(12) United States Patent
Bublot et al.

(10) Patent No.: US 9,114,108 B2
(45) Date of Patent: *Aug. 25, 2015

(54) RECOMBINANT HVT VECTORS EXPRESSING ANTIGENS OF AVIAN PATHOGENS AND USES THEREOF

(71) Applicants: Michel Bublot, Chaponost (FR); Teshome Mebatsion, Watkinsville, GA (US); Joyce Pritchard, Gainesville, GA (US); Perry Linz, Jefferson, GA (US)

(72) Inventors: Michel Bublot, Chaponost (FR); Teshome Mebatsion, Watkinsville, GA (US); Joyce Pritchard, Gainesville, GA (US); Perry Linz, Jefferson, GA (US)

(73) Assignee: MERIAL, INC., Duluth, GA (US)

( * ) Notice: Subject to any disclaimer, the term of this patent is extended or adjusted under 35 U.S.C. 154(b) by 80 days.

This patent is subject to a terminal disclaimer.

(21) Appl. No.: 13/689,625

(22) Filed: Nov. 29, 2012

(65) Prior Publication Data

US 2014/0147457 A1 May 29, 2014

Related U.S. Application Data

(60) Provisional application No. 61/694,957, filed on Aug. 30, 2012, provisional application No. 61/564,877, filed on Nov. 30, 2011.

(51) Int. Cl.
*A61K 39/12* (2006.01)
*C07K 14/005* (2006.01)
*C12N 15/86* (2006.01)
*A61K 39/00* (2006.01)

(52) U.S. Cl.
CPC ................. *A61K 39/12* (2013.01); *C12N 15/86* (2013.01); *A61K 2039/5256* (2013.01); *A61K 2039/552* (2013.01); *A61K 2039/70* (2013.01); *C12N 2710/16334* (2013.01); *C12N 2710/16343* (2013.01); *C12N 2720/10034* (2013.01); *C12N 2760/18134* (2013.01); *C12N 2800/22* (2013.01)

(58) Field of Classification Search
None
See application file for complete search history.

(56) References Cited

U.S. PATENT DOCUMENTS

| | | | |
|---|---|---|---|
| 5,187,087 A | 2/1993 | Sondermeijer et al. | |
| 5,650,153 A | 7/1997 | Ishikawa et al. | |
| 5,853,733 A | 12/1998 | Cochran et al. | |
| 5,980,906 A | 11/1999 | Audonnet et al. | |
| 6,183,753 B1 | 2/2001 | Cochran et al. | |
| 6,299,882 B1 | 10/2001 | Junker | |
| 6,866,852 B2 | 3/2005 | Saitoh et al. | |
| 2007/0212377 A1* | 9/2007 | Okuda et al. | 424/229.1 |
| 2014/0147465 A1* | 5/2014 | Bublot et al. | 424/199.1 |

FOREIGN PATENT DOCUMENTS

| | | |
|---|---|---|
| EP | 1 298 139 | 5/2007 |
| WO | A-87/04463 | 7/1987 |
| WO | WO 2008/038845 | 4/2008 |

OTHER PUBLICATIONS

Taylor et al. (Journal of Virology. 1990; 64 (4): 1441-1450).*
Sequence alignment of instant SEQ ID No: 2 with UniProt database accession No. AAA46675; submitted 1992.*
Sequence alignment of SEQ ID No. 8 with Geneseq database access; No. AAR53527; submitted 1994.*
Sequence alignment of SEQ ID No. 42 with Geneseq database access No. ABR43422, submitted 2003.*
Zelnik et al. (Journal of General Virology. 1994; 75: 2747-2753).*
Tischer et al. (Veterinary Microbiology. 2010; 140: 266-270).*
Sequence alignment of SEQ ID No. 2 with Geneseq accession No: ARL55197, submitted May 2008.*
Zeng, Wei-wei, Y. Wang, and X. Shi. "Optimization of codon usage of F gene enhanced efficacy of Newcastle disease virus DNA vaccine." Chinese Journal of Animal Infectious Diseases 17.2 (2009): 8-16, abstract only.*
Sequence alignment of SEQ ID No. 4 with Geneseq database acc No. ARL55197, submitted May 2008.*
Sequence alignment of SEQ ID No. 33 with Geneseq database acc No. AAR14480, submitted Jun. 2007.*
Sequence alignment of SEQ ID No. 35 with Geneseq database access No. AAR14480, submitted Jun. 2007.*
Sequence alignment of SEQ ID No. 37 with Geneseq database access No. ARL55197, submitted May 2008.*
Slacum et al, 2009, The compatibility of HVT recombinants with other Marek's disease vaccines, 58th Western Poultry Disease Conference, Sacramento, CA, USA, Mar. 23-25, p. 84.
Spatz et al, Virus Gene 42, 3.31-3.38, 2011, "Comparative genomic sequence anabrsis of the Marek's disease vaccine strain SB-1".
Witter et al, 1984, Avian Pathology 13, 75-92, "Polyvalent Marek's disease vaccines: safety, efficacy and protective synergism in chickens with maternal antibodies".
U.S. Appl. No. 13/689,572, Dec. 2014, Bublot et al.
Bublot et al J.Comp. Path.2007,vol. 137, S81-S84, "Use of a Vectored Vaccine against Infectious Bursal Disease of Chickens in the Face of High-Titred maternally Derived Antibody".

(Continued)

*Primary Examiner* — Shanon A Foley
(74) *Attorney, Agent, or Firm* — Judy Jarecki-Black; Ruoying Chen; Merial, Inc.

(57) ABSTRACT

The present invention provides recombinant herpesvirus of turkeys (HVT) vectors that contain and express antigens of avian pathogens, compositions comprising the recombinant HVT vectors, polyvalent vaccines comprising the recombinant HVT vectors and one or more wild type viruses or recombinant vectors. The present invention further provides methods of vaccination against a variety of avian pathogens and method of producing the recombinant HVT vectors.

21 Claims, 77 Drawing Sheets

(56) References Cited

OTHER PUBLICATIONS

Petherbridge, et al., J. Virol. Methods 158, 11-17, 2009, "Cloning of *Gallid herpesvirus* 3 (Marek's disease virus serotype-2) genome as infectious bacterial artificial chromosomes for analysis of viral gene functions".

Jarosinski, et al., J. of Virology 81, 10575-10587, 2007, "Horizontal Transmission of Marek's Disease Virus Requires $U_S2$, the $U_L13$ protein Kinase, and $_gC$".

Jarosinski, et al., J. of Virology 84, 7911-7916, 2010, "Further analysis of Marek's disease virus horizontal transmission confirms that $U_L44$ (gC) and $U_L13$ protein kinase activity are essential, while $U_S2$ is nonessential".

Johnson et al, 2010 Avian Dis 54, 1251-1259, "Protection Against Infectious Laryngotracheitis by In Ovo Vaccination with Commercially Available Viral Vector Recombinant Vaccines".

Morgan et al 1992, Avian dis. 36, 858-70, "Protection of Chickens from Newcastle and Marek's Diseases with a Recombinant Herpesvirus of Turkeys Vaccine Expressing the Newcastle Disease Virus Fusion Protein".

Rudolf Heine 2011; Issues of the Poultry Recombinant Viral Vector Vaccines which May Cause an Effect on the Economic Benefits of those Vaccines; paper presented at the XVII World Veterinary Poultry Association (WVPA) Congress in Cancan, Mexico, Aug. 14-18, 2011.

References Singh et al., Research in Veterinary Science 89, 140-145, 2010, "Comparative efficacy of BAC-derived recombinant SB-1 vaccine and the parent wild type strain in preventing replication, shedding and disease induced by virulent Marek's disease virus".

Database UniProt, EBI accetion No. UNIPROT: Q64957, 1996 & Vakharia et al. "Use of Polymerase chain reaction for efficient cloning of DSRNA infectious bursal disease virus", Avian Disease, vol. 36, No. 3, pp. 736-742, 1996.

Database UniPROT, EBI accession No. UNIPROT A7XL40, 2007 & Miller et al., "Antigenic differences among Newcastle disease virus strains of different genotypes used in vaccine formulation affect viral shedding after a virulent challenge", Vaccine, vol. 25, No. 41, p. 7238-7246, 2007.

Vladimir et al., "Structure and properties of a herpesvirus of turkeys recombinant in which US1, US10 and SORF3 genes have been replaced by a iacZ expression cassette", Journal of General Virology, vol. 76, No. 11, p. 2903-2907, 1995.

Bublot et al., "Use of a vectored vaccine against infectious bursal disease of chickens in the face of high-titred maternally devired antibody", Journal of Comparative Pathology, vol. 137, PS81-S84, 2007.

\* cited by examiner

Figure 1

| SEQ ID NO | Type | Gene |
|---|---|---|
| 1 | DNA | NDV-F VIId codon optimized DNA sequence |
| 2 | Protein | NDV-F protein sequence from codon-optimized VIId strain |
| 3 | DNA | NDV-F VIId wildtype sequence |
| 4 | Protein | NDV-F protein sequence from wildtype VIId strain |
| 5 | DNA | NDV-F Ca02 codon optimized DNA sequence |
| 6 | Protein | NDV-F protein sequence from codon-optimized Ca02 strain |
| 7 | DNA | IBDV DNA encoding VP2 protein |
| 8 | Protein | IBDV VP2 protein |
| 9 | DNA | SV40 promoter |
| 10 | DNA | CMV-IE promoter |
| 11 | DNA | SV40 polyA signal |
| 12 | DNA | Synthetic polyA signal |
| 13 | oligo | MB080 primer |
| 14 | oligo | MB081 primer |
| 15 | oligo | optF primer |
| 16 | oligo | VIIoptF RP primer |
| 17 | oligo | SV40promoterF primer |
| 18 | DNA | Partial plasmid pHM103+Fopt DNA sequence (for vHVT114) |
| 19 | DNA | Partial plasmid pSB1 44 cds SV FCAopt (for vSB1-009) |
| 20 | DNA | Partial plasmid pHVT US2 SV- Fopt-synPA (for vHVT306) |
| 21 | DNA | Partial plasmid pCD046+NDV-F wt (for vHVT110) |
| 22 | DNA | Partial plasmid pHM103+NDV-F wt (for vHVT111) |
| 23 | DNA | Partial plasmid pHM103 + NDV-F CA02 (for vHVT116) |
| 24 | DNA | Partial plasmid HVTIG2 SV Fwt SbfI sequence (for vHVT301) |
| 25 | DNA | Partial plasmid pHVTUS10 cds F opt plasmid (for vHVT302) |
| 26 | DNA | Partial plasmid pHVTUS10 cds F CA02 opt sequence (for vHVT303) |
| 27 | DNA | Partial plasmid HVT IG2 SVFopt syn tail sequence (for vHVT304) |
| 28 | DNA | Partial plasmid pHVT US2 SV-FCA02 opt-synPA (for vHVT307) |
| 29 | DNA | Partial plasmid pCD046+NDV-F VII YZCQ sequence (vHVT112) |
| 30 | DNA | Partial plasmid pCD046+NDV Texas F sequence (for vHVT113) |
| 31 | DNA | Partial plasmid pHM119 sequence (for vHVT039) |
| 32 | DNA | NDV-F Wtnm-Texas wildtype DNA sequence |
| 33 | protein | NDV-F protein from Wtnm-Texas wildtype |
| 34 | DNA | NDV-F YZCQ wildtype DNA sequence |
| 35 | protein | NDV-F protein from wildtype YZCQ strain |
| 36 | DNA | NDV-F Texas wildtype DNA sequence |
| 37 | protein | NDV-F protein from wildtype Texas strain |
| 38 | DNA | MDV gB promoter |

Figure 1 (continued)

| SEQ ID NO | Type | Gene |
|---|---|---|
| 39 | DNA | Partial plasmid HVT SORF3-US2 gpVar-Ewtsyn sequence (for vHVT202) |
| 40 | DNA | Partial plasmid SB1US2 gpVIIdwtsyn sequence (for vSB1-010) |
| 41 | DNA | IBDV DNA encoding VP2 protein of IBDV E strain |
| 42 | protein | IBDV VP2 protein of IBDV E strain |
| 43 | DNA | Guinea pig CMV promoter |
| 44 | oligo | primer HM101 |
| 45 | oligo | Primer HM102 |
| 46 | oligo | primer F-ATG |
| 47 | oligo | Primer F-STOP |

Genomic Structure of HVT, ORFs of the *BamHI* fragment,
and Insertion/Replacement Locations
(GenBank accession number for HVT FC126 sequence: AF291866.1)

Figure 3

Plasmid map of pHM103 containing codon-optimized NDV-F gene

- amp
- Intergene 1 arm
- pHM103 + Fopt
- 7212 bp
- SV40 Promoter
- NotI (2264)
- Intergene 1 arm
- polyA SV 40
- NotI (3941)
- NDV-FconsVIId-CSmut vHVT114 identity PCR Lane 1: no template
Lane 2: FC126 cl2
Lane 3: vHVT114

Dual Immunofluorescent Assay

Panel A is from the pre-MSV passage
Panel B is from the pre-MSV+12 passage

Figure 6

Southern blot using the NDV-F probe

|  1  2  3 | 1  2  3 | 1  2  3 | 1  2  3 |

BamHI    PstI    SphI    NcoI

-- 1.6

1 = pHM103+Fopt donor
2 = vHVT114
3 = FC126 cl2

Immunoprecipitation and Western Blot of vHVT114

Lane M: Pre-Stained Standard (SeeBlue, Invitrogen);
Lane 1: CEF;
Lane 2: vHVT114.

Western blot analysis of immunoprecipitated sample from vHVT306 infected cells

Lane M: pre-stained protein standard (Invitrogen, SeeBlue)
Lane 1: uninfected CEF
Lane 2: vHVT306

Figure 9

Western blot analysis of immunoprecipitated sample
from vSB1-009 infected cells

Lane M: pre-stained protein standard (Invitrogen, SeeBlue)
Lane 1: uninfected CEF
Lane 2: vSB1-009 pre-MSV stock

Figure 10

Challenge study of vHVT304 and vHVT114 against NDV ZJ1 and CA02

Figure 13

Protein sequence alignment of NDV-F

```
                   1                                                      50
SEQ ID NO:2    (1) MGSKPSTRIPAPLMLITRIMLILGCIRPTSSLDGRPLAAAGIVVTGDKAV
SEQ ID NO:33   (1) MGSRSSTRIPVPLMLIIRTALTLSCIRLTSSLDGRPLAAAGIVVTGDKAV
SEQ ID NO:35   (1) MGSRSSTRIPVPLMLIIRTALTLSCIRLTSSLDGRPLAAAGIVVTGDKAV
SEQ ID NO:37   (1) MGSKPSTRIPAPLMLITRIMLILDCIRPTSSLDGRPLAAAGIVVTGDKAV
SEQ ID NO:4    (1) MGSKPSTRIPAPLMLITRIMLILGCIRPTSSLDGRPLAAAGIVVTGDKAV
SEQ ID NO:6    (1) MGSKPSTWISVTLMLITRTMLILSCICPTSSLDGRPLAAAGIVVTGDKAV 51                                                     100
SEQ ID NO:2   (51) NVYTSSQTGSIIVKLLPNMPRDKEACAKAPLEAYNRTLTTLLTPLGDSIR
SEQ ID NO:33  (51) NIYTSSQTGSIIVKLLPNMPKDKEVCAKAPLEAYNRTLTTLLTPLGDSIR
SEQ ID NO:35  (51) NIYTSSQTGSIIVKLLPNMPKDKEVCAKAPLEAYNRTLTTLLTPLGDSIR
SEQ ID NO:37  (51) NVYTSSQTGSIIVKLLPNMPKDKEACAKDPLEAYNRTLTTLLTPLGESIR
SEQ ID NO:4   (51) NVYTSSQTGSIIVKLLPNMPRDKEACAKAPLEAYNRTLTTLLTPLGDSIR
SEQ ID NO:6   (51) NIYTSSQTGSIIIKLLPNMPKDKEACAKAPLEAYNRTLTTLLTPLGDSIR 101                                                    150
SEQ ID NO:2  (101) KIQGSVSTSGGGKQGRLIGAVIGSVALGVATAAQITAAAALIQANQNAAN
SEQ ID NO:33 (101) RIQESVTTSGGRRQRRFIGAIIGSVALGVATAAQITAASALIQANQNAAN
SEQ ID NO:35 (101) RIQESVTTSGGGKQGRLIGAIIGSVALGVATAAQITAASALIQANQNAAN
SEQ ID NO:37 (101) KIQGSVSTSGGGKQGRLIGAVIGSVALGVATAAQITAAAALIQANQNAAN
SEQ ID NO:4  (101) KIQGSVSTSGGGKQGRLIGAVIGSVALGVATAAQITAAAALIQANQNAAN
SEQ ID NO:6  (101) RIQGSATTSGGGKQGRLVGAIIGSVALGVATAAQITAAAALIQANQNAAN 151                                                    200
SEQ ID NO:2  (151) ILRLKESIAATNEAVHEVTDGLSQLSVAVGKMQQFVNDQFNNTARELDCI
SEQ ID NO:33 (151) ILRLKESIAATNEAVHEVTDGLSQLAVAVGKMQQFVNDQFNNTAQELDCI
SEQ ID NO:35 (151) ILRLKESIAATNEAVHEVTDGLSQLAVAVGKMQQFVNDQFNNTAQELDCI
SEQ ID NO:37 (151) ILRLKESIAATNEAVHEVTDGLSQLSVAVGKMQQFVNDQFNNTARELDCI
SEQ ID NO:4  (151) ILRLKESIAATNEAVHEVTDGLSQLSVAVGKMQQFVNDQFNNTARELDCI
SEQ ID NO:6  (151) ILRLKESIAATNDAVHEVTNGLSQLAVAVGKMQQFVNNQFNNTARELDCI 201                                                    250
SEQ ID NO:2  (201) KITQQVGVELNLYLTELTTVFGPQITSPALTQLTIQALYNLAGGNMDYLL
SEQ ID NO:33 (201) KIAQQVGVELNLYLTELTTVFGPQITSPALTQLTIQALYNLAGGNMDYLL
SEQ ID NO:35 (201) KIAQQVGVELNLYLTELTTVFGPQITSPALTQLTIQALYNLAGGNMDYLL
SEQ ID NO:37 (201) KITQQVGVELNLYLTELTTVFGPQITSPALTQLTIQALYNLAGGNMDYLL
SEQ ID NO:4  (201) KITQQVGVELNLYLTELTTVFGPQITSPALTQLTIQALYNLAGGNMDYLL
SEQ ID NO:6  (201) KIAQQVGVELNLYLTELTTVFGPQITSPALTQLTIQALYNLAGGNMDYLL 251                                                    300
SEQ ID NO:2  (251) TKLGIGNNQLSSLIGSGLITGYPILYDSQTQLLGIQVNLPSVGNLNNMRA
SEQ ID NO:33 (251) TKLGVGNNQLSSLIGSGLITGNPILYDSQTQILGIQVTLPSVGNLNNMRA
SEQ ID NO:35 (251) TKLGVGNNQLSSLIGSGLITGNPILYDSQTQILGIQVTLPSVGNLNNMRA
SEQ ID NO:37 (251) TKLGIGNNQLSSLIGSGLITGYPILYDSQTQLLGIQVNLPSVGNLNNMRA
SEQ ID NO:4  (251) TKLGIGNNQLSSLIGSGLITGYPILYDSQTQLLGIQVNLPSVGNLNNMRA
SEQ ID NO:6  (251) TKLGVGNNQLSSLIGSGLITGNPILYDSQTQLLGIQINLPSVGSLNNMRA
```

Figure 13 (continued)

```
                    301                                                350
SEQ ID NO:2    (301) TYLETLSVSTTKGYASALVPKVVTQVGSVIEELDTSYCIESDLDLYCTRI
SEQ ID NO:33   (301) TYLETLSVSTTKGFASALVPKVVTQVGSVIEELDTSYCIGTDLDLYCTRI
SEQ ID NO:35   (301) TYLETLSVSTTKGFASALVPKVVTQVGSVIEELDTSYCIGTDLDLYCTRI
SEQ ID NO:37   (301) TYLETLSVSTAKGYASALVPKVVTQVGSVIEELDTSYCIESDLDLYCTRI
SEQ ID NO:4    (301) TYLETLSVSTTKGYASALVPKVVTQVGSVIEELDTSYCIESDLDLYCTRI
SEQ ID NO:6    (301) TYLETLSVSTTKGFASALVPKVVTQVGSVIEELDTSYCIESDIDLYCTRV 351                                                400
SEQ ID NO:2    (351) VTFPMSPGIYSCLSGNTSACMYSKTEGALTTPYMALKGSVIANCKITTCR
SEQ ID NO:33   (351) VTFPMSPGIYSCLSGNTSACMYSKTEGALTTPYMALKGSVIANCKLTTCR
SEQ ID NO:35   (351) VTFPMSPGIYSCLSGNTSACMYSKTEGALTTPYMALKGSVIANCKLTTCR
SEQ ID NO:37   (351) VTFPMSPGIYSCLSGNTSACMYSKTEGALTTPYMALKGSVIANCKITTCR
SEQ ID NO:4    (351) VTFPMSPGIYSCLSGNTSACMYSKTEGALTTPYMALKGSVIANCKITTCR
SEQ ID NO:6    (351) VTFPMSPGIYSCLSGNTSACMYSKTEGALTTPYMALKGSVIANCKMTTCR 401                                                450
SEQ ID NO:2    (401) CTDPPGIISQNYGEAVSLIDRHSCNVLSLDGITLRLSGEFDATYQKNISI
SEQ ID NO:33   (401) CADPPGIISQNYGEAVSLIDRHSCNVLSLDGITLRLSGEFDATYQKNISI
SEQ ID NO:35   (401) CADPPGIISQNYGEAVSLIDRHSCNVLSLDGITLRLSGEFDATYQKNISI
SEQ ID NO:37   (401) CTDPPGIISQNYGEAVSLIDRHSCNVLSLDGITLRLSGEFDATYQKNISI
SEQ ID NO:4    (401) CTDPPGIISQNYGEAVSLIDRHSCNVLSLDGITLRLSGEFDATYQKNISI
SEQ ID NO:6    (401) CADPPGIISQNYGEAVSLIDKHSCSVLSLDGITLRLSGEFDATYQKNISI 451                                                500
SEQ ID NO:2    (451) LDSQVIVTGNLDISTELGNVNNSISNALDRLAESNSKLEKVNVRLTSTSA
SEQ ID NO:33   (451) LDSQVIVTGNLDISTELGNVNNSISNALNKLEESNSKLDKVNVKLTSTSA
SEQ ID NO:35   (451) LDSQVIVTGNLDISTELGNVNNSISNALNKLEESNSKLDKVNVKLTSTSA
SEQ ID NO:37   (451) LDSQVIVTGNLDISTELGNVNNSISNALDKLAKSNSKLEKVNVRLTSTSA
SEQ ID NO:4    (451) LDSQVIVTGNLDISTELGNVNNSISNALDRLAESNSKLEKVNVRLTSTSA
SEQ ID NO:6    (451) LDSQVIVTGNLDISTELGNVNNSISSTLDKLAESNNKLNKVNVNLTSTSA 501                                                550
SEQ ID NO:2    (501) LITYIVLTVISLVFGALSLVLACYLMYKQKAQQKTLLWLGNNTLDQMRAT
SEQ ID NO:33   (501) LITYIVLTVISLVFGVLSLVLACYLMYKQKAQQKTLLWLGNNTLDQMRAT
SEQ ID NO:35   (501) LITYIVLTVISLVFGVLSLVLACYLMYKQKAQQKTLLWLGNNTLDQMRAT
SEQ ID NO:37   (501) LITYIVLTVISLVFGALSLGLTCYLMYKQKAQQKTLLWLGNNTLDQMRAT
SEQ ID NO:4    (501) LITYIVLTVISLVFGALSLVLACYLMYKQKAQQKTLLWLGNNTLDQMRAT
SEQ ID NO:6    (501) LITYIVLAIVSLAFGVISLVLACYLMYKQRAQQKTLLWLGNNTLDQMRAT

551
SEQ ID NO:2    (551) TRA--
SEQ ID NO:33   (551) TKI--
SEQ ID NO:35   (551) TKI--
SEQ ID NO:37   (551) TRA--
SEQ ID NO:4    (551) TRA--
SEQ ID NO:6    (551) TRT--
```

Figure 13 (continued)

|  | SEQ ID NO:2 | SEQ ID NO:33 | SEQ ID NO:35 | SEQ ID NO:37 | SEQ ID NO:4 | SEQ ID NO:6 |
|---|---|---|---|---|---|---|
| SEQ ID NO:2 |  | 92% | 93% | 98% | 100% | 92% |
| SEQ ID NO:33 |  |  | 99% | 92% | 92% | 91% |
| SEQ ID NO:35 |  |  |  | 92% | 93% | 92% |
| SEQ ID NO:37 |  |  |  |  | 98% | 91% |
| SEQ ID NO:4 |  |  |  |  |  | 92% |
| SEQ ID NO:6 |  |  |  |  |  |  |

Figure 13 (continued)

DNA sequence alignment of NDV-F genes

```
              1                                                  50
SEQ ID NO:1   (1)   ATGGGCAGCAAGCCCAGCACAAGAATCCCAGCCCCCCTGATGCTGATCAC
SEQ ID NO:3   (1)   ATGGGCTCCAAACCTTCTACCAGGATCCCAGCACCTCTGATGCTGATCAC
SEQ ID NO:32  (1)   ATGGGCTCCAGATCTTCTACCAGGATCCCGGTACCTCTAATGCTGATCAT
SEQ ID NO:34  (1)   ATGGGCTCCAGATCTTCTACCAGGATCCCGGTACCTCTAATGCTGATCAT
SEQ ID NO:36  (1)   ATGGGCTCTAAACCTTCTACCAGGATCCCAGCACCTCTGATGCTGATCAC
SEQ ID NO:5   (1)   ATGGGCAGCAAGCCCAGCACCTGGATCAGCGTGACCCTGATGCTGATCAC 51                                                 100
SEQ ID NO:1   (51)  CCGCATCATGCTGATCCTGGGCTGCATCAGACCCACAAGCTCCCTGGATG
SEQ ID NO:3   (51)  CCGGATTATGCTGATATTGGGCTGTATCCGTCCGACAAGCTCTCTTGACG
SEQ ID NO:32  (51)  CCGAACCGCGCTGACACTGAGCTGTATCCGTCTGACAAGCTCTCTTGATG
SEQ ID NO:34  (51)  CCGAACCGCGCTGACACTGAGCTGTATCCGTCTGACAAGCTCTCTTGATG
SEQ ID NO:36  (51)  CCGGATTATGCTGATATTGGACTGTATCCGTCCGACAAGCTCTCTTGACG
SEQ ID NO:5   (51)  CAGAACCATGCTGATCCTGAGCTGCATCTGCCCCACAAGCAGCCTGGACG 101                                                150
SEQ ID NO:1   (101) GACGCCCCTGGCCGCTGCCGGCATCGTGGTGACCGGCGACAAGGCCGTG
SEQ ID NO:3   (101) GCAGGCCTCTTGCAGCTGCAGGAATTGTAGTAACAGGAGATAAGGCAGTC
SEQ ID NO:32  (101) GCAGGCCTCTTGCGGCTGCAGGGATCGTGGTAACAGGAGATAAAGCAGTC
SEQ ID NO:34  (101) GCAGGCCTCTTGCGGCTGCAGGGATCGTGGTAACAGGAGATAAAGCAGTC
SEQ ID NO:36  (101) GCAGGCCTCTTGCAGCTGCAGGAATTGTAGTAACAGGAGATAAGGCAGTC
SEQ ID NO:5   (101) GCAGACCCCTGGCCGCTGCCGGCATCGTGGTGACCGGCGACAAGGCCGTG 151                                                200
SEQ ID NO:1   (151) AACGTGTACACCAGCAGCCAGACCGGCAGCATCATCGTGAAGCTGCTGCC
SEQ ID NO:3   (151) AATGTATACACTTCGTCTCAGACAGGGTCAATCATAGTCAAGTTGCTCCC
SEQ ID NO:32  (151) AACATATACACCTCATCCCAGACAGGGTCAATCATAGTTAAGTTACTCCC
SEQ ID NO:34  (151) AACATATACACCTCATCCCAGACAGGGTCAATCATAGTTAAGTTACTCCC
SEQ ID NO:36  (151) AATGTATATACCTCGTCTCAGACAGGGTCAATCATAGTCAAGTTGCTCCC
SEQ ID NO:5   (151) AACATCTACACCAGCAGCCAGACCGGCAGCATCATCATCAAGCTGCTGCC 201                                                250
SEQ ID NO:1   (201) CAACATGCCCAGAGACAAAGAGGCCTGCGCCAAGGCCCCCCTGGAAGCCT
SEQ ID NO:3   (201) GAATATGCCCAGGGATAAGGAGGCGTGTGCAAAAGCCCCATTAGAGGCAT
SEQ ID NO:32  (201) GAATATGCCCAAGGACAAAGAGGTGTGTGCAAAAGCCCCATTGGAGGCAT
SEQ ID NO:34  (201) GAATATGCCCAAGGACAAAGAGGTGTGTGCAAAAGCCCCATTGGAGGCAT
SEQ ID NO:36  (201) GAATATGCCCAAGGATAAGGAGGCGTGTGCGAAAGCCCATTAGAGGCAT
SEQ ID NO:5   (201) CAACATGCCCAAGGACAAAGAGGCCTGCGCCAAGGCCCCCCTGGAAGCCT 251                                                300
SEQ ID NO:1   (251) ACAACAGAACCCTGACCACCCTGCTGACCCCCCTGGGCGACAGCATCAGA
SEQ ID NO:3   (251) ATAACAGAACACTGACTACTTTGCTCACTCCTCTTGGCGACTCCATCCGC
SEQ ID NO:32  (251) ACAACAGGACACTGACTACTTTACTCACCCCCCTTGGTGATTCTATCCGC
SEQ ID NO:34  (251) ACAACAGGACACTGACTACTTTACTCACCCCCCTTGGTGATTCTATCCGC
SEQ ID NO:36  (251) ATAACAGAACACTGACTACTTTGCTCACTCCTCTTGGCGAATCCATCCGC
SEQ ID NO:5   (251) ACAACAGAACCCTGACCACCCTGCTGACCCCCCTGGGCGACAGCATCAGA
```

Figure 13 (continued)

```
             301                                                350
SEQ ID NO:1  (301) AAGATCCAGGGCTCCGTGAGCACAAGCGGCGGAGGAAAGCAGGGCAGACT
SEQ ID NO:3  (301) AAGATCCAAGGGTCTGTGTCCACATCTGGAGGAGGCAAGCAAGGCCGCCT
SEQ ID NO:32 (301) AGGATACAAGAGTCTGTGACTACTTCCGGAGGAAGGAGACAGAGACGCTT
SEQ ID NO:34 (301) AGGATACAAGAGTCTGTGACTACTTCCGGAGGAGGCAAGCAAGGCCGCCT
SEQ ID NO:36 (301) AAGATCCAAGGGTCTGTGTCCACGTCTGGAGGAGGCAAGCAAGGCCGCCT
SEQ ID NO:5  (301) AGAATCCAGGGCAGCGCCACCACAAGCGGCGGAGGAAAGCAGGGCAGACT 351                                                400
SEQ ID NO:1  (351) GATCGGCGCCGTGATCGGCAGCGTGGCCCTGGGAGTGGCTACAGCTGCCC
SEQ ID NO:3  (351) GATAGGTGCTGTTATTGGCAGTGTAGCTCTTGGGGTTGCAACAGCGGCAC
SEQ ID NO:32 (351) TATAGGTGCCATTATCGGCAGTGTAGCTCTTGGGGTTGCGACAGCTGCAC
SEQ ID NO:34 (351) GATAGGTGCCATTATCGGCAGTGTAGCTCTTGGGGTTGCGACAGCTGCAC
SEQ ID NO:36 (351) GATAGGTGCTGTTATTGGTAGTGTAGCTCTTGGGGTTGCAACAGCGGCAC
SEQ ID NO:5  (351) GGTGGGCGCTATCATCGGGAGCGTGGCCCTGGGCGTGGCCACAGCTGCCC 401                                                450
SEQ ID NO:1  (401) AGATTACCGCTGCAGCCGCCCTGATCCAGGCCAACCAGAACGCCGCCAAC
SEQ ID NO:3  (401) AGATAACAGCAGCTGCGGCCCTAATACAAGCCAACCAGAATGCCGCCAAC
SEQ ID NO:32 (401) AGATAACAGCAGCTTCGGCCCTGATACAAGCCAACCAGAATGCTGCCAAC
SEQ ID NO:34 (401) AGATAACAGCAGCTTCGGCCCTGATACAAGCCAACCAGAATGCTGCCAAC
SEQ ID NO:36 (401) AAATAACAGCAGCTGCGGCCCTAATACAAGCCAACCAGAATGCTGCCAAC
SEQ ID NO:5  (401) AGATTACCGCTGCAGCCGCCCTGATTCAGGCCAATCAGAACGCCGCCAAC 451                                                500
SEQ ID NO:1  (451) ATCCTGAGACTGAAAGAGAGCATTGCCGCCACCAACGAGGCCGTGCACGA
SEQ ID NO:3  (451) ATCCTCCGGCTTAAGGAGAGCATTGCTGCAACCAATGAAGCTGTGCATGA
SEQ ID NO:32 (451) ATCCTCCGGCTTAAAGAGAGCATTGCTGCAACCAATGAAGCTGTGCACGA
SEQ ID NO:34 (451) ATCCTCCGGCTTAAAGAGAGCATTGCTGCAACCAATGAAGCTGTGCACGA
SEQ ID NO:36 (451) ATCCTTCGGCTTAAGGAGAGCATTGCTGCAACCAATGAAGCTGTGCATGA
SEQ ID NO:5  (451) ATCCTGAGACTGAAAGAGAGCATTGCCGCCACCAACGACGCCGTGCACGA 501                                                550
SEQ ID NO:1  (501) AGTGACCGACGGCCTGAGCCAGCTGTCCGTGGCCGTGGGCAAGATGCAGC
SEQ ID NO:3  (501) AGTCACCGACGGATTATCACAACTATCAGTGGCAGTTGGGAAGATGCAGC
SEQ ID NO:32 (501) GGTCACTGACGGATTATCACAACTAGCAGTGGCAGTAGGGAAGATGCAAC
SEQ ID NO:34 (501) GGTCACTGACGGATTATCACAACTAGCAGTGGCAGTAGGGAAGATGCAAC
SEQ ID NO:36 (501) AGTCACCGACGGATTATCACAACTATCAGTGGCAGTTGGGAAGATGCAGC
SEQ ID NO:5  (501) AGTGACAAACGGACTGTCCCAGCTGGCTGTCGCTGTCGGCAAGATGCAGC 551                                                600
SEQ ID NO:1  (551) AGTTCGTGAACGACCAGTTCAACAACACCGCCAGAGAGCTGGACTGCATC
SEQ ID NO:3  (551) AGTTTGTCAATGACCAGTTTAATAATACGGCGCGAGAATTGGACTGTATA
SEQ ID NO:32 (551) AGTTTGTCAATGACCAGTTTAATAATACAGCGCAAGAATTGGACTGTATA
SEQ ID NO:34 (551) AGTTTGTCAATGACCAGTTCAATAATACAGCGCAAGAATTGGACTGTATA
SEQ ID NO:36 (551) AGTTTGTCAATGACCAGTTTAATAATACAGCGCGAGAATTGGACTGTATA
SEQ ID NO:5  (551) AGTTCGTGAACAACCAGTTCAACAACACCGCCAGAGAGCTGGACTGCATC
```

Figure 13 (continued)

```
              601                                              650
SEQ ID NO:1   (601) AAGATCACCCAGCAGGTGGGCGTGGAGCTGAACCTGTACCTGACCGAGCT
SEQ ID NO:3   (601) AAAATCACACAACAGGTTGGTGTAGAACTCAACCTATACCTAACTGAATT
SEQ ID NO:32  (601) AAAATTGCACAGCAGGTCGGTGTAGAACTCAACTTGTACCTAACTGAATT
SEQ ID NO:34  (601) AAAATTGCACAGCAGGTCGGTGTAGAACTCAACTTGTACCTAACTGAATT
SEQ ID NO:36  (601) AAAATCACACAACAGGTTGGTGTAGAACTCAACCTATACCTAACTGAATT
SEQ ID NO:5   (601) AAGATCGCCCAGCAGGTGGGCGTGGAGCTGAACCTGTACCTGACCGAGCT 651                                              700
SEQ ID NO:1   (651) GACCACAGTGTTCGGCCCCCAGATCACAAGCCCAGCCCTGACACAGCTGA
SEQ ID NO:3   (651) GACTACAGTATTCGGGCCACAGATCACCTCCCCTGCATTAACTCAGCTGA
SEQ ID NO:32  (651) GACTACAGTATTTGGGCCACAAATCACTTCCCCTGCCTTAACTCAGCTGA
SEQ ID NO:34  (651) GACTACAGTATTTGGGCCACAAATCACTTCCCCTGCCTTAACTCAGCTGA
SEQ ID NO:36  (651) GACTACAGTATTCGGGCCACAGATCACCTCCCCTGCATTAACTCAGCTGA
SEQ ID NO:5   (651) GACCACAGTGTTCGGCCCCCAGATCACAAGCCCCGCTCTGACCCAGCTGA 701                                              750
SEQ ID NO:1   (701) CCATCCAGGCCCTGTACAACCTGGCTGGCGGCAACATGGACTATCTGCTG
SEQ ID NO:3   (701) CCATCCAGGCACTTTATAATTTAGCTGGTGGCAATATGGATTACTTATTA
SEQ ID NO:32  (701) CTATCCAAGCGCTTTACAATCTAGCTGGTGGTAATATGGATTACTTGCTG
SEQ ID NO:34  (701) CTATCCAAGCGCTTTACAATCTAGCTGGTGGTAATATGGATTACTTGCTG
SEQ ID NO:36  (701) CCATCCAGGCACTTTATAATTTAGCTGGTGGCAATATGGATTACTTATTA
SEQ ID NO:5   (701) CAATCCAGGCCCTGTACAACCTGGCTGGCGGCAACATGGACTATCTGCTG 751                                              800
SEQ ID NO:1   (751) ACAAAGCTGGGAATCGGCAACAACCAGCTGTCCAGCCTGATCGGAAGCGG
SEQ ID NO:3   (751) ACTAAGTTAGGTATAGGGAACAATCAACTCAGCTCGTTAATTGGTAGCGG
SEQ ID NO:32  (751) ACTAAGTTAGGTGTAGGGAACAACCAACTCAGCTCATTAATTGGTAGCGG
SEQ ID NO:34  (751) ACTAAGTTAGGTGTAGGGAACAACCAACTCAGCTCATTAATTGGTAGCGG
SEQ ID NO:36  (751) ACTAAGTTAGGTATAGGGAACAATCAACTCAGCTCATTAATTGGCAGCGG
SEQ ID NO:5   (751) ACTAAGCTGGGAGTGGGCAACAACCAGCTGTCCAGCCTGATCGGGTCCGG 801                                              850
SEQ ID NO:1   (801) CCTGATCACCGGCTACCCCATCCTGTACGACAGCCAGACACAGCTGCTGG
SEQ ID NO:3   (801) CCTGATCACTGGTTACCCTATACTGTATGACTCACAGACTCAACTCTTGG
SEQ ID NO:32  (801) CTTGATCACCGGCAACCCTATTCTGTACGACTCACAGACTCAGATCTTGG
SEQ ID NO:34  (801) CTTGATCACCGGCAACCCTATTCTGTACGACTCACAGACTCAGATCTTGG
SEQ ID NO:36  (801) CCTGATCACTGGTTACCCTATATTGTATGACTCACAGACTCAACTCTTGG
SEQ ID NO:5   (801) GCTGATCACAGGCAACCCCATCCTGTACGACAGCCAGACACAGCTGCTGG 851                                              900
SEQ ID NO:1   (851) GCATCCAGGTGAACCTGCCCAGCGTGGGCAACCTGAACAACATGCGCGCC
SEQ ID NO:3   (851) GCATACAAGTGAATTTACCCTCAGTCGGGAACTTAAATAATATGCGTGCC
SEQ ID NO:32  (851) GTATACAGGTAACTTTGCCTTCAGTTGGGAACCTGAATAATATGCGTGCC
SEQ ID NO:34  (851) GTATACAGGTAACTTTGCCTTCAGTTGGGAACCTGAATAATATGCGTGCC
SEQ ID NO:36  (851) GCATACAAGTGAATTTGCCCTCAGTCGGGAACTTAAATAATATGCGTGCC
SEQ ID NO:5   (851) GCATCCAGATCAACCTGCCATCCGTGGGAAGCCTGAACAACATGAGAGCC
```

Figure 13 (continued)

```
                        901                                              950
SEQ ID NO:1    (901)   ACCTACCTGGAAACCCTGAGCGTGTCCACCACCAAGGGCTACGCCAGCGC
SEQ ID NO:3    (901)   ACCTATTTGGAGACCTTATCTGTAAGTACAACCAAAGGATATGCCTCAGC
SEQ ID NO:32   (901)   ACCTACCTGGAGACCTTATCTGTAAGCACAACCAAGGGATTTGCCTCAGC
SEQ ID NO:34   (901)   ACCTACCTGGAGACCTTATCTGTAAGCACAACCAAGGGATTTGCCTCAGC
SEQ ID NO:36   (901)   ACCTATTTAGAGACCTTATCTGTAAGTACAGCCAAAGGATATGCCTCAGC
SEQ ID NO:5    (901)   ACCTACCTGGAAACCCTGAGCGTGTCCACCACCAAGGGCTTCGCCAGCGC 951                                             1000
SEQ ID NO:1    (951)   CCTGGTGCCCAAGGTGGTGACACAGGTGGGCAGCGTGATCGAGGAACTGG
SEQ ID NO:3    (951)   ACTTGTCCCGAAAGTAGTGACACAAGTCGGTTCCGTGATAGAAGAGCTTG
SEQ ID NO:32   (951)   ACTTGTCCCAAAAGTGGTGACACAGGTCGGTTCCGTGATAGAAGAACTTG
SEQ ID NO:34   (951)   ACTTGTCCCAAAAGTGGTGACACAGGTCGGTTCCGTGATAGAAGAACTTG
SEQ ID NO:36   (951)   ACTTGTTCCAAAAGTAGTGACACAAGTCGGTTCTGTGATAGAAGAGCTTG
SEQ ID NO:5    (951)   CCTGGTGCCCAAGGTGGTGACACAGGTGGGCAGCGTGATCGAGGAACTGG 1001                                             1050
SEQ ID NO:1   (1001)   ACACCAGCTACTGCATCGAGAGCGACCTGGACCTGTACTGCACCAGAATC
SEQ ID NO:3   (1001)   ACACCTCATACTGTATAGAGTCCGATCTGGATTTATATTGTACTAGAATA
SEQ ID NO:32  (1001)   ACACCTCATACTGTATAGGGACCGACTTGGATTTATACTGTACAAGAATA
SEQ ID NO:34  (1001)   ACACCTCATACTGTATAGGGACCGACTTGGATTTATACTGTACAAGAATA
SEQ ID NO:36  (1001)   ACACCTCATACTGTATAGAGTCCGATCTGGATTTATATTGTACTAGAATA
SEQ ID NO:5   (1001)   ACACCAGCTACTGCATCGAGAGCGACATCGACCTGTACTGCACCAGAGTG 1051                                             1100
SEQ ID NO:1   (1051)   GTGACCTTCCCAATGAGCCCCGGCATCTACAGCTGCCTGAGCGGCAACAC
SEQ ID NO:3   (1051)   GTGACATTCCCCATGTCCCCAGGTATTTATTCCTGTTTGAGCGGCAACAC
SEQ ID NO:32  (1051)   GTGACATTCCCTATGTCTCCTGGTATTTATTCTTGTCTGAGCGGTAATAC
SEQ ID NO:34  (1051)   GTGACATTCCCTATGTCTCCTGGTATTTATTCTTGTCTGAGCGGTAATAC
SEQ ID NO:36  (1051)   GTGACATTCCCCATGTCCCCAGGTATTTATTCCTGTTTAAGCGGCAACAC
SEQ ID NO:5   (1051)   GTGACCTTCCCAATGAGCCCCGGCATCTACAGCTGCCTGAGCGGCAACAC 1101                                             1150
SEQ ID NO:1   (1101)   CAGCGCCTGCATGTACAGCAAGACCGAAGGCGCACTGACAACACCCTACA
SEQ ID NO:3   (1101)   ATCAGCTTGCATGTATTCAAAGACTGAAGGCGCACTCACTACGCCGTATA
SEQ ID NO:32  (1101)   ATCGGCTTGCATGTATTCAAAGACTGAAGGCGCACTTACTACGCCATATA
SEQ ID NO:34  (1101)   ATCGGCTTGCATGTATTCAAAGACTGAAGGCGCACTTACTACGCCATATA
SEQ ID NO:36  (1101)   ATCAGCTTGCATGTATTCAAAGACTGAAGGCGCACTCACTACGCCGTATA
SEQ ID NO:5   (1101)   CAGCGCCTGCATGTACAGCAAGACCGAAGGAGCACTGACAACACCCTACA 1151                                             1200
SEQ ID NO:1   (1151)   TGGCCCTGAAGGGAAGCGTGATCGCCAACTGCAAGATCACCACCTGCAGA
SEQ ID NO:3   (1151)   TGGCCCTTAAAGGCTCAGTTATTGCCAATTGTAAAATAACAACATGTAGA
SEQ ID NO:32  (1151)   TGGCTCTCAAAGGCTCAGTTATTGCCAATTGCAAGCTGACAACATGTAGA
SEQ ID NO:34  (1151)   TGGCTCTCAAAGGCTCAGTTATTGCCAATTGCAAGCTGACAACATGTAGA
SEQ ID NO:36  (1151)   TGGCCCTTAAAGGCTCAGTTATTGCCAATTGTAAGATAACAACATGTAGA
SEQ ID NO:5   (1151)   TGGCCCTGAAGGGAAGCGTGATCGCCAACTGCAAGATGACCACCTGCAGA
```

Figure 13 (continued)

```
                    1201                                              1250
SEQ ID NO:1  (1201) TGCACCGACCCCCCAGGCATCATCAGCCAGAACTACGGCGAGGCCGTGAG
SEQ ID NO:3  (1201) TGTACAGACCCTCCTGGTATCATATCGCAAAATTATGGAGAAGCTGTATC
SEQ ID NO:32 (1201) TGTGCAGATCCCCCAGGTATCATATCGCAAAATTATGGAGAAGCTGTGTC
SEQ ID NO:34 (1201) TGTGCAGATCCCCCAGGTATCATATCGCAAAATTATGGAGAAGCTGTGTC
SEQ ID NO:36 (1201) TGTACAGACCCTCCTGGTATCATATCGCAAAATTATGGAGAAGCTGTATC
SEQ ID NO:5  (1201) TGCGCCGACCCCCCAGGCATCATCAGCCAGAACTACGGCGAGGCCGTGAG 1251                                              1300
SEQ ID NO:1  (1251) CCTGATCGATCGCCATTCCTGTAACGTGCTGTCCCTGGACGGCATCACAC
SEQ ID NO:3  (1251) CCTGATAGATAGACATTCGTGCAATGTCTTATCATTAGACGGGATAACTC
SEQ ID NO:32 (1251) CTTAATAGATAGGCACTCATGCAACGTCTTATCCTTAGACGGGATAACTC
SEQ ID NO:34 (1251) CTTAATAGATAGGCACTCATGCAACGTCTTATCCTTAGACGGGATAACTC
SEQ ID NO:36 (1251) CCTGATAGATAGACATTCGTGCAATGTCTTATCATTAGACGGGATAACTC
SEQ ID NO:5  (1251) CCTGATCGACAAACATTCCTGTAGCGTGCTGTCCCTGGATGGCATCACAC 1301                                              1350
SEQ ID NO:1  (1301) TGAGACTGAGCGGCGAGTTCGATGCCACCTACCAGAAGAACATCAGCATC
SEQ ID NO:3  (1301) TAAGGCTCAGTGGGGAATTTGATGCAACTTATCAAAAGAACATCTCAATA
SEQ ID NO:32 (1301) TGAGGCTCAGTGGGGAATTTGATGCAACCTATCAAAAGAATATCTCTATA
SEQ ID NO:34 (1301) TGAGGCTCAGTGGGGAATTTGATGCAACCTATCAAAAGAATATCTCTATA
SEQ ID NO:36 (1301) TGAGGCTCAGTGGAGAATTTGATGCAACTTATCAAAAGAACATCTCAATA
SEQ ID NO:5  (1301) TGAGACTGAGCGGCGAGTTCGACGCCACCTACCAGAAGAACATCAGCATC 1351                                              1400
SEQ ID NO:1  (1351) CTGGACAGCCAGGTGATCGTGACCGGCAACCTGGACATCAGCACCGAGCT
SEQ ID NO:3  (1351) CTAGATTCTCAAGTCATCGTGACAGGCAATCTTGATATATCAACTGAACT
SEQ ID NO:32 (1351) CTAGATTCTCAAGTTATAGTGACAGGCAATCTTGATATATCAACTGAGCT
SEQ ID NO:34 (1351) CTAGATTCTCAAGTTATAGTGACAGGCAATCTTGATATATCAACTGAGCT
SEQ ID NO:36 (1351) CTAGATTCTCAAGTCATCGTGACAGGCAATCTTGATATATCAACTGAACT
SEQ ID NO:5  (1351) CTGGACAGCCAGGTGATCGTGACCGGCAACCTGGACATCAGCACCGAGCT 1401                                              1450
SEQ ID NO:1  (1401) GGGCAACGTGAATAACAGCATCAGCAACGCCCTGGACAGACTGGCCGAGA
SEQ ID NO:3  (1401) TGGAAACGTCAACAATTCAATCAGCAATGCCTTGGATAGGTTGGCAGAAA
SEQ ID NO:32 (1401) TGGGAATGTCAACAACTCAATAAGTAATGCCCTGAATAAGTTAGAGGAAA
SEQ ID NO:34 (1401) TGGGAATGTCAACAACTCAATAAGTAATGCCCTGAATAAGTTAGAGGAAA
SEQ ID NO:36 (1401) TGGAAACGTCAACAATTCAATCAGCAATGCCTTGGATAAGTTGGCAAAAA
SEQ ID NO:5  (1401) GGGCAACGTGAACAACAGCATCAGCAGCACCCTGGACAAGCTGGCCGAGT 1451                                              1500
SEQ ID NO:1  (1451) GCAACAGCAAGCTGGAAAAAGTGAACGTGCGCCTGACATCCACTTCCGCT
SEQ ID NO:3  (1451) GCAACAGCAAGCTAGAAAAAGTCAATGTCAGACTAACCAGCACATCTGCT
SEQ ID NO:32 (1451) GCAACAGCAAACTAGACAAAGTCAATGTCAAACTGACCAGCACATCTGCT
SEQ ID NO:34 (1451) GCAACAGCAAACTAGACAAAGTCAATGTCAAACTGACCAGCACATCTGCT
SEQ ID NO:36 (1451) GCAACAGCAAGCTAGAAAAAGTCAATGTCAGACTAACCAGCACATCCGCT
SEQ ID NO:5  (1451) CCAACAACAAGCTGAACAAAGTGAACGTGAACCTGACCAGCACAAGCGCC
```

Figure 13 (continued)

```
                 1501                                              1550
SEQ ID NO:1   (1501) CTGATCACCTACATCGTGCTGACCGTGATCAGCCTGGTGTTCGGCGCCCT
SEQ ID NO:3   (1501) CTCATTACCTATATTGTTCTAACTGTCATTTCTCTAGTTTTCGGTGCACT
SEQ ID NO:32  (1501) CTCATTACCTACATCGTTTTAACTGTCATATCTCTTGTTTTTGGTGTACT
SEQ ID NO:34  (1501) CTCATTACCTACATCGTTTTAACTGTCATATCTCTTGTTTTTGGTGTACT
SEQ ID NO:36  (1501) CTCATTACCTATATTGTTCTGACTGTCATTTCTCTAGTTTTCGGTGCACT
SEQ ID NO:5   (1501) CTGATCACCTACATCGTGCTGGCCATCGTGTCCCTGGCCTTCGGCGTGAT 1551                                              1600
SEQ ID NO:1   (1551) GAGCCTGGTGCTGGCCTGCTACCTGATGTACAAGCAGAAGGCCCAGCAGA
SEQ ID NO:3   (1551) TAGTCTGGTGTTAGCGTGTTACCTGATGTACAAACAGAAGGCACAACAAA
SEQ ID NO:32  (1551) TAGCCTGGTTCTAGCATGCTACCTGATGTACAAGCAAAAGGCACAACAAA
SEQ ID NO:34  (1551) TAGCCTGGTTCTAGCATGCTACCTGATGTACAAGCAAAAGGCACAACAAA
SEQ ID NO:36  (1551) AAGTCTGGGTTTAACATGTTACCTGATGTACAAACAAAAGGCACAACAAA
SEQ ID NO:5   (1551) CAGCCTGGTGCTGGCCTGCTACCTGATGTACAAGCAGAGAGCCCAGCAGA 1601                                              1650
SEQ ID NO:1   (1601) AAACCCTGCTGTGGCTGGGCAACAACACCCTGGACCAGATGAGAGCCACC
SEQ ID NO:3   (1601) AGACCTTGCTATGGCTTGGGAATAATACCCTCGATCAGATGAGAGCCACT
SEQ ID NO:32  (1601) AGACCTTGTTATGGCTTGGGAATAATACCCTTGATCAGATGAGAGCCACT
SEQ ID NO:34  (1601) AGACCTTGTTATGGCTTGGGAATAATACCCTTGATCAGATGAGAGCCACT
SEQ ID NO:36  (1601) AGACCTTGCTATGGCTTGGGAATAATACCCTCGATCAGATGAGAGCCACT
SEQ ID NO:5   (1601) AAACCCTGCTGTGGCTGGGCAATAACACCCTGGACCAGATGAGGGCCACC 1651      1665
SEQ ID NO:1   (1651) ACCAGAGCCTGATGA
SEQ ID NO:3   (1651) ACAAGAGCATGA---
SEQ ID NO:32  (1651) ACAAAAATATGA---
SEQ ID NO:34  (1651) ACAAAAATATGA---
SEQ ID NO:36  (1651) ACAAGAGCATGA---
SEQ ID NO:5   (1651) ACCAGAACCTGATGA
```

|            | SEQ ID NO:1 | SEQ ID NO:3 | SEQ ID NO:32 | SEQ ID NO:34 | SEQ ID NO:36 | SEQ ID NO:5 |
|---|---|---|---|---|---|---|
| SEQ ID NO:1 |  | 72% | 71% | 71% | 71% | 92% |
| SEQ ID NO:3 |  |  | 88% | 89% | 98% | 69% |
| SEQ ID NO:32 |  |  |  | 99% | 88% | 70% |
| SEQ ID NO:34 |  |  |  |  | 88% | 71% |
| SEQ ID NO:36 |  |  |  |  |  | 69% |
| SEQ ID NO:5 |  |  |  |  |  |  |

Figure 13 (continued)

Protein sequence alignment of IBDV VP2

```
                        1                                                  50
SEQ ID NO:8      (1)    MTNLQDQTQQIVPFIRSLLMPTTGPASIPDDTLEKHTLRSETSTYNLTVG
SEQ ID NO:42     (1)    MTNLQDQTQQIVPFIRSLLMPTTGPASIPDDTLEKHTLRSETSTYNLTVG 51                                                100
SEQ ID NO:8     (51)    DTGSGLIVFFPGFPGSIVGAHYTLQSNGNYKFDQMLLTAQNLPASYNYCR
SEQ ID NO:42    (51)    DTGSGLIVFFPGFPGSIVGAHYTLQSNGNYKFDQMLLTAQNLPASYNYCR 101                                               150
SEQ ID NO:8    (101)    LVSRSLTVRSSTLPGGVYALNGTINAVTFQGSLSELTDVSYNGLMSATAN
SEQ ID NO:42   (101)    LVSRSLTVRSSTLPGGVYALNGTINAVTFQGSLSELTDVSYNGLMSATAN 151                                               200
SEQ ID NO:8    (151)    INDKIGNVLVGEGVTVLSLPTSYDLGYVRLGDPIPAIGLDPKMVATCDSS
SEQ ID NO:42   (151)    INDKIGNVLVGEGVTVLSLPTSYDLGYVRLGDPIPAIGLDPKMVATCDSS 201                                               250
SEQ ID NO:8    (201)    DRPRVYTITAADDYQFSSQYQPGGVTITLFSANIDAITSLSIGGELVFQT
SEQ ID NO:42   (201)    DRPRVYTITAADNYQFSSQYQTGGVTITLFSANIDAITSLSVGGELVFKT 251                                               300
SEQ ID NO:8    (251)    SVQGLVLGATIYLIGFDGTAVITRAVAADNGLTAGTDNLMPFNLVIPTNE
SEQ ID NO:42   (251)    SVQSLVLGATIYLIGFDGTAVITRAVAANNGLTAGIDNLMPFNLVIPTNE 301                                               350
SEQ ID NO:8    (301)    ITQPITSIKLEIVTSKSGGQAGDQMSWSASGSLAVTIHGGNYPGALRPVT
SEQ ID NO:42   (301)    ITQPITSIKLEIVTSKSDGQAGEQMSWSASGSLAVTIHGGNYPGALRPVT 351                                               400
SEQ ID NO:8    (351)    LVAYERVATGSVVTVAGVSNFELIPNPELAKNLVTEYGRFDPGAMNYTKL
SEQ ID NO:42   (351)    LVAYERVATGSVVTVAGVSNFELIPNPELAKNLVTEYGRFDPGAMNYTKL 401                                               450
SEQ ID NO:8    (401)    ILSERDRLGIKTVWPTREYTDFREYFMEVADLNSPLKIAGAFGFKDIIRA
SEQ ID NO:42   (401)    ILSERDRLGIKTVWPTREYTDFREYFMEVADLNSPLKIAGAFGFKDIIRA

451
SEQ ID NO:8    (451)    IRR-
SEQ ID NO:42   (451)    IRR-
```

SEQ ID NO:8 is 98% identical to SEQ ID NO:42

Figure 13 (continued)

DNA sequence alignment of IBDV VP2 gene

```
                        1                                                50
SEQ ID NO:7      (1)    ATGACAAACCTGCAAGATCAAACCCAACAGATTGTTCCGTTCATACGGAG
SEQ ID NO:41     (1)    ATGACAAACCTGCAAGATCAAACCCAACAGATTGTTCCGTTCATACGGAG 51                                               100
SEQ ID NO:7      (51)   CCTTCTGATGCCAACAACCGGACCGGCGTCCATTCCGGACGACACCCTGG
SEQ ID NO:41     (51)   CCTTCTGATGCCAACAACCGGACCGGCGTCCATTCCGGACGACACCCTGG 101                                              150
SEQ ID NO:7      (101)  AGAAGCACACTCTCAGGTCAGAGACCTCGACCTACAATTTGACTGTGGGG
SEQ ID NO:41     (101)  AGAAGCACACTCTCAGGTCAGAGACCTCGACCTACAATTTGACTGTGGGG 151                                              200
SEQ ID NO:7      (151)  GACACAGGGTCAGGGCTAATTGTCTTTTTCCCTGGATTCCCTGGCTCAAT
SEQ ID NO:41     (151)  GACACAGGGTCAGGGCTAATTGTCTTTTTCCCTGGATTCCCTGGCTCAAT 201                                              250
SEQ ID NO:7      (201)  TGTGGGTGCTCACTACACACTGCAGAGCAATGGGAACTACAAGTTCGATC
SEQ ID NO:41     (201)  TGTGGGTGCTCACTACACACTGCAGAGCAATGGGAACTACAAGTTCGATC 251                                              300
SEQ ID NO:7      (251)  AGATGCTCCTGACTGCCCAGAACCTACCGGCCAGCTACAACTACTGCAGA
SEQ ID NO:41     (251)  AGATGCTCCTGACTGCCCAGAACCTACCGGCCAGCTACAACTACTGCAGG 301                                              350
SEQ ID NO:7      (301)  CTAGTGAGTCGGAGTCTCACAGTGAGGTCAAGCACACTCCCTGGTGGCGT
SEQ ID NO:41     (301)  CTAGTGAGTCGGAGTCTCACAGTAAGGTCAAGCACACTCCCTGGTGGCGT 351                                              400
SEQ ID NO:7      (351)  TTATGCACTAAACGGCACCATAAACGCCGTGACCTTCCAAGGAAGCCTGA
SEQ ID NO:41     (351)  TTATGCACTAAACGGCACCATAAACGCCGTGACCTTCCAAGGAAGCCTGA 401                                              450
SEQ ID NO:7      (401)  GTGAACTGACAGATGTTAGCTACAATGGGTTGATGTCTGCAACAGCCAAC
SEQ ID NO:41     (401)  GTGAACTGACAGATGTTAGCTACAACGGGTTGATGTCTGCAACAGCCAAC 451                                              500
SEQ ID NO:7      (451)  ATCAACGACAAAATTGGGAATGTCCTGGTAGGGGAAGGGGTCACTGTCCT
SEQ ID NO:41     (451)  ATCAACGACAAAATTGGGAACGTCCTAGTAGGGGAAGGGGTAACCGTCCT 501                                              550
SEQ ID NO:7      (501)  CAGCCTACCCACATCATATGATCTTGGGTATGTGAGGCTTGGTGACCCCA
SEQ ID NO:41     (501)  CAGCTTACCCACATCATATGATCTTGGGTATGTGAGGCTTGGTGACCCCA 551                                              600
SEQ ID NO:7      (551)  TTCCCGCTATAGGGCTTGACCCAAAAATGGTAGCTACATGCGACAGCAGT
SEQ ID NO:41     (551)  TACCCGCTATAGGGCTTGACCCAAAAATGGTAGCAACATGTGACAGCAGT
```

Figure 13 (continued)

```
                     601                                              650
SEQ ID NO:7    (601) GACAGGCCCAGAGTCTACACCATAACTGCAGCCGATGATTACCAATTCTC
SEQ ID NO:41   (601) GACAGGCCCAGAGTCTACACCATAACTGCAGCCGATAATTACCAATTCTC 651                                              700
SEQ ID NO:7    (651) ATCACAGTACCAACCAGGTGGGGTAACAATCACACTGTTCTCAGCCAACA
SEQ ID NO:41   (651) ATCACAGTACCAAACAGGTGGGGTAACAATCACACTGTTCTCAGCCAACA 701                                              750
SEQ ID NO:7    (701) TTGATGCTATCACAAGCCTCAGCATTGGGGGAGAGCTCGTGTTTCAAACA
SEQ ID NO:41   (701) TTGATGCCATCACAAGTCTCAGCGTTGGGGGAGAGCTCGTGTTCAAAACA 751                                              800
SEQ ID NO:7    (751) AGCGTCCAAGGCCTTGTACTGGGCGCCACCATCTACCTTATAGGCTTTGA
SEQ ID NO:41   (751) AGCGTCCAAAGCCTTGTACTGGGCGCCACCATCTACCTTATAGGCTTTGA 801                                              850
SEQ ID NO:7    (801) TGGGACTGCGGTAATCACCAGAGCTGTAGCCGCAGATAATGGGCTGACGG
SEQ ID NO:41   (801) TGGGACTGCGGTAATCACCAGAGCTGTGGCCGCAAACAATGGGCTGACGG 851                                              900
SEQ ID NO:7    (851) CCGGCACCGACAATCTTATGCCATTCAATCTTGTCATTCCAACCAATGAG
SEQ ID NO:41   (851) CCGGCATCGACAATCTTATGCCATTCAATCTTGTGATTCCAACCAATGAG 901                                              950
SEQ ID NO:7    (901) ATAACCCAGCCAATCACATCCATCAAACTGGAGATAGTGACCTCCAAAAG
SEQ ID NO:41   (901) ATAACCCAGCCAATCACATCCATCAAACTGGAGATAGTGACCTCCAAAAG 951                                              1000
SEQ ID NO:7    (951) TGGTGGTCAGGCAGGGGATCAGATGTCATGGTCGGCAAGTGGGAGCCTAG
SEQ ID NO:41   (951) TGATGGTCAGGCAGGGGAACAGATGTCATGGTCGGCAAGTGGGAGCCTAG 1001                                             1050
SEQ ID NO:7   (1001) CAGTGACGATCCATGGTGGCAACTATCCAGGGGCCCTCCGTCCCGTCACA
SEQ ID NO:41  (1001) CAGTGACGATCCATGGTGGCAACTATCCAGGAGCCCTCCGTCCCGTCACA 1051                                             1100
SEQ ID NO:7   (1051) CTAGTAGCCTACGAAAGAGTGGCAACAGGATCCGTCGTTACGGTCGCTGG
SEQ ID NO:41  (1051) CTAGTGGCCTACGAAAGAGTGGCAACAGGATCTGTCGTTACGGTCGCTGG 1101                                             1150
SEQ ID NO:7   (1101) GGTGAGTAACTTCGAGCTGATTCCAAATCCTGAACTAGCAAAGAACCTGG
SEQ ID NO:41  (1101) GGTGAGCAACTTCGAGCTGATCCCAAATCCTGAACTAGCAAAGAACCTGG 1151                                             1200
SEQ ID NO:7   (1151) TTACAGAATACGGCCGATTTGACCCAGGAGCCATGAACTACACAAAAATTG
SEQ ID NO:41  (1151) TTACAGAATATGGCCGATTTGACCCAGGAGCCATGAACTACACGAAATTG 1201                                             1250
SEQ ID NO:7   (1201) ATACTGAGTGAGAGGGACCGTCTTGGCATCAAGACCGTCTGGCCAACAAG
SEQ ID NO:41  (1201) ATACTGAGTGAGAGGGACCGGCCTTGGCATCAAGACCGTCTGGCCAACAAG
```

Figure 13 (continued)

```
                  1251                                              1300
SEQ ID NO:7  (1251) GGAGTACACTGATTTTCGTGAGTACTTCATGGAGGTGGCCGACCTCAACT
SEQ ID NO:41 (1251) GGAGTACACTGACTTTCGTGAGTACTTCATGGAGGTGGCCGACCTCAACT 1301                                              1350
SEQ ID NO:7  (1301) CTCCCCTGAAGATTGCAGGAGCATTTGGCTTCAAAGACATAATCCGGGCT
SEQ ID NO:41 (1301) CTCCCCTGAAGATTGCAGGAGCATTTGGCTTCAAAGACATAATCCGGGCC 1351    1362
SEQ ID NO:7  (1351) ATAAGGAGGTAA
SEQ ID NO:41 (1351) ATAAGGAGGTGA
```

SEQ ID NO:7 is 97% identical to SEQ ID NO:41

Figure 14

DNA and protein sequences

NDV-F codon optimized DNA (SEQ ID NO:1)
atgggcagcaagcccagcacaagaatcccagcccccctgatgctgatcacccgcatcat
gctgatcctgggctgcatcagacccacaagctccctggatggacgcccctggccgctg
ccggcatcgtggtgaccggcgacaaggccgtgaacgtgtacaccagcagccagaccggc
agcatcatcgtgaagctgctgcccaacatgccagagacaaagaggcctgcgccaaggc
cccctggaagcctacaacagaaccctgaccaccctgctgacccccctgggcgacagca
tcagaaagatccagggctccgtgagcacaagcggcggaggaaagcagggcagactgatc
ggcgccgtgatcggcagcgtggccctgggagtggctacagctgcccagattaccgctgc
agccgccctgatccaggccaaccagaacgccgccaacatcctgagactgaaagagagca
ttgccgccaccaacgaggccgtgcacgaagtgaccgacggcctgagccagctgtccgtg
gccgtgggcaagatgcagcagttcgtgaacgaccagttcaacaacaccgccagagagct
ggactgcatcaagatcacccagcaggtgggcgtggagctgaacctgtacctgaccgagc
tgaccacagtgttcggcccccagatcacaagcccagccctgacacagctgaccatccag
gccctgtacaacctggctggcggcaacatggactatctgctgacaaagctgggaatcgg
caacaaccagctgtccagcctgatcggaagcggcctgatcaccggctaccccatcctgt
acgacagccagacacagctgctgggcatccaggtgaacctgcccagcgtgggcaacctg
aacaacatgcgcgccacctacctggaaaccctgagcgtgtccaccaccaagggctacgc
cagcgccctggtgcccaaggtggtgacacaggtgggcagcgtgatcgaggaactggaca
ccagctactgcatcgagagcgacctggacctgtactgcaccagaatcgtgaccttccca
atgagccccggcatctacagctgcctgagcggcaacaccagcgcctgcatgtacagcaa
gaccgaaggcgcactgacaacaccctacatggccctgaagggaagcgtgatcgccaact
gcaagatcaccacctgcagatgcaccgacccccaggcatcatcagccagaactacggc
gaggccgtgagcctgatcgatcgccattcctgtaacgtgctgtccctggacggcatcac
actgagactgagcggcgagttcgatgccacctaccagaagaacatcagcatcctggaca
gccaggtgatcgtgaccggcaacctggacatcagcaccgagctgggcaacgtgaataac
agcatcagcaacgccctggacagactggccgagagcaacagcaagctggaaaaagtgaa
cgtgcgcctgacatccacttccgctctgatcacctacatcgtgctgaccgtgatcagcc
tggtgttcggcgccctgagcctggtgctggcctgctacctgatgtacaagcagaaggcc
cagcagaaaaccctgctgtggctgggcaacaacaccctggaccagatgagagccaccac
cagagcctgatga

NDV-F protein (SEQ ID NO:2)
MGSKPSTRIPAPLMLITRIMLILGCIRPTSSLDGRPLAAAGIVVTGDKAVNVYTSSQTGSIIVKL
LPNMPRDKEACAKAPLEAYNRTLTTLLTPLGDSIRKIQGSVSTSGGGKQGRLIGAVIGSVALGVA
TAAQITAAAALIQANQNAANILRLKESIAATNEAVHEVTDGLSQLSVAVGKMQQFVNDQFNNTAR
ELDCIKITQQVGVELNLYLTELTTVFGPQITSPALTQLTIQALYNLAGGNMDYLLTKLGIGNNQL
SSLIGSGLITGYPILYDSQTQLLGIQVNLPSVGNLNNMRATYLETLSVTTKGYASALVPKVVTQ
VGSVIEELDTSYCIESDLDLYCTRIVTFPMSPGIYSCLSGNTSACMYSKTEGALTTPYMALKGSV
IANCKITTCRCTDPPGIISQNYGEAVSLIDRHSCNVLSLDGITLRLSGEFDATYQKNISILDSQV
IVTGNLDISTELGNVNNSISNALDRLAESNSKLEKVNVRLTSTSALITYIVLTVISLVFGALSLV
LACYLMYKQKAQQKTLLWLGNNTLDQMRATTRA*

Figure 14 (Continued)

DNA sequence of NDV-F VIId wildtype (SEQ ID NO:3)
atgggctccaaaccttctaccaggatcccagcacctctgatgctgatcacccggattat
gctgatattgggctgtatccgtccgacaagctctcttgacggcaggcctcttgcagctg
caggaattgtagtaacaggagataaggcagtcaatgtatacacttcgtctcagacaggg
tcaatcatagtcaagttgctcccgaatatgcccagggataaggaggcgtgtgcaaaagc
cccattagaggcatataacagaacactgactactttgctcactcctcttggcgactcca
tccgcaagatccaagggtctgtgtccacatctggaggaggcaagcaaggccgcctgata
ggtgctgttattggcagtgtagctcttggggttgcaacagcggcacagataacagcagc
tgcggccctaatacaagccaaccagaatgccgccaacatcctccggcttaaggagagca
ttgctgcaaccaatgaagctgtgcatgaagtcaccgacggattatcacaactatcagtg
gcagttgggaagatgcagcagtttgtcaatgaccagtttaataatacggcgcgagaatt
ggactgtataaaaatcacacaacaggttggtgtagaactcaacctatacctaactgaat
tgactacagtattcgggccacagatcacctcccctgcattaactcagctgaccatccag
gcactttataatttagctggtggcaatatggattacttattaactaagttaggtatagg
gaacaatcaactcagctcgttaattggtagcggcctgatcactggttaccctatactgt
atgactcacagactcaactcttgggcatacaagtgaatttaccctcagtcgggaactta
aataatatgcgtgccacctatttggagaccttatctgtaagtacaaccaaaggatatgc
ctcagcacttgtcccgaaagtagtgacacaagtcggttccgtgatagaagagcttgaca
cctcatactgtatagagtccgatctggatttatattgtactagaatagtgacattcccc
atgtccccaggtatttattcctgtttgagcggcaacacatcagcttgcatgtattcaaa
gactgaaggcgcactcactacgccgtatatggcccttaaaggctcagttattgccaatt
gtaaaataacaacatgtagatgtacagaccctcctggtatcatatcgcaaaattatgga
gaagctgtatccctgatagatagacattcgtgcaatgtcttatcattagacgggataac
tctaaggctcagtggggaatttgatgcaacttatcaaaagaacatctcaatactagatt
ctcaagtcatcgtgacaggcaatcttgatatatcaactgaacttggaaacgtcaacaat
tcaatcagcaatgccttggataggttggcagaaagcaacagcaagctagaaaaagtcaa
tgtcagactaaccagcacatctgctctcattacctatattgttctaactgtcatttctc
tagttttcggtgcacttagtctggtgttagcgtgttacctgatgtacaaacagaaggca
caacaaaagaccttgctatggcttgggaataatacccctcgatcagatgagagccactac
aagagcatga

Amino Acid sequence of NDV-F VIId wildtype (SEQ ID NO:4)
```
  1    MGSKPSTRIP  APLMLITRIM  LILGCIRPTS  SLDGRPLAAA  GIVVTGDKAV
 51    NVYTSSQTGS  IIVKLLPNMP  RDKEACAKAP  LEAYNRTLTT  LLTPLGDSIR
101    KIQGSVSTSG  GGKQGRLIGA  VIGSVALGVA  TAAQITAAAA  LIQANQNAAN
151    ILRLKESIAA  TNEAVHEVTD  GLSQLSVAVG  KMQQFVNDQF  NNTARELDCI
201    KITQQVGVEL  NLYLTELTTV  FGPQITSPAL  TQLTIQALYN  LAGGNMDYLL
251    TKLGIGNNQL  SSLIGSGLIT  GYPILYDSQT  QLLGIQVNLP  SVGNLNNMRA
301    TYLETLSVST  TKGYASALVP  KVVTQVGSVI  EELDTSYCIE  SDLDLYCTRI
351    VTFPMSPGIY  SCLSGNTSAC  MYSKTEGALT  TPYMALKGSV  IANCKITTCR
401    CTDPPGIISQ  NYGEAVSLID  RHSCNVLSLD  GITLRLSGEF  DATYQKNISI
451    LDSQVIVTGN  LDISTELGNV  NNSISNALDR  LAESNSKLEK  VNVRLTSTSA
501    LITYIVLTVI  SLVFGALSLV  LACYLMYKQK  AQQKTLLWLG  NNTLDQMRAT
551    TRA*
```

Figure 14 (Continued)

DNA sequence of NDV-F-CAO2-CSmut (SEQ ID NO:5) for HVT116
atgggcagcaagcccagcacctggatcagcgtgaccctgatgctgatcaccagaaccat
gctgatcctgagctgcatctgccccacaagcagcctggacggcagacccctggccgctg
ccggcatcgtggtgaccggcgacaaggccgtgaacatctacaccagcagccagaccggc
agcatcatcatcaagctgctgcccaacatgcccaaggacaaagaggcctgcgccaaggc
ccccctggaagcctacaacagaaccctgaccaccctgctgacccccctgggcgacagca
tcagaagaatccagggcagcgccaccacaagcggcggaggaaagcagggcagactggtg
ggcgctatcatcgggagcgtggccctgggcgtggccacagctgcccagattaccgctgc
agccgccctgattcaggccaatcagaacgccgccaacatcctgagactgaaagagagca
ttgccgccaccaacgacgccgtgcacgaagtgacaaacggactgtcccagctggctgtc
gctgtcggcaagatgcagcagttcgtgaacaaccagttcaacaacaccgccagagagct
ggactgcatcaagatcgcccagcaggtgggcgtggagctgaacctgtacctgaccgagc
tgaccacagtgttcggcccccagatcacaagccccgctctgacccagctgacaatccag
gccctgtacaacctggctggcggcaacatggactatctgctgactaagctgggagtggg
caacaaccagctgtccagcctgatcgggtccggctgatcacaggcaacccatcctgt
acgacagccagacacagctgctgggcatccagatcaacctgccatccgtgggaagcctg
aacaacatgagagccacctacctggaaaccctgagcgtgtccaccaccaagggcttcgc
cagcgccctggtgcccaaggtggtgacacaggtgggcagcgtgatcgaggaactggaca
ccagctactgcatcgagagcgacatcgacctgtactgcaccagagtggtgaccttccca
atgagccccggcatctacagctgcctgagcggcaacaccagcgcctgcatgtacagcaa
gaccgaaggagcactgacaacaccctacatggccctgaagggaagcgtgatcgccaact
gcaagatgaccacctgcagatgcgccgacccccaggcatcatcagccagaactacggc
gaggccgtgagcctgatcgacaaacattcctgtagcgtgctgtccctggatggcatcac
actgagactgagcggcgagttcgacgccacctaccagaagaacatcagcatcctggaca
gccaggtgatcgtgaccggcaacctggacatcagcaccgagctgggcaacgtgaacaac
agcatcagcagcaccctggacaagctggccgagtccaacaacaagctgaacaaagtgaa
cgtgaacctgaccagcacaagcgccctgatcacctacatcgtgctggccatcgtgtccc
tggccttcggcgtgatcagcctggtgctggcctgctacctgatgtacaagcagagagcc
cagcagaaaaccctgctgtggctgggcaataacaccctggaccagatgagggccaccac
cagaacctgatga

Amino Acid sequence of NDV-F-CAO2-CSmut (SEQ ID NO:6) for HVT116

```
  1    MGSKPSTWIS  VTLMLITRTM  LILSCICPTS  SLDGRPLAAA  GIVVTGDKAV
 51    NIYTSSQTGS  IIIKLLPNMP  KDKEACAKAP  LEAYNRTLTT  LLTPLGDSIR
101    RIQGSATTSG  GGKQGRLVGA  IIGSVALGVA  TAAQITAAAA  LIQANQNAAN
151    ILRLKESIAA  TNDAVHEVTN  GLSQLAVAVG  KMQQFVNNQF  NNTARELDCI
201    KIAQQVGVEL  NLYLTELTTV  FGPQITSPAL  TQLTIQALYN  LAGGNMDYLL
251    TKLGVGNNQL  SSLIGSGLIT  GNPILYDSQT  QLLGIQINLP  SVGSLNNMRA
301    TYLETLSVST  TKGFASALVP  KVVTQVGSVI  EELDTSYCIE  SDIDLYCTRV
351    VTFPMSPGIY  SCLSGNTSAC  MYSKTEGALT  TPYMALKGSV  IANCKMTTCR
401    CADPPGIISQ  NYGEAVSLID  KHSCSVLSLD  GITLRLSGEF  DATYQKNISI
451    LDSQVIVTGN  LDISTELGNV  NNSISSTLDK  LAESNNKLNK  VNVNLTSTSA
501    LITYIVLAIV  SLAFGVISLV  LACYLMYKQR  AQQKTLLWLG  NNTLDQMRAT
551    TRT*
```

Figure 14 (Continued)

DNA coding for IBDV VP2 protein (SEQ ID NO:7)
ATGACAAACCTGCAAGATCAAACCCAACAGATTGTTCCGTTCATACGGAGCCTTCTGAT
GCCAACAACCGGACCGGCGTCCATTCCGGACGACACCCTGGAGAAGCACACTCTCAGGT
CAGAGACCTCGACCTACAATTTGACTGTGGGGACACAGGGTCAGGGCTAATTGTCTTT
TTCCCTGGATTCCCTGGCTCAATTGTGGGTGCTCACTACACACTGCAGAGCAATGGGAA
CTACAAGTTCGATCAGATGCTCCTGACTGCCCAGAACCTACCGGCCAGCTACAACTACT
GCAGACTAGTGAGTCGGAGTCTCACAGTGAGGTCAAGCACACTCCCTGGTGGCGTTTAT
GCACTAAACGGCACCATAAACGCCGTGACCTTCCAAGGAAGCCTGAGTGAACTGACAGA
TGTTAGCTACAATGGGTTGATGTCTGCAACAGCCAACATCAACGACAAAATTGGGAATG
TCCTGGTAGGGGAAGGGGTCACTGTCCTCAGCCTACCCACATCATATGATCTTGGGTAT
GTGAGGCTTGGTGACCCCATTCCCGCTATAGGGCTTGACCCAAAAATGGTAGCTACATG
CGACAGCAGTGACAGGCCCAGAGTCTACACCATAACTGCAGCCGATGATTACCAATTCT
CATCACAGTACCAACCAGGTGGGGTAACAATCACACTGTTCTCAGCCAACATTGATGCT
ATCACAAGCCTCAGCATTGGGGAGAGCTCGTGTTTCAAACAAGCGTCCAAGGCCTTGT
ACTGGGCGCCACCATCTACCTTATAGGCTTTGATGGGACTGCGGTAATCACCAGAGCTG
TAGCCGCAGATAATGGGCTGACGGCCGGCACCGACAATCTTATGCCATTCAATCTTGTC
ATTCCAACCAATGAGATAACCCAGCCAATCACATCCATCAAACTGGAGATAGTGACCTC
CAAAAGTGGTGGTCAGGCAGGGGATCAGATGTCATGGTCGGCAAGTGGGAGCCTAGCAG
TGACGATCCATGGTGGCAACTATCCAGGGGCCCTCCGTCCCGTCACACTAGTAGCCTAC
GAAAGAGTGGCAACAGGATCCGTCGTTACGGTCGCTGGGGTGAGTAACTTCGAGCTGAT
TCCAAATCCTGAACTAGCAAAGAACCTGGTTACAGAATACGGCCGATTTGACCCAGGAG
CCATGAACTACACAAAATTGATACTGAGTGAGAGGGACCGTCTTGGCATCAAGACCGTC
TGGCCAACAAGGGAGTACACTGATTTTCGTGAGTACTTCATGGAGGTGGCCGACCTCAA
CTCTCCCCTGAAGATTGCAGGAGCATTTGGCTTCAAAGACATAATCCGGGCTATAAGGA
GGTAA

IBDV VP2 protein (SEQ ID NO:8)
MTNLQDQTQQIVPFIRSLLMPTTGPASIPDDTLEKHTLRSETSTYNLTVGDTGSGLIVF
FPGFPGSIVGAHYTLQSNGNYKFDQMLLTAQNLPASYNYCRLVSRSLTVRSSTLPGGVY
ALNGTINAVTFQGSLSELTDVSYNGLMSATANINDKIGNVLVGEGVTVLSLPTSYDLGY
VRLGDPIPAIGLDPKMVATCDSSDRPRVYTITAADDYQFSSQYQPGGVTITLFSANIDA
ITSLSIGGELVFQTSVQGLVLGATIYLIGFDGTAVITRAVAADNGLTAGTDNLMPFNLV
IPTNEITQPITSIKLEIVTSKSGGQAGDQMSWSASGSLAVTIHGGNYPGALRPVTLVAY
ERVATGSVVTVAGVSNFELIPNPELAKNLVTEYGRFDPGAMNYTKLILSERDRLGIKTV
WPTREYTDFREYFMEVADLNSPLKIAGAFGFKDIIRAIRR

Sv40 Promoter (SEQ ID NO:9)
gaattcgagctcggtacagcttggctgtggaatgtgtgtcagttagggtgtggaaagtc
cccaggctccccagcaggcagaagtatgcaaagcatgcatctcaattagtcagcaacca
ggtgtggaaagtccccaggctccccagcaggcagaagtatgcaaagcatgcatctcaat
tagtcagcaaccatagtcccgcccctaactccgcccatcccgcccctaactccgcccag
ttccgcccattctccgcccatggctgactaattttttttatttatgcagaggccgagg
ccgcctcggcctctgagctattccagaagtagtgaggaggcttttttggaggcctaggc
ttttgcaaaaagct Figure 14 (Continued)

CMV-IE promoter (SEQ ID NO:10)
aactccgcccgttttatgactagaaccaatagttttttaatgccaaatgcactgaaatcc
cctaatttgcaaagccaaacgcccctatgtgagtaatacggggactttttacccaatt
tcccaagcggaaagccccctaatacactcatatggcatatgaatcagcacggtcatgca
ctctaatggcggcccatagggactttccacataggggggcgttcaccatttcccagcata
ggggtggtgactcaatggcctttacccaagtacattgggtcaatgggaggtaagccaat
gggttttccattactggcaagcacactgagtcaaatgggactttccactgggttttg
cccaagtacattgggtcaatgggaggtgagccaatgggaaaaacccattgctgccaagt
acactgactcaatagggactttccaatgggttttccattgttggcaagcataaggt
caatgtgggtgagtcaatagggactttccattgtattctgcccagtacataaggtcaat
agggggtgaatcaacaggaaagtcccattggagccaagtacactgcgtcaatagggact
ttccattgggttttgcccagtacataaggtcaatagggggtgagtcaatgggaaaaacc
cattggagccaagtacactgactcaatagggactttccattgggttttgcccagtacat
aaggtcaatagggggtgagtcaacaggaaagtcccattggagccaagtacattgagtca
atagggactttccaatgggttttgcccagtacataaggtcaatgggaggtaagccaatg
ggttttccattactggcacgtatactgagtcattagggactttccaatgggttttgc
ccagtacataaggtcaatagggggtgaatcaacaggaaagtcccattggagccaagtaca
ctgagtcaatagggactttccattgggttttgcccagtacaaaggtcaatagggggtg
agtcaatggttttcccattattggcacgtacataaggtcaatagggggtgagtcattg
gttttcagccaatttaattaaaacgccatgtactttccaccattgacgtcaatgg
gctattgaaactaatgcaacgtgacctttaaacggtactttcccatagctgattaatgg
gaaagtaccgttctcgagccaatacacgtcaatgggaagtgaaagggcagccaaaacgt
aacaccgccccggttttccctggaaattccatattggcacgcattctattggctgagc
tgcgttctacgtgggtataagaggcgcgaccagcgtcggtaccgtcgcagtcttcggtc
tgaccaccgtagaacgcagagctcctcgctgcag

SV40 polyA signal (SEQ ID NO:11)
Ggggatccagacatgataagatacattgatgagtttggacaaaccacaactagaatgca
gtgaaaaaatgctttatttgtgaaatttgtgatgctattgctttatttgtaaccatta
taagctgcaataaacaagttaacaacaacaattgcattgattttatgtttcaggttcag
ggggaggtgtgggaggttttttcggatcctctagagtcgac

Synthetic polyA signal (SEQ ID NO:12)
aataaaatatctttattttcattacatctgtgtgttggttttttgtgtgaatcgatagt
actaacatacgctctccatcaaaacaaaacgaaacaaaacaaactagcaaaataggctg
tccccagtgcaagtgcaggtgccagaacatttctctt Figure 14 (Continued)

The nucleotide sequence of the cloned NDV Texas F gene (wild type non-modified) (SEQ ID NO:32)

ATGGGCTCCAGATCTTCTACCAGGATCCCGGTACCTCTAATGCTGATCATCCGAACCGC
GCTGACACTGAGCTGTATCCGTCTGACAAGCTCTCTTGATGGCAGGCCTCTTGCGGCTG
CAGGGATCGTGGTAACAGGAGATAAAGCAGTCAACATATACACCTCATCCCAGACAGGG
TCAATCATAGTTAAGTTACTCCCGAATATGCCCAAGGACAAAGAGGTGTGTGCAAAAGC
CCCATTGGAGGCATACAACAGGACACTGACTACTTTACTCACCCCCCTTGGTGATTCTA
TCCGCAGGATACAAGAGTCTGTGACTACTTCCGGAGGAAGGAGACAGAGACGCTTTATA
GGTGCCATTATCGGCAGTGTAGCTCTTGGGGTTGCGACAGCTGCACAGATAACAGCAGC
TTCGGCCCTGATACAAGCCAACCAGAATGCTGCCAACATCCTCCGGCTTAAAGAGAGCA
TTGCTGCAACCAATGAAGCTGTGCACGAGGTCACTGACGGATTATCACAACTAGCAGTG
GCAGTAGGGAAGATGCAACAGTTTGTCAATGACCAGTTCAATAATACAGCGCAAGAATT
GGACTGTATAAAAATTGCACAGCAGGTCGGTGTAGAACTCAACTTGTACCTAACTGAAT
TGACTACAGTATTTGGGCCACAAATCACTTCCCCTGCCTTAACTCAGCTGACTATCCAA
GCGCTTTACAATCTAGCTGGTGGTAATATGGATTACTTGCTGACTAAGTTAGGTGTAGG
GAACAACCAACTCAGCTCATTAATTGGTAGCGGCTTGATCACCGGCAACCCTATTCTGT
ACGACTCACAGACTCAGATCTTGGGTATACAGGTAACTTTGCCTTCAGTTGGGAACCTG
AATAATATGCGTGCCACCTACCTGGAGACCTTATCTGTAAGCACAACCAAGGGATTTGC
CTCAGCACTTGTCCCAAAAGTGGTGACACAGGTCGGTTCCGTGATAGAAGAACTTGACA
CCTCATACTGTATAGGGACCGACTTGGATTTATACTGTACAAGAATAGTGACATTCCCT
ATGTCTCCTGGTATTTATTCTTGTCTGAGCGGTAATACATCGGCTTGCATGTATTCAAA
GACTGAAGGCGCACTTACTACGCCATATATGGCTCTCAAAGGCTCAGTTATTGCCAATT
GCAAGCTGACAACATGTAGATGTGCAGATCCCCCAGGTATCATATCGCAAAATTATGGA
GAAGCTGTGTCCTTAATAGATAGGCACTCATGCAACGTCTTATCCTTAGACGGGATAAC
TCTGAGGCTCAGTGGGGAATTTGATGCAACCTATCAAAAGAATATCTCTATACTAGATT
CTCAAGTTATAGTGACAGGCAATCTTGATATATCAACTGAGCTTGGGAATGTCAACAAC
TCAATAAGTAATGCCCTGAATAAGTTAGAGGAAAGCAACAGCAAACTAGACAAAGTCAA
TGTCAAACTGACCAGCACATCTGCTCTCATTACCTACATCGTTTTAACTGTCATATCTC
TTGTTTTTGGTGTACTTAGCCTGGTTCTAGCATGCTACCTGATGTACAAGCAAAAGGCA
CAACAAAAGACCTTGTTATGGCTTGGGAATAATACCCTTGATCAGATGAGAGCCACTAC
AAAAATATGA

The amino acid sequence of the cloned NDV Texas F gene (wild type non-modified; cleavage site underlined) (SEQ ID NO:33)

MGSRSSTRIPVPLMLIIRTALTLSCIRLTSSLDGRPLAAAGIVVTGDKAVNIYTSSQTG
SIIVKLLPNMPKDKEVCAKAPLEAYNRTLTTLLTPLGDSIRRIQESVTTSGGRRQRRFI
GAIIGSVALGVATAAQITAASALIQANQNAANILRLKESIAATNEAVHEVTDGLSQLAV
AVGKMQQFVNDQFNNTAQELDCIKIAQQVGVELNLYLTELTTVFGPQITSPALTQLTIQ
ALYNLAGGNMDYLLTKLGVGNNQLSSLIGSGLITGNPILYDSQTQILGIQVTLPSVGNL
NNMRATYLETLSVSTTKGFASALVPKVVTQVGSVIEELDTSYCIGTDLDLYCTRIVTFP
MSPGIYSCLSGNTSACMYSKTEGALTTPYMALKGSVIANCKLTTCRCADPPGIISQNYG
EAVSLIDRHSCNVLSLDGITLRLSGEFDATYQKNISILDSQVIVTGNLDISTELGNVNN
SISNALNKLEESNSKLDKVNVKLTSTSALITYIVLTVISLVFGVLSLVLACYLMYKQKA
QQKTLLWLGNNTLDQMRATTKI

Figure 14 (Continued)

NDV-F YZCQ wildtype DNA sequence (SEQ ID NO:34)
atgggctccagatcttctaccaggatcccggtacctctaatgctgatcatccgaaccgc
gctgacactgagctgtatccgtctgacaagctctcttgatggcaggcctcttgcggctg
cagggatcgtggtaacaggagataaagcagtcaacatatacacctcatcccagacaggg
tcaatcatagttaagttactcccgaatatgcccaaggacaaagaggtgtgtgcaaaagc
cccattggaggcatacaacaggacactgactactttactcaccccttggtgattcta
tccgcaggatacaagagtctgtgactacttccggaggaggcaagcaaggccgcctgata
ggtgccattatcggcagtgtagctcttggggttgcgacagctgcacagataacagcagc
ttcggccctgatacaagccaaccagaatgctgccaacatcctccggcttaaagagagca
ttgctgcaaccaatgaagctgtgcacgaggtcactgacggattatcacaactagcagtg
gcagtagggaagatgcaacagtttgtcaatgaccagttcaataatacagcgcaagaatt
ggactgtataaaaattgcacagcaggtcggtgtagaactcaacttgtacctaactgaat
tgactacagtatttgggccacaaatcacttcccctgccttaactcagctgactatccaa
gcgctttacaatctagctggtggtaatatggattacttgctgactaagttaggtgtagg
gaacaaccaactcagctcattaattggtagcggcttgatcaccggcaaccctattctgt
acgactcacagactcagatcttgggtatacaggtaactttgccttcagttgggaacctg
aataatatgcgtgccacctacctggagaccttatctgtaagcacaaccaagggatttgc
ctcagcacttgtcccaaaagtggtgacacaggtcggttccgtgatagaagaacttgaca
cctcatactgtatagggaccgacttggatttatactgtacaagaatagtgacattccct
atgtctcctggtatttattcttgtctgagcggtaatacatcggcttgcatgtattcaaa
gactgaaggcgcacttactacgccatatatggctctcaaaggctcagttattgccaatt
gcaagctgacaacatgtagatgtgcagatccccaggtatcatatcgcaaaattatgga
gaagctgtgtccttaatagataggcactcatgcaacgtcttatccttagacgggataac
tctgaggctcagtggggaatttgatgcaacctatcaaaagaatatctctatactagatt
ctcaagttatagtgacaggcaatcttgatatcaactgagcttgggaatgtcaacaac
tcaataagtaatgccctgaataagttagaggaaagcaacagcaaactagacaaagtcaa
tgtcaaactgaccagcacatctgctctcattacctacatcgttttaactgtcatatctc
ttgttttggtgtacttagcctggttctagcatgctacctgatgtacaagcaaaaggca
caacaaaagaccttgttatggcttgggaataatacccttgatcagatgagagccactac
aaaaatatga

NDV-F protein from wildtype YZCQ strain (Amino Acid Sequence of NDV-F of Texas strain with lentogenic cleavage site sequence) (SEQ ID NO:35)

mgsrsstripvplmliirtaltlscirltssldgrplaaagivvtgdkavniytssqtg
siivkllpnmpkdkevcakapleaynrtltlltplgdsirriqesvttsgggkqgrli
gaiigsvalgvataaqitaasaliqanqnaanilrlkesiaatneavhevtdglsqlav
avgkmqqfvndqfnntaqeldcikiaqqvgvelnlyltelttvfgpqitspaltqltiq
alynlaggnmdyllltklgvgnnqlssligsglitgnpilydsqtqilgiqvtlpsvgnl
nnmratyletlsvsttkgfasalvpkvvtqvgsvieeldtsycigtdldlyctrivtfp
mspgiysclsgntsacmysktegalttpymalkgsviancklttcrcadppgiisqnyg
eavslidrhscnvlsldgitlrlsgefdatyqknisildsqvivtgnldistelgnvnn
sisnalnkleesnskldkvnvkltstsalityivltvislvfgvlslvlacylmykqka
qqktllwlgnntldqmrattki*

Figure 14 (Continued)

NDV-F Texas wildtype DNA sequence (SEQ ID NO:36)

```
atgggctctaaaccttctaccaggatcccagcacctctgatgctgatcacccggattat
gctgatattggactgtatccgtccgacaagctctcttgacggcaggcctcttgcagctg
caggaattgtagtaacaggagataaggcagtcaatgtatatacctcgtctcagacaggg
tcaatcatagtcaagttgctcccgaatatgcccaaggataaggaggcgtgtgcgaaaga
cccattagaggcatataacagaacactgactactttgctcactcctcttggcgaatcca
tccgcaagatccaagggtctgtgtccacgtctggaggaggcaagcaaggccgcctgata
ggtgctgttattggtagtgtagctcttggggttgcaacagcggcacaaataacagcagc
tgcggccctaatacaagccaaccagaatgctgccaacatccttcggcttaaggagagca
ttgctgcaaccaatgaagctgtgcatgaagtcaccgacggattatcaactatcagtg
gcagttgggaagatgcagcagtttgtcaatgaccagtttaataatacagcgcgagaatt
ggactgtataaaaatcacacaacaggttggtgtagaactcaacctatacctaactgaat
tgactacagtattcgggccacagatcacctccctgcattaactcagctgaccatccag
gcactttataatttagctggtggcaatatggattacttattaactaagttaggtatagg
gaacaatcaactcagctcattaattggcagcggcctgatcactggttaccctatattgt
atgactcacagactcaactcttgggcatacaagtgaatttgccctcagtcgggaactta
aataatatgcgtgccacctatttagagaccttatctgtaagtacagccaaggatatgc
ctcagcacttgttccaaaagtagtgacacaagtcggttctgtgatagaagagcttgaca
cctcatactgtatagagtccgatctggatttatattgtactagaatagtgacattcccc
atgtccccaggtatttattcctgtttaagcggcaacacatcagcttgcatgtattcaaa
gactgaaggcgcactcactacgccgtatatggcccttaaaggctcagttattgccaatt
gtaagataacaacatgtagatgtacagaccctcctggtatcatatcgcaaaattatgga
gaagctgtatccctgatagatagacattcgtgcaatgtcttatcattagacgggataac
tctgaggctcagtggagaatttgatgcaacttatcaaaagaacatctcaatactagatt
ctcaagtcatcgtgacaggcaatcttgatatatcaactgaacttggaaacgtcaacaat
tcaatcagcaatgccttggataagttggcaaaaagcaacagcaagctagaaaaagtcaa
tgtcagactaaccagcacatccgctctcattacctatattgttctgactgtcatttctc
tagttttcggtgcactaagtctgggtttaacatgttacctgatgtacaaacaaaaggca
caacaaaagaccttgctatggcttgggaataataccctcgatcagatgagagccactac
aagagcatga
```

NDV-F protein from wildtype Texas strain (Amino Acid Sequence of NDV-F VIId wt YZCQ with lentogenic cleavage site sequence) (SEQ ID NO:37)

```
mgskpstripaplmlitrimlildcirptssldgrplaaagivvtgdkavnvytssqtg
siivkllpnmpkdkeacakdpleaynrtltttlltplgesirkiqgsvstsgggkqgrli
gavigsvalgvataaqitaaaaliqanqnaanilrlkesiaatneavhevtdglsqlsv
avgkmqqfvndqfnntareldcikitqqvgvelnlylttelttvfgpqitspaltqltiq
alynlaggnmdyllltklgignnqlssligsglitgypilydsqtqllgiqvnlpsvgnl
nnmratyletlsvstakgyasalvpkvvtqvgsvieeldtsyciesdldlyctrivtfp
mspgiysclsgntsacmysktegalttpymalkgsvianckittcrctdppgiisqnyg
eavslidrhscnvlsldgitlrlsgefdatyqknisildsqvivtgnldistelgnvnn
sisnaldklaksnsklekvnvrltstsalityivltvislvfgalslgltcylmykqka
qqktllwlgnntldqmrattra*
```

Figure 14 (Continued)

MDV gB promoter (SEQ ID NO:38)
CGATGTTTAGTCACGATAGACATCGGTTCGCCCAGCCGTCGAATACAGCATTATATTTT
AGTGTTGAAAATGTAGGGCTGCTTCCTCACTTAAAGGAGGAAATGGCTCGATTCATGTT
TCATAGCAGTAGAAAAACAGATTGGACCGTCAGTAAGTTTAGAGGGTTTTATGACTTTA
GCACTATAGATAATGTAACTGCGGCCCATCGCATGGCTTGGAAATATATCAAAGAACTG
ATTTTTGCAACAGCTTTATTTTCTTCTGTATTTAAATGTGGCGAATTGCACATCTGTCG
TGCCGACAGTTTGCAGATCAACAGCAATGGAGACTATGTATGGAAAAATGGAATATATA
TAACATATGAAACCGAATATCCACTTATAATGATTCTGGGGTCAGAATCAAGCACTTCA
GAAACGCAAAATATGACTGCAATTATTGATACAGATGTTTTTCGTTGCTTTATTCTAT
TTTGCAGTATATGGCCCCCGTTACGGCAGATCAGGTGCGAGTAGAACAGATTACCAACA
GCCACGCCCCCATCTGACCCGTCCAATATTCTTGTGTCCCTGCATTTTATCTCACACAA
TTTATGAACAGCATCATTAAGATCATCTCACT

IBDV DNA encoding VP2 protein of IBDV E strain (SEQ ID NO:41)
atgacaaacctgcaagatcaaacccaacagattgttccgttcatacggagccttctgat
gccaacaaccggaccggcgtccattccggacgacaccctggagaagcacactctcaggt
cagagacctcgacctacaatttgactgtggggacacagggtcaggctaattgtcttt
ttccctggattccctggctcaattgtgggtgctcactacacactgcagagcaatgggaa
ctacaagttcgatcagatgctcctgactgcccagaacctaccggccagctacaactact
gcaggctagtgagtcggagtctcacagtaaggtcaagcacactccctggtggcgtttat
gcactaaacggcaccataaacgccgtgaccttccaaggaagcctgagtgaactgacaga
tgttagctacaacggggttgatgtctgcaacagccaacatcaacgacaaaattgggaacg
tcctagtaggggaaggggtaaccgtcctcagcttacccacatcatatgatcttgggtat
gtgaggcttggtgaccccatacccgctatagggcttgacccaaaaatggtagcaacatg
tgacagcagtgacaggcccagagtctacaccataactgcagccgataattaccaattct
catcacagtaccaaacaggtggggtaacaatcacactgttctcagccaacattgatgcc
atcacaagtctcagcgttggggagagctcgtgttcaaaacaagcgtccaaagccttgt
actgggcgccaccatctaccttataggctttgatgggactgcggtaatcaccagagctg
tggccgcaaacaatgggctgacggccggcatcgacaatcttatgccattcaatcttgtg
attccaaccaatgagataacccagccaatcacatccatcaaactggagatagtgacctc
caaaagtgatggtcaggcagggaacagatgtcatggtcggcaagtgggagcctagcag
tgacgatccatggtggcaactatccaggagccctccgtcccgtcacactagtggcctac
gaaagagtggcaacaggatctgtcgttacggtcgctggggtgagcaacttcgagctgat
cccaaatcctgaactagcaaagaacctggttacagaatatggccgatttgacccaggag
ccatgaactacacgaaattgatactgagtgagagggaccgccttggcatcaagaccgtc
tggccaacaagggagtacactgactttcgtgagtacttcatggaggtggccgacctcaa
ctctcccctgaagattgcaggagcatttggcttcaaagacataatccgggccataagga
ggtga Figure 14 (Continued)

IBDV VP2 protein of IBDV E strain (SEQ ID NO:42)

mtnlqdqtqqivpfirsllmpttgpasipddtlekhtlrsetstynltvgdtgsglivf
fpgfpgsivgahytlqsngnykfdqmlltaqnlpasynycrlvsrsltvrsstlpggvy
alngtinavtfqgslseltdvsynglmsatanindkignvlvgegvtvlslptsydlgy
vrlgdpipaigldpkmvatcdssdrprvytitaadnyqfssqyqtggvtitlfsanida
itslsvggelvfktsvqslvlgatiyligfdgtavitravaanngltagidnlmpfnlv
iptneitqpitsikleivtsksdgqageqmswsasgslavtihggnypgalrpvtlvay
ervatgsvvtvagvsnfelipnpelaknlvteygrfdpgamnytklilserdrlgiktv
wptreytdfreyfmevadlnsplkiagafgfkdiirairr*

Guinea pig CMV promoter (SEQ ID NO:43)

ttagtcatatgttacttggcagaggccgcatggaaagtccctggacgtgggacatctga
ttaatacgtgaggaggtcagccatgttcttttggcaaaggactacggtcattggacgt
ttgattggcatgggatagggtcagccagagttaacagtgttcttttggcaaagggatac
gtggaaagtcccgggccatttacagtaaactgatacggggacaaagcacagccatattt
agtcatgtattgcttggcagagggtctatggaaagtccctggacgtgggacgtctgatt
aatatgaagaaggtcagccagaggtagctgtgtccttttggcaaagggatacggtta
tgggacgtttgattggactgggatagggtcagccagagttaacagtgttcttttggcaa
aggaaacgtggaaagtcccgggccatttacagtaaactgatactgggacaaagtacacc
catatttagtcatgttcttttggcaaagagcatctggaaagtcccgggcagcattata
gtcacttggcagagggaaagggtcactcagagttaagtacatctttccagggccaatat
tccagtaaattacacttagttttatgcaaatcagccacaagggggattttcccggtcaa
ttatgacttttccttagtcatgcggtatccaattactgccaaattggcagtacatact
aggtgattcactgacatttggccgtcctctggaaagtccctggaaaccgctcaagtact
gtatcatggtgactttgcattttggagagcacgccccactccaccattggtccacgta
ccctatggggagtggtttatgagtatataaggggctccggtttagaagccgggcaga Figure 14 (Continued)

Partial plasmid pHM103+Fopt DNA sequence (SEQ ID NO:18)
*Green and Italic* = Arms
Black and bold = NDV Fopt
BLUE AND UPPERCASE = SV40 PROMOTER
*Red and Italic and underlined* = SV40 polyA

*gagctcagggtatgatactcagctgttattgtggccgaccaggaggactccaat*
*gcttagcattcataagaacgctagagatgctatttaacgatgtgctgtcgtcta*
*aagaatttgtgcatttagcctttaaatgtaaaaccaatgacgcattcactacgc*
*tcgtgcgtgcaatttctgggccagggtatgcatattccataacagaaatcgaca*
*cttgagaagaggatctgactgtttgggataaaggtcgtttgggtctgtcctagc*
*gatataatttatatgacgatatacattaaacatctgtgtgcagtacttaggtat*
*ttaatcatgtcgatgaaatgttatgtgtaaatatcggacaatatagataacggg*
*cacgctgctattgtaacgtgcgcccgcgcgctagtgctgactaatagtgtggat*
*gatgtatacagtatattacaaacggaaatgatacgtaataaattatgtactctt*
*attgatttataaaaacatacatgcagtgttgctatgtcacataattagcctcgc*
*ccgtctacgctccactgaagataatgggctcccgctgttcaaaaaaatcagcgt*
*gcgtcgataagactttggtgcagtctcttcggggtcgcaatttagatttgccgc*
*atggagggtatctggggatttttgccaatgctggagcgacgactgtacgattcg*
*tcccatcgggatctagcagaccaatgatgttgacacacatcggccatgcatgta*
*cggacggtctattgcgcgagtttgttattttcgaaggacaagatggaagtgtat*
*atggaaccgacaataatgttagtttgcatttcttagggcggaatctacatgata*
*tcttatccaagcggggtatgagccagagagatgtgatggtcataaagggtaaat*
*tttttagatctgaaataacgcagttgcccaaacaacgatcgcgattaaaagaaa*
*aatcggatggttcaattaggacatgcatggattctgtgcgcataaaccataacc*
*gcagcactgttgggcacttcggtaactcaaatgcgaagcgttgcacgtctgcga*
*taactacgcctactatgcacattgttactcctgcatcttaaaatatatcctgt*
*agtaattttcacagcaatgtcataacatcatctcgctaaagaatgacctgggat*
*tggagaagtaatgaatatttgcaaccaatgcattgaataaactaacattaaac*G
AATTCGAGCTCGGTACAGCTTGGCTGTGGAATGTGTGTCAGTTAGGGTGTGGAA
AGTCCCCAGGCTCCCCAGCAGGCAGAAGTATGCAAAGCATGCATCTCAATTAGT
CAGCAACCAGGTGTGGAAAGTCCCCAGGCTCCCCAGCAGGCAGAAGTATGCAAA
GCATGCATCTCAATTAGTCAGCAACCATAGTCCCGCCCCTAACTCCGCCCATCC
CGCCCCTAACTCCGCCCAGTTCCGCCCATTCTCCGCCCCATGGCTGACTAATTT
TTTTATTTATGCAGAGGCCGAGGCCGCCTCGGCCTCTGAGCTATTCCAGAAGT
AGTGAGGAGGCTTTTTTGGAGGCCTAGGCTTTTGCAAAAAGCTgcggccgccac
catgggcagcaagcccagcacaagaatcccagccccccctgatgctgatcacccg
catcatgctgatcctgggctgcatcagacccacaagctccctggatggacgccc
cctggccgctgccggcatcgtggtgaccggcgacaaggccgtgaacgtgtacac
cagcagccagaccggcagcatcatcgtgaagctgctgcccaacatgcccagaga
caaagaggcctgcgccaaggccccccctggaagcctacaacagaaccctgaccac
cctgctgacccccctgggcgacagcatcagaaagatccagggctccgtgagcac
aagcggcggaggaaagcagggcagactgatcggcgccgtgatcggcagcgtggc
cctgggagtggctacagctgcccagattaccgctgcagccgccctgatccaggc

Figure 14 (Continued)

caaccagaacgccgccaacatcctgagactgaaagagagcattgccgccaccaa
cgaggccgtgcacgaagtgaccgacggcctgagccagctgtccgtggccgtggg
caagatgcagcagttcgtgaacgaccagttcaacaacaccgccagagagctgga
ctgcatcaagatcacccagcaggtgggcgtggagctgaacctgtacctgaccga
gctgaccacagtgttcggcccccagatcacaagcccagccctgacacagctgac
catccaggccctgtacaacctggctggcggcaacatggactatctgctgacaaa
gctgggaatcggcaacaaccagctgtccagcctgatcggaagcggcctgatcac
cggctaccccatcctgtacgacagccagacacagctgctgggcatccaggtgaa
cctgcccagcgtgggcaacctgaacaacatgcgcgccacctacctggaaaccct
gagcgtgtccaccaccaagggctacgccagcgccctggtgcccaaggtggtgac
acaggtgggcagcgtgatcgaggaactggacaccagctactgcatcgagagcga
cctggacctgtactgcaccagaatcgtgaccttcccaatgagccccggcatcta
cagctgcctgagcggcaacaccagcgcctgcatgtacagcaagaccgaaggcgc
actgacaacaccctacatggccctgaagggaagcgtgatcgccaactgcaagat
caccacctgcagatgcaccgaccccccaggcatcatcagccagaactacggcga
ggccgtgagcctgatcgatcgccattcctgtaacgtgctgtccctggacggcat
cacactgagactgagcggcgagttcgatgccacctaccagaagaacatcagcat
cctggacagccaggtgatcgtgaccggcaacctggacatcagcaccgagctggg
caacgtgaataacagcatcagcaacgccctggacagactggccgagagcaacag
caagctggaaaaagtgaacgtgcgcctgacatccacttccgctctgatcaccta
catcgtgctgaccgtgatcagcctggtgttcggcgccctgagcctggtgctggc
ctgctacctgatgtacaagcagaaggcccagcagaaaccctgctgtggctggg
caacaacaccctggaccagatgagagccaccaccagagcctgatgagcggccgc
ggggatccagacatgataagatacattgatgagtttggacaaaccacaactaga
atgcagtgaaaaaatgctttatttgtgaatttgtgatgctattgctttattt
gtaaccattataagctgcaataaacaagttaacaacaacaattgcattgatttt
atgtttcaggttcaggggaggtgtgggaggttttttcggatcctctagagtcg
acaattatttatttaataacatatagcccaaagacctctatgaacatttagtt
tcccgtatactcaacggcgcgtgtacacgcatctctttgcatagcgatgaag
tttgttcggcagcagaaatgcagatatccaacaatctggagaaaacttatcat
cacagtggcagtggaaacataccccctctatattcatggtataattatcgtcta
cagcgtccaggatagtggcgtgagaaatggagatctgcagccctccttccat
ggcatgccgctttattgttcattaaacgcacaatggtctcaacgccagatatgg
gcatagattctgaagaacccgttgacaatccgaagaagaaggcgtgcaggtctt
tggaagactcgcacgttggtcttataatgtatgatcgagatgtcaccctaatgc
cacatggtacaggcttatcgcggtcatggcgatcggacttgtaatttgcaacga
tgggcaaaggatcgacgacatgccaaacattctgaacccgtagagatgttaacg
atgacgaggatgaatatccatgctcgctgccatagtatcaagtacaccgcgaa
taaggacgcgtccaacatcgttatatgcacacaatgggctacacgtgactaaca
cccccgaatattagtcatatgtgagtttcagtctggctcccatatagcctgtag
actatttgtggtttaagtgtgaacgaggcgctgtgaacgagactcgggccgatt
gtaagaacaagcaaatgcactttccatttaacaagaagtgtagagagaatactc
aacctctttggatgtatcctcgag Figure 14 (Continued)

Partial plasmid pSB1 44cds SV FCAopt sequence for vSB1-009 (SEQ ID NO:19)

- SB1 UL44 arm
- SV40 promoter
- NDV-F-CA02-CSmut
- SB1 UL44 arm pSB1 44 cds SV CaF opt

*Green and Italic = UL44 Recombination Arms*
BLUE AND UPPERCASE = SV40 PROMOTER
Black and Bold = NDV-F-CAO2-CSmut sequence

*Cttttgtcatgctcggagctctgatcgcatcttatcattacgtctgcatagcaacgtct*
*ggagacgtgacgtggaagaccgggttttagttgtggcggcagggacgattgccggcat*
*cacggctccgtatggagacatttctcctctagccggctttctttcggcgtatacggcgt*
*tagctattcacgtggtcagagacgccagtcggtctctaatgaacacgtgctactaccgt*
*gcacgtcgggaaattactgtgaacggtgcatatcgcctcggtcgcgcgcgtctcccgcc*
*cagcacggacgccgaggcgacgcgcgaagaagacgtatccagttacgatacgctggggg*
*ggaatattcctacgataattctgagcctcatagcggtcatctcgattccagccatagcc*
*agctttcaaaagtacatgtcgaacgcaactaagcaccagtcaacattgactgacacgtt*
*acgcagtatatgcggtttcttggtgggtacaagtgtcgcgatattccttccgtcgcgct*
*accacgaggttctgttccgtccaattcttgtattactgttaatattcggggcaatggct*
*actaccttagccggcttcggtttacttctcgggccgacattgttttcgcgacagccgc*
*ggttctgtgctgctacacttgtataaatgtacgcaacgcgaatagcggaataaagcaat*
*tggcggccgccgcagctggtaaatgcatattaggaactgccatctcgagcatgttggtt*
*tgcgtgttaatacaatattcctgatcgcggagcgattaattttatatcatgtgctcat*
*agcgttctttcgaactgcgaataaaactttcgtggctactaaaggggcctatcgtgggt*
*ttatgcgctgtcgaaaacatgaaagggccgatttaaagctaagttgcgcaggcagagc*
*cactccatatacgctctcggagacgcggctcgcacgccagctgaaatattttccccct*
gcaggtcgaccCAATTCGAGCTCGGTACAGCTTGGCTGTGGAATGTGTGTCAGTTAGGG
TGTGGAAAGTCCCCAGGCTCCCCAGCAGGCAGAAGTATGCAAAGCATGCATCTCAATTA
GTCAGCAACCAGGTGTGGAAAGTCCCCAGGCTCCCCAGCAGGCAGAAGTATGCAAAGCA
TGCATCTCAATTAGTCAGCAACCATAGTCCCGCCCCTAACTCCGCCCATCCCGCCCCTA
ACTCCGCCCAGTTCCGCCCATTCTCCGCCCCATGGCTGACTAATTTTTTTATTTATGC
AGAGGCCGAGGCCGCCTCGGCCTCTGAGCTATTCCAGAAGTAGTGAGGAGGCTTTTTG
GAGGCCTAGGCTTTTGCAAAAAGCTcccggggcggccgccaccatgggcagcaagccca
gcacctggatcagcgtgaccctgatgctgatcaccagaaccatgctgatcctgagctgc
atctgccccacaagcagcctggacggcagaccctggccgctgccggcatcgtggtgac
cggcgacaaggccgtgaacatctacaccagcagccagaccggcagcatcatcatcaagc
tgctgcccaacatgcccaaggacaaagaggcctgcgccaaggcccccctggaagcctac

Figure 14 (Continued)

```
aacagaaccctgaccaccctgctgacccccctgggcgacagcatcagaagaatccaggg
cagcgccaccacaagcggcggaggaaagcagggcagactggtgggcgctatcatcggga
gcgtggccctgggcgtggccacagctgcccagattaccgctgcagccgccctgattcag
gccaatcagaacgccgccaacatcctgagactgaaagagagcattgccgccaccaacga
cgccgtgcacgaagtgacaaacggactgtcccagctggctgtcgctgtcggcaagatgc
agcagttcgtgaacaaccagttcaacaacaccgccagagagctggactgcatcaagatc
gcccagcaggtgggcgtggagctgaacctgtacctgaccgagctgaccacagtgttcgg
cccccagatcacaagccccgctctgacccagctgacaatccaggccctgtacaacctgg
ctggcggcaacatggactatctgctgactaagctgggagtgggcaacaaccagctgtcc
agcctgatcgggtccgggctgatcacaggcaaccccatcctgtacgacagccagacaca
gctgctgggcatccagatcaacctgccatccgtgggaagcctgaacaacatgagagcca
cctacctggaaaccctgagcgtgtccaccaccaagggcttcgccagcgccctggtgccc
aaggtggtgacacaggtgggcagcgtgatcgaggaactggacaccagctactgcatcga
gagcgacatcgacctgtactgcaccagagtggtgaccttcccaatgagccccggcatct
acagctgcctgagcggcaacaccagcgcctgcatgtacagcaagaccgaaggagcactg
acaacaccctacatggccctgaagggaagcgtgatcgccaactgcaagatgaccacctg
cagatgcgccgaccccccaggcatcatcagccagaactacggcgaggccgtgagcctga
tcgacaaacattcctgtagcgtgctgtccctggatggcatcacactgagactgagcggc
gagttcgacgccacctaccagaagaacatcagcatcctggacagccaggtgatcgtgac
cggcaacctggacatcagcaccgagctgggcaacgtgaacaacagcatcagcagcaccc
tggacaagctggccgagtccaacaacaagctgaacaaagtgaacgtgaacctgaccagc
acaagcgccctgatcacctacatcgtgctggccatcgtgtccctggccttcggcgtgat
cagcctggtgctggcctgctacctgatgtacaagcagagagcccagcagaaaccctgc
tgtggctgggcaataacccctggaccagatgagggccaccaccagaacctgatga
```
gcggccgcgatacctgcagg*tttgcggtgacattgatctggctcattatatgccccgagctc*
*ttgtaacatcgcggacgcgatttccgtagtaggcacatctcaaatgcaaaagcggcatg*
*tcaaccgtataggtacatccggccctgcttacagtcggtagggcatatatccaccggaa*
*aacttcagctttagactcctcaggtgatgaggaatagtatgtaaccctctagcagtacg*
*gtatttctaaaaaaggtagatccttttccacacggcacagactaaataacgtacacta*
*cacaggttctctcgaacttcgtttggaccggaattattccctcggcagcgcctaaaaag*
*caaacctctagagtagataagtgtcagtgaacctaggccttcttttgttccacggctgga*
*aagctaagggacgaggtacacgcgaccccagccacgcacgaacagagtttaacggaagc*
*gtcgtttgcgggataaggttgtcggacccgcgggtcgttgaaaagtggctgcgcgcc*
*taccgacgaatacgtcggtaacaattttagaaatcgaatatgactgcgagtaccgtaca*
*atcgcgaaatacggtctctatatagctactcggtccttaaatatgtaagtatgatgtcc*
*cctactcccgaagacgaccgcgacttggtcgcagtacgtgggctgctccggatgatgga*
*cgagaccacatctgagcgacacaaacgttcgcgttcaggatgccccggttgttatgcg*
*gttgtacgatcgggatcgctcttactgtgttcgtcatcacagctacggtcgtgctagct*
*tcgctgtttgcattctcttacatgtccctggagtccggtacatgtcctcacgaatggat*
*cggtttaggctatagttgtatgcgcgcgatggggagcaacgctaccgagctagaagccc*
*tagatacgtgctcccgacataacagcaagcttgtcgactttactcatgcgaaaattcta*
*atcgaagctatcgc*

Figure 14 (Continued)

Partial plasmid pHVT US2 SV-Fopt-SynPA for vHVT306 (SEQ ID NO:20)

pHVT US2 SV-Fopt-synPA

*Green and Italic = SORF3 and US2 Recombination Arms*
BLUE AND UPPERCASE = SV40 PROMOTER
Black and Bold = NDV-FconsVIId-CSmut sequence
<u>Red and Italic and Underlined = Synthetic Poly A tail</u>

*taaaatgggatctatcattacattcgttaagagtctggataatttactgtttgccagc*
*ttcgatcttggaacgtactgtggatagtgccttacttggaatcgtgaaaatttgaaacg*
*tccattatttggatatcttccggttgtcccatatcccgccctggtaccgctcggatacc*
*ttgcccgtatggattcgtattgacagtcgcgcaatggggaccaacaacgcgtgggtcc*
*acactcattcggaaattttccgatgattctgaatatttattgccgctcgttacgagtcg*
*ttggacatatctgtaatacatttcttcttctgaaggatcgctgcacatttgatctatac*
*attggccaggatgttcaagtctcagatgttgcattctggcacagcacaactttatggca*
*tttccgatgtaatcgtccggcagcctgggggagttctatattcgcatattgggatggt*
*aaggacaatagcagatctcgcaacctccagggaggctataataacgtttttaaaggatg*
*gatttctcataaaaatctgtcgcaaattacactgagaatatcctttactagcgccgatt*
*gagagcatcgtcgtccaattttctaaatggaaagaaaacaaggcgggcaagagtgttcc*
*aaacattttcattttcggcgaatctctcaaatcccatggcgtgcaattgattgcaaaat*
*tggcacttccgttcacgtttgtatctccaaactctaagacacttttaattgaaaaacta*
*cgttctagtgtggaaagaaacctataggcagaccatagaactatttgacaccacatatc*
*tttttgtatgtcaaactgaccatgatcgtatgttgctgaatgcactagggcaattcgct*
*cgcgcgactccatacattgaataattccacacgtcagctcatcggttagcaaggtccag*
*tagttgaagtcatttattttccccgcggctggccaaatctacctctgggaatatccaa*
*gttgtcgaatatgatcgcaccggctctggtcatggtgaaggaacttgtagcataaagac*
*gcaggtatcataggggtaatatttttttattcactcacatactaaaagtaacgcatatt*
*agcaccatgtatggctatcaattgacatttgcgtagcactacatcacgattatgtaca*
*acataatgggacaacatatg*cctgcaggtcgacccAATTCGAGCTCGGTACAGCTTGGC
TGTGGAATGTGTGTCAGTTAGGGTGTGGAAAGTCCCCAGGCTCCCCAGCAGGCAGAAGT
ATGCAAAGCATGCATCTCAATTAGTCAGCAACCAGGTGTGGAAAGTCCCCAGGCTCCCC
AGCAGGCAGAAGTATGCAAAGCATGCATCTCAATTAGTCAGCAACCATAGTCCCGCCCC
TAACTCCGCCCATCCCGCCCCTAACTCCGCCCAGTTCCGCCCATTCTCCGCCCCATGGC
TGACTAATTTTTTTTATTTATGCAGAGGCCGAGGCCGCCTCGGCCTCTGAGCTATTCCA
GAAGTAGTGAGGAGGCTTTTTTGGAGGCCTAGGCTTTTGCAAAAAGCTcccggggcggc Figure 14 (Continued)

cgccaccatgggcagcaagcccagcacaagaatcccagccccctgatgctgatcaccc
gcatcatgctgatcctgggctgcatcagacccacaagctccctggatggacgcccctg
gccgctgccggcatcgtggtgaccggcgacaaggccgtgaacgtgtacaccagcagcca
gaccggcagcatcatcgtgaagctgctgcccaacatgcccagagacaagaggcctgcg
ccaaggccccctggaagcctacaacagaaccctgaccaccctgctgaccccctgggc
gacagcatcagaaagatccagggctccgtgagcacaagcggcggaggaaagcagggcag
actgatcggcgccgtgatcggcagcgtggccctgggagtggctacagctgcccagatta
ccgctgcagccgccctgatccaggccaaccagaacgccgccaacatcctgagactgaaa
gagagcattgccgccaccaacgaggccgtgcacgaagtgaccgacggcctgagccagct
gtccgtggccgtgggcaagatgcagcagttcgtgaacgaccagttcaacaacaccgcca
gagagctggactgcatcaagatcacccagcaggtgggcgtggagctgaacctgtacctg
accgagctgaccacagtgttcggccccagatcacaagcccagccctgacacagctgac
catccaggccctgtacaacctggctggcggcaacatggactatctgctgacaaagctgg
gaatcggcaacaaccagctgtccagcctgatcggaagcggcctgatcaccggctacccc
atcctgtacgacagccagacacagctgctgggcatccaggtgaacctgcccagcgtggg
caacctgaacaacatgcgcgccaccacctggaaaccctgagcgtgtccaccaccaagg
gctacgccagcgccctggtgcccaaggtggtgacacaggtgggcagcgtgatcgaggaa
ctggacaccagctactgcatcgagagcgacctggacctgtactgcaccagaatcgtgac
cttcccaatgaccccggcatctacagctgcctgagcggcaacaccagcgcctgcatgt
acagcaagaccgaaggcgcactgacaacacccctacatggccctgaagggaagcgtgatc
gccaactgcaagatcaccacctgcagatgcaccgaccccccaggcatcatcagccagaa
ctacggcgaggccgtgagcctgatcgatcgccattcctgtaacgtgctgtccctggacg
gcatcacactgagactgagcggcgagttcgatgccacctaccagaagaacatcagcatc
ctggacagccaggtgatcgtgaccggcaacctggacatcagcaccgagctgggcaacgt
gaataacagcatcagcaacgccctggacagactggccgagagcaacagcaagctggaaa
aagtgaacgtgcgcctgacatccacttccgctctgatcacctacatcgtgctgaccgtg
atcagcctggtgttcggcgccctgagcctggtgctggcctgctacctgatgtacaagca
gaaggcccagcagaaaaccctgctgtggctgggcaacaaccctggaccagatgagag
ccaccaccagagcctgatgagcggccgcgatatc<u>aataaatatctttatttcattac
atctgtgtgttggtttttgtgtgaatcgatagtactaacatacgctctccatcaaaac
aaaacgaaacaaacaaactagcaaaataggctgtccccagtgcaagtgcaggtgccag
aacatttctctt</u>ctagacctgcaggcccggg*caagtagatgcaatttcctcacactagt
tgggtttatctactattgaattttccctatctgtgatacacttgggagcctctacaag
catattgccatcatgtacgtttttatctactgtcttaacgcccatgggaacggaggcgt
cgtcgtcatgtattggacggcaacataggcagcaacacaaattgcgtttaggtggggtg
catgtggactcgataccaagcccctgcagctggggaacgtctggtggagagccgataat
ttgatatacgcacgccatattactgtcgttgaagtacgccttatcttctatgttttcaa
atttaggttcccaagtggacgtgagaagtgtttgtatctcacatggaatggcccaaggc
attccagcccaggtgcctggtactttaatggcaaacaaacgttttggtagaggtattga
ttctattgcagttctgcagatatctgcagccccgagtatccacaggctatacgatacgt
tatcggaggcctccgattctagcattacatagccggtcagtagatcctgccattcggta
gcgcaaccggctacatcttcaaacagtctcacaataaatgcatctctcgttcctgccaa
tccggaaccgggcataccactcccgcctgccgatttaattctcacaattgggcgatgcc
ggcggggcaaaacgaatgtggatttggcaaaccgacacaggtctgctgtacggactaat*

Figure 14 (Continued)

*atgggcacacccacatcattcttcagatgctccatgcattgttctatgagaaagatcca*
*tagggtggaggcagcgtcacgagatcgcccaggcaatcgatcgcattcgtctagtaaag*
*tgacgagagttatcatgcacacccat*

Figure 14 (Continued)

plasmid pCD046+NDV-F wt for vHVT110 (SEQ ID NO:21)
*Green and Italic = BamHI fragment I intergenic Recombination Arms*
BLUE AND UPPERCASE = MCMV PROMOTER
Black and Bold = NDV-F VIId wildtype consensus sequence
*Red and Italic and Underlined = SV40 Poly A tail*

```
                              NDV-F VIId wt
                                    polyA SV 40
Intergene 1 arm    pMCMV                    Intergene 1 arm
``` pCD046+NDV-F wt

*gagctcagggtatgatactcagctgttattgtggccgaccaggaggactccaatgctta
gcattcataagaacgctagagatgctatttaacgatgtgctgtcgtctaaagaatttgt
gcattagcctttaaatgtaaaaccaatgacgcattcactacgctcgtgcgtgcaattt
ctgggccagggtatgcatattccataacagaaatcgacacttgagaagaggatctgact
gtttgggataaaggtcgtttgggtctgtcctagcgatataattatatgacgataca
ttaaacatctgtgtgcagtacttaggtatttaatcatgtcgatgaaatgttatgtgtaa
atatcggacaatatagataacgggcacgctgctattgtaacgtgcgcccgcgcgctagt
gctgactaatagtgtggatgatgtatacagtatattacaaacggaaatgatacgtaata
aattatgtactcttattgatttataaaaacatacatgcagtgttgctatgtcacataat
tagcctcgcccgtctacgctccactgaagataatgggctccgctgttcaaaaaaatca
gcgtgcgtcgataagactttggtgcagtctcttcggggtcgcaatttagatttgccgca
tggagggtatctggggattttgccaatgctggagcgacgactgtacgattcgtcccat
cgggatctagcagaccaatgatgttgacacacatcggccatgcatgtacggacggtcta
ttgcgcgagtttgttattttcgaaggacaagatggaagtgtatatggaaccgacaataa
tgttagtttgcatttcttagggcggaatctacatgatatcttatccaagcggggtatga
gccagagagatgtgatggtcataaagggtaaattttttagatctgaaataacgcagttg
cccaaacaacgatcgcgattaaaagaaaaatcggatggttcaattaggacatgcatgga
ttctgtgcgcataaaccataaccgcagcactgttgggcacttcggtaactcaaatgcga
agcgttgcacgtctgcgataactacgcctactatgcacattgttactcctgcatcttaa
aaatatatcctgtagtaattttcacagcaatgtcataacatcatctcgctaaagaatga
cctgggattggagaagtaatgaatatttgcaaccaatgcattgaataaactaacattaa
acgaattc*AATAGTGGATCCCCCAACTCCGCCCGTTTTATGACTAGAACCAATAGTTTT
TAATGCCAAATGCACTGAAATCCCCTAATTTGCAAAGCCAAACGCCCCCTATGTGAGTA
ATACGGGGACTTTTTACCCAATTTCCCACGCGGAAAGCCCCCTAATACACTCATATGGC
ATATGAATCAGCACGGTCATGCACTCTAATGGCGGCCCATAGGGACTTTCCACATAGGG
GGCGTTCACCATTTCCCAGCATAGGGGTGGTGACTCAATGGCCTTTACCCAAGTACATT
GGGTCAATGGGAGGTAAGCCAATGGGTTTTTCCCATTACTGGCAAGCACACTGAGTCAA
ATGGGACTTTCCACTGGGTTTTGCCCAAGTACATTGGGTCAATGGGAGGTGAGCCAATG
GGAAAAACCCATTGCTGCCAAGTACACTGACTCAATAGGGACTTTCCAATGGGTTTTTC Figure 14 (Continued)

```
CATTGTTGGCAAGCATATAAGGTCAATGTGGGTGAGTCAATAGGGACTTTCCATTGTAT
TCTGCCCAGTACATAAGGTCAATAGGGGGTGAATCAACAGGAAAGTCCCATTGGAGCCA
AGTACACTGCGTCAATAGGGACTTTCCATTGGGTTTTGCCCAGTACATAAGGTCAATAG
GGGATGAGTCAATGGGAAAAACCCATTGGAGCCAAGTACACTGACTCAATAGGGACTTT
CCATTGGGTTTTGCCCAGTACATAAGGTCAATAGGGGGTGAGTCAACAGGAAAGTTCCA
TTGGAGCCAAGTACATTGAGTCAATAGGGACTTTCCAATGGGTTTTGCCCAGTACATAA
GGTCAATGGGAGGTAAGCCAATGGGTTTTTCCCATTACTGGCACGTATACTGAGTCATT
AGGGACTTTCCAATGGGTTTTGCCCAGTACATAAGGTCAATAGGGGTGAATCAACAGGA
AAGTCCCATTGGAGCCAAGTACACTGAGTCAATAGGGACTTTCCATTGGGTTTTGCCCA
GTACAAAAGGTCAATAGGGGGTGAGTCAATGGGTTTTTCCCATTATTGGCACGTACATA
AGGTCAATAGGGGTGAGTCATTGGGTTTTTCCAGCCAATTTAATTAAAACGCCATGTAC
TTTCCCACCATTGACGTCAATGGGCTATTGAAACTAATGCAACGTGACCTTTAAACGGT
ACTTTCCCATAGCTGATTAATGGGAAAGTACCGTTCTCGAGCCAATACACGTCAATGGG
AAGTGAAAGGGCAGCCAAAACGTAACACCGCCCGGTTTTCCCCTGGAAATTCCATATT
GGCACGCATTCTATTGGCTGAGCTGCGTTCTACGTGGGTATAAGAGGCGCGACCAGCGT
CGGTACCGTCGCAGTCTTCGGTCTGACCACCGTAGAACGCAGAGCTCCTCGCTGCAGgc
ggccgcatgggctccaaaccttctaccaggatcccagcacctctgatgctgatcaccg
gattatgctgatattgggctgtatccgtccgacaagctctcttgacggcaggcctcttg
cagctgcaggaattgtagtaacaggagataaggcagtcaatgtatacacttcgtctcag
acagggtcaatcatagtcaagttgctcccgaatatgcccagggataaggaggcgtgtgc
aaaagccccattagaggcatataacagaacactgactactttgctcactcctcttggcg
actccatccgcaagatccaagggtctgtgtccacatctggaggaggcaagcaaggccgc
ctgataggtgctgttattggcagtgtagctcttgggggttgcaacagcggcacagataac
agcagctgcggccctaatacaagccaaccagaatgccgccaacatcctccggcttaagg
agagcattgctgcaaccaatgaagctgtgcatgaagtcaccgacggattatcacaacta
tcagtggcagttgggaagatgcagcagtttgtcaatgaccagtttaataatacggcgcg
agaattggactgtataaaaatcacacaacaggttggtgtagaactcaacctatacctaa
ctgaattgactacagtattcgggccacagatcacctcccctgcattaactcagctgacc
atccaggcactttataatttagctggtggcaatatggattacttattaactaagttagg
tatagggaacaatcaactcagctcgttaattggtagcggcctgatcactggttaccta
tactgtatgactcacagactcaactcttgggcatacaagtgaatttaccctcagtcggg
aacttaaataatatgcgtgccacctatttggagaccttatctgtaagtacaaccaaagg
atatgcctcagcacttgtcccgaaagtagtgacacaagtcggttccgtgatagaagagc
ttgacacctcatactgtatagagtccgatctggatttatattgtactagaatagtgaca
ttccccatgtccccaggtatttattcctgtttgagcggcaacacatcagcttgcatgta
ttcaaagactgaaggcgcactcactacgccgtatatggcccttaaaggctcagttattg
ccaattgtaaaataacaacatgtagatgtacagaccctcctggtatcatatcgcaaaat
tatggagaagctgtatccctgatagatagacattcgtgcaatgtcttatcattagacgg
gataactctaaggctcagtggggaatttgatgcaacttatcaaaagaacatctcaatac
tagattctcaagtcatcgtgacaggcaatcttgatatatcaactgaacttggaaacgtc
aacaattcaatcagcaatgccttggataggttggcagaaagcaacagcaagctagaaaa
agtcaatgtcagactaaccagcacatctgctctcattacctatattgttctaactgtca
tttctctagttttcggtgcacttagtctggtgttagcgtgttacctgatgtacaaacag
aaggcacaacaaagaccttgctatggcttgggaataatacctcgatcagatgagagc
```

Figure 14 (Continued)

cactacaagagcatgagcggccgc*ggggatccagacatgataagatacattgatgagtt*
*tggacaaaccacaactagaatgcagtgaaaaaaatgctttatttgtgaaatttgtgatg*
*ctattgctttatttgtaaccattataagctgcaataaacaagttaacaacaacaattgc*
*attgatttatgtttcaggttcaggggaggtgtgggaggttttttcggatcctctaga*
gtcgac*aattatttatttaataacatatagcccaaagacctctatgaacatttagttt*
*cccgtatactcaacggcgcgtgtacacacgcatctctttgcatagcgatgaagtttgtt*
*cggcagcagaaaatgcagatatccaacaatctggagaaaacttatcatcacagtggcag*
*tggaaacatacccctctatattcatggtataattatcgtctacagcgtccaggatagt*
*ggcgtgagaaaatggagatctgcagccctcctttccatggcatgccgctttattgttca*
*ttaaacgcacaatggtctcaacgccagatatgggcatagattctgaagaacccgttgac*
*aatccgaagaagaaggcgtgcaggtctttggaagactcgcacgttggtcttataatgta*
*tgatcgagatgtcaccctaatgccacatggtacaggcttatcgcggtcatggcgatcgg*
*acttgtaatttgcaacgatgggcaaaggatcgacgacatgccaaacattctgaacccgt*
*agagatgttaacgatgacgaggatgaatatcccatgctcgctgccatagtatcaagtac*
*accgcgaataaggacgcgtccaacatcgttatgcacacaatgggctacacgtgacta*
*acaccccgaatattagtcatatgtgagtttcagtctggctcccatatagcctgtagac*
*tatttgtggtttaagtgtgaacgaggcgctgtgaacgagactcgggccgattgtaagaa*
*caagcaaatgcactttccatttaacaagaagtgtagagagaatactcaacctctttgga*
*tgtatcctcgag*

Figure 14 (Continued)
Partial plasmid pHM103+NDV-F wt sequence for vHVT111 (SEQ ID NO:22)

pHM103 + NDV-F wt

*Green and Italic = BamHI fragment I intergenic Recombination Arms*
BLUE AND UPPERCASE = SV40 PROMOTER
Black and Bold = NDV-F VIId wildtype consensus sequence
*Red and Italic and Underlined = SV40 Poly A tail*

*gagctcagggtatgatactcagctgttattgtggccgaccaggaggactccaatgctta*
*gcattcataagaacgctagagatgctatttaacgatgtgctgtcgtctaaagaatttgt*
*gcatttagcctttaaatgtaaaaccaatgacgcattcactacgctcgtgcgtgcaattt*
*ctgggccagggtatgcatattccataacagaaatcgacacttgagaagaggatctgact*
*gtttgggataaaggtcgtttgggtctgtcctagcgatataatttatatgacgatataca*
*ttaaacatctgtgtgcagtacttaggtatttaatcatgtcgatgaaatgttatgtgtaa*
*atatcggacaatatagataacgggcacgctgctattgtaacgtgcgcccgcgcgctagt*
*gctgactaatagtgtggatgatgtatacagtatattacaaacggaaatgatacgtaata*
*aattatgtactcttattgatttataaaaacatacatgcagtgttgctatgtcacataat*
*tagcctcgcccgtctacgctccactgaagataatgggctcccgctgttcaaaaaaatca*
*gcgtgcgtcgataagactttggtgcagtctcttcggggtcgcaatttagatttgccgca*
*tggagggtatctggggattttttgccaatgctggagcgacgactgtacgattcgtcccat*
*cgggatctagcagaccaatgatgttgacacacatcggccatgcatgtacggacggtcta*
*ttgcgcgagtttgttatttcgaaggacaagatggaagtgtatatggaaccgacaataa*
*tgttagtttgcatttcttagggcggaatctacatgatatcttatccaagcggggtatga*
*gccagagagatgtgatggtcataaagggtaaattttttagatctgaaataacgcagttg*
*cccaaacaacgatcgcgattaaaagaaaaatcggatggttcaattaggacatgcatgga*
*ttctgtgcgcataaaccataaccgcagcactgttgggcacttcggtaactcaaatgcga*
*agcgttgcacgtctgcgataactacgctactatgcacattgttactcctgcatcttaa*
*aaatatcctgtagtaattttcacagcaatgtcataacatcatctcgctaaagaatga*
*cctgggattggagaagtaatgaatatttgcaaccaatgcattgaataaactaacattaa*
*ac*gaattcGAGCTCGGTACAGCTTGGCTGTGGAATGTGTGTCAGTTAGGGTGTGGAAAG
TCCCCAGGCTCCCCAGCAGGCAGAAGTATGCAAAGCATGCATCTCAATTAGTCAGCAAC
CAGGTGTGGAAAGTCCCCAGGCTCCCCAGCAGGCAGAAGTATGCAAAGCATGCATCTCA
ATTAGTCAGCAACCATAGTCCCGCCCCTAACTCCGCCCATCCCGCCCCTAACTCCGCCC
AGTTCCGCCCATTCTCCGCCCCATGGCTGACTAATTTTTTTTATTTATGCAGAGGCCGA
GGCCGCCTCGGCCTCTGAGCTATTCCAGAAGTAGTGAGGAGGCTTTTTTGGAGGCCTAG Figure 14 (Continued)

```
GCTTTTGCAAAAGCTgcggccgcatgggctccaaaccttctaccaggatcccagcacc
tctgatgctgatcaccggattatgctgatattgggctgtatccgtccgacaagctctc
ttgacggcaggcctcttgcagctgcaggaattgtagtaacaggagataaggcagtcaat
gtatacacttcgtctcagacagggtcaatcatagtcaagttgctcccgaatatgcccag
ggataaggaggcgtgtgcaaaagccccattagaggcatataacagaacactgactactt
tgctcactcctcttggcgactccatccgcaagatccaagggtctgtgtccacatctgga
ggaggcaagcaaggccgcctgataggtgctgttattggcagtgtagctcttggggttgc
aacagcggcacagataacagcagctgcggccctaatacaagccaaccagaatgccgcca
acatcctccggcttaaggagagcattgctgcaaccaatgaagctgtgcatgaagtcacc
gacggattatcacaactatcagtggcagttgggaagatgcagcagtttgtcaatgacca
gtttaataatacggcgcgagaattggactgtataaaatcacacaacaggttggtgtag
aactcaacctatacctaactgaattgactacagtattcgggccacagatcacctcccct
gcattaactcagctgaccatccaggcactttataatttagctggtggcaatatggatta
cttattaactaagttaggtatagggaacaatcaactcagctcgttaattggtagcggcc
tgatcactggttaccctatactgtatgactcacagactcaactcttgggcatacaagtg
aatttaccctcagtcgggaacttaaataatatgcgtgccacctatttggagaccttatc
tgtaagtacaaccaaaggatatgcctcagcacttgtcccgaaagtagtgacacaagtcg
gttccgtgatagaagagcttgacacctcatactgtatagagtccgatctggatttatat
tgtactagaatagtgacattccccatgtccccaggtatttattcctgtttgagcggcaa
cacatcagcttgcatgtattcaaagactgaaggcgcactcactacgccgtatatggccc
ttaaaggctcagttattgccaattgtaaaataacaacatgtagatgtacagaccctcct
ggtatcatatcgcaaaattatggagaagctgtatccctgatagatagacattcgtgcaa
tgtcttatcattagacgggataactctaaggctcagtggggaatttgatgcaacttatc
aaaagaacatctcaatactagattctcaagtcatcgtgacaggcaatcttgatatatca
actgaacttggaaacgtcaacaattcaatcagcaatgccttggataggttggcagaaag
caacagcaagctagaaaaagtcaatgtcagactaaccagcacatctgctctcattacct
atattgttctaactgtcatttctctagttttcggtgcacttagtctggtgttagcgtgt
tacctgatgtacaaacagaaggcacaacaaaagaccttgctatggcttgggaataatac
cctcgatcagatgagagccactacaagagcatgagcggccgcggggatccagacatgat
aagatacattgatgagtttggacaaaccacaactagaatgcagtgaaaaaaatgcttta
tttgtgaaatttgtgatgctattgctttatttgtaaccattataagctgcaataaacaa
gttaacaacaacaattgcattgatttatgtttcaggttcaggggaggtgtgggaggt
tttttcggatcctctagagtcgacaattatttatttaataacatatagcccaaagacc
tctatgaacatttagtttcccgtatactcaacggcgcgtgtacacacgcatctctttgc
atagcgatgaagtttgttcggcagcagaaatgcagatatccaacaatctggagaaaac
ttatcatcacagtggcagtggaaacataccccctctatattcatggtataattatcgtc
tacagcgtccaggatagtggcgtgagaaatggagatctgcagccctcctttccatggc
atgccgctttattgttcattaaacgcacaatggtctcaacgccagatatgggcatagat
tctgaagaacccgttgacaatccgaagaagaaggcgtgcaggtctttggaagactcgca
cgttggtcttataatgtatgatcgagatgtcacctaatgccacatggtacaggcttat
cgcggtcatggcgatcggacttgtaatttgcaacgatgggcaaggatcgacgacatgc
caaacattctgaacccgtagagatgttaacgatgacgaggatgaatatccatgctcgc
tgccatagtatcaagtacaccgcgaataaggacgcgtccaacatcgttatatgcacaca
atgggctacacgtgactaacaccccgaatattagtcatatgtgagtttcagtctggct
```

Figure 14 (Continued)

```
cccatatagcctgtagactatttgtggtttaagtgtgaacgaggcgctgtgaacgagac
tcgggccgattgtaagaacaagcaaatgcactttcatttaacaagaagtgtagagaga
atactcaacctctttggatgtatcctcgag
```

Figure 14 (Continued)
Partial plasmid pHM103+NDV-F CA02 for vHVT116 (SEQ ID NO:23)

```
                    NDV-F-CA02-CSmut
      SV40 Promoter                      polyA SV 40
Intergene 1 arm                                    Intergene 1 arm
``` pHM103 + NDV-F CA02

*Green and Italic = BamHI fragment I intergenic Recombination Arms*
BLUE AND UPPERCASE = SV40 PROMOTER
Black and Bold = NDV-F-CA02-CSmut sequence
*Red and Italic and Underlined = SV40 Poly A tail*

*gagctcagggtatgatactcagctgttattgtggccgaccaggaggactccaatgctta*
*gcattcataagaacgctagagatgctatttaacgatgtgctgtcgtctaaagaatttgt*
*gcatttagcctttaaatgtaaaaccaatgacgcattcactacgctcgtgcgtgcaattt*
*ctggggccagggtatgcatattccataacagaaatcgacacttgagaagaggatctgact*
*gtttgggataaaggtcgtttgggtctgtcctagcgatataatttatatgacgataca*
*ttaaacatctgtgtgcagtacttaggtatttaatcatgtcgatgaaatgttatgtgtaa*
*atatcggacaatatagataacgggcacgctgctattgtaacgtgcgcccgcgcgctagt*
*gctgactaatagtgtggatgatgtatacagtatattacaaacggaaatgatacgtaata*
*aattatgtactcttattgatttataaaaacatacatgcagtgttgctatgtcacataat*
*tagcctcgccgtctacgctccactgaagataatgggctcccgctgttcaaaaaaatca*
*gcgtgcgtcgataagactttggtgcagtctcttcggggtcgcaatttagatttgccgca*
*tggagggtatctggggattttgccaatgctggagcgacgactgtacgattcgtccat*
*cgggatctagcagaccaatgatgttgacacacatcggccatgcatgtacggacggtcta*
*ttgcgcgagtttgttatttcgaaggacaagatggaagtgtatatggaaccgacaataa*
*tgttagtttgcatttcttagggcggaatctacatgatatcttatccaagcggggtatga*
*gccagagagatgtgatggtcataagggtaaattttttagatctgaaataacgcagttg*
*cccaaacaacgatcgcgattaaaagaaaaatcggatggttcaattaggacatgcatgga*
*ttctgtgcgcataaaccataaccgcagcactgttgggcacttcggtaactcaaatgcga*
*agcgttgcacgtctgcgataactacgcctactatgcacattgttactcctgcatcttaa*
*aaatatatcctgtagtaattttcacagcaatgtcataacatcatctcgctaaagaatga*
*cctgggattggagaagtaatgaatatttgcaaccaatgcattgaataaactaacattaa*
*ac*gaattcGAGCTCGGTACAGCTTGGCTGTGGAATGTGTGTCAGTTAGGGTGTGGAAAG
TCCCCAGGCTCCCCAGCAGGCAGAAGTATGCAAAGCATGCATCTCAATTAGTCAGCAAC
CAGGTGTGGAAAGTCCCCAGGCTCCCCAGCAGGCAGAAGTATGCAAAGCATGCATCTCA
ATTAGTCAGCAACCATAGTCCCGCCCCTAACTCCGCCCATCCCGCCCCTAACTCCGCCC
AGTTCCGCCCATTCTCCGCCCCATGGCTGACTAATTTTTTTTATTTATGCAGAGGCCGA
GGCCGCCTCGGCCTCTGAGCTATTCCAGAAGTAGTGAGGAGGCTTTTTTGGAGGCCTAG Figure 14 (Continued)

```
GCTTTTGCAAAAGCTgcggccgccaccatgggcagcaagcccagcacctggatcagcg
tgaccctgatgctgatcaccagaaccatgctgatcctgagctgcatctgccccacaagc
agcctggacggcagacccctggccgctgccggcatcgtggtgaccggcgacaaggccgt
gaacatctacaccagcagccagaccggcagcatcatcatcaagctgctgcccaacatgc
ccaaggacaaagaggcctgcgccaaggcccccctggaagcctacaacagaaccctgacc
accctgctgaccccctgggcgacagcatcagaagaatccagggcagcgccaccacaag
cggcggaggaaagcagggcagactggtgggcgctatcatcgggagcgtggccctgggcg
tggccacagctgcccagattaccgctgcagccgccctgattcaggccaatcagaacgcc
gccaacatcctgagactgaaagagagcattgccgccaccaacgacgccgtgcacgaagt
gacaaacggactgtcccagctggctgtcgctgtcggcaagatgcagcagttcgtgaaca
accagttcaacaacaccgccagagagctggactgcatcaagatcgcccagcaggtgggc
gtggagctgaacctgtacctgaccgagctgaccacagtgttcggccccagatcacaag
ccccgctctgacccagctgacaatccaggccctgtacaacctggctggcggcaacatgg
actatctgctgactaagctgggagtgggcaacaaccagctgtccagcctgatcgggtcc
gggctgatcacaggcaaccccatcctgtacgacagccagacacagctgctgggcatcca
gatcaacctgccatccgtgggaagcctgaacaacatgagagccacctacctggaaaccc
tgagcgtgtccaccaccaagggcttcgccagcgccctggtgcccaaggtggtgacacag
gtgggcagcgtgatcgaggaactggacaccagctactgcatcgagagcgacatcgacct
gtactgcaccagagtggtgaccttcccaatgagccccggcatctacagctgcctgagcg
gcaacaccagcgcctgcatgtacagcaagaccgaaggagcactgacaacaccctacatg
gccctgaagggaagcgtgatcgccaactgcaagatgaccacctgcagatgcgccgaccc
cccaggcatcatcagccagaactacggcgaggccgtgagcctgatcgacaaacattcct
gtagcgtgctgtccctggatggcatcacactgagactgagcggcgagttcgacgccacc
taccagaagaacatcagcatcctggacagccaggtgatcgtgaccggcaacctggacat
cagcaccgagctgggcaacgtgaacaacagcatcagcagcaccctggacaagctggccg
agtccaacaacaagctgaacaaagtgaacgtgaacctgaccagcacaagcgccctgatc
acctacatcgtgctggccatcgtgtccctggccttcggcgtgatcagcctggtgctggc
ctgctacctgatgtacaagcagagagcccagcagaaaccctgctgtggctgggcaata
acaccctggaccagatgagggccaccaccagaacctgatgagcggccgcggggatccag
acatgataagatacattgatgagtttggacaaaccacaactagaatgcagtgaaaaaaa
tgctttatttgtgaaatttgtgatgctattgctttatttgtaaccattataagctgcaa
taaacaagttaacaacaacaattgcattgattttatgtttcaggttcaggggaggtgt
gggaggttttttcggatcctctagagtcgacaattatttatttaataacatatagccc
aaagacctctatgaacatttagtttcccgtatactaacggcgcgtgtacacacgcatc
tctttgcatagcgatgaagtttgttcggcagcagaaatgcagatatccaacaatctgg
agaaaacttatcatcacagtggcagtggaaacataccccctctatattcatggtataat
tatcgtctacagcgtccaggatagtggcgtgagaaatggagatctgcagccctccttt
ccatggcatgccgctttattgttcattaaacgcacaatggtctcaacgccagatatggg
catagattctgaagaacccgttgacaatccgaagaagaaggcgtgcaggtctttggaag
actcgcacgttggtcttataatgtatgatcgagatgtcacctaatgccacatggtaca
ggcttatcgcggtcatggcgatcggacttgtaatttgcaacgatgggcaaggatcgac
gacatgccaaacattctgaacccgtagagatgttaacgatgacgaggatgaatatccca
tgctcgctgccatagtatcaagtacaccgcgaataaggacgcgtccaacatcgttatat
gcacacaatgggctacacgtgactaacaccccgaatattagtcatatgtgagtttcag
```

Figure 14 (Continued)

*tctggctcccatatagcctgtagactatttgtggtttaagtgtgaacgaggcgctgtga
acgagactcgggccgattgtaagaacaagcaaatgcactttccatttaacaagaagtgt
agagagaatactcaacctctttggatgtatcctcgag*

Figure 14 (Continued)

Partial plasmid HVTIG2 SV Fwt SbfI sequence for vHVT301 (SEQ ID NO:24)

*Green and Italic = gp070 and gp066 Recombination Arms*
BLUE AND UPPERCASE = SV40 PROMOTER
Black and Bold = NDV-F VIId wildtype consensus sequence
<u>Red and Underlined = SV40 Poly A tail</u>

*tgtttcgcaccatatccaagctggctgtccctaagagcttattcctgcaagacctcata*
*cggaataattgcccgaccaatacttattacggacataggtaggccgataaatattatgt*
*tgactggaggatggaaaggaggttttgtaacagctacatcgctcgttcatcagcaagcg*
*atactttggatatccgagcttcaaaagccgcataaaccccgctttatttctgaatacgc*
*cccaacagtaacacatgcgtggttcctggcacttggaacgccgtgttttataggcaaga*
*acatactacccaaagaggtcttgggatttctggcgcgtcgttgcaatgaagaaatgaat*
*tctttgttccttgaaatgccgacaactctaaaaacggtattcgagcaccattactttac*
*gcgtggatctgaagtaaatccagcgttgttgatggagcctaacagattttgcaactga*
*tggattcgcggaaaatcctatgtttatacgaatccgctatgtgcgacaaccccggagct*
*cagggtatgatactcagctgttattgtggccgaccaggaggactccaatgcttagcatt*
*cataagaacgctagagatgctatttaacgatgtgctgtcgtctaaagaatttgtgcatt*
*tagcctttaaatgtaaaaccaatgacgcattcactacgctcgtgcgtgcaatttctggg*
*ccagggtatgcatattccataacagaaatcgacacttgagaagaggatctgactgtttg*
*ggataaaggtcgtttgggtctgtcctagcgatataatttatatgacgatatacattaaa*
*catctgtgtgcagtacttaggtatttaatcatgtcgatgaaatgttatgtgtaaatatc*
*ggacaatatagataacgggcacgctgctattgtaacgtgcgcccgcgcgctagtgctga*
*ctaatagtgtggatgatgtatacagtatattacaaacggaaatgatacgtaataaa*cct
gcaggtcgaccCAATTCGAGCTCGGTACAGCTTGGCTGTGGAATGTGTGTCAGTTAGGG
TGTGGAAAGTCCCCAGGCTCCCCAGCAGGCAGAAGTATGCAAAGCATGCATCTCAATTA
GTCAGCAACCAGGTGTGGAAAGTCCCCAGGCTCCCCAGCAGGCAGAAGTATGCAAAGCA
TGCATCTCAATTAGTCAGCAACCATAGTCCCGCCCCTAACTCCGCCCATCCCGCCCCTA
ACTCCGCCCAGTTCCGCCCATTCTCCGCCCCATGGCTGACTAATTTTTTTTATTTATGC
AGAGGCCGAGGCCGCCTCGGCCTCTGAGCTATTCCAGAAGTAGTGAGGAGGCTTTTTTG
GAGGCCTAGGCTTTTGCAAAAGCTgcggccgcatgggctccaaaccttctaccaggat
cccagcacctctgatgctgatcaccggattatgctgatattgggctgtatccgtccga
caagctctcttgacggcaggcctcttgcagctgcaggaattgtagtaacaggagataag
gcagtcaatgtatacacttcgtctcagacagggtcaatcatagtcaagttgctcccgaa

Figure 14 (Continued)

tatgcccagggataaggaggcgtgtgcaaaagccccattagaggcatataacagaacac
tgactactttgctcactcctcttggcgactccatccgcaagatccaagggtctgtgtcc
acatctggaggaggcaagcaaggccgcctgataggtgctgttattggcagtgtagctct
tggggttgcaacagcggcacagataacagcagctgcggccctaatacaagccaaccaga
atgccgccaacatcctccggcttaaggagagcattgctgcaaccaatgaagctgtgcat
gaagtcaccgacggattatcacaactatcagtggcagttgggaagatgcagcagtttgt
caatgaccagtttaataatacggcgcgagaattggactgtataaaatcacacaacagg
ttggtgtagaactcaacctatacctaactgaattgactacagtattcgggccacagatc
acctcccctgcattaactcagctgaccatccaggcactttataatttagctggtggcaa
tatggattacttattaactaagttaggtatagggaacaatcaactcagctcgttaattg
gtagcggcctgatcactggttaccctatactgtatgactcacagactcaactcttgggc
atacaagtgaatttaccctcagtcgggaacttaaataatatgcgtgccacctatttgga
gaccttatctgtaagtacaaccaaaggatatgcctcagcacttgtcccgaaagtagtga
cacaagtcggttccgtgatagaagagcttgacacctcatactgtatagagtccgatctg
gatttatattgtactagaatagtgacattccccatgtccccaggtatttattcctgttt
gagcggcaacacatcagcttgcatgtattcaaagactgaaggcgcactcactacgccgt
atatggcccttaaaggctcagttattgccaattgtaaaataacaacatgtagatgtaca
gaccctcctggtatcatatcgcaaaattatggagaagctgtatccctgatagatagaca
ttcgtgcaatgtcttatcattagacgggataactctaaggctcagtggggaatttgatg
caacttatcaaaagaacatctcaatactagattctcaagtcatcgtgacaggcaatctt
gatatcaactgaacttggaaacgtcaacaattcaatcagcaatgccttggataggtt
ggcagaaagcaacagcaagctagaaaagtcaatgtcagactaaccagcacatctgctc
tcattacctatattgttctaactgtcatttctctagttttcggtgcacttagtctggtg
ttagcgtgttacctgatgtacaaacagaaggcacaacaaaagaccttgctatggcttgg
gaataatccctcgatcagatgagagccactacaagagcatga<u>gcggccgcggggatcc</u>
<u>agacatgataagatacattgatgagtttggacaaaccacaactagaatgcagtgaaaaa</u>
<u>aatgctttatttgtgaaatttgtgatgctattgctttatttgtaaccattataagctgc</u>
<u>aataaacaagttaacaacaacaattgcattgattttatgtttcaggttcaggggaggt</u>
<u>gtgggaggtttttcggatcctctagaggggatt</u>aatcctgcagg*ttatgtactcttat*
*tgatttataaaacatacatgcagtgttgctatgtcacataattagcctcgccgtcta*
*cgctccactgaagataatgggctcccgctgttcaaaaaatcagcgtgcgtcgataaga*
*ctttggtgcagtctcttcggggtcgcaatttagatttgccgcatggagggtatctgggg*
*atttttgccaatgctggagcgacgactgtacgattcgtcccatcgggatctagcagacc*
*aatgatgttgacacatcggccatgcatgtacggacggtctattgcgcgagtttgtta*
*ttttcgaaggacaagatggaagtgtatatggaaccgacaataatgttagtttgcatttc*
*ttagggcggaatctacatgatatcttatccaagcggggtatgagccagagagatgtgat*
*ggtcataaagggtaaattttagatctgaaataacgcagttgcccaaacaacgatcgc*
*gattaaaagaaaatcggatggttcaattaggacatgcatggattctgtgcgcataaac*
*cataacgcagcactgttgggcacttcggtaactcaaatgcgaagcgttgcacgtctgc*
*gataactacgcctactatgcacattgttactcctgcatcttaaaaatatatcctgtagt*
*aattttcacagcaatgtcataacatcatctcgcta*

Figure 14 (Continued)

Partial plasmid pHVTUS10 cds F opt plasmid for vHVT302 (SEQ ID NO:25)

*Green and Italic = US10 cds Recombination Arms*
Black and Bold = NDV-FconsVIId-CSmut sequence

*tcccttacggcggatcgaaacgacattaggcatactcgggtaccattttgcattccgat*
*cagcacggatgaaattaggcaggaatgcggtttatattatgcggcattggacaaacgat*
*atggcattgattggcagtttatgaatgtcttcatgttgggcgtaaacggattcctattg*
*gttcagaagacaacgacgatatatttagagagaaaaagctacccagcataggataaaca*
*cacattgagcattgagagacataggtatcggtatggatgggaaaactacacacgtgaac*
*accaaacgacttatatactcgagcggtgatactactgagcaagaatgcactgcatctga*
*gccactgaatgaagactgtgatgaaaatgtgaccatcgatggaattggagaagaatatg*
*cgcagttcttcatgtccccgcaatgggtcccaaatctacatcgcttgagcgaggatacc*
*aaaaaggtataccgatgtatggtttccaacagactcaattattttccctattatgaggc*
*gttcaggcggtctttgtttgatatgtatgctaggtcggttggggcgtcgacttaagc*
*gatctgactggagactattatgcatctgtcaccaacgcaaagtcggcgtctacataga*
*actttaagatttgtggagcgtagaattatccatctaacagttatatacgcacatcggg*
*ccacgttccgccttcgagggcacttccgacagatacgaatttaaagatggatgaataat*
*taaattggaaagagtaactacattaatcgagcgtcatgacggcgtcccgtgaaaatggg*
*aattttctactcgaaacaccgtgacatttgacagacctggaattgttattctgatatat*
*agtgggtgtgtctggccggcaacatacataatgtgcatgcgaaaccacttttcagtgt*
*acgctgacattgtgcaacacggaggggtagcatctacatacaatatatgttgatta*cct
gcagggcggccgccacc**atgggcagcaagcccagcacaagaatcccagccccctgatg
ctgatcacccgcatcatgctgatcctgggctgcatcagacccacaagctccctggatgg
acgccccctggccgctgccggcatcgtggtgaccggcgacaaggccgtgaacgtgtaca
ccagcagccagaccggcagcatcatcgtgaagctgctgcccaacatgcccagagacaaa
gaggcctgcgccaaggcccccctggaagcctacaacagaaccctgaccaccctgctgac
ccccctgggcgacagcatcagaaagatccagggctccgtgagcacaagcggcggaggaa
agcagggcagactgatcggcgccgtgatcggcagcgtggccctgggagtggctacagct
gcccagattaccgctgcagccgccctgatccaggccaaccagaacgccgccaacatcct
gagactgaaagagagcattgccgccaccaacgaggccgtgcacgaagtgaccgacggcc
tgagccagctgtccgtggccgtgggcaagatgcagcagttcgtgaacgaccagttcaac
aacaccgccagagagctggactgcatcaagatcacccagcaggtgggcgtggagctgaa
cctgtacctgaccgagctgaccacagtgttcggcccccagatcacaagcccagccctga**

Figure 14 (Continued)

```
cacagctgaccatccaggccctgtacaacctggctggcggcaacatggactatctgctg
acaaagctgggaatcggcaacaaccagctgtccagcctgatcggaagcggcctgatcac
cggctaccccatcctgtacgacagccagacacagctgctgggcatccaggtgaacctgc
ccagcgtgggcaacctgaacaacatgcgcgccacctacctggaaaccctgagcgtgtcc
accaccaagggctacgccagcgccctggtgcccaaggtggtgacacaggtgggcagcgt
gatcgaggaactggacaccagctactgcatcgagagcgacctggacctgtactgcacca
gaatcgtgaccttcccaatgagccccggcatctacagctgcctgagcggcaacaccagc
gcctgcatgtacagcaagaccgaaggcgcactgacaacacccatcatggccctgaaggg
aagcgtgatcgccaactgcaagatcaccacctgcagatgcaccgacccccaggcatca
tcagccagaactacggcgaggccgtgagcctgatcgatcgccattcctgtaacgtgctg
tccctggacggcatcacactgagactgagcggcgagttcgatgccacctaccagaagaa
catcagcatcctggacagccaggtgatcgtgaccggcaacctggacatcagcaccgagc
tgggcaacgtgaataacagcatcagcaacgccctggacagactggccgagagcaacagc
aagctggaaaaagtgaacgtgcgcctgacatccacttccgctctgatcacctacatcgt
gctgaccgtgatcagcctggtgttcggcgccctgagcctggtgctggcctgctacctga
tgtacaagcagaaggcccagcagaaaccctgctgtggctgggcaacaacaccctggac
cagatgagagccaccaccagagcctgatgagcggccgccccgggcctgcaggcataggc
acgctctgatgttacagaccacaataccgcatacatttattgtaaggttgttaataaag
gtttattctatgtaagactacaatactttcgacattgcttgtatacatattaaatactt
tctcaagttcctattacataaatgggatctatcattacattcgttaagagtctggata
atttactgtttgccagcttcgatcttggaacgtactgtggatagtgccttacttggaa
tcgtgaaaatttgaaacgtccattatttggatatcttccggttgtcccatatcccgccc
tggtaccgctcggataccttgcccgtatggattcgtattgacagtcgcgcaatcgggga
ccaacaacgcgtgggtccacactcattcggaaattttccgatgattctgaatatttatt
gccgctcgttacgagtcgttggacatatctgtaatacatttcttcttgaaggatcgc
tgcacatttgatctatacattggccaggatgttcaagtctcagatgttgcattctggca
cagcacaactttatggcatttccgatgtaatcgtccggcagccctgggggagttctata
ttcgcatattgggatggtaaggacaatagcagatctcgcaacctccagggaggctataa
taacgtttttaaaggatggatttctcataaaaatctgtcgcaaattacactgagaatat
cctttactagcgccgattgagagcatcgtcgtccaattttctaaatggaaagaaaacaa
ggcgggcaagagtgttccaaacattttcattttcggcgaatctctcaaatcccatggcg
tgcaattgattgcaaaattggcacttccgttcacgtttgtatctccaaactctaagaca
cttttaattgaaaaactacgttctagtgtggaaagaaacctataggcagaccatagaac
tatttgacaccacatatcttttgtatgtcaaactgaccatgatcgtat
```

Figure 14 (Continued)

Partial plasmid pHVT US10 cds F CA02 opt sequence for vHVT303 (SEQ ID NO:26)

```
Green and Italic = US10 cds Recombination Arms
Black and Bold = NDV-F-CA02-CSmut sequence
```

*tccct tacggcggatcgaaacgacat taggcatactcggg taccat t t tgcat tccgat
cagcacggatgaaat taggcaggaatgcggt t tatat tatgcggcat tggacaaacgat
atggcat tgat tggcagt t tatgaatgtct tcatgt tgggcgtaaacggat tcctat tg
gt tcagaagacaacgacgatatat tagagagaaaaagctaccagcataggataaaca
cacat tgagcat tgagagacataggtatcggtatggatgggaaaactacacacgtgaac
accaaacgact tatatactcgagcggtgatactactgagcaagaatgcactgcatctga
gccactgaatgaagactgtgatgaaatgtgaccatcgatggaat tggagaagaatatg
cgcagt tct tcatgtcccgcaatgggtcccaaatctacatcgct tgagcgaggatacc
aaaaaggtataccgatgtatggt t tccaacagactcat tat t tcctat tatgagc
gt tcaggcggtct t tgt t tgatatgtatatgctaggtcggt tgggcgtcgact taagc
gatctgactgggagactat tatgcatctgtcaccaacgcaaagtcggcgtctacataga
act t taagat t tgtggagcgtagaat tatccatctaacagt tatatacgcacatcggg
ccacgt tccgcct tcgagggcact tccgacagatacgaat t taaagatggatgaataat
taat tggaaagagtaactacat taatcgagcgtcatgacggcgtcccgtgaaatggg
aat t tctactcgaaacaccgtgacat tgacagacctggaat tgt tat tctgatatat
agtgggtgtgtctggccggcaacatacataatgtgcatgcgaaaccact t t t tcagtgt
acgctgacat tgtgcaacacggaggggtagcatctacatacaatatatgt tgat ta*cct
gcagggcggccgccacc**atgggcagcaagcccagcacctggatcagcgtgaccctgatg
ctgatcaccagaaccatgctgatcctgagctgcatctgccccacaagcagcctggacgg
cagacccctggccgctgccggcatcgtggtgaccggcgacaaggccgtgaacatctaca
ccagcagccagaccggcagcatcatcatcaagctgctgcccaacatgcccaaggacaaa
gaggcctgcgccaaggccccctggaagcctacaacagaaccctgaccaccctgctgac
ccccctgggcgacagcatcagaagaatccagggcagcgccaccacaagcggcggaggaa
agcagggcagactggtgggcgctatcatcgggagcgtggccctgggcgtggccacagct
gcccagattaccgctgcagccgccctgattcaggccaatcagaacgccgccaacatcct
gagactgaaagagagcat tgccgccaccaacgacgccgtgcacgaagtgacaaacggac
tgtcccagctggctgtcgctgtcggcaagatgcagcagttcgtgaacaaccagttcaac
aacaccgccagagagctggactgcatcaagatcgcccagcaggtgggcgtggagctgaa
cctgtacctgaccgagctgaccacagtgttcggcccccagatcacaagccccgctctga
cccagctgacaatccaggccctgtacaacctggctggcggcaacatggactatctgctg**

Figure 14 (Continued)

actaagctgggagtgggcaacaaccagctgtccagcctgatcgggtccgggctgatcac
aggcaaccccatcctgtacgacagccagacacagctgctgggcatccagatcaacctgc
catccgtgggaagcctgaacaacatgagagccacctacctggaaaccctgagcgtgtcc
accaccaagggcttcgccagcgccctggtgcccaaggtggtgacacaggtgggcagcgt
gatcgaggaactggacaccagctactgcatcgagagcgacatcgacctgtactgcacca
gagtggtgaccttcccaatgagccccggcatctacagctgcctgagcggcaacaccagc
gcctgcatgtacagcaagaccgaaggagcactgacaacaccctacatggccctgaaggg
aagcgtgatcgccaactgcaagatgaccacctgcagatgcgccgaccccccaggcatca
tcagccagaactacggcgaggccgtgagcctgatcgacaaacattcctgtagcgtgctg
tccctggatggcatcacactgagactgagcggcgagttcgacgccacctaccagaagaa
catcagcatcctggacagccaggtgatcgtgaccggcaacctggacatcagcaccgagc
tgggcaacgtgaacaacagcatcagcagcaccctggacaagctggccgagtccaacaac
aagctgaacaaagtgaacgtgaacctgaccagcacaagcgccctgatcacctacatcgt
gctggccatcgtgtccctggccttcggcgtgatcagcctggtgctggcctgctacctga
tgtacaagcagagagcccagcagaaaaccctgctgtggctgggcaataacaccctggac
cagatgagggccaccaccagaacctgatga*gcggccgccccgggcctgcagcataggc*
*acgctctgatgttacagaccacaataccgcatacatttattgtaaggttgttaataaag*
*gttattctatgtaagactacaatactttcgacattgcttgtatacatattaaatactt*
*tctcaagttcctattacataaaatgggatctatcattacattcgttaagagtctggata*
*attttactgtttgccagcttcgatcttgaacgtactgtggatagtgccttacttggaa*
*tcgtgaaatttgaaacgtccattatttggatatcttccggttgtcccatatcccgccc*
*tggtaccgctcggataccttgcccgtatggattcgtattgacagtcgcgcaatcgggga*
*ccaacaacgcgtgggtccacactcattcggaaattttccgatgattctgaatatttatt*
*gccgctcgttacgagtcgttggacatatctgtaatacattcttcttctgaaggatcgc*
*tgcacatttgatctatacattggccaggatgttcaagtctcagatgttgcattctgca*
*cagcacaactttatggcatttccgatgtaatcgtccggcagccctggggagttctata*
*ttcgcatattgggatggtaaggacaatagcagatctcgcaacctccagggaggctataa*
*taacgtttttaaaggatggatttctcataaaatctgtcgcaaattacactgagaatat*
*cctttactagcgccgattgagagcatcgtcgtccaattttctaaatggaaagaaaacaa*
*ggcgggcaagagtgttccaaacatttcattttcggcgaatctctcaaatcccatggcg*
*tgcaattgattgcaaaattggcacttcgttcacgtttgtatctccaaactctaagaca*
*cttttaattgaaaactacgttctagtgtggaaagaaacctataggcagaccatagaac*
*tatttgacaccacatatcttttgtatgtcaaactgaccatgatcgtat*

Figure 14 (Continued)

Partial plasmid HVT IG2 SVFopt syn tail sequence for vHVT304 (SEQ ID NO:27)

```
         NDV-F VIId-CSmut
SV40 Promoter              Syn Poly a tail
  gp070                        gp066
```

HVT IG2 SVFopt syn tail.

*Green and italic = gp070 and gp066 Recombination Arms*
BLUE AND UPPERCASE = SV40 PROMOTER
Black and Bold = NDV-FconsVIId-CSmut sequence
Red and Underlined = Synthetic Poly A tail

*Tgtttcgcaccatatccaagctggctgtccctaagagcttattcctgcaagacctcata*
*cggaataattgcccgaccaatacttattacggacataggtaggccgataaatattatgt*
*tgactggaggatggaaggaggttttgtaacagctacatcgctcgttcatcagcaagcg*
*atactttggatatccgagcttcaaaagccgcataaacccgctttatttctgaatacgc*
*cccaacagtaacacatgcgtggttcctggcacttggaacgccgtgttttataggcaaga*
*acatactacccaagaggtcttgggatttctggcgcgtcgttgcaatgaagaaatgaat*
*tctttgttccttgaaatgccgacaactctaaaaacggtattcgagcaccattactttac*
*gcgtggatctgaagtaaatccagcgttgttgatggagcctaacagattttgcaactga*
*tggattcgcggaaaatcctatgtttatacgaatccgctatgtcgacaaccccggagct*
*cagggtatgatactcagctgttattgtggccgaccaggaggactccaatgcttagcatt*
*cataagaacgctagagatgctatttaacgatgtgctgtcgtctaaagaatttgtcatt*
*tagcctttaaatgtaaaaccaatgacgcattcactacgctcgtgcgtgcaatttctggg*
*ccagggtatgcatattccataacagaaatcgacacttgagaagaggatctgactgttg*
*ggataaaggtcgtttgggtctgtcctagcgatataatttatgacgatatacattaaa*
*catctgtgtgcagtacttaggtatttaatcatgtcgatgaaatgttatgtgtaaatatc*
*ggacaatatagataacgggcacgctgctattgtaacgtgcgcccgcgcgctagtgctga*
*ctaatagtgtggatgatgtatacagtatattacaaacggaaatgatacgtaataaa*cct
gcaggtcgaccCAATTCGAGCTCGGTACAGCTTGGCTGTGGAATGTGTGTCAGTTAGGG
TGTGGAAAGTCCCCAGGCTCCCCAGCAGGCAGAAGTATGCAAAGCATGCATCTCAATTA
GTCAGCAACCAGGTGTGGAAAGTCCCCAGGCTCCCCAGCAGGCAGAAGTATGCAAAGCA
TGCATCTCAATTAGTCAGCAACCATAGTCCCGCCCCTAACTCCGCCCATCCCGCCCCTA
ACTCCGCCCAGTTCCGCCCATTCTCCGCCCCATGGCTGACTAATTTTTTTTATTTATGC
AGAGGCCGAGGCCGCCTCGGCCTCTGAGCTATTCCAGAAGTAGTGAGGAGGCTTTTTTG
GAGGCCTAGGCTTTTGCAAAAAGCTcccggggcggccgccaccatgggcagcaagccca
gcacaagaatcccagccccctgatgctgatcacccgcatcatgctgatcctgggctgc
atcagacccacaagctccctggatggacgccccctggccgctgccggcatcgtggtgac

Figure 14   (Continued)

cggcgacaaggccgtgaacgtgtacaccagcagccagaccggcagcatcatcgtgaagc
tgctgcccaacatgcccagagacaaagaggcctgcgccaaggcccccctggaagcctac
aacagaaccctgaccaccctgctgacccccctgggcgacagcatcagaaagatccaggg
ctccgtgagcacaagcggcggaggaaagcagggcagactgatcggcgccgtgatcggca
gcgtggccctgggagtggctacagctgcccagattaccgctgcagccgccctgatccag
gccaaccagaacgccgccaacatcctgagactgaaagagagcattgccgccaccaacga
ggccgtgcacgaagtgaccgacggcctgagccagctgtccgtggccgtgggcaagatgc
agcagttcgtgaacgaccagttcaacaacaccgccagagagctggactgcatcaagatc
acccagcaggtgggcgtggagctgaacctgtacctgaccgagctgaccacagtgttcgg
cccccagatcacaagcccagccctgacacagctgaccatccaggccctgtacaacctgg
ctggcggcaacatggactatctgctgacaaagctgggaatcggcaacaaccagctgtcc
agcctgatcggaagcggcctgatcaccggctaccccatcctgtacgacagccagacaca
gctgctgggcatccaggtgaacctgcccagcgtgggcaacctgaacaacatgcgcgcca
cctacctggaaaccctgagcgtgtccaccaccaagggctacgccagcgccctggtgccc
aaggtggtgacacaggtgggcagcgtgatcgaggaactggacaccagctactgcatcga
gagcgacctggacctgtactgcaccagaatcgtgaccttcccaatgagccccggcatct
acagctgcctgagcggcaacaccagcgcctgcatgtacagcaagaccgaaggcgcactg
acaacaccctacatggccctgaagggaagcgtgatcgccaactgcaagatcaccacctg
cagatgcaccgaccccccaggcatcatcagccagaactacggcgaggccgtgagcctga
tcgatcgccattcctgtaacgtgctgtccctggacggcatcacactgagactgagcggc
gagttcgatgccacctaccagaagaacatcagcatcctggacagccaggtgatcgtgac
cggcaacctggacatcagcaccgagctgggcaacgtgaataacagcatcagcaacgccc
tggacagactggccgagagcaacagcaagctggaaaaagtgaacgtgcgcctgacatcc
acttccgctctgatcacctacatcgtgctgaccgtgatcagcctggtgttcggcgccct
gagcctggtgctggcctgctacctgatgtacaagcagaaggcccagcagaaaccctgc
tgtggctgggcaacaacaccctggaccagatgagagccaccaccagagcctgatga<u>cg
gccgcgatatcaataaatatctttattttcattacatctgtgtgttggttttttgtgt
gaatcgatagtactaacatacgctctccatcaaaacaaaacgaaacaaaacaaactagc
aaaataggctgtccccagtgcaagtgcaggtgccagaacatttctctt</u>ctagacctgca
gg*ttatgtactcttattgatttataaaacatacatgcagtgttgctatgtcacataat
tagcctcgcccgtctacgctccactgaagataatgggctccgctgttcaaaaaaatca
gcgtgcgtcgataagactttggtgcagtctcttcggggtcgcaatttagatttgccgca
tggagggtatctggggattttgccaatgctggagcgacgactgtacgattcgtccat
cgggatctagcagaccaatgatgttgacacatcggccatgcatgtacggacggtcta
ttgcgcgagtttgttattttcgaaggacaagatggaagtgtatatggaaccgacaataa
tgttagtttgcatttcttaggcggaatctacatgatatcttatccaagcggggtatga
gccagagagatgtgatggtcataaagggtaaattttagatctgaaataacgcagttg
cccaaacaacgatcgcgattaaagaaaaatcggatggttcaattaggacatgcatgga
ttctgtgcgcataaaccataaccgcagcactgttgggcacttcggtaactcaaatgcga
agcgttgcacgtctgcgataactacgcctactatgcacattgttactcctgcatcttaa
aaatatatcctgtagtaattttcacagcaatgtcataacatcatctcgctaa*

Partial plasmid pHVT US2 SV-FCA02 opt-synPA for vHVT307 (SEQ ID NO:28)

pHVT US2 SV-FCAO2opt-synPA

*Green and Italic = US2 and SORF3 Recombination Arms*
BLUE AND UPPERCASE = SV40 PROMOTER
Black and Bold = NDV-F-CAO2-CSmut sequence
Red and underlined = Synthetic Poly A tail

*tatctccacatcgtattcaggcccacggaagtcttcgttatcgaagctattgttactag*
*tatctggcgacatcgacggttctgcaaccgtcgtaccgctttcgatattttcacagaca*
*atacccatattcgaggcacttactttcgaagactcaacatctacttccatcgccgccac*
*gtatgtaatttcgggacgttggatgatataaatatatagtacgcgtccgggtatacac*
*ctgtgcgaaagtagtacgagaccggcagtcaaaaagacgtttccgatcttccacagctc*
*cagttattcggaaggcgtgggcatgggtgtgtgcatgataactctcgtcactttactag*
*acgaatgcgatcgattgcctgggcgatctcgtgacgctgcctccaccctatggatcttt*
*ctcatagaacaatgcatggagcatctgaagaatgatgtgggtgtgcccatattagtccg*
*tacagcagacctgtgtcggtttgccaaatccacattcgttttgccccgccggcatcgcc*
*caattgtgagaattaaatcggcaggcgggagtggtatgcccggttccggattggcagga*
*acgagagatgcatttattgtgagactgtttgaagatgtagccggttgcgctaccgaatg*
*gcaggatctactgaccggctatgtaatgctagaatcggaggcctccgataacgtatcgt*
*atagcctgtggatactcggggctgcagatatctgcagaactgcaatagaatcaatacct*
*ctaccaaaacgtttgtttgccattaaagtaccaggcacctgggctggaatgccttgggc*
*cattccatgtgagatacaaacacttctcacgtccacttgggaacctaaatttgaaaaca*
*tagaagataaggcgtacttcaacgacagtaatatggcgtgcgtatatcaaattatcggc*
*tctccaccagacgttccccagctgcaggggcttggtatcgagtccacatgcaccccacc*
*taaacgcaatttgtgttgctgcctatgttgccgtccaatacatgacgacgacgcctccg*
*ttcccatgggcgttaagacagtagataaaaacgtacatgatggcaatatgcttgtagag*
*gctcccaagtgtatcacagataggggaaaattcaatagtagataaacccaactagtgtg*
*aggaaattgcatctacttgc*ccccgggcctgcaggtcgaccCAATTCGAGCTCGGTACA
GCTTGGCTGTGGAATGTGTGTCAGTTAGGGTGTGGAAAGTCCCCAGGCTCCCCAGCAGG
CAGAAGTATGCAAAGCATGCATCTCAATTAGTCAGCAACCAGGTGTGGAAAGTCCCCAG
GCTCCCCAGCAGGCAGAAGTATGCAAAGCATGCATCTCAATTAGTCAGCAACCATAGTC
CCGCCCCTAACTCCGCCCATCCCGCCCCTAACTCCGCCCAGTTCCGCCCATTCTCCGCC
CCATGGCTGACTAATTTTTTTTATTTATGCAGAGGCCGAGGCCGCCTCGGCCTCTGAGC
TATTCCAGAAGTAGTGAGGAGGCTTTTTTGGAGGCCTAGGCTTTTGCAAAAAGCTcccg
gggcggccgccaccatgggcagcaagcccagcacctggatcagcgtgaccctgatgctg

Figure 14 (Continued)

atcaccagaaccatgctgatcctgagctgcatctgccccacaagcagcctggacggcag
acccctggccgctgccggcatcgtggtgaccggcgacaaggccgtgaacatctacacca
gcagccagaccggcagcatcatcatcaagctgctgcccaacatgcccaaggacaaagag
gcctgcgccaaggccccctggaagcctacaacagaaccctgaccaccctgctgacccc
cctgggcgacagcatcagaagaatccagggcagcgccaccacaagcggcggaggaaagc
agggcagactggtgggcgctatcatcgggagcgtggccctgggcgtggccacagctgcc
cagattaccgctgcagccgccctgattcaggccaatcagaacgccgccaacatcctgag
actgaaagagagcattgccgccaccaacgacgccgtgcacgaagtgacaaacggactgt
cccagctggctgtcgctgtcggcaagatgcagcagttcgtgaacaaccagttcaacaac
accgccagagagctggactgcatcaagatcgcccagcaggtgggcgtggagctgaacct
gtacctgaccgagctgaccacagtgttcggccccagatcacaagcccgctctgaccc
agctgacaatccaggccctgtacaacctggctggcggcaacatggactatctgctgact
aagctggagtgggcaacaaccagctgtccagcctgatcgggtccggctgatcacagg
caaccccatcctgtacgacagccagacacagctgctgggcatccagatcaacctgccat
ccgtgggaagcctgaacaacatgagagccacctacctggaaaccctgagcgtgtccacc
accaagggcttcgccagcgccctggtgcccaaggtggtgacacaggtgggcagcgtgat
cgaggaactggacaccagctactgcatcgagagcgacatcgacctgtactgcaccagag
tggtgaccttcccaatgagccccggcatctacagctgcctgagcggcaacaccagcgcc
tgcatgtacagcaagaccgaaggagcactgacaacaccctacatggccctgaagggaag
cgtgatcgccaactgcaagatgaccacctgcagatgcgccgacccccaggcatcatca
gccagaactacggcgaggccgtgagcctgatcgacaaacattcctgtagcgtgctgtcc
ctggatggcatcacactgagactgagcggcgagttcgacgccacctaccagaagaacat
cagcatcctggacagccaggtgatcgtgaccggcaacctggacatcagcaccgagctgg
gcaacgtgaacaacagcatcagcagcaccctggacaagctggccgagtccaacaacaag
ctgaacaaagtgaacgtgaacctgaccagcacaagcgccctgatcacctacatcgtgct
ggccatcgtgtccctggccttcggcgtgatcagcctggtgctggcctgctacctgatgt
acaagcagagagcccagcagaaaaccctgctgtggctgggcaataaccctggaccag
atgagggccaccaccagaacctgatgagcggccgcgatatcaataaaatatctttattt
tcattacatctgtgtgttggtttttgtgtgaatcgatagtactaacatacgctctcca
tcaaaacaaaacgaaacaaaacaaactagcaaaataggctgtccccagtgcaagtgcag
gtgccagaacatttctcttctagacctgcaggcatatgttgtccattatgttgtacat
aatcgtgatgtagtgctacgcaaatgtcaattgatagcccatacatggtgctaatatgc
gttacttagtatgtgagtgaataaaaaatattaccctatgatacctgcgtcttta
tgctacaagttccttcaccatgaccagagccggtgcgatcatattcgacaacttggata
ttcccagaggtagatttggccagccgcggggaaaataaatgacttcaactactggacc
ttgctaaccgatgagctgacgtgtggaattattcaatgtatggagtcgcgcgagcgaat
tgccctagtgcattcagcaacatacgatcatggtcagtttgacatacaaaagatatgt
ggtgtcaaatagttctatggtctgcctataggtttctttccacactagaacgtagtttt
tcaattaaaagtgtcttagagtttggagatacaaacgtgaacggaagtgccaattttgc
aatcaattgcacgccatgggatttgagagattcgccgaaaatgaaatgtttggaacac
tcttgcccgccttgtttctttccatttagaaaattggacgacgatgctctcaatcggc
gctagtaaaggatattctcagtgtaatttgcgacagattttatgagaaatccatcctt
taaaaacgttattatagcctcctggaggttgcgagatctgctattgtccttaccatcc
caatatgcgaatatagaactccccagggctgccggacgattacatcggaaatgccata
aagttgtgctgtgccagaatgcaacatctgagacttgaacatcctggccaatgtataga Figure 14 (Continued)

```
tcaaatgtgcagcgatccttcagaagaagaaatgtattacagatatgtccaacgactcg
taacgagcggcaataaatattcagaatcatcggaaaatttccgaatgagtgtggaccca
cgcgttgttggtccccgattgcgcgactgtcaatacgaatccatacgggcaaggtatcc
gagcggtaccagggcgggatatgggacaaccggaagatatccaaataatggacgtttca
aattttcacgattccaagtaaggcactatccacagtacgttccaagatcgaagctggca
aacagtaaaattatccagactcttaacgaatgtaatgatagatcccatttta
```

Figure 14 (Continued)

Partial plasmid pCD046+NDV-F VII YZCQ for vHVT112 (SEQ ID NO:29)

*Green and Italic* = Flanking Arms
BLUE AND UPPERCASE = mCMV IE
Black and Bold = NDV-F VIId wt YZCQ
Red and underlined = SV40 Poly A

*gagctcagggtatgatactcagctgttattgtggccgaccaggaggactccaatgctta
gcattcataagaacgctagagatgctatttaacgatgtgctgtcgtctaaagaatttgt
gcatttagcctttaaatgtaaaaccaatgacgcattcactacgctcgtgcgtgcaattt
ctgggccagggtatgcatattccataacagaaatcgacacttgagaagaggatctgact
gtttgggataaaggtcgtttgggtctgtcctagcgatataatttatatgacgatataca
ttaaacatctgtgtgcagtacttaggtatttaatcatgtcgatgaaatgttatgtgtaa
atatcggacaatatagataacgggcacgctgctattgtaacgtgcgcccgcgcgctagt
gctgactaatagtgtggatgatgtatacagtatattacaaacggaaatgatacgtaata
aattatgtactcttattgatttataaaaacatacatgcagtgttgctatgtcataat
tagcctcgcccgtctacgctccactgaagataatgggctcccgctgttcaaaaaaatca
gcgtgcgtcgataagactttggtgcagtctcttcggggtcgcaatttagatttgccgca
tggagggtatctggggattttgccaatgctggagcgacgactgtacgattcgtcccat
cgggatctagcagaccaatgatgttgacacacatcggccatgcatgtacggacggtcta
ttgcgcgagtttgttatttcgaaggacaagatggaagtgtatatggaaccgacaataa
tgttagtttgcatttcttagggcggaatctacatgatatcttatccaagcggggtatga
gccagagagatgtgatggtcataagggtaaattttttagatctgaaataacgcagttg
cccaaacaacgatcgcgattaaaagaaaaatcggatggttcaattaggacatgcatgga
ttctgtgcgcataaaccataaccgcagcactgttgggcacttcggtaactcaaatgcga
agcgttgcacgtctgcgataactacgcctactatgcacattgttactcctgcatcttaa
aaatatatcctgtagtaattttcacagcaatgtcataacatcatctcgctaaagaatga
cctgggattggagaagtaatgaatatttgcaaccaatgcattgaataaactaacattaa
ac*GAATTCAATAGTGGATCCCCCAACTCCGCCCGTTTTATGACTAGAACCAATAGTTTT
TAATGCCAAATGCACTGAAATCCCCTAATTTGCAAAGCCAAACGCCCCCTATGTGAGTA
ATACGGGGACTTTTTACCCAATTTCCCACGCGGAAAGCCCCCTAATACACTCATATGGC
ATATGAATCAGCACGGTCATGCACTCTAATGGCGGCCCATAGGGACTTTCCACATAGGG
GGCGTTCACCATTTCCCAGCATAGGGGTGGTGACTCAATGGCCTTTACCCAAGTACATT
GGGTCAATGGGAGGTAAGCCAATGGGTTTTTCCCATTACTGGCAAGCACACTGAGTCAA
ATGGGACTTTCCACTGGGTTTTGCCCAAGTACATTGGGTCAATGGGAGGTGAGCCAATG
GGAAAAACCCATTGCTGCCAAGTACACTGACTCAATAGGGACTTTCCAATGGGTTTTTC
CATTGTTGGCAAGCATATAAGGTCAATGTGGGTGAGTCAATAGGGACTTTCCATTGTAT
TCTGCCCAGTACATAAGGTCAATAGGGGGTGAATCAACAGGAAAGTCCCATTGGAGCCA
AGTACACTGCGTCAATAGGGACTTTCCATTGGGTTTTGCCCAGTACATAAGGTCAATAG
GGGATGAGTCAATGGGAAAAACCCATTGGAGCCAAGTACACTGACTCAATAGGGACTTT
CCATTGGGTTTTGCCCAGTACATAAGGTCAATAGGGGGTGAGTCAACAGGAAAGTTCCA
TTGGAGCCAAGTACATTGAGTCAATAGGGACTTTCCAATGGGTTTTGCCCAGTACATAA
GGTCAATGGGAGGTAAGCCAATGGGTTTTTCCCATTACTGGCACGTATACTGAGTCATT Figure 14 (Continued)

```
AGGGACTTTCCAATGGGTTTTGCCCAGTACATAAGGTCAATAGGGGTGAATCAACAGGA
AAGTCCCATTGGAGCCAAGTACACTGAGTCAATAGGGACTTTCCATTGGGTTTTGCCCA
GTACAAAAGGTCAATAGGGGGTGAGTCAATGGGTTTTTCCCATTATTGGCACGTACATA
AGGTCAATAGGGGTGAGTCATTGGGTTTTTCCAGCCAATTTAATTAAAACGCCATGTAC
TTTCCCACCATTGACGTCAATGGGCTATTGAAACTAATGCAACGTGACCTTTAAACGGT
ACTTTCCCATAGCTGATTAATGGGAAAGTACCGTTCTCGAGCCAATACACGTCAATGGG
AAGTGAAAGGGCAGCCAAAACGTAACACCGCCCCGGTTTTCCCCTGGAAATTCCATATT
GGCACGCATTCTATTGGCTGAGCTGCGTTCTACGTGGGTATAAGAGGCGCGACCAGCGT
CGGTACCGTCGCAGTCTTCGGTCTGACCACCGTAGAACGCAGAGCTCCTCGCTGCAG
```
*gc ggccgc*atgggctctaaaccttctaccaggatcccagcacctctgatgctgatcacccg gattatgctgatattggactgtatccgtccgacaagctctcttgacggcaggcctcttg cagctgcaggaattgtagtaacaggagataaggcagtcaatgtatatacctcgtctcag acagggtcaatcatagtcaagttgctcccgaatatgcccaaggataaggaggcgtgtgc gaaagacccattagaggcatataacagaacactgactactttgctcactcctcttggcg aatccatccgcaagatccaagggtctgtgtccacgtctggaggaggcaagcaaggccgc ctgataggtgctgttattggtagtgtagctcttggggttgcaacagcggcacaaataac agcagctgcggccctaatacaagccaaccagaatgctgccaacatccttcggcttaagg agagcattgctgcaaccaatgaagctgtgcatgaagtcaccgacggattatcacaacta tcagtggcagttgggaagatgcagcagtttgtcaatgaccagtttaataatacagcgcg agaattggactgtataaaaatcacacaacaggttggtgtagaactcaacctatacctaa ctgaattgactacagtattcgggccacagatcacctcccctgcattaactcagctgacc atccaggcactttataatttagctggtggcaatatggattacttattaactaagttagg tatagggaacaatcaactcagctcattaattggcagcggcctgatcactggttacccta tattgtatgactcacagactcaactcttgggcatacaagtgaatttgccctcagtcggg aacttaaataatatgcgtgccacctatttagagaccttatctgtaagtacagccaaagg atatgcctcagcacttgttccaaaagtagtgacacaagtcggttctgtgatagaagagc ttgacacctcatactgtatagagtccgatctggatttatattgtactagaatagtgaca ttccccatgtccccaggtatttattcctgtttaagcggcaacacatcagcttgcatgta ttcaaagactgaaggcgcactcactacgccgtatatggcccttaaaggctcagttattg ccaattgtaagataacaacatgtagatgtacagaccctcctggtatcatatcgcaaaat tatggagaagctgtatccctgatagatagacattcgtgcaatgtcttatcattagacgg gataactctgaggctcagtggagaatttgatgcaacttatcaaaagaacatctcaatac tagattctcaagtcatcgtgacaggcaatcttgatatatcaactgaacttggaaacgtc aacaattcaatcagcaatgccttggataagttggcaaaaagcaacagcaagctagaaaa agtcaatgtcagactaaccagcacatccgctctcattacctatattgttctgactgtca tttctctagttttcggtgcactaagtctgggtttaacatgttacctgatgtacaaacaa aaggcacaacaaaagaccttgctatggcttgggaataatacctcgatcagatgagagc cactacaagagcatga*gcggccgc*gggatccagacatgataagatacattgatgagtt tggacaaaccacaactagaatgcagtgaaaaaatgctttatttgtgaaatttgtgatg ctattgctttatttgtaaccattataagctgcaataaacaagttaacaacaacaattgc attgatttatgtttcaggttcaggggaggtgtgggaggttttttcggatcctctaga gtcgacaattatttattaataacatatagcccaaagacctctatgaacatttagttt cccgtatactcaacggcgcgtgtacacacgcatctctttgcatagcgatgaagtttgtt cggcagcagaaatgcagatatccaacaatctggagaaaacttatcatcacagtggcag Figure 14 (Continued)

```
tggaaacatacccctctatattcatggtataattatcgtctacagcgtccaggatagt
ggcgtgagaaaatggagatctgcagccctcctttccatggcatgccgctttattgttca
ttaaacgcacaatggtctcaacgccagatatgggcatagattctgaagaacccgttgac
aatccgaagaagaaggcgtgcaggtctttggaagactcgcacgttggtcttataatgta
tgatcgagatgtcaccctaatgccacatggtacaggcttatcgcggtcatggcgatcgg
acttgtaatttgcaacgatgggcaaggatcgacgacatgccaaacattctgaacccgt
agagatgttaacgatgacgaggatgaatatcccatgctcgctgccatagtatcaagtac
accgcgaataaggacgcgtccaacatcgttatgcacacaatgggctacacgtgacta
acaccccgaatattagtcatatgtgagtttcagtctggctcccatatagcctgtagac
tatttgtggtttaagtgtgaacgaggcgctgtgaacgagactcgggccgattgtaagaa
caagcaaatgcactttccatttaacaagaagtgtagagagaatactcaacctctttgga
tgtatcctcgag
```

Figure 14 (Continued)

Partial plasmid pCD046 + NDV Texas F for vHVT113 (SEQ ID NO:30)

*Green and Italic = Flanking Arms*
BLUE AND UPPERCASE = mCMV IE
Black and Bold = NDV Texas F
Red and underlined = SV40 Poly A

*gagctcagggtatgatactcagctgttattgtggccgaccaggaggactccaatgctta
gcattcataagaacgctagagatgctatttaacgatgtgctgtcgtctaaagaatttgt
gcatttagcctttaaatgtaaaaccaatgacgcattcactacgctcgtgcgtgcaattt
ctgggccagggtatgcatattccataacagaaatcgacacttgagaagaggatctgact
gtttgggataaaggtcgtttgggtctgtcctagcgatataattatatgacgatataca
ttaaacatctgtgtgcagtacttaggtatttaatcatgtcgatgaaatgttatgtgtaa
atatcggacaatatagataacgggcacgctgctattgtaacgtgcgcccgcgcgctagt
gctgactaatagtgtggatgatgtatacagtatattacaaacggaaatgatacgtaata
aattatgtactcttattgatttataaaaacatacatgcagtgttgctatgtcacataat
tagcctcgcccgtctacgctccactgaagataatgggctcccgctgttcaaaaaaatca
gcgtgcgtcgataagactttggtgcagtctcttcggggtcgcaatttagatttgccgca
tggagggtatctggggattttgccaatgctggagcgacgactgtacgattcgtcccat
cgggatctagcagaccaatgatgttgacacacatcggccatgcatgtacggacggtcta
ttgcgcgagtttgttatttcgaaggacaagatggaagtgtatatggaaccgacaataa
tgttagtttgcatttcttagggcggaatctacatgatatcttatccaagcggggtatga
gccagagagatgtgatggtcataaagggtaaattttttagatctgaaataacgcagttg
cccaaacaacgatcgcgattaaaagaaaatcggatggttcaattaggacatgcatgga
ttctgtgcgcataaaccataaccgcagcactgttgggcacttcggtaactcaaatgcga
agcgttgcacgtctgcgataactacgcctactatgcacattgttactcctgcatcttaa
aaatatcctgtagtaattttcacagcaatgtcataacatcatctcgctaaagaatga
cctgggattggagaagtaatgaatatttgcaaccaatgcattgaataaactaacattaa
ac*GAATTCAATAGTGGATCCCCCAACTCCGCCCGTTTTATGACTAGAACCAATAGTTTT
TAATGCCAAATGCACTGAAATCCCCTAATTTGCAAAGCCAAACGCCCCCTATGTGAGTA
ATACGGGGACTTTTTACCCAATTTCCCACGCGGAAAGCCCCCTAATACACTCATATGGC
ATATGAATCAGCACGGTCATGCACTCTAATGGCGGCCCATAGGGACTTTCCACATAGGG
GGCGTTCACCATTTCCCAGCATAGGGGTGGTGACTCAATGGCCTTTACCCAAGTACATT
GGGTCAATGGGAGGTAAGCCAATGGGTTTTTCCCATTACTGGCAAGCACACTGAGTCAA
ATGGGACTTTCCACTGGGTTTTGCCCAAGTACATTGGGTCAATGGGAGGTGAGCCAATG
GGAAAAACCCATTGCTGCCAAGTACACTGACTCAATAGGGACTTTCCAATGGGTTTTTC
CATTGTTGGCAAGCATATAAGGTCAATGTGGGTGAGTCAATAGGGACTTTCCATTGTAT
TCTGCCCAGTACATAAGGTCAATAGGGGGTGAATCAACAGGAAAGTCCCATTGGAGCCA
AGTACACTGCGTCAATAGGGACTTTCCATTGGGTTTTGCCCAGTACATAAGGTCAATAG
GGGATGAGTCAATGGGAAAAACCCATTGGAGCCAAGTACACTGACTCAATAGGGACTTT
CCATTGGGTTTTGCCCAGTACATAAGGTCAATAGGGGTGAGTCAACAGGAAAGTTCCA
TTGGAGCCAAGTACATTGAGTCAATAGGGACTTTCCAATGGGTTTTGCCCAGTACATAA Figure 14 (Continued)

```
GGTCAATGGGAGGTAAGCCAATGGGTTTTTCCCATTACTGGCACGTATACTGAGTCATT
AGGGACTTTCCAATGGGTTTTGCCCAGTACATAAGGTCAATAGGGGTGAATCAACAGGA
AAGTCCCATTGGAGCCAAGTACACTGAGTCAATAGGGACTTTCCATTGGGTTTTGCCCA
GTACAAAAGGTCAATAGGGGGTGAGTCAATGGGTTTTTCCCATTATTGGCACGTACATA
AGGTCAATAGGGGTGAGTCATTGGGTTTTTCCAGCCAATTTAATTAAAACGCCATGTAC
TTTCCCACCATTGACGTCAATGGGCTATTGAAACTAATGCAACGTGACCTTTAAACGGT
ACTTTCCATAGCTGATTAATGGGAAGTACCGTTCTCGAGCCAATACACGTCAATGGG
AAGTGAAAGGGCAGCCAAAACGTAACACCGCCCCGGTTTTCCCCTGGAAATTCCATATT
GGCACGCATTCTATTGGCTGAGCTGCGTTCTACGTGGGTATAAGAGGCGCGACCAGCGT
CGGTACCGTCGCAGTCTTCGGTCTGACCACCGTAGAACGCAGAGCTCCTCGCTGCAGgc
ggccgcatgggctccagatcttctaccaggatcccggtacctctaatgctgatcatccg
aaccgcgctgacactgagctgtatccgtctgacaagctctcttgatggcaggcctcttg
cggctgcagggatcgtggtaacaggagataaagcagtcaacatatacacctcatcccag
acagggtcaatcatagttaagttactcccgaatatgcccaaggacaaagaggtgtgtgc
aaaagccccattggaggcatacaacaggacactgactactttactcacccccttggtg
attctatccgcaggatacaagagtctgtgactacttccggaggaggcaagcaaggccgc
ctgataggtgccattatcggcagtgtagctcttggggttgcgacagctgcacagataac
agcagcttcggccctgatacaagccaaccagaatgctgccaacatcctccggcttaaag
agagcattgctgcaaccaatgaagctgtgcacgaggtcactgacggattatcaaacta
gcagtggcagtagggaagatgcaacagtttgtcaatgaccagttcaataatacagcgca
agaattggactgtataaaaattgcacagcaggtcggtgtagaactcaacttgtacctaa
ctgaattgactacagtatttgggccacaaatcacttcccctgccttaactcagctgact
atccaagcgctttacaatctagctggtggtaatatggattacttgctgactaagttagg
tgtagggaacaaccaactcagctcattaattggtagcggcttgatcaccggcaaccta
ttctgtacgactcacagactcagatcttgggtatacaggtaactttgccttcagttggg
aacctgaataatatgcgtgccacctacctggagaccttatctgtaagcacaaccaaggg
atttgcctcagcacttgtcccaaaagtggtgacacaggtcggttccgtgatagaagaac
ttgacacctcatactgtatagggaccgacttggatttatactgtacaagaatagtgaca
ttccctatgtctcctggtatttattcttgtctgagcggtaatacatcggcttgcatgta
ttcaaagactgaaggcgcacttactacgccatatatggctctcaaaggctcagttattg
ccaattgcaagctgacaacatgtagatgtgcagatcccccaggtatcatatcgcaaaat
tatggagaagctgtgtccttaatagataggcactcatgcaacgtcttatccttagacgg
gataactctgaggctcagtggggaatttgatgcaacctatcaaaagaatatctctatac
tagattctcaagttatagtgacaggcaatcttgatatatcaactgagcttgggaatgtc
aacaactcaataagtaatgccctgaataagttagaggaaagcaacagcaaactagacaa
agtcaatgtcaaactgaccagcacatctgctctcattacctacatcgttttaactgtca
tatctcttgttttggtgtacttagcctggttctagcatgctacctgatgtacaagcaa
aaggcacaacaaagaccttgttatggcttgggaataatacccttgatcagatgagagc
cactacaaaaatgagcggccgcgggatccagacatgataagatacattgatgagtt
tggacaaaccacaactagaatgcagtgaaaaaatgctttatttgtgaaatttgtgatg
ctattgctttatttgtaaccattataagctgcaataaacaagttaacaacaacaattgc
attgattttatgtttcaggttcaggggaggtgtgggaggttttttcggatcctctaga
gtcgacaattattttatttaataacatatagcccaaagacctctatgaacatttagttt
cccgtatactcaacggcgcgtgtacacacgcatctctttgcatagcgatgaagtttgtt
```

Figure 14 (Continued)

*cggcagcagaaaatgcagatatccaacaatctggagaaaacttatcatcacagtggcag*
*tggaaacatacccctctatattcatggtataattatcgtctacagcgtccaggatagt*
*ggcgtgagaaaatggagatctgcagccctcctttccatggcatgccgctttattgttca*
*ttaaacgcacaatggtctcaacgccagatatgggcatagattctgaagaacccgttgac*
*aatccgaagaagaaggcgtgcaggtctttggaagactcgcacgttggtcttataatgta*
*tgatcgagatgtcaccctaatgccacatggtacaggcttatcgcggtcatggcgatcgg*
*acttgtaatttgcaacgatgggcaaaggatcgacgacatgccaaacattctgaacccgt*
*agagatgttaacgatgacgaggatgaatatccatgctcgctgccatagtatcaagtac*
*accgcgaataaggacgcgtccaacatcgttatatgcacacaatgggctacacgtgacta*
*acaccccgaatattagtcatatgtgagtttcagtctggctcccatatagcctgtagac*
*tatttgtggtttaagtgtgaacgaggcgctgtgaacgagactcgggccgattgtaagaa*
*caagcaaatgcactttccatttaacaagaagtgtagagagaatactcaacctctttgga*
*tgtatcctcgag*

Figure 14 (Continued)

Partial plasmid pHM119 sequence for vHVT039 (SEQ ID NO:31)

*Green and Italic = BamHI fragment I intergenic Recombination Arms*
BLUE AND UPPERCASE = MDV gB PROMOTER
Black and Bold = NDV-F wild type unmodified Texas strain sequence
*Red and Italic and Underlined = SV40 Poly A tail*

*gagctcagggtatgatactcagctgttattgtggccgaccaggaggactccaatgctta*
*gcattcataagaacgctagagatgctatttaacgatgtgctgtcgtctaaagaatttgt*
*gcatttagcctttaaatgtaaaaccaatgacgcattcactacgctcgtgcgtgcaattt*
*ctgggccagggtatgcatattccataacagaaatcgacacttgagaagaggatctgact*
*gtttgggataaaggtcgtttgggtctgtcctagcgatataatttatatgacgatataca*
*ttaaacatctgtgtgcagtacttaggtatttaatcatgtcgatgaaatgttatgtgtaa*
*atatcggacaatatagataacgggcacgctgctattgtaacgtgcgcccgcgcgctagt*
*gctgactaatagtgtggatgatgtatacagtatattacaaacggaaatgatacgtaata*
*aattatgtactcttattgatttataaaaacatacatgcagtgttgctatgtcacataat*
*tagcctcgcccgtctacgctccactgaagataatgggctcccgctgttcaaaaaaatca*
*gcgtgcgtcgataagactttggtgcagtctcttcggggtcgcaatttagatttgccgca*
*tggagggtatctggggattttgccaatgctggagcgacgactgtacgattcgtcccat*
*cgggatctagcagaccaatgatgttgacacacatcggccatgcatgtacggacggtcta*
*ttgcgcgagtttgttattttcgaaggacaagatggaagtgtatatggaaccgacaataa*
*tgttagtttgcatttcttagggcggaatctacatgatatcttatccaagcggggtatga*
*gccagagagatgtgatggtcataaagggtaaatttttagatctgaaataacgcagttg*
*cccaaacaacgatcgcgattaaaagaaaaatcggatggttcaattaggacatgcatgga*
*ttctgtgcgcataaaccataaccgcagcactgttgggcacttcggtaactcaaatgcga*
*agcgttgcacgtctgcgataactacgcctactatgcacattgttactcctgcatcttaa*
*aaatatatcctgtagtaattttcacagcaatgtcataacatcatctcgctaaagaatga*
*cctgggattggagaagtaatgaatatttgcaaccaatgcattgaataaactaacattaa*
*ac*gaattcCGATGTTTAGTCACGATAGACATCGGTTCGCCCAGCCGTCGAATACAGCAT
TATATTTTAGTGTTGAAAATGTAGGGCTGCTTCCTCACTTAAAGGAGGAAATGGCTCGA
TTCATGTTTCATAGCAGTAGAAAAACAGATTGGACCGTCAGTAAGTTTAGAGGGTTTTA
TGACTTTAGCACTATAGATAATGTAACTGCGGCCCATCGCATGGCTTGGAAATATATCA
AAGAACTGATTTTTGCAACAGCTTTATTTTCTTCTGTATTTAAATGTGGCGAATTGCAC
ATCTGTCGTGCCGACAGTTTGCAGATCAACAGCAATGGAGACTATGTATGGAAAAATGG
AATATATATAACATATGAAACCGAATATCCACTTATAATGATTCTGGGGTCAGAATCAA
GCACTTCAGAAACGCAAAATATGACTGCAATTATTGATACAGATGTTTTTTCGTTGCTT
TATTCTATTTTGCAGTATATGGCCCCCGTTACGGCAGATCAGGTGCGAGTAGAACAGAT
TACCAACAGCCACGCCCCCATCTGACCCGTCCAATATTCTTGTGTCCCTGCATTTTATC
TCACACAATTTATGAACAGCATCATTAAGATCATCTCACTgcggccgcaag**atgggctc
cagatcttctaccaggatcccggtacctctaatgctgatcatccgaaccgcgctgacac
tgagctgtatccgtctgacaagctctcttgatggcaggcctcttgcggctgcagggatc**

Figure 14 (Continued)

```
gtggtaacaggagataaagcagtcaacatatacacctcatcccagacagggtcaatcat
agttaagttactcccgaatatgcccaaggacaaagaggtgtgtgcaaaagccccattgg
aggcatacaacaggacactgactactttactcacccccttggtgattctatccgcagg
atacaagagtctgtgactacttccggaggaaggagacagagacgctttataggtgccat
tatcggcagtgtagctcttggggttgcgacagctgcacagataacagcagcttcggccc
tgatacaagccaaccagaatgctgccaacatcctccggcttaaagagagcattgctgca
accaatgaagctgtgcacgaggtcactgacggattatcacaactagcagtggcagtagg
gaagatgcaacagtttgtcaatgaccagttcaataatacagcgcaagaattggactgta
taaaaattgcacagcaggtcggtgtagaactcaacttgtacctaactgaattgactaca
gtatttgggccacaaatcacttcccctgccttaactcagctgactatccaagcgcttta
caatctagctggtggtaatatggattacttgctgactaagttaggtgtagggaacaacc
aactcagctcattaattggtagcggcttgatcaccggcaaccctattctgtacgactca
cagactcagatcttgggtatacaggtaactttgccttcagttgggaacctgaataatat
gcgtgccacctacctggagaccttatctgtaagcacaaccaagggatttgcctcagcac
ttgtcccaaaagtggtgacacaggtcggttccgtgatagaagaacttgacacctcatac
tgtatagggaccgacttggatttatactgtacaagaatagtgacattccctatgtctcc
tggtatttattcttgtctgagcggtaatacatcggcttgcatgtattcaaagactgaag
gcgcacttactacgccatatatggctctcaaaggctcagttattgccaattgcaagctg
acaacatgtagatgtgcagatccccaggtatcatatcgcaaaattatggagaagctgt
gtccttaatagataggcactcatgcaacgtcttatccttagacgggataactctgaggc
tcagtggggaatttgatgcaacctatcaaaagaatatctctatactagattctcaagtt
atagtgacaggcaatcttgatatatcaactgagcttgggaatgtcaacaactcaataag
taatgccctgaataagttagaggaaagcaacagcaaactagacaaagtcaatgtcaaac
tgaccagcacatctgctctcattacctacatcgttttaactgtcatatctcttgttttt
ggtgtacttagcctggttctagcatgctacctgatgtacaagcaaaaggcacaacaaaa
gaccttgttatggcttgggaataataccttgatcagatgagagccactacaaaaatat
gagcggccgcgggatccagacatgataagatacattgatgagtttggacaaaccacaa
ctagaatgcagtgaaaaaatgctttatttgtgaaatttgtgatgctattgctttattt
gtaaccattataagctgcaataaacaagttaacaacaacaattgcattcatttatgtt
tcaggttcaggggaggtgtgggaggttttttcggatcctctagagtcgacaattattt
tatttaataacatatagcccaaagacctctatgaacatttagtttccgtatactcaac
ggcgcgtgtacacacgcatctctttgcatagcgatgaagtttgttcggcagcagaaaat
gcagatatccaacaatctggagaaaacttatcatcacagtggcagtggaaacatacccc
ctctatattcatggtataattatcgtctacagcgtccaggatagtggcgtgagaaaatg
gagatctgcagccctcctttccatggcatgccgctttattgttcattaaacgcacaatg
gtctcaacgccagatatgggcatagattctgaagaacccgttgacaatccgaagaagaa
ggcgtgcaggtctttggaagactcgcacgttggtcttataatgtatgatcgagatgtca
ccctaatgccacatggtacaggcttatcgcggtcatggcgatcggacttgtaatttgca
acgatgggcaaaggatcgacgacatgccaaacattctgaacccgtagagatgttaacga
tgacgaggatgaatatccatgctcgctgccatagtatcaagtacaccgcgaataagga
cgcgtccaacatcgttatatgcacacaatgggctacacgtgactaacaccccgaatat
tagtcatatgtgagtttcagtctggctcccatatagcctgtagactatttgtggtttaa
gtgtgaacgaggcgctgtgaacgagactcgggccgattgtaagaacaagcaaatgcact
ttccatttaacaagaagtgtagagagaatactcaacctctttggatgtatcctcgag
```

Figure 14 (Continued)

Partial plasmid SORF3-US2 gpVar-Ewtsyn sequence (for vHVT202) (SEQ ID NO:39)

*Green and Italic* = Flanking Arms
BLUE AND UPPERCASE = GPCMV
Black and Bold = Varient E wt
*Red and Italic and Underlined = Syn Poly A*

*taaaatgggatctatcattacattcgttaagagtctggataatttactgtttgccagc*
*ttcgatcttggaacgtactgtggatagtgccttacttggaatcgtgaaaatttgaacg*
*tccattatttggatatcttccggttgtcccatatcccgcctggtaccgctcggatacc*
*ttgcccgtatggattcgtattgacagtcgcgcaatcggggaccaacaacgcgtgggtcc*
*acactcattcggaattttccgatgattctgaatatttattgccgctcgttacgagtcg*
*ttggacatatctgtaatacatttcttcttctgaaggatcgctgcacatttgatctatac*
*attggccaggatgttcaagtctcagatgttgcattctggcacagcacaactttatggca*
*tttccgatgtaatcgtccggcagccctgggggagttctatattcgcatattgggatggt*
*aaggacaatagcagatctcgcaacctccagggaggctataataacgttttaaaggatg*
*gatttctcataaaaatctgtcgcaaattacactgagaatatcctttactagcgccgatt*
*gagagcatcgtcgtccaattttctaaatggaaagaaaacaaggcgggcaagagtgttcc*
*aaacattttcatttcggcgaatctctcaaatcccatggcgtgcaattgattgcaaaat*
*tggcacttccgttcacgtttgtatctccaaactctaagacacttttaattgaaaacta*
*cgttctagtgtggaaagaaacctataggcagaccatagaactatttgacaccacatatc*
*tttttgtatgtcaaactgaccatgatcgtatgttgctgaatgcactagggcaattcgct*
*cgcgcgactccatacattgaataattccacacgtcagctcatcggttagcaaggtccag*
*tagttgaagtcatttattttccccgcggctggccaaatctacctctgggaatatccaa*
*gttgtcgaatatgatcgcaccggctctggtcatggtgaaggaacttgtagcataaagac*
*gcaggtatcataggggtaatatttttttattcactcacatactaaaagtaacgcatatt*
*agcaccatgtatgggctatcaattgacatttgcgtagcactacatcacgattatgtaca*
*acataatgggacaacatatg*cctgcagg*TTAGTCATATGTTACTTGGCAGAGGCCGCAT
GGAAAGTCCCTGGACGTGGGACATCTGATTAATACGTGAGGAGGTCAGCCATGTTCTTT
TTGGCAAAGGACTACGGTCATTGGACGTTTGATTGGCATGGGATAGGGTCAGCCAGAGT
TAACAGTGTTCTTTTGGCAAAGGGATACGTGGAAAGTCCCGGGCCATTTACAGTAAACT
GATACGGGGACAAAGCACAGCCATATTTAGTCATGTATTGCTTGGCAGAGGGTCTATGG
AAAGTCCCTGGACGTGGGACGTCTGATTAATATGAAAGAAGGTCAGCCAGAGGTAGCTG
TGTCCTTTTTGGCAAAGGGATACGGTTATGGGACGTTTGATTGGACTGGGATAGGGTCA
GCCAGAGTTAACAGTGTTCTTTTGGCAAAGGAAACGTGGAAAGTCCCGGGCCATTTACA
GTAAACTGATACTGGGACAAAGTACACCCATATTTAGTCATGTTCTTTTTGGCAAAGAG
CATCTGGAAAGTCCCGGGCAGCATTATAGTCACTTGGCAGAGGGAAAGGGTCACTCAGA
GTTAAGTACATCTTTCCAGGGCCAATATTCCAGTAAATTACACTTAGTTTTATGCAAAT
CAGCCACAAAGGGGATTTTCCCGGTCAATTATGACTTTTCCTTAGTCATGCGGTATCC
AATTACTGCCAAATTGGCAGTACATACTAGGTGATTCACTGACATTTGGCCGTCCTCTG
GAAAGTCCCTGGAAACCGCTCAAGTACTGTATCATGGTGACTTTGCATTTTTGGAGAGC
ACGCCCCACTCCACCATTGGTCCACGTACCCTATGGGGAGTGGTTTATGAGTATATAA
GGGGCTCCGGTTTAGAAGCCGGGCAGA*gcggccgc*atgacaaacctgcaagatcaaacc

Figure 14 (Continued)

```
caacagattgttccgttcatacggagccttctgatgccaacaaccggaccggcgtccat
tccggacgacaccctggagaagcacactctcaggtcagagacctcgacctacaatttga
ctgtgggggacacagggtcagggctaattgtcttttccctggattccctggctcaatt
gtgggtgctcactacacactgcagagcaatgggaactacaagttcgatcagatgctcct
gactgcccagaacctaccggccagctacaactactgcaggctagtgagtcggagtctca
cagtaaggtcaagcacactccctggtggcgtttatgcactaaacggcaccataaacgcc
gtgaccttccaaggaagcctgagtgaactgacagatgttagctacaacgggttgatgtc
tgcaacagccaacatcaacgacaaaattgggaacgtcctagtaggggaaggggtaaccg
tcctcagcttacccacatcatatgatcttgggtatgtgaggcttggtgacccataccc
gctatagggcttgacccaaaaatggtagcaacatgtgacagcagtgacaggcccagagt
ctacaccataactgcagccgataattaccaattctcatcacagtaccaaacaggtgggg
taacaatcacactgttctcagccaacattgatgccatcacaagtctcagcgttggggga
gagctcgtgttcaaaacaagcgtccaaagccttgtactgggcgccaccatctaccttat
aggctttgatgggactgcggtaatcaccagagctgtggccgcaaacaatgggctgacgg
ccggcatcgacaatcttatgccattcaatcttgtgattccaaccaatgagataacccag
ccaatcacatccatcaaactggagatagtgacctccaaaagtgatggtcaggcagggga
acagatgtcatggtcggcaagtgggagcctagcagtgacgatccatggtggcaactatc
caggagccctccgtcccgtcacactagtggcctacgaaagagtggcaacaggatctgtc
gttacggtcgctggggtgagcaacttcgagctgatcccaaatcctgaactagcaagaa
cctggttacagaatatggccgatttgacccaggagccatgaactacacgaaattgatac
tgagtgagagggaccgccttggcatcaagaccgtctggccaacaagggagtacactgac
tttcgtgagtacttcatggaggtggccgacctcaactctccctgaagattgcaggagc
atttggcttcaaagacataatccgggccataaggaggtgagcggccgcgatatcaataa
aatatctttatttcattacatctgtgtgttggttttttgtgtgaatcgatagtactaa
catacgctctccatcaaaacaaaacgaaacaaaacaaactagcaaaataggctgtcccc
agtgcaagtgcaggtgccagaacatttctcttctagacctgcaggcccgggcaagtag
atgcaatttcctcacactagttgggtttatctactattgaattttcccctatctgtgat
acacttgggagcctctacaagcatattgccatcatgtacgtttttatctactgtcttaa
cgccatgggaacggaggcgtcgtcgtcatgtattggacggcaacataggcagcaacac
aaattgcgtttaggtggggtgcatgtggactcgataccaagcccctgcagctggggaac
gtctggtggagagccgataatttgatatacgcacgccatattactgtcgttgaagtacg
cctatcttctatgttttcaaatttaggttccaagtggacgtgagaagtgtttgtatc
tcacatggaatggcccaaggcattccagcccaggtgcctggtactttaatggcaaacaa
acgttttggtagaggtattgattctattgcagttctgcagatatctgcagccccgagta
tccacaggctatacgatacgttatcggaggcctccgattctagcattacatagccggtc
agtagatcctgccattcggtagcgcaaccggctacatcttcaaacagtctcacaataaa
tgcatctctcgttcctgccaatccggaaccgggcataccactcccgcctgccgatttaa
ttctcacaattgggcgatgccggcggggcaaaacgaatgtggatttggcaaaccgacac
aggtctgctgtacggactaatatgggcacaccacatcattcttcagatgctccatgca
ttgttctatgagaaagatccataggggtggaggcagcgtcacgagatcgccaggcaatc
gatcgcattcgtctagtaaagtgacgagagttatcatgcacacacccatgcccacgcct
tccgaataactggagctgtggaagatcggaaacgtcttttgactgccggtctcgtact
actttcgcacaggtgtataccggacgcgtactatatatttatatcatccaacgtccc
gaaattacatacgtggcggcgatggaagtagatgttgagtcttcgaaagtaagtgcctc
```

Figure 14  (Continued)

```
gaatatgggtattgtctgtgaaaatatcgaaagcggtacgacggttgcagaaccgtcga
tgtcgccagatactagtaacaatagcttcgataacgaagacttccgtgggcctgaatac
gatgtggagata
```

Figure 14 (Continued)

Partial plasmid SB1US2 gpVIIdwtsyn sequence (for vSB1-010) (SEQ ID NO:40)

*Green and Italic* = Flanking Arms
BLUE AND UPPERCASE = GPCMV
Black and Bold = NDV-F VIId wt
*Red and Italic and Underlined = Syn Poly A*

*tctcgtctaaaacgctccagtgctttacagttcgataatctggacctggggacgcgtat
aggatcgttcctccacatgcgctgctgtcggtatctcgaatccccggtattcagttgaa
tcgttggcggagtgtcctcctggactctgcaatgttccctagccgtcttcactatctcg
tgcaaggctctataatacagttcctctgcagacccgtcgttgctcttccttctgcgtc
gttagttatttctgtaggctccagacgatttgcctgcatttgtgcgcaacataatctga
ttgcattccctatctcgtcttccggtaatcccataggtgttcggtattcgcagataggt
agagaaagcaccactgcaaatcgtgcaatttccattgccccaaccaatattttttttaa
gaacggcatcgccgttaatgtacctcgggcattgtgacgatcgaaaccctatggatgc
ctaaagagagcattgcggtccagttctccaggtgaaaagagaatagcgcgggtagaaac
gggccgattagttttatcttcgccgcgtccctaatatcccaagttctgcagtataactt
ccatcgtccgttttcgacaaggtccggcgcgacatagtttgaaatgtcatctatcagaa
acatctcgcccatcgtagaaaaaacctgtacgcagaccataaaaccattcggtaccac
atatccttgtgtatatcaaacgatatgttggttatgtcgttggcggatgttgtatgaaa
tagagctaagcgttctctggattccacgcactgaacgattccgttagtcaattcatctg
ctaacataggccaaaagtttattcgtgttacttttctcggcggtttggcaaaacgcccc
cttggcacatccatgtcattaaatacagcggcataactcctactcatgtgttccatagc
ccaggtttctgttcggtctgctactacgatcagatcagtggcgcgatcagatgcgtggg
atgaatgaagtgtatccgaaagcagttttgagatatacgctaaactgtacgacgattgt
ggcactaaacgaagctttgcgcgaccccatcccacgc*cctgcagg**TTAGTCATATGTT
ACTTGGCAGAGGCCGCATGGAAAGTCCCTGGACGTGGGACATCTGATTAATACGTGAGG
AGGTCAGCCATGTTCTTTTTGGCAAAGGACTACGGTCATTGGACGTTTGATTGGCATGG
GATAGGGTCAGCCAGAGTTAACAGTGTTCTTTTGGCAAAGGGATACGTGGAAAGTCCCG
GGCCATTTACAGTAAACTGATACGGGGACAAAGCACAGCCATATTTAGTCATGTATTGC
TTGGCAGAGGGTCTATGGAAAGTCCCTGGACGTGGGACGTCTGATTAATATGAAAGAAG
GTCAGCCAGAGGTAGCTGTGTCCTTTTTGGCAAAGGGATACGGTTATGGGACGTTTGAT
TGGACTGGGATAGGGTCAGCCAGAGTTAACAGTGTTCTTTTGGCAAAGGAAACGTGGAA
AGTCCCGGGCCATTTACAGTAAACTGATACTGGGACAAAGTACACCCATATTTAGTCAT
GTTCTTTTTGGCAAAGAGCATCTGGAAAGTCCCGGGCAGCATTATAGTCACTTGGCAGA
GGGAAAGGGTCACTCAGAGTTAAGTACATCTTTCCAGGGCCAATATTCCAGTAAATTAC
ACTTAGTTTTATGCAAATCAGCCACAAAGGGGATTTTCCGGTCAATTATGACTTTTTC
CTTAGTCATGCGGTATCCAATTACTGCCAAATTGGCAGTACATACTAGGTGATTCACTG
ACATTTGGCCGTCCTCTGGAAAGTCCCTGGAAACCGCTCAAGTACTGTATCATGGTGAC
TTTGCATTTTTGGAGAGCACGCCCCACTCCACCATTGGTCCACGTACCCTATGGGGGAG
TGGTTTATGAGTATATAAGGGCTCCGGTTTAGAAGCCGGGCAGA**gcggccgcatgggc
tccaaaccttctaccaggatcccagcacctctgatgctgatcaccggattatgctgat
attgggctgtatccgtccgacaagctctcttgacggcaggcctcttgcagctgcaggaa
ttgtagtaacaggagataaggcagtcaatgtatacacttcgtctcagacagggtcaatc**

Figure 14 (Continued)

atagtcaagttgctcccgaatatgcccagggataaggaggcgtgtgcaaaagccccatt
agaggcatataacagaacactgactactttgctcactcctcttggcgactccatccgca
agatccaagggtctgtgtccacatctggaggaggcaagcaaggccgcctgataggtgct
gttattggcagtgtagctcttggggttgcaacagcggcacagataacagcagctgcggc
cctaatacaagccaaccagaatgccgccaacatcctccggcttaaggagagcattgctg
caaccaatgaagctgtgcatgaagtcaccgacggattatcacaactatcagtggcagtt
gggaagatgcagcagtttgtcaatgaccagtttaataatacggcgcgagaattggactg
tataaaaatcacacaacaggttggtgtagaactcaacctatacctaactgaattgacta
cagtattcgggccacagatcacctcccctgcattaactcagctgaccatccaggcactt
tataatttagctggtggcaatatggattacttattaactaagttaggtatagggaacaa
tcaactcagctcgttaattggtagcggcctgatcactggttaccctatactgtatgact
cacagactcaactcttgggcatacaagtgaatttaccctcagtcgggaacttaaataat
atgcgtgccacctatttggagaccttatctgtaagtacaaccaaaggatatgcctcagc
acttgtcccgaaagtagtgacacaagtcggttccgtgatagaagagcttgacacctcat
actgtatagagtccgatctggatttatattgtactagaatagtgacattccccatgtcc
ccaggtatttattcctgtttgagcggcaacacatcagcttgcatgtattcaaagactga
aggcgcactcactacgccgtatatggcccttaaaggctcagttattgccaattgtaaaa
taacaacatgtagatgtacagaccctcctggtatcatatcgcaaaattatggagaagct
gtatccctgatagatagacattcgtgcaatgtcttatcattagacgggataactctaag
gctcagtggggaatttgatgcaacttatcaaaagaacatctcaatactagattctcaag
tcatcgtgacaggcaatcttgatatatcaactgaacttggaaacgtcaacaattcaatc
agcaatgccttggataggttggcagaaagcaacagcaagctagaaaaagtcaatgtcag
actaaccagcacatctgctctcattacctatattgttctaactgtcatttctctagttt
tcggtgcacttagtctggtgttagcgtgttacctgatgtacaaacagaaggcacaacaa
aagaccttgctatggcttgggaataatacctcgatcagatgagagccactacaagagc
atgagcggccgcgatatc*aataaaatatctttatttcattacatctgtgtgttggttt*
*tttgtgtgaatcgatagtactaacatacgctctccatcaaaacaaaacgaaacaaaaca*
*aactagcaaaataggctgtccccagtgcaagtgcaggtgccagaacatttctctt*ctag
acctgcagg*ggagtctgtgcaaggttaatgaccctcgcagttcattcggaagttataac*
*tgccgccttcgcacatttcttttttgtcctgttttgtattgccataacagataggaattg*
*aaacctgatcctcctgttttttgcagcatggccagcaacagaatactttgtcggatcga*
*ctacttgcgcgagatggttccgttcttggaggtttcggcgggtcggtggagaacctat*
*tattttatacacacgtcataccgttgtcgcgaaatgttctttgtcttctgccgtct*
*cgaacgtcggttcccacgtagacgttaggagcgttggaatggtatcaggaagagccac*
*ggcatgccggaccaagtacccgctactttgaccgcgagcagtctcttcggtaatgggat*
*gtattccagagcagcgcggcagagatcagcggccccactatccacagactgtatgaag*
*tgttttctgaaacatcggactccaacatcaaatatccagacataacatcttgccattcg*
*gaagcacatccgccgacatcttcaaatagcctaactataaacgagtctctagttcctgc*
*taacccagtacctcgaatgccagtccatccggtgggttcgtcctgataatcggtctct*
*gacgccgaggaagaactaaaaggggtctggaaaagcggaacagatctgcagaccgaacg*
*actacagacacgcccacatcatcatgtatctgttccatgcattgctttatgagaaaat*
*ccataaggccgaggcggcatctctagatctcccggggagtctctcgcactcatctagga*
*gagtgacgacagttatcatagacacgcccatttgtgcaccaaacgaaaagttcctgtac*
*tggtggagcgtcggcgcgggaatcggtccgtgctctgaaaccagtgtctagacagaaga*

Figure 14 (Continued)

```
ccatccggtaaattctggtgtatgaactgacggtctccagacgaacgtcgaagacatta
acgatggaaactaacgagctttcttcaaaagtgtctgattacaacgctaatagaccta
cgaaactatacgcagcgataccagtgacacagatccgtcggtgtcg
```

RECOMBINANT HVT VECTORS EXPRESSING ANTIGENS OF AVIAN PATHOGENS AND USES THEREOF

CROSS-REFERENCE TO RELATED APPLICATIONS

This application claims priority to U.S. provisional application 61/564,877 filed on Nov. 30, 2011 and U.S. provisional application 61/694,957 filed on Aug. 30, 2012.

FIELD OF THE INVENTION

The invention relates to recombinant viral vectors for the insertion and expression of foreign genes for use as safe immunization vehicles to protect against a variety of pathogens. It also relates to multivalent composition or vaccine comprising one or more recombinant viral vectors for protection against a variety of pathogens. The present invention relates to methods of making and using the recombinant viral vectors.

BACKGROUND OF THE INVENTION

Poultry vaccination is widely used to protect poultry flocks against devastating diseases including Newcastle disease (ND), infectious bursal disease (IBD), Marek's disease (MD), infectious bronchitis (IB), infectious laryngotracheitis (ILT) and avian influenza (AI). ND is caused by the avian paramyxovirus 1 (APMV-1) also designated ND virus (NDV) belonging to the Paramyxoviridae family. MD is caused by Gallid herpesvirus 2 (Herpesviridae family) also designated as MD virus serotype 1 (MDV1). IB is caused by IB virus (IBV) belonging to the Coronaviridae family, ILT is caused by Gallid herpesvirus 1 (Herpesviridae family) also designated ILT virus (ILTV) and AI is caused by AI virus (AIV) belonging to the Orthomyxoviridae family.

A number of recombinant avian viral vectors have been proposed with a view to vaccinating birds against these avian pathogens. The viral vectors used comprise avipox viruses, especially fowlpox (EP-A-0,517,292), Marek's virus, such as serotypes 2 and 3 (HVT) (WO-A-87/04463), or alternatively the ITLV, NDV and avian adenovirus. When some of these recombinant avian viral vectors were used for vaccination, they display variable levels of protection.

Several recombinant herpesvirus of turkeys (HVT, also designated Meleagrid herpesvirus 1 or MDV serotype 3) vectors expressing antigens from various pathogens (U.S. Pat. Nos. 5,980,906, 5,853,733, 6,183,753, 5,187,087) including IBDV, NDV, ILTV and AIV have been developed and licensed. Of particular interest is a HVT vector-expressing IBDV VP2 protective gene that has shown clear advantages over classical IBD vaccines (Bublot et al J. Comp. Path. 2007, Vol. 137, S81-S84; U.S. Pat. No. 5,980,906). Other HVT vectors of interest are those expressing either NDV (Morgan et al 1992, Avian dis. 36, 858-70; U.S. Pat. No. 6,866,852; U.S. Pat. No. 5,650,153) or ILTV (Johnson et al, 2010 Avian Dis 54, 1251-1259; U.S. Pat. No. 6,299,882; U.S. Pat. No. 5,853,733) protective gene(s). One of the practical problems of using several HVT-based recombinant vaccines together is their interference. Lower protection is induced at least against one of the disease when two HVT recombinants expressing different antigens are mixed (Rudolf Heine 2011; Issues of the Poultry Recombinant Viral Vector Vaccines which May Cause an Effect on the Economic Benefits of those Vaccines; paper presented at the XVII World Veterinary Poultry Association (WVPA) Congress in Cancun, Mexico, Aug. 14-18, 2011; Slacum G, Hein R. and Lynch P., 2009, The compatibility of HVT recombinants with other Marek's disease vaccines, 58th Western Poultry Disease Conference, Sacramento, Calif., USA, March 23rd-25th, p 84).

The combination of HVT and SB-1, a Gallid herpesvirus 3 (MDV serotype 2 or MDV-2) vaccine strain, has shown a synergistic effect on MD protection (Witter and Lee, 1984, Avian Pathology 13, 75-92). To address the interference problem, it is of interest to evaluate the HVT virus as a vaccine vector to express one or more protective antigen(s) against a variety of avian pathogens.

The SB-1 genome was cloned and characterized in bacterial artificial chromosome (BAC) (Petherbridge, et al., J. Virol. Methods 158, 11-17, 2009; Singh et al., Research in Veterinary Science 89, 140-145, 2010). The MDV2 SB-1 sequence was recently obtained and analyzed (Spatz and Schat, Virus Gene 42, 331-338, 2011). A glycoprotein E deletion of SB-1 virus was described by Petherbridge, et al. (J. Virol. Methods 158, 11-17, 2009). However, no research has been reported using SB-1 as a viral vector expressing foreign protective genes.

Considering the potential effect of animal pathogens, such as NDV and IBDV on veterinary public health and the economy, efficient methods of preventing infection and protecting animals are needed. There is a need for a solution of combined effective vector vaccines and a suitable method for making the vaccine that could alleviate the problem of interference observed between two HVT-based vector vaccines.

SUMMARY OF THE INVENTION

The present invention showed surprising result when polyvalent compositions or vaccines comprising single or double HVT vector were effective to protect animals against a variety of avian pathogens without interference. Surprising results were also observed when various combinations of promoters, codon-optimized gene, polyA tails and insertion sites conferred different levels of efficacy and stability to the expression of one or more heterologous genes in vivo.

The present invention relates to a recombinant HVT vector comprising one or more heterologous polynucleotides coding for and expressing at least one antigen of an avian pathogen.

The present invention provides a composition or vaccine comprising one or more recombinant HVT vectors comprising one or more heterologous polynucleotides coding for and expressing at least one antigen of an avian pathogen.

The present invention provides a polyvalent composition or vaccine comprising one or more recombinant HVT vectors comprising heterologous polynucleotides coding for and expressing at least one antigen of an avian pathogen and one or more recombinant SB1 vectors comprising heterologous polynucleotides coding for and expressing at least one antigen of an avian pathogen.

The present invention relates to a method of vaccinating an animal, or inducing an immunogenic or protective response in an animal, comprising at least one administration of the composition or vector of the present invention.

BRIEF DESCRIPTION OF THE DRAWINGS

The following detailed description, given by way of example, and which is not intended to limit the invention to specific embodiments described, may be understood in conjunction with the accompanying figures, incorporated herein by reference, in which:

FIG. 1 is a table showing the SEQ ID NO assigned to each DNA and protein sequence.

FIG. 3 depicts the plasmid map of pHM103.

FIG. 5A1 and FIG. 5A2 are from the pre-MSV passage. FIG. 5B1 and FIG. 5B2 are from the pre-MSV+12 passage.

FIG. 6 depicts the Southern blot results of vHVT114.

FIG. 9 depicts the Western blot analysis of immunoprecipitated sample from vSB1-009 infected cells.

FIG. 10 depicts the result of challenge study of vHVT304 and vHVT114 against NDV ZJ1 and CA02.

FIG. 11 depicts the viral shedding result after NDV CA02 and ZJ1 challenge.

FIG. 13 shows the sequence alignment and percentage identity.

DETAILED DESCRIPTION OF THE INVENTION

Figure 2:
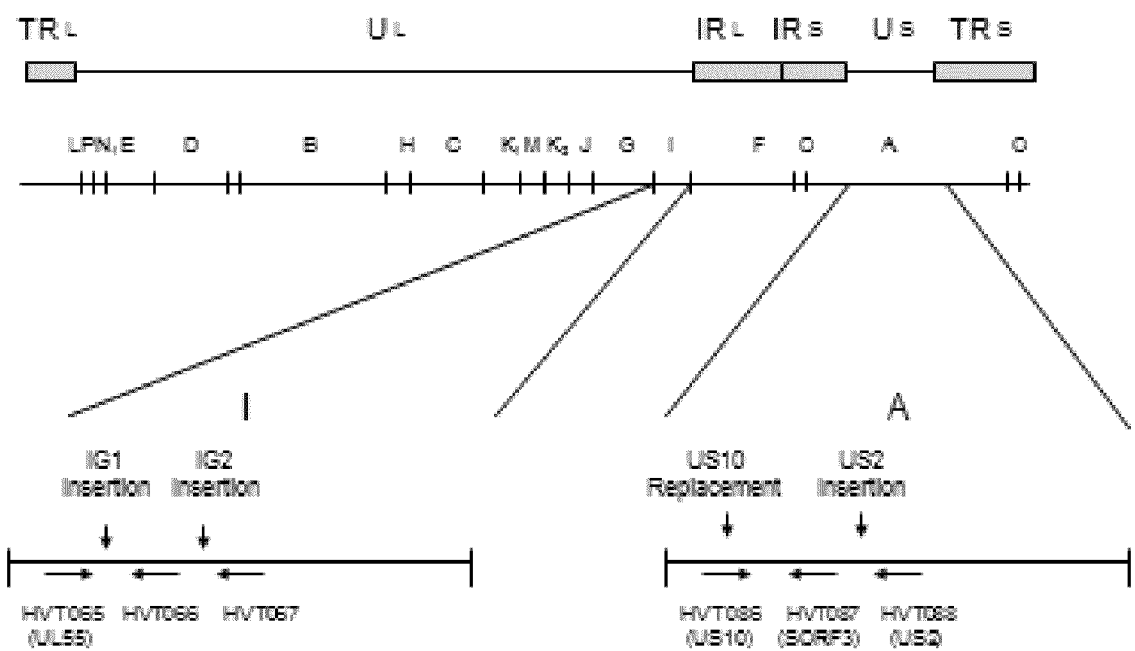
FIG. 2 depicts the genome structure of HVT and its insertion sites.
Figure 4:
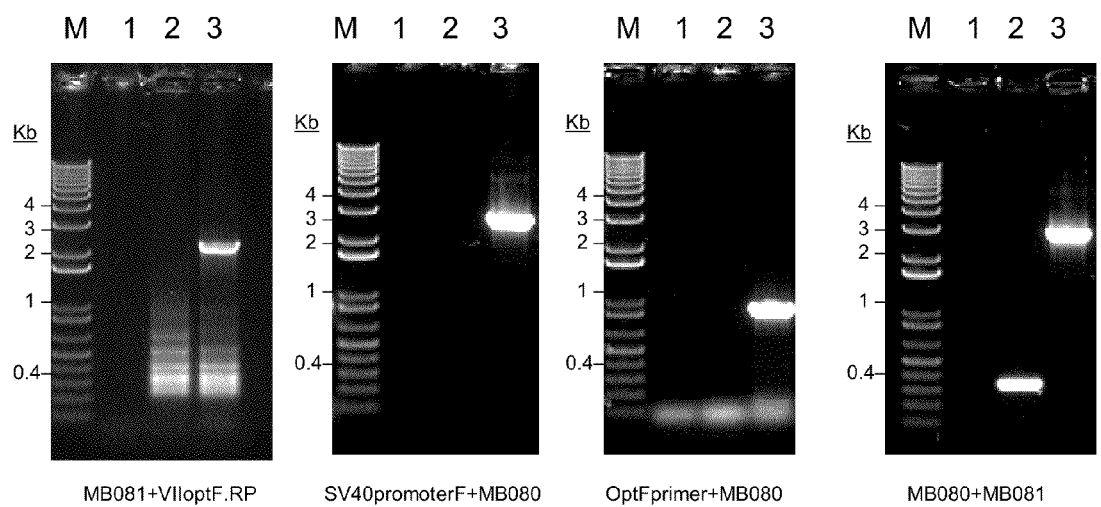
FIG. 4 depicts the PCR analysis results of vHVT114.
Figure 5:
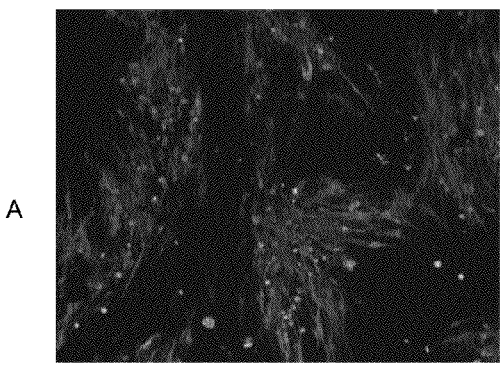
FIG. 5 shows the dual immunofluorescent assay results.
Figure 5:
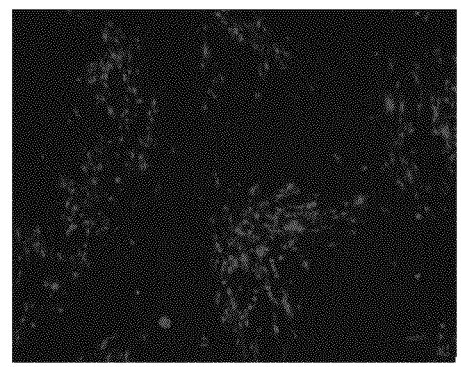
Figure 5:
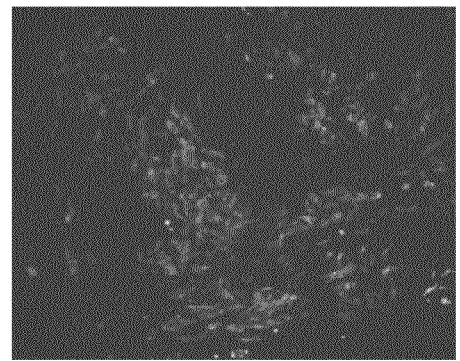
Figure 5:
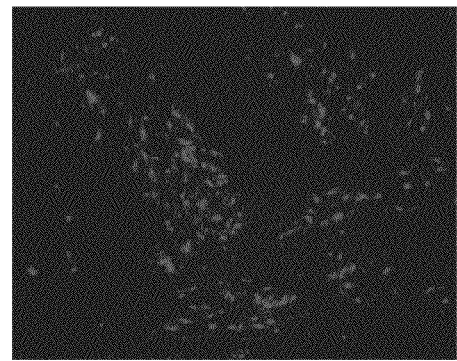
Figure 7:
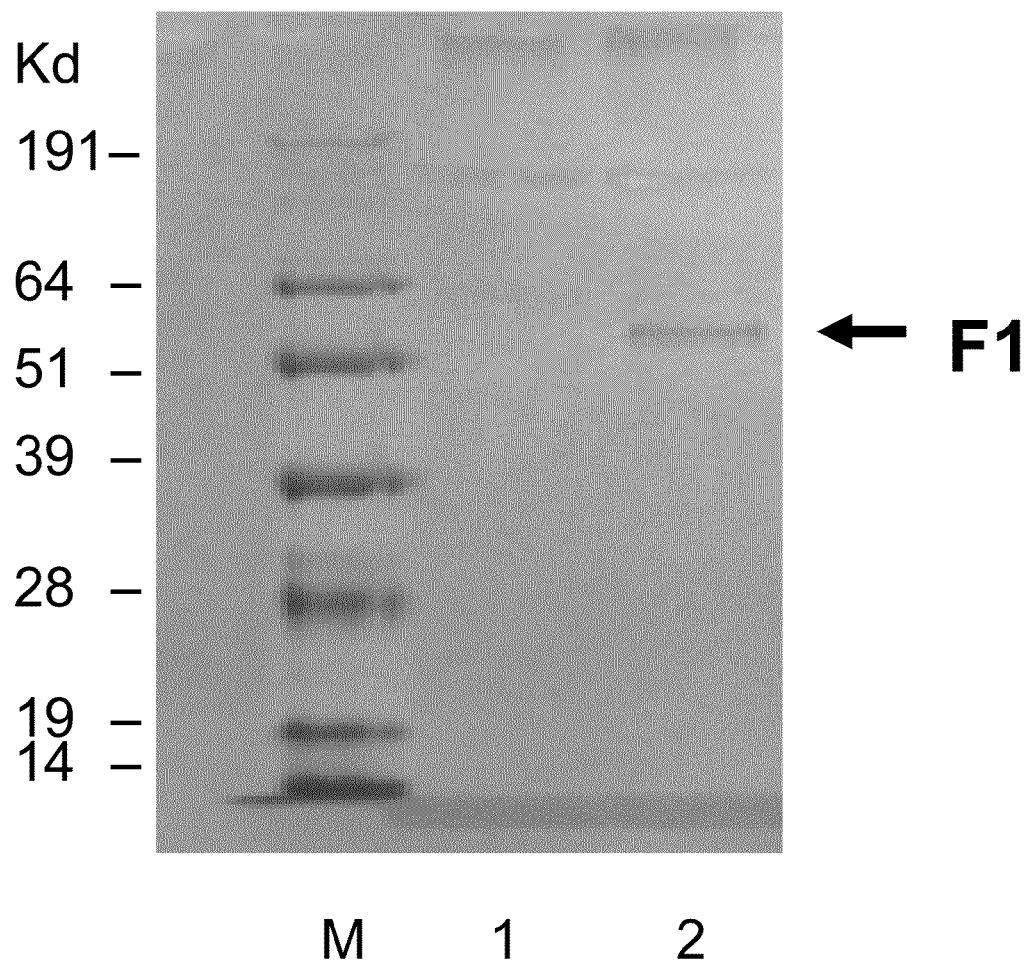
FIG. 7 depicts the immunoprecipitation and Western blot analysis results of vHVT114.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), swine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The terms "polypeptide" and "protein" are used interchangeably herein to refer to a polymer of consecutive amino acid residues.

The term "nucleic acid", "nucleotide", and "polynucleotide" are used interchangeably and refer to RNA, DNA, cDNA, or cRNA and derivatives thereof, such as those containing modified backbones. It should be appreciated that the invention provides polynucleotides comprising sequences complementary to those described herein. The "polynucleotide" contemplated in the present invention includes both the forward strand (5' to 3') and reverse complementary strand (3' to 5'). Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "genomic DNA" or "genome" is used interchangeably and refers to the heritable genetic information of a host organism. The genomic DNA comprises the DNA of the nucleus (also referred to as chromosomal DNA) but also the DNA of the plastids (e.g., chloroplasts) and other cellular organelles (e.g., mitochondria). The genomic DNA or genome contemplated in the present invention also refers to the RNA of a virus. The RNA may be a positive strand or a negative strand RNA. The term "genomic DNA" contemplated in the present invention includes the genomic DNA containing sequences complementary to those described herein. The term "genomic DNA" also refers to messenger RNA (mRNA), complementary DNA (cDNA), and complementary RNA (cRNA).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.; Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "heterologous DNA" as used herein refers to the DNA derived from a different organism, such as a different cell type or a different species from the recipient. The term also refers a DNA or fragment thereof on the same genome of the host DNA wherein the heterologous DNA is inserted into a region of the genome which is different from its original location.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The term "immunogenic protein or peptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Similarly, conformational epitopes are readily identified by determining spatial conformation of amino acids such as by, e.g., x-ray crystallography and 2-dimensional nuclear magnetic resonance.

The term "immunogenic protein or peptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) nonpolar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "recombinant" and "genetically modified" are used interchangeably and refer to any modification, alteration or engineering of a polynucleotide or protein in its native form or structure, or any modification, alteration or engineering of a polynucleotide or protein in its native environment or surrounding. The modification, alteration or engineering of a polynucleotide or protein may include, but is not limited to, deletion of one or more nucleotides or amino acids, deletion of an entire gene, codon-optimization of a gene, conservative substitution of amino acids, insertion of one or more heterologous polynucleotides.

The term "double HVT construct" or "double HVT vector" refers to an HVT viral vector comprising two heterologous polynucleotides.

The terms "polyvalent vaccine or composition", "combination or combo vaccine or composition" and "multivalent vaccine or composition" are used interchangeably to refer to a composition or vaccine containing more than one composition or vaccines. The polyvalent vaccine or composition may contain two, three, four or more compositions or vaccines. The polyvalent vaccine or composition may comprise recombinant viral vectors, active or attenuated or killed wild-type viruses, or a mixture of recombinant viral vectors and wild-type viruses in active or attenuated or killed forms.

One embodiment of the invention provides a recombinant HVT viral vector comprising one or more heterologous polynucleotides coding for and expressing at least one antigen or polypeptide of an avian pathogen. The HVT strains used for the recombinant viral vector may be any HVT strains, including, but not limited to, the HVT strain FC126 (Igarashi T. et al., J. Gen. Virol. 70, 1789-1804, 1989).

Another embodiment of the invention provides a recombinant SB-1 viral vector comprising one or more heterologous polynucleotides coding for and expressing at least one antigen or polypeptide of an avian pathogen. The SB-1 strains may be any SB-1 strains, including, but not limited to, the commercial Marek's Disease Vaccine (SB-1 vaccine) (Merial Select Inc., Gainesville, Ga. 30503, USA), the SB-1 strain having the genome sequence as defined by GenBank Accession Number HQ840738.1.

The genes coding for antigen or polypeptide may be those coding for Newcastle Disease Virus fusion protein (NDV-F), Newcastle Disease Virus hemagglutinin neuraminidase (NDV-HN), Marek's Disease Virus glycoprotein C (gC), Marek's Disease Virus glycoprotein B (gB), Marek's Disease Virus glycoprotein E (gE), Marek's Disease Virus glycoprotein I (gI), Marek's Disease Virus glycoprotein H (gH) or Marek's Disease Virus glycoprotein L (gL), Infectious Bursal Disease Virus (IBDV) VP2, IBDV VPX, IBDV VP3, IBDV VP4, ILTV glycoprotein B, ILTV glycoprotein I, ILTV UL32, ILTV glycoprotein D, ILTV glycoprotein E, ILTV glycoprotein C, influenza hemaglutinin (HA), influenza neuraminidase (NA), protective genes derived from *Mycoplasma gallisepticum* (MG), or *Mycoplasma synoviae* (MS), or combinations thereof. The antigen or polypeptide may be any antigen from the poultry pathogen selected form the group consisting of avian encephalomyelitis virus, avian reovirus, avian paramyxovirus, avian metapneumovirus, avian influenza virus, avian adenovirus, fowl pox virus, avian coronavirus, avian rotavirus, chick anemia virus, avian astrovirus, avian parvovirus, coccidiosis (*Eimeria* sp.), *Campylobacter* sp., *Salmonella* sp., *Pasteurella* sp., *Avibacterium* sp., *Mycoplasma gallisepticum, Mycoplasma synoviae, Clostridium* sp., and *E. coli*.

Moreover, homologs of aforementioned antigen or polynucleotides are intended to be within the scope of the present invention. As used herein, the term "homologs" includes orthologs, analogs and paralogs. The term "analogs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type polypeptide can differ from the wild-type polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the polynucleotide or polypeptide sequences of antigens described above, and will exhibit a similar function.

In one embodiment, the present invention provides a recombinant HVT or SB-1 viral vector comprising one or more heterologous polynucleotides coding for and expressing the NDV-F antigen or polypeptide. In one aspect of the embodiment, the NDV-F antigen or polypeptide has at least 70%, 75%, 80%, 85%, 90%, 95%, 96%, 97%, 98% or 99% sequence identity to a polypeptide having the sequence as set forth in SEQ ID NO:2, 4, 6, 33, 35, or 37, or a conservative variant, an allelic variant, a homolog or an immunogenic fragment comprising at least eight or at least ten consecutive amino acids of one of these polypeptides, or a combination of these polypeptides. In another aspect of the embodiment, the heterologous polynucleotide encoding an NDV-F antigen or polypeptide having at least 70%, 75%, 80%, 85%, 90%, 95%, 96%, 97%, 98% or 99% sequence identity to a polypeptide having the sequence as set forth in SEQ ID NO:2, 4, 6, 33, 35, or 37. In yet another aspect of the embodiment, the heterologous polynucleotide has at least 70%, 75%, 80%, 85%, 90%, 95%, 96%, 97%, 98% or 99% sequence identity to a polynucleotide having the sequence as set forth in SEQ ID NO:1, 3, 5, 32, 34, or 36.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene of interest, are intended to be within the scope of the invention.

The term "identity" with respect to sequences can refer to, for example, the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman). The sequence identity or sequence similarity of two amino acid sequences, or the sequence identity between two nucleotide sequences can be determined using Vector NTI software package (Invitrogen, 1600 Faraday Ave., Carlsbad, Calif.). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for NDV-F polypeptides, the DNA sequence of the NDV-F protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of NDV F protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the NDV-F polypeptide encoded by the nucleotide sequence is functionally unchanged.

Successful expression of the heterologous polynucleotides by the recombinant/modified infectious virus requires two conditions. First, the heterologous polynucleotides must be inserted or introduced into a region of the genome of the virus in order that the modified virus remains viable. The second condition for expression of inserted heterologous polynucleotides is the presence of a regulatory sequences allowing expression of the gene in the viral background (for instance: promoter, enhancer, donor and acceptor splicing sites and intron, Kozak translation initiation consensus sequence, polyadenylation signals, untranslated sequence elements).

The insertion site may be any non-essential region of the HVT genome, including, but not limited to, the region between the ATG of ORF UL55 and the junction of UL with the adjacent repeat region (U.S. Pat. No. 5,980,906), the IG1 locus, the IG2 locus, the IG3 locus, the UL43 locus, the US10 locus, the SORF3/US2 locus (see FIG. 2)

In general, it is advantageous to employ a strong promoter functional in eukaryotic cells. The promoters include, but are not limited to, an immediate early cytomegalovirus (CMV) promoter, guinea pig CMV promoter, an SV40 promoter, Pseudorabies Virus promoters such as that of glycoprotein X promoter, Herpes Simplex Virus-1 such as the alpha 4 promoter, Marek's Disease Viruses (including MDV-1, MDV-2 and HVT) promoters such as those driving glycoproteins gC, gB, gE, or gI expression, Infectious Laryngotracheitis Virus promoters such as those of glycoprotein gB, gE, gI, gD genes, or other herpesvirus promoters.

One embodiment of the invention provides a recombinant HVT vector comprising a heterologous polynucleotide coding for and expressing the NDV-F antigen or polypeptide. In one aspect of the embodiment, the polynucleotide encoding the NDV-F polypeptide is operably linked to the SV40 promoter having the sequence as set forth in SEQ ID NO:9 and therefore the expression of the NDV-F antigen or polypeptide is regulated by the SV40 promoter. In another aspect of the embodiment, the expression of NDV-F antigen or polypeptide is regulated by the SV40 polyA signal having the sequence as set forth in SEQ ID NO:11. In yet another aspect of the embodiment, the polynucleotide encoding the NDV-F polypeptide is operably linked to the MDV gB promoter having the sequence as set forth in SEQ ID NO:38 and therefore the expression of the NDV-F antigen or polypeptide is regulated by the MDV gB promoter.

Another embodiment of the invention provides a recombinant double HVT vector comprising a first heterologous polynucleotide coding for and expressing the NDV-F antigen or polypeptide and a second polynucleotide coding for and expressing the IBDV VP2 antigen or polypeptide. In one aspect of the embodiment, the NDV-F antigen or polypeptide has at least 70%, 75%, 80%, 85%, 90%, 95%, 96%, 97%, 98% or 99% sequence identity to a polypeptide having the sequence as set forth in SEQ ID NO:2, 4, 6, 33, 35, or 37. In another aspect of the embodiment, the IBDV VP2 antigen or polypeptide has at least 70%, 75%, 80%, 85%, 90%, 95%, 96%, 97%, 98% or 99% sequence identity to a polypeptide having the sequence as set forth in SEQ ID NO:8 or 42. In another aspect, the polynucleotide encoding the NDV-F polypeptide is operably linked to the SV40 promoter having the sequence as set forth in SEQ ID NO:9 and the expression of NDV-F antigen or polypeptide is regulated by the SV40 promoter. In yet another aspect, the expression of NDV-F antigen or polypeptide is regulated by the SV40 polyA signal having the sequence as set forth in SEQ ID NO:11, or the synthetic polyA signal having the sequence as set forth in SEQ ID NO:12. In another aspect, the expression of IBDV VP2 antigen or polypeptide is regulated by the CMV-IE promoter having the sequence as set forth in SEQ ID NO:10 and the SV40 polyA signal having the sequence as set forth in SEQ ID NO:11.

Yet another embodiment of the invention provides a recombinant double HVT vector comprising two polynucleotides coding for and expressing the IBDV VP2 antigens or polypeptides. In one aspect of the embodiment, the IBDV VP2 antigen or polypeptide has at least 70%, 75%, 80%, 85%, 90%, 95%, 96%, 97%, 98% or 99% sequence identity to a polypeptide having the sequence as set forth in SEQ ID NO:8 or 42. In one aspect, the polynucleotide encoding a first IBDV VP2 antigen or polypeptide is operably linked to the CMV-IE promoter having the sequence as set forth in SEQ ID NO:10, and the polynucleotide encoding a second IBDV VP2 antigen or polypeptide is operably linked to the guinea pig CMV promoter having the sequence as set forth in SEQ ID NO:43. In another aspect, the expression of a first IBDV VP2 antigen or polypeptide is regulated by the CMV-IE promoter having the sequence as set forth in SEQ ID NO:10 and the SV40 polyA signal having the sequence as set forth in SEQ ID NO:11, and the expression of a second IBDV VP2 antigen or polypeptide is regulated by the guinea pig CMV promoter having the sequence as set forth in SEQ ID NO:43 and the synthetic polyA signal having the sequence as set forth in SEQ ID NO:12. In yet another aspect of the embodiment, the polynucleotides encoding the IBDV VP2 antigen or polypeptide may be inserted in one or more locus regions selected from the group consisting of IG1, IG2, US10, SORF3-US2 and gD of HVT genome. In one embodiment, the present invention relates to a pharmaceutical composition or vaccine comprising one or more recombinant HVT or SB-1 rival vectors of the present invention and a pharmaceutically or veterinarily acceptable carrier, excipient, vehicle or adjuvant.

In another embodiment, the present invention provides a composition or vaccine comprising an HVT viral vector comprising a polynucleotide encoding an NDV-F antigen, an SV40 promoter, and optionally a pharmaceutically or veterinarily acceptable carrier, excipient, vehicle or adjuvant. In another embodiment, the present invention provides a pharmaceutical composition or vaccine comprising a first HVT vector comprising a polynucleotide encoding an NDV-F antigen, a second HVT vector comprising a polynucleotide encoding an IBDV VP2 antigen, and optionally a pharmaceutically or veterinarily acceptable carrier, excipient, vehicle or adjuvant. In another embodiment, the present invention provides a pharmaceutical composition or vaccine comprising an HVT vector comprising a polynucleotide encoding an NDV-F antigen, an SB-1 vector comprising a polynucleotide encoding an NDV-F antigen, optionally a pharmaceutically or veterinarily acceptable carrier, excipient, vehicle or adjuvant. The pharmaceutical composition or vaccine of the present invention may comprise a first HVT vector comprising a polynucleotide encoding an NDV-F antigen, a second HVT vector comprising a polynucleotide encoding an IBDV VP2 antigen, an SB-1 vector comprising a polynucleotide encoding an NDV-F antigen, optionally a pharmaceutically or veterinarily acceptable carrier, excipient, vehicle or adjuvant.

In yet another embodiment, the present invention provides a composition or vaccine comprising a double HVT viral vector comprising: i) a first heterologous polynucleotide coding for and expressing an NDV-F antigen or polypeptide; ii) a second polynucleotide coding for and expressing an IBDV VP2 antigen or polypeptide; and iii) optionally a pharmaceutically or veterinarily acceptable carrier, excipient, vehicle or adjuvant. In another embodiment, the present invention provides a composition or vaccine comprising a double HVT viral vector comprising two polynucleotides coding for and expressing the IBDV VP2 antigens or polypeptides, and optionally a pharmaceutically or veterinarily acceptable carrier, excipient, vehicle or adjuvant. In yet another embodiment, the composition comprising the double HVT viral vector further comprises an HVT vector comprising a polynucleotide encoding an IBDV VP2 antigen, or an SB-1 vector comprising a polynucleotide encoding an NDV-F antigen, or a combination thereof. The pharmaceutically or veterinarily acceptable carriers or adjuvant or vehicles or excipients are well known to the one skilled in the art. For example, a pharmaceutically or veterinarily acceptable carrier or adjuvant or vehicle or excipient can be Marek's disease vaccine diluent used for MD vaccines. Other pharmaceutically or veterinarily acceptable carrier or adjuvant or vehicle or excipients that can be used for methods of this invention include, but are not limited to, 0.9% NaCl (e.g., saline) solution or a phosphate buffer, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro), or facilitating transfection or infection and/or improve preservation of the vector (or protein). Doses and dose volumes are herein discussed in the general description and can also be determined by the skilled artisan from this disclosure read in conjunction with the knowledge in the art, without any undue experimentation.

Optionally other compounds may be added as pharmaceutically or veterinarily acceptable carriers or adjuvant or vehicles or excipients, including, but not limited to, alum; CpG oligonucleotides (ODN), in particular ODN 2006, 2007, 2059, or 2135 (Pontarollo R. A. et al., *Vet. Immunol. Immunopath*, 2002, 84: 43-59; Wernette C. M. et al., *Vet. Immunol. Immunopath*, 2002, 84: 223-236; Mutwiri G. et al., *Vet. Immunol. Immunopath*, 2003, 91: 89-103); polyA-polyU, dimethyldioctadecylammonium bromide (DDA) ("Vaccine Design The Subunit and Adjuvant Approach", edited by Michael F. Powell and Mark J. Newman, *Pharmaceutical Biotechnology*, 6: p. 03, p. 157); N,N-dioctadecyl-N',N'-bis (2-hydroxyethyl) propanediamine (such as AVRIDINE®) (Ibid, p. 148); carbomer, chitosan (see U.S. Pat. No. 5,980,912 for example).

The pharmaceutical compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

Another aspect of the invention relates to a method for inducing an immunological response in an animal against one or more antigens or a protective response in an animal against one or more avian pathogens, which method comprises inoculating the animal at least once with the vaccine or pharmaceutical composition of the present invention. Yet another aspect of the invention relates to a method for inducing an immunological response in an animal to one or more antigens or a protective response in an animal against one or more avian pathogens in a prime-boost administration regimen, which is comprised of at least one primary administration and at least one booster administration using at least one common polypeptide, antigen, epitope or immunogen. The immunological composition or vaccine used in primary administration may be same, may be different in nature from those used as a booster.

The avian pathogens may be Newcastle Disease Virus (NDV), Infectious Bursal Disease Virus (i.e., IBDV or Gumboro Disease virus), Marek's Disease Virus (MDV), Infectious Laryngotracheitis Virus (ILTV), avian encephalomyelitis virus, avian reovirus, avian paramyxovirus, avian metapneumovirus, avian influenza virus, avian adenovirus, fowl pox virus, avian coronavirus, avian rotavirus, avian parvovirus, avian astrovirus and chick anemia virus coccidiosis (*Eimeria* sp.), *Campylobacter* sp., *Salmonella* sp., *Mycoplasma gallisepticum*, *Mycoplasma synoviae*, *Pasteurella* sp., *Avibacterium* sp., *E. coli* or *Clostridium* sp.

Usually, one administration of the vaccine is performed either at one day-of-age by the subcutaneous or intramuscular route or in ovo in 17-19 day-old embryo. A second administration can be done within the first 10 days of age. The animals are preferably at least 17 day-embryo or one day old at the time of the first administration.

A variety of administration routes in day-old chicks may be used such as subcutaneously or intramuscularly, intradermally, transdermally. The in ovo vaccination can be performed in the amniotic sac and/or the embryo. Commercially available in ovo and SC administration devices can be used for vaccination.

The invention will now be further described by way of the following non-limiting examples.

EXAMPLES

Construction of DNA inserts, plasmids and recombinant viral vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989).

Example 1

Construction of Recombinant vHVT114 Expressing NDV-F

Preparation of Donor Plasmid pHM103+Fopt

The plasmid pHM103 (Merial Limited) containing the Intergenic I arms of HVT FC126 (see FIG. 2), SV40 promoter and SV40 poly A was digested with NotI, dephosphorylated, and the 5.6 kb fragment was gel extracted. A NotI flanked 1.7 kb fragment of a chemically synthesized codon-optimized genotype VIId NDV-F gene (SEQ ID NO:1, coding for SEQ ID NO:2) was also NotI digested and the 1.7 kb fragment was gel extracted. The 5.6 and 1.7 kb fragments were ligated to create pHM103+Fopt (FIG. 3).

Generation of Recombinant HVT Viral Vector

An in vitro recombination (IVR) was performed by co-electroporation of secondary chicken embryo fibroblast cells (2° CEF cells) using pHM103+Fopt as the donor plasmid and viral DNA isolated from the HVT strain FC126. Co-electroporation was performed using $1 \times 10^7$ 2° CEF in 300 ul Opti-MEM and shocked at 150 volts with 950 capacitance in a 2 mm electroporation cuvette. The transfected cells were seeded into 96-well plate and incubated for 5 days. The cells grown in the 96-well plate were then duplicated into two 96-well plates. One set of 96-well plates was used for IFA using chicken polyclonal sera against NDV-F to identify positive wells containing recombinants and another set of 96-well plates was used for recovering the infected cells from the positive wells.

The recombinant viral purification was performed first by 96-well plate duplication and IFA selection for the wells containing the most IFA positive plaques with the least amount of IFA negative plaques. Wells matching those criteria were then harvested and adjusted to 1 ml in DMEM+2% FBS. From the 1 ml stock, 5-20 ul were removed and mixed with $1 \times 10^7$ CEFs in 10 ml DMEM+2% FBS and aliquoted onto a new 96-well plate to have single HVT plaques per well. The supernatant of the wells that contained single plaques were tested for the absence of parental virus by PCR. After five rounds of plaque purification, a recombinant virus designated as vHVT114 was isolated and the purity was tested by IFA and PCR to confirm NDV-F expression and the absence of parental virus.

PCR Analysis of Recombinant vHVT114

DNA was extracted from vHVT114 by phenol/chloroform extraction, ethanol precipitated, and was resuspended in 20 mM HEPES. PCR primers (shown in Table 1) were designed to specifically identify the presence of the codon optimized NDV-F, the SV40 promoter, as well as, the purity of the recombinant virus from FC126 CL2 parental virus. PCR was performed using 200 ng of DNA template along with the specified primers pairs indicted in Table 1. PCR cycling conditions are as follows: 94° C. for 2 mins; 30 cycles of 94° C. for 30 secs, 55° C. for 30 secs, 68° C. for 3 mins; 68° C. for 5 mins. The expected PCR products are shown in Table 2. The PCR results are shown in FIG. 4. As shown in FIG. 4, the sizes of PCR products after gel electrophoresis correspond well with the expected sizes and the banding patterns.

TABLE 1

| primer | SEQ ID NO | Sequence 5'-3' |
|---|---|---|
| MB080 | 13 | CGA ACA AAC TTC ATC GCT ATG C |
| MB081 | 14 | TAA CTC AAA TGC GAA GCG TTG C |
| optF | 15 | ACT GAC AAC ACC CTA CAT GGC |
| VlloptF RP | 16 | GCC AGC ACC AGG CTC AGG G |
| SV40promoterF | 17 | AGC TTG GCT GTG GAA TGT |

TABLE 2

| Primer pairs | Expected size (bp) FC126 CL21 | vHVT114 |
|---|---|---|
| MB081 + VIIoptF.RP | — | 2138 |
| SV40promoterF + MB080 | — | 2368 |
| OptFprimer + MB080 | — | 872 |
| MB080 + MB081 | 323 | 2578 |

Expression Analysis of Recombinant vHVT114

Immunofluorescence testing was performed using the vHVT114 which was passaged over ten times beyond an experimental pre-master seed (pre-MSV). The pre-MSV and pre-MSV+12 materials were diluted 1:100 in media. Fifty microliters of the diluted virus was added to 10 ml of DMEM+2% FBS with $1\times10^7$ CEFs and then aliquoted onto a 96 well plate (100 ul/well). The plates were incubated for 3 days at 37° C.+5% $CO_2$ until viral plaques were visible. The plates were fixed with 95% ice-cold acetone for three minutes and washed three times with PBS. Chicken anti-sera against Newcastle Disease Virus (lot#C0139, Charles Rivers Laboratory) at 1:1000 were added along with monoclonal antibody L-78 (Merial Limited) at 1:3000 and the plates were incubated at 37° C. for 1 hour. After the 1 hour incubation the plates were washed three times with PBS and FITC anti-chicken (cat# F8888, Sigma) was added along with Alexz Fluor 568 donkey anti-mouse (IgG) (cat# A 10037, Molecular Probe) at 1:500. Again the plates were incubated at 37° C. for 1 hour. After the 1 hour incubation the cells were rinsed three times with PBS. A small amount of PBS was added to prevent the monolayer from drying and causing auto fluorescence. The cells were then visualized with a fluorescent microscope using both the tetramethylrhodamine isothiocyanate (TRITC) and fluorescein isothiocyanate (FITC) filters in combination.

The vHVT114 viral plaques were visualized using both the TRITC and FITC filters for the dual staining. The FITC test showed the NDV-F expression and the TRITC test showed the HVT expression. Because of the small wells of the 96 well plates, each well was recorded with the plaques first counted with the TRITC filter and then recounted with the FITC filter. Over 500 plaques were counted for the pre-MSV and pre-MSV+12 passage. All the plaques were positive for both the FITC and TRITC on both plates. (FIG. 5)

Southern Blot Analysis of Recombinant vHVT114

Total genomic DNA was extracted from HVT FC126 and vHVT114 according to the standard genomic DNA extraction protocol. For each restriction digest, 3 μg of genomic DNA (1 ng for the donor plasmid) was used with a total digestion volume of 20 μl for each sample. The genomic DNA of HVT FC126 (negative control), pHM103+Fopt donor plasmid, and vHVT114 were each digested overnight at 37° C. with BamHI, PstI, SphI, and NcoI restriction endonucleases. The restriction fragments of HVT FC126 (negative control), pHM103+Fopt donor plasmid, and vHVT114 genomic DNA were separated by a 1% agarose gel and transferred to a positively charged Nylon membrane. Following the North2South Chemiluminescent Hybridization and Detection Kit (Thermo Scientific) manufacturers' instructions, the membrane was pre-hybridized for 1 hr and then hybridized with a biotinylated NDV-F probe overnight at 55° C. Following the overnight hybridization, several stringency washes were performed until the membrane was placed in blocking buffer with the addition of Streptavidin-HRP. After rinsing the membrane of any unbound Streptavidin-HRP the substrate solution of Luminal and peroxide were added. The membrane was then exposed to X-ray film and developed. Areas where the biotinylated probe bound to the DNA were chemiluminescent and were captured by the X-ray film. Table 3 shows the expected Southern blot bands using the NDV-F probe. The Southern blot results showed the digestion patterns as expected (FIG. 6).

TABLE 3

| NDV-F Probe | | | |
|---|---|---|---|
| Restriction Endonuclease | Donor plasmid pHM103 + Fopt | vHVT114 | FC126 CL2 |
| BamHI | 7.014 | 6.630 | — |
| | 0.198 | 1.259 | |
| | | 0.198 | |
| PstI | 5.481 | 6.359 | — |
| | 0.947 | 0.947 | |
| | 0.784 | 0.784 | |
| SphI | 4.763 | 2.377 | — |
| | 2.377 | 2.119 | |
| | 0.072 | 0.072 | |
| NcoI | 4.931 | 3.753 | — |
| | 2.157 | 2.157 | |
| | 0.124 | 0.124 | |

Sequence Analysis of the Inserted Region in Recombinant vHVT114

Analysis of vHVT114 genomic DNA region was performed by PCR amplification. Total of 10 primers were used to amplify the entire cassette, as well as, beyond the flanking BamHI-I arms used in the donor plasmid. The 4.727 kb PCR product was gel purified and the entire fragment was sequenced using the sequencing primers. The sequence result confirmed that the vHVT114 contains the correct SV40 promoter, the codon-optimized NDV-F and the SV40 polyA sequences that match exactly the sequence described for the donor plasmid pHM103+Fopt in SEQ ID NO:18.

Western Blot Analysis of Recombinant vHVT114

Approximately $2\times10^6$ chicken fibroblast cells were infected at ~0.1 MOI with vHVT114 Pre-MSV. After two days of incubation at 37° C., infected as well as uninfected cells were harvested using a cell scraper after removing the media and rinsing with PBS. The cells were harvested with 1 ml of PBS and centrifuged. The cell pellets were lysed by following the Pierce Classic IP Kit (cat#26146, Thermo Scientific). 100 μl of the anti-NDV-F monoclonal antibody 001C3 (Merial Limited) was used to form the immune complex. The antibody/lysate sample was added to Protein A/G Plus Agarose to capture the immune complex. The immune complex was washed three times to remove non-bound material and then eluted in 50 ul volume using sample buffer elution under non-reducing condition. After boiling for 5 minutes, 10 μl of the samples were loaded into a 10% Acrylamide gel (Invitrogen). The PAGE gel was run in MOPS buffer (Invitrogen) at 200 volts for 1 hour. Then the gel was transferred onto a PVDF membrane.

The Protein Detector Western Blot Kit TMB System (KPL, cat#54-11-50) was used for blotting the PVDF membrane by using the reagents and following manufacturer's directions. After blocking the membrane for 1 hour at room temperature, the membrane was then rinsed three times in 1× Wash Buffer, five minutes each and then soaked in blocking buffer containing 1:1000 dilution of chicken serum raised against NDV virus (Lot # C0139, Charles River Laboratories). After washing three times in a washing buffer, the membrane was incubated with a peroxidase labeled goat anti-chicken IgG (KPL, cat#14-24-06) at a dilution of 1:2000 for 1 hour at room temperature. The membrane was then rinsed three times in 1× Wash Buffer, five minutes each. 5 ml of TMB membrane peroxidase substrate was added to the membrane and gently rocked for about 1 minute. The developing reaction was stopped by placing the membrane into water.

The immunoprecipitation and Western blot technique detected an approximately 55 kD protein in vHVT114 sample that corresponds to the expected size of F1 component of the NDV-F protein (FIG. 7).

Example 2

Construction of Recombinant vHVT110, vHVT111, vHVT112, vHVT113 and vHVT116 Expressing NDV-F Generation and characterization of HVT recombinants vHVT110, vHVT111, vHVT112, vHVT113, and vHVT116 was essentially done in the same way as for vHVT114 described in example 1. Table 4 shows the features unique to each construct around the expression cassettes, including the respective sequences.

TABLE 4

Characteristics of the expression cassettes of single HVT recombinants

| Name | Parental virus | Promoter | F gene | Poly-A | Locus |
|---|---|---|---|---|---|
| vHVT039 | HVT | MDV gB | Wtnm-Texas | SV40 | IG1 |
| vHVT110 | HVT | mCMV IE | Wt-VIId | SV40 | IG1 |
| vHVT111 | HVT | SV40 | Wt-VIId | SV40 | IG1 |
| vHVT112 | HVT | MCMV IE | Wt-YZCQ | SV40 | IG1 |
| vHVT113 | HVT | MCMV IE | Wt-Texas | SV40 | IG1 |
| vHVT114 | HVT | SV40 | Opt-VIId | SV40 | IG1 |
| vHVT116 | HVT | SV40 | Opt-Ca02 | SV40 | IG1 | vHVT110

The plasmid pCD046 (Merial proprietary material) containing the Intergenic I arms of HVT FC126, mouse CMV promoter and SV40 poly A was digested with NotI, dephosphorylated, and a 6.6 kb fragment was gel extracted. A NotI flanked 1.7 kb fragment of a chemically synthesized NDV-F gene containing wild-type F sequence (SEQ ID NO:3, coding for SEQ ID NO:4) was also NotI digested and the 1.7 kb fragment was gel extracted. The 6.6 and 1.7 kb fragments were ligated to create a donor plasmid pCD046+NDV-F wt (SEQ ID NO:21 for vHVT110) used in transfection to generate recombinant vHVT110. Sequencing of the insert region confirmed that vHVT110 contains the correct sequences of mCMV promoter, the wildtype NDV-F gene and the SV40 polyA. The sequence also exactly matches the sequence described for the donor plasmid pCD046+NDV-F wt in SEQ ID NO:21.

vHVT111

The plasmid pHM103 plasmid (Merial proprietary material) containing the Intergenic I arms of HVT FC126, SV40 promoter and SV40 polyA was digested with NotI, dephosphorylated, and the 5.6 kb fragment was gel extracted. A NotI flanked 1.7 kb fragment of a chemically synthesized NDV-F gene containing wildtype F sequence (SEQ ID NO:3, coding for SEQ ID NO:4) was also NotI digested and a 1.7 kb fragment was gel extracted. The 5.6 and 1.7 kb fragments were ligated to create a donor plasmid (SEQ ID NO:22 for vHVT1110) used in transfection to generate recombinant vHVT111. Sequencing of the insert region confirmed that vHVT111 contains the correct sequences of SV40 promoter, the wildtype NDV-F gene and the SV40 polyA as shown in the sequence of the donor plasmid pHM103+NDV-F wt (SEQ ID NO:22).

vHVT112

A fragment encompassing the synthetic NDV-F YZCQ wild type gene (SEQ ID NO:34 encoding SEQ ID NO:35) was excised from pUC57 NDV-F YZCQ plasmid (synthesized by GeneScript) using NotI and inserted into the same site of pCD046 plasmid containing mCMV promoter and SV40 polyA tail. Ligated material was transformed using Top10 Oneshot kit (cat#C404002, Invitrogen). Bacterial colonies were grown in LBamp broth, plasmid extracted by using Qiagens MiniSpin Prep kit, and screened for insert orientation. The correct donor plasmid was designated pCD046+NDV-F VII YZCQ. Large scale cultures were grown and plasmid extraction was done by using Qiagens Maxi Prep kit. Transient expression of the maxi preps was verified using Fugene Transfection Reagent in Chicken Embryo Fibroblast Cells (CEF's) and chicken polyclonal sera against NDV.

Plasmid pCD046+NDV-F VII YZCQ (SEQ ID NO:29) was used in transfection to generate recombinant vHVT112. Sequencing of the insert region confirmed that vHVT112 contains the correct sequences of mCMV promoter, the wildtype NDV-F YZCQ gene and the SV40 polyA. The sequence also exactly matches the sequence described for the donor plasmid pCD046+NDV-F VII YZCQ in SEQ ID NO:29.

vHVT113

A fragment encompassing the synthetic NDV Texas F gene (SEQ ID NO:36 encoding SEQ ID NO:37) was excised from pUC57 NDV Texas F plasmid (synthesized by GeneScript) using NotI and inserted into the same site of pCD046 plasmid containing mCMV promoter and SV40 polyA tail. Ligated material was transformed using Top10 Oneshot kit (cat#C404002, Invitrogen). Bacterial colonies were grown in LBamp broth, plasmid extracted by using Qiagens MiniSpin Prep kit, and screened for insert orientation. The correct donor plasmid was designated pCD046+Texas NDV-F. Large scale cultures were grown and plasmid extraction was done by using Qiagens Maxi Prep kit. Transient expression of the maxi preps was verified using Fugene Transfection Reagent in Chicken Embryo Fibroblast Cells (CEF's) and chicken polyclonal sera against NDV.

Plasmid pCD046+Texas NDV-F (SEQ ID NO:30) was used in transfection to generate recombinant vHVT113. Sequencing of the insert region confirmed that vHVT113 contains the correct sequences of mCMV promoter, the wild-type NDV-F Texas F gene and the SV40 polyA. The sequence also exactly matches the sequence described for the donor plasmid pCD046+Texas NDV-F in SEQ ID NO:30.

vHVT039

The MDV gB promoter (SEQ ID NO:38) was amplified from MDV1 RB1B strain extracted DNA by PCR using the primers HM101 (5'-CCG-GAA-TTC-CGA-TGT-TTA-GTC-ACG-ATA-GAC-3') (SEQ ID NO:44) and HM102 (5'-ATA-AGA-GCG-GCC-GCA-GTG-AGA-TGA-TCT-TAA-TGA-TG-3') (SEQ ID NO:45). The former contains an EcoRI site and the latter contains a NotI site for ligation of the EcoRI/NotI digested 630 bp PCR product into EcoRI/NotI digested pCD046 plasmid. The ligation product was used to transform DH5α competent cells. Colonies were picked and screened for the presence of the inserted PCR fragment by restriction analysis with EcoRI and NotI. The resulting plasmid was designated pHM102.

The velogenic NDV Texas strain (genotype IV) was grown on 11-day-old SPF embryonated eggs and semi-purified. Total RNA was extracted and an RT PCR was performed using two primers F-ATG (5' TAT-AGC-GGC-CGC-AAG-ATG-GGC-TCC-AGA-TCT-TCT-ACC-AG 3') (SEQ ID NO:46) and F-STOP (5' CGA-GGC-GGC-CGC-TCA-TAT-TTT-TGT-AGT-GGC-TCT-C 3') (SEQ ID NO:47). They allow the whole amplification of the NDV F gene with addition of NotI site upstream ATG and downstream STOP codons. The 1.7 kb PCR fragment was digested with NotI and ligated into NotI-digested pHM102. The resulting plasmid was designated pHM119 and was used as a donor plasmid in in vitro recombination study by co-transfection of CEF cells with HVT parental DNA to generate vHVT039 as described above. Sequencing of the insert region confirmed that vHVT039 contains the correct sequences of MDV gB promoter, the wildtype unmodified NDV-F gene from Texas strain (SEQ ID NO:32 encoding SEQ ID NO:33) and the SV40 polyA as shown in the partial sequence of the donor plasmid pHM119 (SEQ ID NO:31).

vHVT116

The plasmid pHM103 plasmid (Merial proprietary material) containing the Intergenic I arms of HVT FC126, SV40 promoter and SV40 polyA was digested with NotI, dephosphorylated, and the 5.6 kb fragment was gel extracted. A NotI flanked 1.7 kb fragment of a chemically synthesized, codon-optimized, CA02 genotype V NDV-F gene (SEQ ID NO:5, coding for SEQ ID NO:6) was also NotI digested and the 1.7 kb fragment was gel extracted. The 5.6 and 1.7 kb fragments were ligated to create pHM103+NDV-F CA02 (SEQ ID NO:23 for vHVT116) used in transfection to generate recombinant vHVT116. Sequencing of the insert region confirmed that vHVT116 contains the correct sequences of SV40 promoter, the codon-optimized CA02 NDV-F gene and the SV40 polyA as shown in the sequence of the donor plasmid pHM103+NDV-F wt (SEQ ID NO:23).

Discussion

Various cassettes under mCMV or non-CMV promoter were inserted at different loci of HVT genome (Table 4). Despite repeated attempts, generating a construct with a combination of mCMV and codon-optimized F sequence was not successful beyond passage 2. However, when wild-type sequence was driven by mCMV a stable construct, vHVT110 could be generated. In addition, recombinant vHVT111 with wild-type F sequence under SV40 promoter was also stable for more than 10 in vitro passages. Surprisingly, a codon-optimized F sequence under SV40 promoter was similarly found to be stable for more than 10 in vitro passages (e.g. vHVT114 and vHVT116). These results indicate the delicate balance between the strength of the promoter and the nature of the gene they control (codon-optimized or not optimized) in generating a genetically stable HVT construct.

Example 3

Construction of vHVT306, a Double HVT Vector Expressing NDV-F and IBDV VP2

The donor plasmid pHVT US2 SV-Fopt-synPA was constructed containing SV40 promoter, synthetic NDV F codon optimized VII gene, synthetic polyA tail flanked by the SORF3 and US2 arm sequences of HVT FC126.

Generation of Recombinant Virus

A standard homologous recombination procedure was followed by co-electroporation of secondary CEF cells using donor plasmid pHVT US2 SV-Fopt-synPA and viral DNA isolated from vHVT13 (an HVT vector expressing the IBDV VP2 gene, Merial Limited). Essentially the procedure described in example 1 for vHVT114 was followed to generate, plaque purify and characterize recombinants by immunofluorescence.

After five rounds of plaque purification, pure recombinant virus (vHVT306) was isolated and the purity of vHVT306 was tested and confirmed by IFA and PCR.

PCR Analysis

Viral DNA was extracted from vHVT306 pre-master seed virus (pre-MSV) stock by QIA DNeasy Blood & Tissue Kit (Qiagen cat#69506). PCR primers were designed to identify the presence of the NDV F optimized, the NDV F wild type, the SV40 promoter, the mCMV promoter, the flanking arms of US2 HVT virus and SB-1 virus.

PCR amplification with various primers confirmed that the vHVT306 has the expected amplification patterns and amplicons.

Expression Analysis

Indirect immunofluorescent assay (IFA) was performed on the vHVT306 pre-MSV stock. The CEFs that were inoculated with vHVT306 were fixed with ice-cold 95% acetone for three minutes at room temperature and air-dried for 10 min. After three washes with PBS, two primary antibodies, chicken anti-Newcastle Disease Virus sera (Charles Rivers Laboratories cat#10100641, lot#C0117A) at 1:500 dilution and L78 monoclonal antibody against HVT (Merial Select, Gainesville, Ga.) at 1:3000 dilution were added and incubated for 45 min at 37° C. After three washes with PBS, two secondary antibodies, goat anti-chicken IgG-fluorescein (KPL cat#.02-24-06, lot#110020) at 1:500 dilution and donkey anti-mouse IgG-Alexa Fluor 568 (Molecular Probe

A10037, lot#989784) at 1:300 dilution were added. The plates were incubated at 37° C. for 45 min and followed by three washes with PBS. The cells were observed to identify the IFA positive plaques with a fluorescent microscope using fluorescein isothiocyanate (FITC)- and tetramethylrhodamine isothiocyanate (TRITC)-filters of Nikon Eclipse Ti inverted microscope.

Similarly the expression of IBDV VP2 protein (SEQ ID NO:8 encoded by SEQ ID NO:7) of vHVT306 were examined by IFA using chicken anti-IBDV sera (Charles River Laboratories cat#10100610 lot#G0117) (1:500 dilution) and anti-NDV F monoclonal antibody 001C3 (Asceitic fluid, Batch 10/09/044, 02/11/2010) (1:300 dilution) as primary antibodies; followed by goat anti-chicken IgG-fluorescein (KPL cat#.02-24-06, lot#110020) (1:500 dilution) and donkey anti-mouse IgG-Alexa Fluor 568 (Molecular Probe #A10037, lot#989784) (1:300 dilution) as secondary antibodies.

IFA results indicate that vHVT306 expresses the NDV F genes in virus-infected CEFs.

Over 400 vHVT306 plaques were counted using the FITC-filter and TRITC-filter of microscope. The overall expression of NDV F gene and IBDV VP2 match with the HVT plaques (Table 5).

TABLE 5

Dual IFA of vHVT306

| Virus | IFA #1 (total 453 plaques) | | IFA#2 (total 478 plaques) | |
|---|---|---|---|---|
| | Anti-NDV serum positive plaques | Anti-HVT MAb positive plaques | Anti-NDV F MAb positive plaques | Anti-IBDV serum positive plaques |
| vHVT306 pre-MSV | 453 | 453 | 478 | 478 |

Southern Blot Analysis

Total genomic DNA was extracted from vHVT306 pre-MSV stock infected CEFs. The Southern blot analysis was performed according to the standard protocol.

A total 3 probes were used to confirm the NDV F cassette (SV40 promoter, NDV F codon optimized gene, synthetic polyA tail) between SORF3 and US2 of vHVT306 as well as retention of IBDV VP2 cassette (mCMV promoter, IBDV VP2 gene, SV40 poly A tail).

The Southern blot results showed the digestion patterns as expected based on Vector NTI (Invitrogen, 1600 Faraday Ave., Carlsbad, Calif.) map analysis. The NDV F cassette (SV40 promoter, NDV F codon optimized gene, synthetic poly A tail) is located between SORF3 and US2, and IBDV VP2 cassette (mCMV promoter, IBDV VP2 gene, SV40 poly A tail) is intact like the parent virus (vHVT13).

Genomic Analysis

The genomic DNA of vHVT306 pre-MSV stock was sequenced to verify the sequence of the recombination arm region as well as inserted gene cassette.

Primers were designed to amplify the entire inserted gene cassette including recombination arm used in donor plasmid. Analysis of vHVT306 genomic DNA was performed by PCR amplification and followed by nucleotide sequence determination.

The vHVT306 (donor plasmid pHVT US2 SV-Fopt-synPA) containing the recombinant arms, SV40 promoter and NDV F codon-optimized gene was confirmed to be correct as shown in SEQ ID NO:20.

Western Blot Analysis

The CEF monolayer was infected with vHVT306 pre-MSV at MOI ~0.1. After a 4-day incubation, the CEFs were pelleted and washed with PBS followed by lysis with IP Lysis/Wash buffer of Pierce Classic IP Kit (Thermo Scientific cat#26146) according to the manufacturer's protocols. The lysate was pre-cleared and incubated with 100 ul of anti-NDV F monoclonal antibody 001C3 to make the immune complex. The immune complex was captured by Protein A/G Plus Agarose and after removing of the un-bounded immune complex by washing steps, the 50 ul of sample buffer was used to elute under non-reducing conditions. The uninfected CEFs were included as controls. The 20 ul of eluted samples were separated in a 10% Bis-Tris Gels by electrophoresis. After the electrophoresis, the separated proteins were transferred onto PVDF membrane. The Protein Detection TMB Western Blot Kit (KPL cat#54-11-50) was used to detect the NDV antigens on PVDF membrane with chicken anti-NDV serum (Charles River Laboratories cat#10100641, lot#C0117A), and goat anti-chicken IgG-peroxidase conjugate (KPL. cat#414-24-06) following the manufacturers' protocols.

Figure 8:
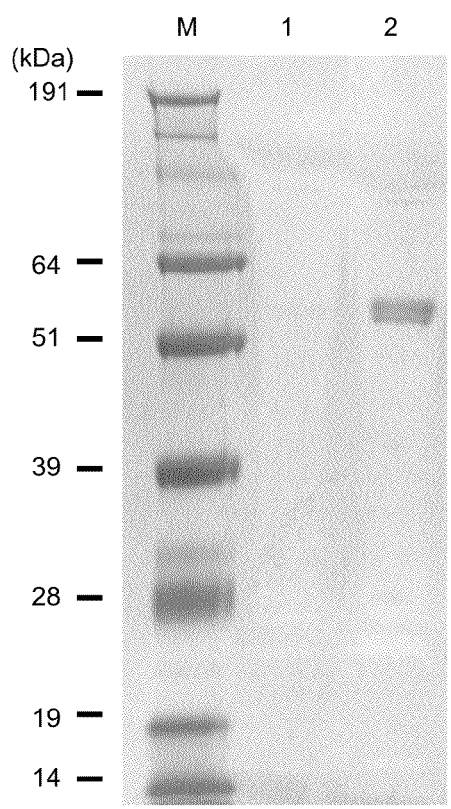
FIG. 8 depicts the Western blot analysis of immunoprecipitated sample from vHVT306 infected cells.

The NDV F protein expression of vHVT306 was confirmed by two-step immunodetection. First, the expressed NDV F proteins from vHVT306 infected CEF were captured by the immunoprecipitation using anti-NDV F monoclonal antibody 001C3. Subsequently Western blot analysis using anti-NDV polyclonal serum (Charles River Laboratories cat#10100641, lot#C0117A) was applied to detect the NDV F protein in the captured samples (NDV F protein-monoclonal antibody complex) (FIG. 8). A 55 kDa protein in vHVT306 pre-MSV lysates was detected by anti-NDV serum which corresponds to the expected size of NDV F1 fusion protein (FIG. 8).

Example 4

Construction of Double HVT Vectors vHVT301, vHVT302, vHVT303, vHVT304 and vHVT307 Expressing NDV-F and IBDV VP2, and Double HVT Vector vHVT202 Expressing IBDV VP2 Variants Example 4.1

Construction of vHVT301, vHVT302, vHVT303, vHVT304 and vHVT307

Generation and characterization of double HVT recombinants vHVT301, vHVT302, vHVT303, vHVT304, and vHVT307 were essentially done in the same way as for vHVT306 described in example 3. Table 6.1 shows the features unique to each construct around the expression cassettes, including the respective sequences.

TABLE 6.1

Characteristics of the expression cassettes of double HVT recombinants

| Name | Parental virus | Promoter | NDV-F gene | Poly-A | Locus |
|---|---|---|---|---|---|
| vHVT301 | vHVT13 | SV40 | Wt-VIId NDV-F | SV40 | IG2 |
| vHVT302 | vHVT13 | US10 | Opt-VIId NDV-F | US10 | US10 |
| vHVT303 | vHVT13 | US10 | Opt-V NDV-F | US10 | US10 |
| vHVT304 | vHVT13 | SV40 | Opt-VIId NDV-F | Synthetic | IG2 |

TABLE 6.1-continued

Characteristics of the expression cassettes of double HVT recombinants

| Name | Parental virus | Promoter | NDV-F gene | Poly-A | Locus |
|---|---|---|---|---|---|
| vHVT306 | vHVT13 | SV40 | Opt-VIId NDV-F | Synthetic | SORF3-US2 |
| vHVT307 | vHVT13 | SV40 | Opt-V NDV-F | Synthetic | SORF3-US2 | vHVT301

The plasmid pHVT IG2 SbfI (Merial proprietary material) containing the Intergenic 2 arm sequences of vHVT13 was digested with SmaI, dephosphorylated, and the 4.3 kb fragment was gel extracted. The donor plasmid pHM103+NDV-F wt containing an SV40 promoter, wildtype NDV-F genotype VIId, SV40 poly A tail was EcoRI and SalI digested, klenow treated, and the 2.3 kb fragment was gel extracted. The two fragments were ligated to create a donor plasmid pHVT IG2 SV Fwt SbfI (SEQ ID NO: 24) used in transfection to generate recombinant vHVT301.

vHVT302

A synthetically synthesized plasmid, pHVT US10 cds, containing the US10 arm sequences of vHVT13 was digested with NotI, dephosphorylated, and the 4.7 kb fragment was gel extracted. A NotI flanked 1.7 kb fragment of a chemically synthesized, codon-optimized, NDV-F genotype VIId was NotI digested and gel extracted. The two fragments were ligated to create a donor plasmid pHVT US10 cds F opt used in transfection to generate recombinant vHVT302. The transcription of the inserted F gene should be driven by the native US10 promoter and be stopped by the native US10 polyA signal. No exogenous promoter or polyA is added to express this insert. Sequencing of the insert region confirmed that vHVT302 contains the correct sequence of the codon-optimized VIId NDV-F gene as shown in the sequence of the donor plasmid pHVT US10 cds F opt (SEQ ID NO: 25).

vHVT303

The synthetically synthesized plasmid pHVT US10 cds containing the US10 arm sequences of vHVT13 was digested with NotI, dephosphorylated, and the 4.7 kb fragment was gel extracted. A NotI flanked 1.7 kb fragment of a chemically synthesized, codon-optimized, NDV-F genotype V was NotI digested and gel extracted. The two fragments were ligated to create a donor plasmid pHVT US10 cds F CAO2 opt used in transfection to generate recombinant vHVT303. As with vHVT302, the transcription of this inserted F gene should also be driven by the native US10 promoter and be stopped by the native US10 polyA signal. No exogenous promoter or polyA is added to express this insert. Sequencing of the insert region confirmed that vHVT303 contains the correct sequence of the codon-optimized NDV-F genotype V as shown in the sequence of the donor plasmid pHVT US10 cds F CA02 (SEQ ID NO: 26).

vHVT304

The donor plasmid pHVT IG2 SbfI containing the Intergenic 2 arm sequences of vHVT13 was digested with SbfI, dephosphorylated, and the 4.3 kb fragment was gel extracted. A synthetically synthesized plasmid containing an SV40 promoter+codon optimized NDV-F genotype VIId+synthetic polyA tail flanked by SbfI was digested with SbfI and the 2.3 kb fragment was gel extracted. The two fragments were ligated to create a donor plasmid pHVT IG2 SV Fopt syn tail used in transfection to generate recombinant vHVT304. Sequencing of the insert region confirmed that vHVT304 contains the correct sequences of SV40 promoter, the codon-optimized VIId NDV-F gene, and the synthetic poly A tail as shown in the sequence of the donor plasmid pHVT IG2 SV Fopt syn tail (SEQ ID NO:27).

vHVT307

The donor plasmid pHVT US2-SORF3 containing the US2 and SORF3 arm sequences of vHVT13 was digested with SbfI, dephosphorylated, and the 5.1 kb fragment was gel extracted. The plasmid SB-1 UL55 SV CaF syn tail SbfI containing an SV40 promoter+codon optimized NDV-F genotype V+synthetic polyA tail flanked by SbfI was digested with SbfI and the 2.3 kb fragment was gel extracted. The two fragments were ligated to create a donor plasmid pHVT US2 SV-FCA02 opt-synPA used in transfection to generate recombinant vHVT307. Sequencing of the insert region confirmed that vHVT307 contains the correct sequences of SV40 promoter, the codon-optimized VIId NDV-F gene, and the synthetic poly A tail as shown in the sequence of the donor plasmid pHVT US2 SV-FCA02 opt-synPA (SEQ ID NO: 28).

Discussion

One of the main goals of this work was to develop a multivalent avian Herpesvirus-based vector by incorporating multiple protective genes of interest to one avian Herpesvirus backbone (e.g. HVT). A prerequisite for this approach is to define expression cassettes containing appropriate promoter-gene-polyA combinations and evaluate for their genetic stability and ability to protect against the specific disease.

For the purpose of creating an efficacious MD-IBD-ND trivalent vector vaccine, either codon-optimized or non-optimized Newcastle Disease Virus (NDV)-F gene sequences were cloned into vHVT13 backbone (HVT-IBD, a licensed vaccine to simultaneously protect chickens against MD and IBD) under human CMV (mouse CMV is already used in vHVT13). All vHVT-IBD-F constructs under human CMV promoter lost F-protein expression within six passages whether or not the NDV-F sequence is codon-optimized and regardless of the insertion site. The loss of F protein expression was rapid (within two passes) when hCMV was combined with codon-optimized F protein as compared to a combination of hCMV with wild-type F-sequence (loss of F protein expression within 6 passages). Taken together, the data shows that human CMV is not an ideal promoter for the generation of stable HVT recombinants expressing NDV-F protein. Surprisingly, this example shows that SV40 promoter and HVT endogenous promoter (US10 promoter) generated stable HVT recombinants expressing NDV-F protein.

Example 4.2

Construction of vHVT202

Donor Plasmid HVT SORF3-US2 gpVar-Ewtsyn Construction

A fragment encompassing the synthetic Varient E wild type IBDV VP2 gene (SEQ ID NO:41 encoding SEQ ID NO:42) was excised from pUC57 Varient E wt plasmid (synthesized by GeneScript) using NotI and inserted into the same site of SORF3 and US2 plasmid containing gpCMV promoter and synthetic polyA tail. Ligated material was transformed using Top10 Oneshot kit (cat#C404002, Invitrogen). Bacterial colonies were grown in LBamp broth, plasmid extracted by using Qiagens MiniSpin Prep kit, and screened for insert orientation using SacI+HindIII digestion. The correct donor plasmid was designated pHVT SORF3-US2 gpVar-Ewt Syn. Table 6.2 shows the features unique to the construct around the expression cassettes, including the respective sequences.

Large scale cultures were grown and plasmid extraction was done by using Qiagens Maxi Prep kit. Transient expression of the maxi preps was verified using Fugene Transfection Reagent in Chicken Embryo Fibroblast Cells (CEF's) and chicken polyclonal sera against IBDV.

TABLE 6.2

Characteristics of the expression cassettes of double HVT recombinants

| Name | Parental virus | Promoter | IBDV VP2 gene | Poly-A | Locus |
|---|---|---|---|---|---|
| vHVT202 | vHVT306 | Guinea pig CMV | IBDV E VP2 | Synthetic | SORF3-US2 |

Recombinant Generation

A standard homologous recombination procedure was followed by co-electroporation of secondary CEF cells using pHVTSORF3-US2 gpVar-Ewt Syn donor plasmid and viral DNA isolated from vHVT306 and digested with SbfI. vHVT306, expressing classical VP2 of IBDV and NDV-F, was chosen as a parent to simplify the section process as described below. The variant E VP2 donor plasmid was designed to replace the F gene and recombinants were initially selected for the absence of F gene expression and later by PCR for the presence of variant E VP2. Co-electroporation was performed using $1\times10^7$ 2° CEF in 300 μl Opti-MEM and shocked at 150 volts with 950 capacitance in a 2 mm electroporation cuvette. The transfected cells were seeded into 96-well plate and incubated for 5-7 days. The cells grown in the 96-well plate were then duplicated into two 96-well plates and incubated for 5 more days. One set of 96-well plates was used for IFA using chicken polyclonal sera against NDV-F to identify positive wells containing the vHVT306 parents and another set of 96-well plates was used for recovering the infected cells from the IFA negative wells.

The recombinant viral purification methods were preformed first by 96-well plate duplication and IFA selection for the wells containing the most IFA negative (against NDV-F) plaques with the least amount of IFA positive plaques. Wells matching those criteria were then harvested and adjusted to 1 ml in DMEM+2% FBS. From the 1 ml stock 5-20 μl (depending on the number of visible plaques) were removed and mixed with $1\times10^7$ CEFs in 10 ml DMEM+2% FBS and aliquoted onto a new 96-well plate in an attempt to have single HVT plaques per well. The 96-well plates were duplicated after 4 days of incubation and wells that contained plaques were tested for the presence of recombinant HVT and absence of parental virus by IFA and PCR. Again the wells that appeared to have more recombinant virus and less parent virus, by comparing the PCR banding results, were harvested and adjusted to 1 ml and aliquoted onto new 96-well plates (the same as before). After five rounds of purification of virus infected cells, recombinant HVT carrying two IBDV VP2 proteins was isolated and the purity of the recombinant virus was tested by PCR to confirm the absence of parental virus.

Sequencing of the insert region confirmed that vHVT202 contains the correct sequences of guinea pig CMV promoter, the IBDV Varient E wildtype VP2 gene, and the synthetic poly A tail as shown in the sequence of the donor plasmid HVT SORF3-US2 gpVar-Ewtsyn (SEQ ID NO:39).

Analysis of Recombinant by PCR

DNA was extracted from a stock virus by phenol/chloroform extraction, ethanol precipitated, and resuspended in 20 mM HEPES. PCR primers were designed to specifically identify the Varient E wt gene, the promoter, the polyA, as well as, the purity of the recombinant virus from HVT parental virus. PCR was performed using 200 μg of DNA template along with the specified primers pairs indicated in Table 1. PCR cycling conditions are as follows (unless otherwise noted): 94° C.-2 min; 30 cycles of 94° C.-30 sec, 55° C.-30 sec, 68° C.-3 min; 68° C.-5 min.

Purity of recombinant virus was verified by PCR using primer pairs that are specific to the HVT flanking arms, the gpCMV promoter, the Varient E gene and the syn tail. Primers, specific to SB1, MDV serotype 2 (SB1US1.FP+ SB1Sorf4.RP) were also included in the analysis. The PCR results demonstrate that recombinant virus vHVT202 carries the intended expression cassette and the virus stock is free from detectable amounts of parental HVT virus.

Immunofluorescent Staining of Recombinant vHVT202 Virus Expressing Two VP2 Proteins of IBDV For immunofluorescence testing, the P3 material was diluted 1:100 in media. Approximately 50 μl of the diluted virus was added to 10 ml of DMEM+2% FBS with $1\times10^7$ CEFs and then aliquoted onto a 96 well plate (100 μl/well). The plates were incubated for 4 days at 37° C.+5% $CO_2$ until viral plaques were visible. The plates were fixed with 95% ice-cold acetone for three minutes and washed three times with PBS. One well was used for chicken anti-sera against Newcastle Disease Virus (lot#C0139, Charles Rivers Laboratory) at 1:1000 was added and the plates were incubated at 37° C. for 1 hour. The other well was used for chicken anti-sera against IBDV (lot#G0117) After one hour incubation, the plates were washed three times with PBS and FITC anti-chicken (cat# F8888, Sigma) was added at 1:500. Again the plates were incubated at 37° C. for 1 hour. After one hour incubation the cells were rinsed three times with PBS and visualized with a fluorescent microscope using fluorescein isothiocyanate (FITC) filter.

The immunofluorescent staining results indicate that vHVT202 exhibited a very strong expression of the VP2 protein when the polyclonal sera against both classical and variant E VP2 proteins were used.

Conclusion

Based on PCR and immunofluorescence analysis, vHVT202 is a recombinant HVT in which a VP2 gene of variant E IBDV under the control of gpCMV promoter was successfully inserted into a recombinant HVT background that already expresses the VP2 gene of classical IBDV. Consequently vHVT202 carries both VP2 genes of variant E and classical IBDV and it is free of any detectable parental vHVT306 virus.

Example 5

Construction of Recombinant vSB1-009, vSB1-004, vSB1-006, vSB1-007, vSB1-008, and vSB1-010 Expressing NDV-F Example 5.1

Construction of vSB1-009, vSB1-004, vSB1-006, vSB1-007, and vSB1-008

The aim of the study is to construct a recombinant SB-1 viral vector vSB1-009 in which an expression cassette containing SV40 promoter and Newcastle disease virus fusion protein (NDV-F) is inserted to replace UL44 coding sequence (gC) of SB-1.

A donor plasmid pSB1 44 cds SV FCAopt was constructed containing UL44 flanking arms of SB1 virus, SV40 promoter and NDV F codon optimized gene sequence (SEQ ID NO:5, coding for SEQ ID NO:6).

Generation of Recombinant Virus

A standard homologous recombination procedure was followed by co-electroporation of secondary CEF cells using donor plasmid pSB1 44 cds SV FCAopt and viral DNA isolated from SB-1 virus infected CEFs. Essentially the procedure described in example 1 for vHVT114 was followed to generate, plaque purify and characterize recombinants by immunofluorescence.

After five rounds of plaque purification, pure recombinant virus (vSB1-009) was isolated and the purity of vSB1-009 was tested by IFA and PCR to validate the appropriate insertion as well as no remnant parental virus.

PCR Analysis

Viral DNA was extracted from vSB1-009 pre-master seed virus (pre-MSV) stock by QIA DNeasy Blood & Tissue Kit (Qiagen cat#69506). PCR primers were designed to identify the presence of the NDV F optimized, the NDV F wild type, the SV40 promoter, the mCMV promoter, the UL44 flanking arms of SB-1 virus and HVT virus. PCR amplifications were performed using approximately 200 ng of DNA template along with the primer pairs.

PCR amplification with various primers confirmed that the vSB1-009 has the expected amplification patterns and amplicons.

Expression Analysis

Indirect immunofluorescent assay (IFA) was performed on the vSB1-009 pre-MSV stock to examine the expression of NDV F gene and SB-1 virus antigen. The CEFs that were inoculated with vSB1-009 were fixed with ice-cold 95% acetone for three minutes at room temperature and air-dried for 10 min. The plates were washed with PBS, then two primary antibodies, chicken anti-Newcastle Disease Virus sera (Charles Rivers Laboratories cat#10100641, lot#C0117A) at 1:500 dilution and Y5.9 monoclonal antibody against SB-1 virus (Merial Select, Gainesville, Ga.) at 1:3000 dilution were added and the plates were incubated for 45 min at 37° C. After three washes with PBS, two secondary antibodies, goat anti-chicken IgG-fluorescein (KPL cat#.02-24-06, lot#110020) at 1:500 dilution and donkey anti-mouse IgG-Alexa Fluor 568 (Molecular Probe #A10037, lot#989784) at 1:250 dilution were added. The plates were incubated at 37° C. for 45 min and followed by three washes with PBS. The wells were screened for IFA positive plaques with a fluorescent microscope using fluorescein isothiocyanate (FITC) and tetramethylrhodamine isothiocyanate (TRITC)-filters of Nikon Eclipse Ti inverted microscope. Similarly, reactivity of vSB1-009 with NDV F Mab was examined by Dual IFA using anti-MDV serum (Charles River Laboratories, cat#10100628, lot#D0111) (1/300 dilution) and anti-NDV F monoclonal antibody (1/300 dilution) as primary antibody. The goat anti-chicken IgG-fluorescein (KPL cat#.02-24-06, lot#110020) (1:500 dilution) and donkey anti-mouse IgG-Alexa Fluor 568 (Molecular Probe #A10037, lot#989784) (1:250 dilution) were used as secondary antibodies. The wells were observed to identify the IFA positive plaques with a fluorescent microscope using FITC- and TRITC-filters of Nikon Eclipse Ti inverted microscope.

IFA results indicate that vSB1-009 expresses the NDV F protein in virus-infected CEF. Over 500 vSB1-009 plaques were counted for NDV F protein expression as well as SB-1 virus specific protein expression with dual IFA. The expression of NDV F protein completely matched with SB-1 virus antigen expression in each virus plaque (Table 7).

TABLE 7

Dual IFA of vSB1-009

| Virus | Dual IFA plate#1 (total 189 plaques) | | Dual IFA plate#2 (total 361 plaques) | |
|---|---|---|---|---|
| | Anti-NDV serum positive plaques | Anti-SB-1 MAb positive plaques | Anti-NDV serum positive plaques | Anti-SB-1 MAb positive plaques |
| vSB1-009 pre-MSV | 189 | 189 | 361 | 361 |

NDV F Mab reactivity was confirmed by Dual IFA. Over 200 vSB1-009 plaques were examined for NDV F Mab reactivity as well as anti-MDV serum reactivity. The reactivity with NDV F Mab completely matched with anti-MDV serum reactivity in each virus plaque (Table 8).

TABLE 8

Reactivity of vSB1-009 with anti-NDV F Mab

| | Dual IFA (total 254 plaques) | |
|---|---|---|
| Virus | Anti-MDV serum positive plaques | Anti-NDV F MAb positive plaques |
| vSB1-009 pre-MSV | 254 | 254 |

Southern Blot Analysis

Total genomic DNA was extracted from vSB1-009 pre-MSV stock infected CEFs. The genomic DNA of vSB1-009, SB-1 virus (negative control), pSB1 44 cds SV FCA opt donor plasmid were digested at 37° C. with EcoRI, NcoI, and KpnI restriction endonucleases separately. The restriction fragments were separated by a 0.8% agarose gel electrophoresis and transferred onto a positively charged Nylon membrane. After transfer, the membrane was treated with 0.4M NaOH and then neutralized with 2×SSC-HCl buffer. The membrane was then air dried and UV crosslinked.

Following the North2South Chemiluminescent Hybridization and Detection Kit (Thermo Scientific cat#89880) manufacturers' instructions, the membrane was pre-hybridized for 1 hr and then hybridized with the probe at 55° C. for overnight. For hybridization, two probes were used; 1) the SbfI fragment of pSB1 44 cds SV FCA opt as NDV F cassette probe, 2) the SmaI-EcoRI fragment of pUC57 SB1 44 arm (GenScript) as recombination arm probe. After the overnight hybridization, several stringency washes were conducted until the membrane was placed in blocking buffer with the addition of Streptavidin-HRP. After rinsing the membrane of any unbound Streptavidin-HRP, the substrate solution of Luminal and peroxide were added. The membrane was then exposed to X-ray film and the film was developed.

The Southern blot results were as expected based on Vector NTI map analysis. The NDV F cassette (SV40 promoter, NDV-F CA02 codon optimized gene) replaced the UL44 coding sequences of SB-1 virus.

Genomic Analysis

The genomic DNA of vSB1-009 pre-MSV stock was conducted by nucleotide sequence determination of the region of recombination arm as well as inserted gene cassette. Primers were designed and used to amplify the entire NDV-F gene cassette including the recombination arms.

The vSB1-009 sequence (donor plasmid pSB1 44 cds SV FCAopt) containing the recombinant arms, SV40 promoter and NDV F codon-optimized gene was confirmed to be correct as shown in SEQ ID NO:19.

Western Blot Analysis

The CEF monolayer was infected with vSB1-009 pre-MSV at MOI ~0.1. After a 5-day incubation, the CEFs were pelleted and washed with PBS followed by lysis with IP Lysis/Wash buffer of Pierce Classic IP Kit (Thermo Scientific cat#26146) according to the manufacturers' protocols. The lysate was pre-cleared and incubated with 100 μl of anti-NDV F monoclonal antibody to make the immune complex. The immune complex was captured by Protein A/G Plus Agarose and after removing of the un-bounded immune complex by washing steps, the 50 μl of sample buffer was used to elute under non-reducing conditions. The uninfected CEFs were included as a control. The 20 μl of eluted samples were separated in 10% Bis-Tris gels by electrophoresis. After the electrophoresis, the separated proteins in a gel were transferred onto PVDF membrane. The Protein Detection TMB Western Blot Kit (KPL cat#54-11-50) was used to detect the NDV antigens onto PVDF membrane with chicken anti-NDV serum (Charles River Laboratories cat#10100641, lot#C0117A), and goat anti-chicken IgG-peroxidase conjugate (KPL cat#14-24-06) following the manufacturers' protocols.

The NDV F protein expression of vSB1-009 was confirmed by two-step immunodetection. First, the expressed NDV F proteins from vSB1-009 infected CEF lysate were captured by the immunoprecipitation using anti-NDV F monoclonal antibody 001C3. Subsequently Western blot analysis using anti-NDV polyclonal serum (Charles River Laboratories cat#10100641, lot#C0117A) was applied to detect the NDV F protein in the captured samples (NDV F protein-monoclonal antibody complex) (FIG. 9). An approximately 55 kDa protein in vSB1-007 pre-MSV lysates was detected by anti-NDV serum that corresponding the expected size of NDV F1 fusion protein (FIG. 9).

Generation and characterization of HVT recombinants vSB1-004, vSB1-006, vSB1-007 and vSB1-008 were essentially done in the same way as for vSB1-009 described in this example. Table 9.1 shows the features unique to each construct around the expression cassettes, including the respective sequences. The generation and characterization of recombinant SB1 viral vectors were also described in U.S. patent application Ser. No. 13/689,572 filed on Nov. 29, 2012 (Merial limited), which is incorporated herein by reference in its entirety.

TABLE 9.1

Characteristics of the expression cassettes of SB1 recombinants

| Name | Parental virus | Promoter | F gene | Locus |
|---|---|---|---|---|
| vSB1-009 | SB1 | SV40 | Opt-CA02 | UL44 (gC) |
| vSB1-004 | SB1 | mCMV IE | Wt-VIId | US10 |
| vSB1-006 | SB1 | SV40 | Opt-VIId | UL55/LORF5 |
| vSB1-007 | SB1 | SV40 | Opt-VIId | UL44 (gC) |
| vSB1-008 | SB1 | SV40 | Opt-CA02 | UL55/LORF5 |

Example 5.2

Construction of Double Construct vSB1-010

Donor Plasmid SB1US2 gpVIIdwtsyn Construction

Using the plasmid HVT SOrf3-US2 gpVar-Ewt Syn, the gpCMV, Varient E, Syn tail was removed by SbfI digestion. This fragment was ligated into the SB1 US2 donor plasmid. The Varient E gene was cut out by NotI and replaced by NDV-F VIId wt. The synthetic NDV-F VIId wild type gene (SEQ ID NO:3 encoding SEQ ID NO:4) was excised from pUC57 NDV-F VIId wt plasmid (synthesized by GeneScript) using NotI digestion. Ligated material was transformed using Top10 Oneshot kit (cat#C404002, Invitrogen). Bacterial colonies were grown in LBamp broth, plasmid extracted by using Qiagens MiniSpin Prep kit, and screened for insert orientation using NcoI+SalI digestion. The correct donor plasmid was designated pSB1 US2 gpVIIdwt Syn. Table 9.2 shows the features unique to the construct around the expression cassettes, including the respective sequences. Large scale cultures were grown and plasmid extraction was done by using Qiagens Maxi Prep kit. Transient expression of the maxi preps was verified using Fugene Transfection Reagent in Chicken Embryo Fibroblast Cells (CEF's) and chicken polyclonal sera against NDV-F.

Recombinant Generation

A standard homologous recombination procedure was followed by co-electroporation of secondary CEF cells using pSB1 US2 gpVIIdWt Syn donor plasmid and viral DNA isolated from vSB1-009 (vSB1-009 is already a recombinant virus expressing CA02 F gene of NDV). Essentially the procedure described in example 1 for vHVT114 was followed to generate, plaque purify and characterize recombinants by immunofluorescence.

After five rounds of plaque purification, pure recombinant virus (vSB1-010) was isolated and the purity of vSB1-010 was tested by IFA and PCR to validate the appropriate insertion as well as no remnant parental virus.

TABLE 9.2

Characteristics of the expression cassette of vSB1-010

| Name | Parental virus | Promoter | F gene | Locus |
|---|---|---|---|---|
| vSB1-010 | vSB1-009 | Guinea pig CMV | NDV-F VIId | SORF4-US2 |

Sequencing of the insert region confirmed that vSB1-010 contains the correct sequences of guinea pig CMV promoter and the NDV-F VIId wt gene as shown in the sequence of the donor plasmid SB1US2 gpVIIdwtsyn (SEQ ID NO:40).

Analysis of Recombinant by PCR

DNA was extracted from a stock virus by phenol/chloroform extraction, ethanol precipitated, and resuspended in 20 mM HEPES. PCR primers were designed to specifically identify the NDV-F VIId wt gene, the promoter, the polyA, as well as, the purity of the recombinant virus from SB1 parental virus. PCR was performed using 200 μg of DNA template along with the specified primers pairs indicted in Table 1. PCR cycling conditions are as follows (unless otherwise noted): 94° C.-2 min; 30 cycles of 94° C.-30 sec, 55° C.-30 sec, 68° C.-3 min; 68° C.-5 min.

Purity of recombinant virus was verified by PCR using primer pairs that are specific to the SB1 flanking arms, the gpCMV promoter, the NDV-F VIId wt gene and the syn tail. Primers, specific to HVT, MDV serotype 3 (MB080+MB081) were also included in the analysis. The PCR results demonstrate that recombinant virus vSB1-010 carries the intended expression cassette and the virus stock is free from detectable amounts of parental SB1-009 virus.

Immunofluorescent Staining of Recombinant vSB1-010 Virus Expressing Two NDV-F Proteins For immunofluorescence testing, the P3 material was diluted 1:100 in media. Approximately 50 μl of the diluted virus was added to 10 ml of DMEM+2% FBS with $1\times10^7$ CEFs and then aliquoted onto a 96 well plate (100 μl/well). The plates were incubated for 5 days at 37° C.+5% $CO_2$ until viral plaques were visible. The plates were fixed with 95% ice-cold acetone for three minutes and washed three times with PBS. Chicken anti-sera against Newcastle Disease Virus (lot#C0139, Charles Rivers Laboratory) at 1:1000 was added and the plates were incubated at 37° C. for 1 hour. After one hour incubation, the plates were washed three times with PBS and FITC anti-chicken (cat# F8888, Sigma) was added at 1:500. Again the plates were incubated at 37° C. for 1 hour. After one hour incubation the cells were rinsed three times with PBS and visualized with a fluorescent microscope using fluorescein isothiocyanate (FITC) filter.

The immunofluorescent staining results indicate that vSB1-010 exhibited a very strong expression of the NDV-F protein when the polyclonal sera against both CA02 and VIId F proteins of NDV were used.

Conclusion

Based on PCR testing and immunofluorescence analysis, vSB1-010 is a recombinant SB-1 in which VIId-F gene of NDV under the control of gpCMV promoter was successfully inserted into a vSB1-009, which already expresses the CA02-F gene of NDV. Consequently vSB1-010 carries both VIId and CA02 F genes of NDV genotypes and it is free of any detectable parental vSB1-009.

Example 6

Efficacy of vHVT110, vHVT111, vHVT114 and vSB1-004 Expressing the NDV F Gene Against Challenges with NDV Chimalhuacan and Malaysian (MAL04-01) Strains at 14 Days of Age in SPF Chickens The aim of the study was to assess the efficacy of three HVT recombinant constructs (vHVT110, vHVT111 and vHVT114) and one SB1 recombinant construct (vSB1-004) expressing the NDV F gene against Newcastle disease challenges (Chimalhuacan and Malaysian virus strains) performed at 14 days of age in SPF chickens.

The characteristics of these 5 vaccine candidates are described in Table 10 below.

TABLE 10

Characteristics of the vectors used in the challenge study

| Name | Parental virus | Promoter | F gene | Poly-A | Locus |
|---|---|---|---|---|---|
| vHVT110 | HVT | mCMV IE | Wt-VIId | SV40 | IG1 |
| vHVT111 | HVT | SV40 | Wt-VIId | SV40 | IG1 |
| vHVT114 | HVT | SV40 | Opt-VIId | SV40 | IG1 |
| vSB1-004 | SB-1 | mCMV IE | Wt-VIId | SV40 | US10 |

On D0, 100 one-day-old SPF chickens were randomly allocated into 10 groups of 10 birds. The birds were injected by subcutaneous injection in the neck at D0 with 0.2 mL of recombinant vaccines containing a target dose of 2000 pfu as described in Table 11 below. It should be mentioned that the titer of vSB1-004 (31600 pfu) administered to birds of groups 6 was well above the target. The birds were challenged by the intramuscular route on D14 with velogenic ND Malaysia (genotype VIId) strain (sub-groups "a") or with virulent ND Chimalhuacan (genotype V) strain (sub-groups "b").

TABLE 11

Challenge study with vHVT110, vHVT111, vHVT114 and vSB1-004

| Group | Vaccine at day-old (D0) | NDV serology at D14* | % protection against mortality/ morbidity after Newcastle challenge at 14 days of age (D14): Malaysian strain | Chimalhuacan strain |
|---|---|---|---|---|
| G1a | — | 0/10 | 0%/0% | — |
| G1b | — | | — | 0%/0% |
| G2a | vHVT110 | 7/10 | 100%/89% | — |
| G2b | vVHT110 | | | 100%/70% |
| G3a | vHVT111 | 2/10 | 30%/20% | — |
| G3b | vHVT111 | | — | 67%/11% |
| G4a | vHVT114 | 9/10 | 100%/100% | — |
| G4b | vHVT114 | | — | 89%/89% |
| G5a | vSB1-004 | 3/10 | 70%/50% | — |
| G5b | vSB1-004 | | — | 40%/30% |

*Number of birds positive by NDV HI test/total tested

Each group was monitored before and after challenge. Clinical signs after challenge were scored daily as follows: healthy/with specific symptoms (ruffled feathers, prostration, torticollis, tremor)/dead. On D14, serum samples were taken in each group for serology (Newcastle Disease virus hemagglutination inhibition (HI) test).

As expected, the unvaccinated animals (G1a and G1b) displayed no NDV antibodies on D14. A low titer seroconversion (mean HI titer <0.6 log 10) was obtained in each vaccinated group (sub-groups "a" and "b" of G2 to G5) confirming the vaccine takes. The number of positive birds/total tested was group-dependent and was the highest (90%) in vHVT114 vaccinated birds (see Table above).

Percentages of protection against mortality and morbidity are reported in the table above. Full susceptibility was observed in the control groups G1a and G1b thus validating the high severity of both challenges. Lowest protection levels were observed in the groups vaccinated with vHVT111 or vSB1-004. Highest protection rates against morbidity and mortality were obtained in the groups vaccinated with vHVT110 or vHVT114 whatever the challenge strain used (homologous strain i.e. Malaysian genotype VIId or heterologous strain i.e. Chimalhuacan genotype V). There was a correlation between the % of birds positive by HI test before challenge and the % protection.

The difference of protection obtained between vHVT110 and vHVT111 clearly illustrates the importance of the promoter, the mCMV IE promoter being more potent than the SV40 promoter for the transcription of the wild type (wt) genotype VIId F gene. The difference of protection obtained between vHVT111 and vHVT114 illustrates the importance of the nucleotide sequence of the F gene, the optimized sequence being more potent than the wild type (or native) sequence.

In conclusion, the results of this study showed the importance of the promoter and the nucleotide sequence of the F gene in the ND protection induced by Marek's disease vector vaccines. An optimal combination of these factors needs to be found to reach the best efficacy performances as for vHVT114.

Example 7

Efficacy of vHVT114, vHVT116, vHVT301, vHVT302 and vHVT303 Expressing the NDV F Gene Against Challenges with NDV Texas GB Strain at 14 Days of Age in SPF Chickens The aim of the study was to assess the efficacy of 2 single HVT recombinant constructs (vHVT114 and vHVT116)

expressing the NDV F gene and 3 double HVT recombinant constructs (vHVT-301, vHVT302 and vHVT303) expressing both NDV F and IBDV VP2 genes against Newcastle disease challenge (Texas GB strain, genotype II) performed at 14 days of age in SPF chickens.

The characteristics of these 4 vaccine candidates are described in Table 12 below.

TABLE 12

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vHVT116 | HVT | SV40 | Opt-V | SV40 | IG1 |
| vHVT301 | vHVT13* | SV40 | Wt-VIId | SV40 | IG2 |
| vHVT302 | vHVT13 | US10 | Opt-VIId | US10 | US10 |
| vHVT303 | vHVT13 | US10 | Opt-V | US10 | US10 |

*vHVT13 is the active ingredient of the licensed Vaxxitek HVT-IBD vaccine based on an HVT vector expressing the IBDV VP2 gene (see U.S. Pat. No. 5,980,906 and EP 0 719 864).

On D0, 120 one-day-old SPF chickens were randomly allocated into 6 groups of 20 birds. The birds were injected by subcutaneous injection in the neck at D0 with 0.2 mL of recombinant vaccines containing a target dose of 1000 pfu as described in Table 13 below. The birds were challenged by the intramuscular route on D14 with 4.5 log 10 EID50 velogenic ND Texas GB (genotype II) strain.

TABLE 13

Results of efficacy

| Group | Vaccine at day-old (D0) | % clinical protection (number infected/total) after Newcastle challenge at 14 days of age (D14) |
|---|---|---|
| G1 | — | 0% (20/20) |
| G2 | vHVT114 | 80% (4/20) |
| G3 | vHVT116 | 70% (6/20) |
| G4 | vHVT301 | 15% (17/20) |
| G5 | vHVT302 | 52.6% (9/19)* |
| G6 | vHVT303 | 15% (17/20) |

*1 bird died before challenge

Each group was monitored before and after challenge. NDV clinical signs and mortality were recorded after challenge.

Percentages of clinical protection are reported in the table above. Full susceptibility was observed in the non-vaccinated challenged control group G1 thus validating the high severity of both challenges. Partial protection was observed for the 5 vaccine candidates, the best performances being obtained with vHVT114 and vHVT116. Among the double HVT recombinants, the vHVT302 was the most protective. It performed better than vHVT303 suggesting that the optimized genotype VIId NDV F gene may be better cross-protective against genotype II challenge than the optimized genotype V NDV F gene. A similar tendency was observed with single HVT, the vHVT114 (VIId gene) performing slightly better than vHVT116 (V gene) but the difference was less pronounced. These results indicated that both genotypes VIId and V NDV F genes inserted in the HVT vector provide cross-protection against a heterologous genotype II NDV challenge; the VIId gene may potentially be more cross-protective. The vHVT302 induced a better ND protection than vHVT301 confirming the importance of the promoter, poly-A and locus of insertion. In conclusion, the results of this study showed the very good early ND protection induced by tested Marek's disease vector vaccines, especially for the tested single HVT-ND.

Example 8

Efficacy of vHVT114, vHVT116, vSB1-007, vSB1-008 (Alone or with vHVT13) and vHVT 304 Against Challenges with NDV ZJ1 (Genotype VIId) and California/02 (Genotype V) at 21 Days of Age in SPF Chickens The aim of the study was to assess the efficacy of 2 single HVT recombinant constructs (vHVT114 and vHVT116), 2 SB1 recombinant constructs (vSB1-007 & vSB1-008) expressing the NDV F gene and a double HVT recombinant (vHVT304) against Newcastle disease challenge with NDV ZJ1 (genotype VIId) and California/02 (genotype V) performed at 21 days of age in SPF chickens.

The characteristics of these 5 vaccine candidates are described in Table 14 below.

TABLE 14

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vHVT116 | HVT | SV40 | Opt-V | SV40 | IG1 |
| vSB1-007 | SB-1 | SV40 | Opt-VIId | gC | UL44 (gC) |
| vSB1-008 | SB-1 | SV40 | Opt-V | SV40 | IG1 |
| vHVT304 | vHVT13* | SV40 | Opt-VIId | Synth | IG2 |

*vHVT13 is the active ingredient of the licensed Vaxxitek HVT-IBD vaccine based on an HVT vector expressing the IBDV VP2 gene (see U.S. Pat. No. 5,980,906 and EP 0 719 864).

On D0, 158 one-day-old SPF chickens were randomly allocated into 6 groups of 24 birds (vaccinated) and 1 group of 12 birds (non-vaccinated controls). The birds were injected by subcutaneous injection in the neck at D0 with 0.2 mL of recombinant vaccines containing a target dose of 1000 pfu as described in Table 15 below. The birds were then separated into two sub-groups, each sub-group being challenged by the intramuscular route on D21 with 5 log 10 EID50 of either NDV ZJ1 (genotype VIId) or California/02 (genotype V) velogenic strain.

TABLE 15

Results of efficacy

| | | % clinical protection | |
|---|---|---|---|
| Group | Vaccine at day-old (D0) | CA/02 (genotype V) | ZJ1 (genotype VIId) |
| G1 | — | 0% | 0% |
| G2 | vHVT114 | 100% | 100% |
| G3 | vHVT116 | 100% | 90% |
| G4 | vSB1-007 | 92% | 100% |
| G5 | vSB1-008 | 100% | 100% |
| G6 | vSB1-008 + vHVT13 | 100% | 83% |
| G7 | vHVT304 | 92% | 75% |

Each group was monitored before and after challenge. Technical problems observed with isolators reduced the number of birds in group 2 (vHVT114: from 24 to 14) and in group 3 (vHVT116: from 24 to 20). NDV clinical signs were recorded after challenge. Serum was collected from blood samples taken from birds of groups 2 and 7 before challenge (D21) for NDV serology by HI test using each challenge strains as antigen.

Mean serologic HI titers in G2 and G7 before challenge are shown in FIG. 10. HI titers were higher with the ZJ1 antigen in both groups. The HI titers induced by vHVT114 were higher than those induced by vHVT304.

Percentages of protection against mortality and morbidity are reported in the table above. Full susceptibility was observed in the non-vaccinated challenged control group G1 thus validating the high severity of both challenges. All vaccines induced high levels (≥75%) of protection against both challenges. Full clinical protection against both challenges was induced by vHVT114 and vSB1-008. Following a similar tendency as the HI titers, the ND protection induced by vHVT304 was slightly lower than that induced by vHVT114.

Figure 11A:
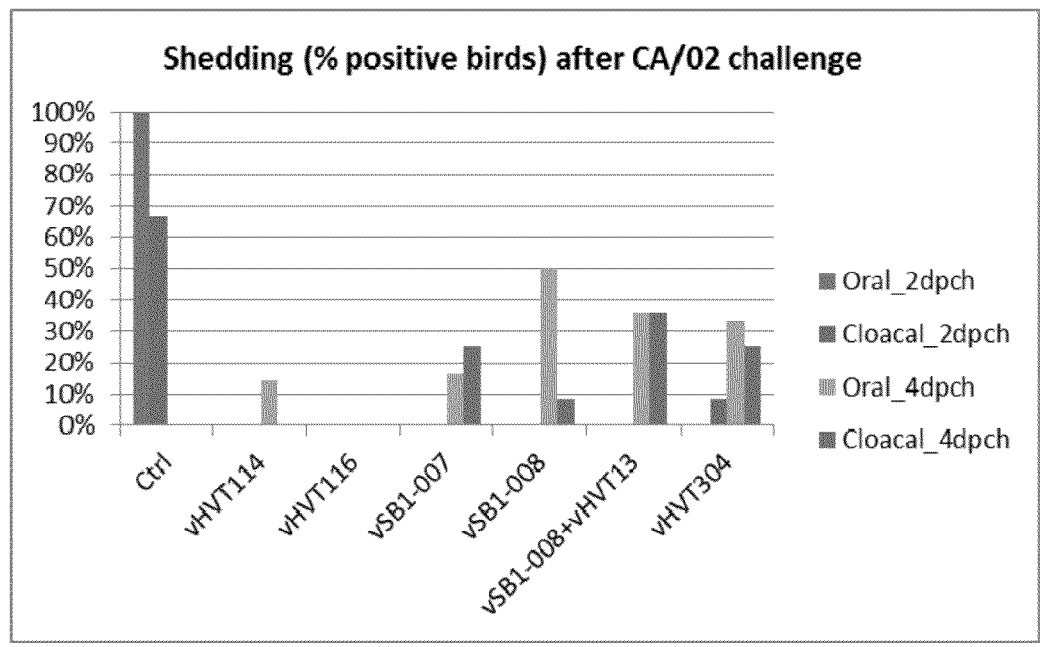
FIG. 11A depicts the vial shedding result after CA/02 challenge.
Figure 11B:
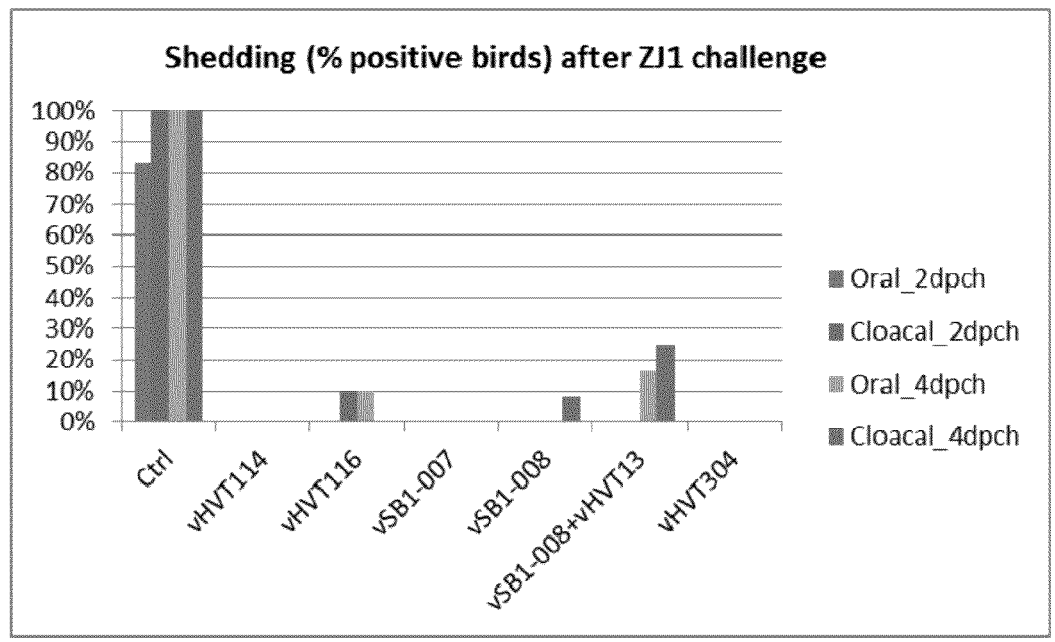
FIG. 11B depicts the vial shedding result after ZJ1 challenge.

The shedding was evaluated after challenge by real time RT-PCR in oral and cloacal swabs taken 2 and 4 days post-challenge. Percentage of positive (Ct<40) birds are shown for both challenges in FIGS. 11A and 11B. Note that all 6 birds were dead at 4 dpch in the control group challenged with the CA/02 isolate and only one bird (out of 6) was still alive at 4 dpch in the control group challenged with ZJ1. Shedding was detected in all control birds. Reduction of the percentage of birds positive for shedding was observed in all vaccinated groups.

In conclusion, the results of this study showed the very good ND protection at 3 weeks of age induced by tested Marek's disease vector vaccines.

Example 9

Efficacy of vHVT114, vSB1-007, vSB1-009, vHVT306 and vHVT307 Vaccines Against Challenges with NDV Texas GB Strain at 28 Days of Age in SPF Chickens The aim of the study was to assess the efficacy of combinations of different Marek's disease vector vaccines expressing the NDV F and/or the IBDV VP2 gene against Newcastle disease challenge (Texas GB strain, genotype II) performed at 28 days of age in SPF chickens.

The characteristics of the 5 recombinant vaccine candidates tested in this study are described in Table 16 below.

TABLE 16

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vSB1-007 | SB-1 | SV40 | Opt-VIId | gC | UL44 (gC) |
| vSB1-009 | SB-1 | SV40 | Opt-V | gC | UL44 (gC) |
| vHVT306 | vHVT13 | SV40 | Opt-VIId | Synth | SORF3-US2 |
| vHVT307 | vHVT13 | SV40 | Opt-V | Synth | SORF3-US2 |

The Marek's disease virus serotype 1 (CVI988 (or Rispens) strain; Gallid herpesvirus 2) and serotype 2 (SB-1 strain; gallid herpesvirus 3) vaccines were used also in combination with recombinant viruses in some of the groups.

On D0, 135 one-day-old SPF chickens were randomly allocated into 9 groups of 15 birds. The birds were injected by subcutaneous injection in the neck at D0 with 0.2 mL containing a target dose of 2000 pfu for recombinant vaccines (vSB1-007, vSB1-009, vHVT13, vHVT306, vHVT307, vHVT114), and 1000 pfu for parental Marek's disease vaccine strains (SB-1 and CVI988). The design of the 9 groups is shown in Table 17 below. The birds were challenged by the intramuscular route on D28 with 4.0 log 10 EID50 velogenic ND Texas GB (genotype II) strain.

TABLE 17

Results of efficacy

| Group | Vaccine at day-old (D0) | % ND protection after Newcastle disease challenge at 28 days of age |
|---|---|---|
| G1 | — | 0% |
| G2 | vSB1-007 + vHVT13 | 80% |
| G3 | vSB1-009 | 100% |
| G4 | vSB1-009 + vHVT13 | 86% |
| G5 | vSB1-009 + vHVT13 + CVI988 | 93% |
| G6 | vHVT306 + SB-1 | 100% |
| G7 | vHVT307 | 100% |
| G8 | vHVT307 + SB-1 | 93% |
| G9 | vHVT114 + vHVT13 + SB-1 | 100% |

Each group was monitored before and after challenge. NDV clinical signs after challenge were recorded.

Percentages of protection against mortality and morbidity are reported in the table above. Full susceptibility was observed in the non-vaccinated challenged control group G1 thus validating the high severity of challenge. Excellent levels of protection were observed in all vaccinated groups. Birds from G3, G6, G7 and G9 were fully protected. This study shows that the vSB1-ND candidates can be co-administered with vHVT13 and CVI988 and still provide a very good ND protection. Similarly, double HVT-IBD+ND are compatible with SB-1 and vHVT-ND (vHVT114) is compatible with vHVT13 and SB-1.

In conclusion, the results of this study showed the lack of interference on ND protection induced by the tested Marek's disease parental and vector vaccines.

Example 10

Efficacy of vHVT114, vHVT307, vSB1-007 and vSB1-009 in Combination with vHVT13 Against Challenges with NDV Chimalhuacan Strain (Genotype V) at D28 in SPF Chickens The aim of the study was to assess the efficacy of 1 HVT recombinant construct (vHVT114) and 2 SB 1 recombinant constructs (vSB1-007 and vSB1-009) expressing the NDV F gene in combination with vHVT-IBD (vHVT13), as well as a double HVT vHVT307 expressing both NDV F and IBDV VP2 against Newcastle disease challenge (Chimalhuacan, genotype V) performed at 28 days of age in SPF chickens.

The characteristics of these 4 vaccine candidates are described in Table 18 below.

TABLE 18

Characteristics of the vectors used in the challenge study

| Name | Parental virus | Promoter | F gene | Poly-A | Locus |
|---|---|---|---|---|---|
| vHVT114 | HVT | SV40 | Opt-VIId | SV40 | IG1 |
| vSB1-007 | SB-1 | SV40 | Opt-VIId | gC | UL44 (gC) |
| vSB1-009 | SB-1 | SV40 | Opt-V | gC | UL44 (gC) |
| vHVT307 | vHVT13 | SV40 | Opt-V | Synth | SORF3-US2 |

On D0, 45 one-day-old SPF chickens were randomly allocated into 4 groups of 10 birds and 1 group of 5 birds (unvaccinated control group). The birds were injected by subcutaneous injection in the neck at D0 with 0.2 mL of recombinant vaccines containing a target dose of 2000 pfu as described in Table 19 below. The birds were challenged by the intramuscular route on D28 with 5.0 log 10 EID50 velogenic Chimalhuacan (genotype V) strain.

TABLE 19

Results of efficacy

| Group | Vaccine at day-old (D0) | % protection against mortality | % protection against morbidity |
|---|---|---|---|
| G1 | — | 0% | 0% |
| G2 | vHVT114 + vHVT13 | 100% | 100% |
| G3 | vHVT307 | 80% | 80% |
| G4 | vSB1-007 + vHVT13 | 90% | 90% |
| G5 | vSB1-009 + vHVT13 | 90% | 90% |

Each group was monitored before and after challenge. NDV clinical signs were recorded after challenge. Oropharyngeal swabs were taken in the vaccinated groups at 5 and 7 days post-challenge to evaluate the viral load by real time RT-PCR.

Percentages of protection against mortality and morbidity are reported in the table above. Full susceptibility was observed in the non-vaccinated challenged control group G1 thus validating the high severity of challenge. Very good protection was observed in all 4 vaccinated groups, a full clinical protection being induced by vHVT114+vHVT13.

Figure 12A:
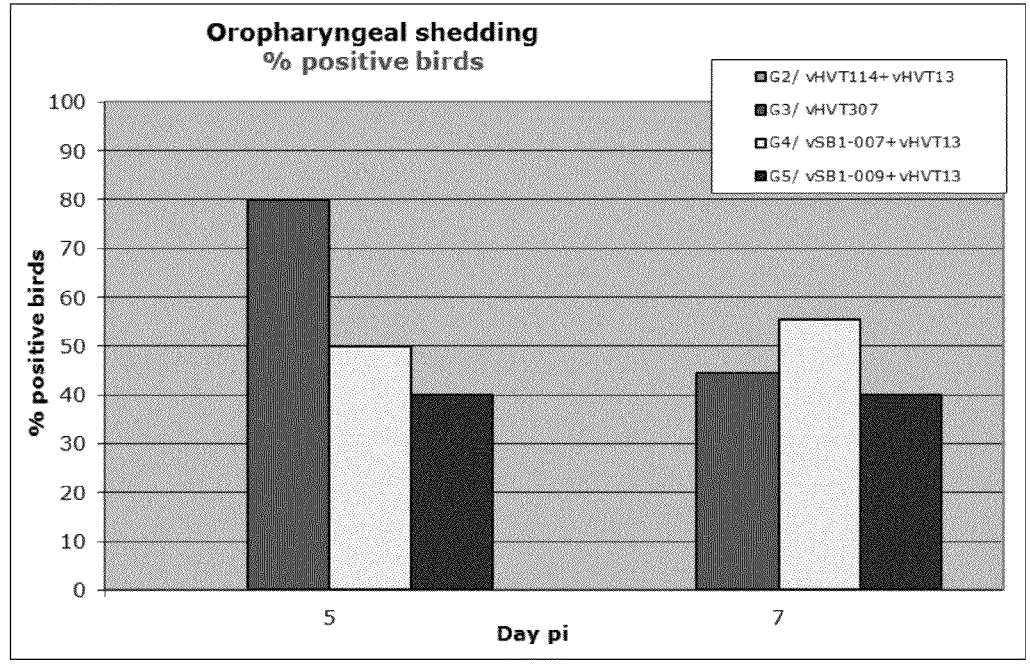
FIG. 12A and FIG. 12B depict the viral shedding result after NDV Chimalhuacan challenge.
Figure 12B:
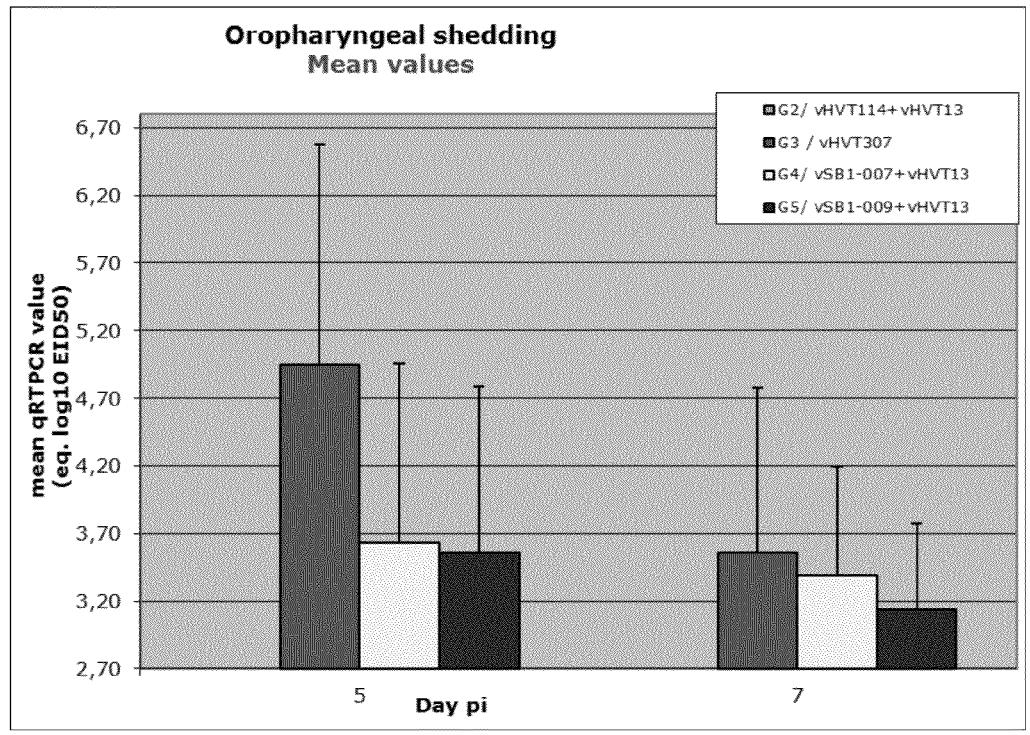
Figure 14:
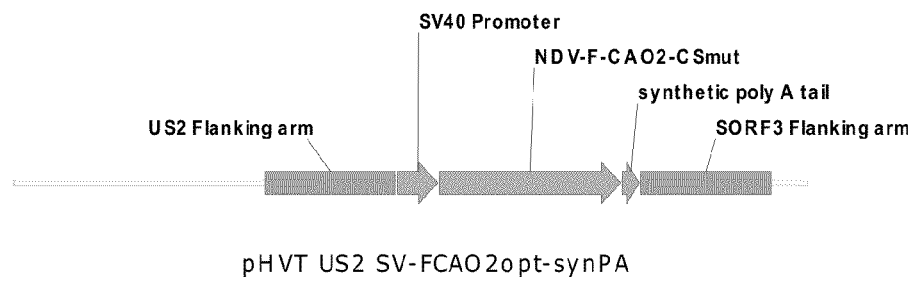
FIG. 14 shows the DNA and protein sequences.

The percentage of positive birds and the mean shedding titer (expressed as log 10 EID50 equivalent per mL) are shown in FIGS. 12A and 12B. Surprisingly, no shedding was detected in G2 indicating a complete (against both clinical signs and shedding) ND protection induced by vHVT114 even if co-administered with vHVT13, in the tested conditions. The shedding levels detected in the other vaccinated groups were low with a slightly higher level detected in G3 (vHVT307) at 5 days post-infection (pi) only.

In conclusion, this example further illustrates the excellent ND protection induced by double HVT-IBD+ND recombinant or a combination of SB1-ND or HVT-ND and HVT-IBD (vHVT13) recombinant viruses. Contrary to the general belief in the field that a second HVT vaccine (regular HVT vaccines or recombinant HVT vaccines) interferes with the immunity to the foreign genes inserted into the first recombinant HVT vaccine, the present invention showed surprising result that vHVT114 in combination with vHVT13 offered excellent protection against NDV and no interference effect was observed.

Example 11

Efficacy of vHVT306, vSB1-008 in Combination with vHVT13 Administered by SC or in Ovo Route Against Challenge with NDV Chimalhuacan Strain (Genotype V) at D28 in SPF Chickens The aim of the study was to assess the efficacy of the vHVT306 double HVT expressing both NDV F and IBDV VP2 genes, and the vSB1-008 SB1 recombinant expressing the NDV F gene in combination with vHVT-IBD (vHVT13), administered by the in ovo or by the subcutaneous route against Newcastle disease challenge (Chimalhuacan, genotype V) performed at 28 days of age in SPF chickens.

The characteristics of these 2 ND vaccine candidates are reported in the table 14 (vSB1-008) and in table 16 (vHVT306).

The design of the groups is shown on Table 20. Sixty SPF embryonated eggs (after approximately 18 days and 18 hours of incubation; D-3) were used for the in ovo administration (20 per group for G1, G2 and G3). Fifty microliters of vaccine containing 2000 PFU were administered by the in ovo route using the IntelliLab System device from AviTech LLC (Salisbury, Md., USA). Hatchability and survival were recorded after in ovo administration. On D0, 20 one-day-old SPF chickens were randomly allocated into 2 groups of 10 birds (G4 and G5). The birds were injected by subcutaneous (SC) injection in the neck at D0 with 0.2 mL of recombinant vaccines containing a target dose of 2000 pfu as described in Table 20 below. Ten birds per group were challenged by the intramuscular route on D28 with 5.0 log 10 EID50 velogenic Chimalhuacan (genotype V) strain.

TABLE 20

Study design and results of ND efficacy

| Group | Vaccine at day-old (D0) | Admin. route | % protection against mortality | % protection against morbidity |
|---|---|---|---|---|
| G1 | vHVT13 | In ovo | 0% | 0% |
| G2 | vHVT306 | In ovo | 100% | 100% |
| G3 | vSB1-008 + vHVT13 | In ovo | 78% | 68% |
| G4 | vHVT306 | SC | 100% | 100% |
| G5 | vSB1-008 + vHVT13 | SC | 100% | 70% |

Each group was monitored before and after challenge. NDV clinical signs were recorded after challenge. Oropharyngeal swabs were taken in the vaccinated groups at 5 and 7 days post-challenge to evaluate the viral load by real time RT-PCR.

Full hatchability and viability were recorded up to D28 (challenge day) for birds of groups G1 and G2. Hatchability in G3 was 85% and one additional bird died after hatching in this group. The lower hatchability of that group may be due to egg incubator problems. Body weights of males and females in G1, G2 and G3 were similar at D1 and at D28.

Percentages of protection against mortality and morbidity are reported in the table 20. Full susceptibility was observed in the non-vaccinated challenged control group G1 thus validating the high severity of challenge. Very good protection was observed in all 4 vaccinated groups, a full clinical protection being induced by vHVT306 administered by both routes.

The percentage of positive birds and the mean shedding titer (expressed as log 10 EID50 equivalent per mL) are shown in Table 21. Absence of detectable or very low shedding was observed in G2 and G4 vaccinated with vHVT306. The shedding levels detected in the groups vaccinated with vSB1-008+vHVT13 were higher especially at 5 days post-infection (pi).

TABLE 21

Results of protection against shedding (percentage of birds with detectable shedding and mean viral load in log10) evaluated at D5 and D7 after NDV challenge

| Group | Vaccine at day-old (D0) | Admin. Route | Percent of positive birds (D5/D7 pi) | Mean viral load* (D5/D7 pi) |
|---|---|---|---|---|
| G2 | vHVT306 | In ovo | 0/0% | 2.7/2.7 |
| G3 | vSB1-008 + vHVT13 | In ovo | 100/38% | 5.2/3.2 |
| G4 | vHVT306 | SC | 20/10% | 3.2/2.9 |
| G5 | vSB1-008 + vHVT13 | SC | 80/50% | 4.6/3.4 |

*Mean quantitative real time PCR value expressed in equivalent log10 EID50; the threshold is set at 2.7 log10.

In conclusion, this example shows excellent ND protection induced by vHVT306 double HVT recombinant administered either by in ovo or by SC routes. The performance of vSB1-008+vHVT13 was slightly lower especially after in ovo administration, but it may be at least partially due to egg incubator problems. Indeed, the in ovo safety testing of another SB1-ND recombinant (vSB1-009) at 1000 or 4000 PFU associated with 6000 PFU of vHVT13 did not show any difference in hatchability and early survival with a group receiving 6000 PFU of vHVT13 only.

Example 12

Efficacy of vHVT304, vHVT306, vSB1-007 and vSB1-008 in Combination with vHVT13 Against Challenge with NDV Chimalhuacan Strain (Genotype V) at D42 in Commercial Broiler Chickens The aim of the study was to assess the efficacy of two double HVT (vHVT304 and vHVT306) expressing both NDV F and IBDV VP2 genes, and two SB1 recombinants (vSB1-007 and vSB1-008) expressing the NDV F gene in combination with vHVT-IBD (vHVT13) against Newcastle disease challenge (Chimalhuacan, genotype V) performed at 42 days of age in commercial broiler chickens.

The characteristics of these 4 ND vaccine candidates are reported in tables 14 and 16. The design of the groups is shown on Table 22. On D0, 55 one-day-old commercial broiler chickens were randomly allocated into 5 groups of 11 birds. The birds were injected by subcutaneous (SC) injection in the neck at D0 with 0.2 mL of recombinant vaccines containing a target dose of 2000 pfu as described in Table 22 below. Ten birds per group were challenged by the intramuscular route on D42 with 5.0 log 10 EID50 velogenic Chimalhuacan (genotype V) strain.

TABLE 22

Study design and results of ND efficacy

| Group | Vaccine at day-old (D0) | % protection against mortality | % protection against morbidity |
|---|---|---|---|
| G1 | vHVT13 | 0% | 0% |
| G2 | vHVT304 | 82% | 82% |
| G3 | vHVT306 | 100% | 100% |
| G4 | vSB1-007 + vHVT13 | 100% | 100% |
| G5 | vSB1-008 + vHVT13 | 91% | 91% |

Each group was monitored before and after challenge. NDV clinical signs were recorded during 14 days after challenge. Oropharyngeal swabs were taken in the vaccinated groups at 5 and 7 days post-challenge to evaluate the viral load by real time RT-PCR.

Percentages of protection against mortality and morbidity are reported in the table 22. Full susceptibility was observed in the non-vaccinated challenged control group G1 thus validating the high severity of challenge. Very good protection was observed in all 4 vaccinated groups, a full clinical protection being induced by vHVT306 and by vSB1-007+vHVT13.

The percentage of positive birds and the mean shedding titer (expressed as log 10 EID50 equivalent per mL) are shown in Table 23. The best reduction of shedding was induced by vHVT306 and vSB1-007+vHVT13, which were also the best candidates for clinical protection.

TABLE 23

Results of protection against shedding (percentage of birds with detectable shedding and mean viral load in log10) evaluated at D5 and D7 after NDV challenge (pi)

| Group | Vaccine at day-old (D0) | Percent of positive birds (D5/D7 pi) | Mean viral load* (D5/D7 pi) |
|---|---|---|---|
| G2 | vHVT304 | 100/100% | 5.4/4.6 |
| G3 | vHVT306 | 40/50% | 3.5/3.7 |
| G4 | vSB1-007 + vHVT13 | 80/70% | 3.8/4.8 |
| G5 | vSB1-008 + vHVT13 | 100/100% | 4.8/4.3 |

*Mean quantitative real time PCR value expressed in equivalent log10 EID50; the threshold was set at 2.7 log10.

The vHVT306 ND protection was found to be better than that of vHVT304. These two double HVT contain the same NDV F expression cassette but inserted in two different loci, the IBDV VP2 one being inserted at the same position. This example therefore illustrates the importance of the locus of insertion in the design of HVT recombinants. The vSB1-007+vHVT13 was better than vSB1-008+vHVT13. The vSB1-007 genomic structure differs from that of vSB1-008 in different aspects: locus of insertion, promoter, poly-adenylation signal and F gene origin. The combination of these foreign sequences and locus of insertion in vSB1-007 were likely responsible for its better ND protection performances.

In summary, this example illustrates the importance of the locus of insertion and other regulatory sequences of the NDV expression cassette in the ND protection induced by HVT and MDV serotype 2 vectors.

Example 13

Efficacy of Double HVT-ND+IBD (vHVT304 and vHVT306) or SB1-ND (vSB1-008) in Combination with vHVT13 Recombinant Vaccines, Against Challenge with a Classical IBDV Isolate on D14 in SPF Chickens The aim of the study was to assess the early IBD efficacy of double HVT recombinants vHVT304 and vHVT306 as well as that of vHVT13 co-administered with a SB1-ND (vSB1-008) recombinant constructs against a virulent infectious bursal disease virus (vIBDV) challenge (Faragher 52/70 strain) performed at 14 days of age in SPF chickens.

The characteristics of the double HVT and SB1 recombinants used in this study are shown in Tables 14 and 16.

On D0, 95 one-day-old SPF chickens were randomly allocated into 9 groups of 10 birds and 1 group of 5 birds (unvaccinated unchallenged control group). The birds were injected by subcutaneous injection in the neck at D0 with 0.2 mL of recombinant vaccines containing a target dose of 300 or 1000 pfu as described in the Table 24 below. On D14, blood sample was collected from 5 birds per group for serological testing with the Kit ProFLOK® plus IBD (Synbiotics Corp). The birds (10 birds per group except for group 7 in which 1 bird died before challenge) were challenged by the eye drop (0.05 mL per bird) on D14 with 2.5 log 10 EID50.

TABLE 24

Study design and results of IBD efficacy

| Group | Vaccine at day-old (dose in PFU) | IBD+ ELISA titer at D14[1] | Number Dead/Sick[2] | % protect-tion[3] | Mean bursal/body weight ratio[4] |
|---|---|---|---|---|---|
| G1 | vSB1-008 (1000) | 0.2 | 7/10 | 0% | 0.0013 |
| G2 | vHVT13 (300) | 2.7 | 0/0 | 100% | 0.0051 |
| G3 | vHVT13 (1000) | 2.7 | 0/0 | 90% | 0.0049 |
| G4 | vHVT13 + vSB1-008 (300) | 1.9 | 1/1 | 60% | 0.0041 |
| G5 | vHVT13 + vSB1-008 (1000) | 2.4 | 0/0 | 70% | 0.0041 |
| G6 | vHVT304 (300) | 2.9 | 0/0 | 60% | 0.0037 |
| G7 | vHVT304 (1000) | 2.2 | 0/0 | 67% | 0.0047 |
| G8 | vHVT306 (300) | 2.4 | 0/0 | 80% | 0.0033 |
| G9 | vHVT306 (1000) | 2.7 | 0/0 | 40% | 0.0026 |

[1]Mean IBD+ ELISA titers expressed in log10 in the serum of 5 birds per group sampled at D14 before challenge;
[2]Birds sick for more than 2 days or still sick on D25 were considered as sick.
[3]Protection against clinical signs and severe bursal lesion (bursal score <3)
[4]The bursal/body weight ratio of the unvaccinated/unchallenged group was 0.0047.

Each group was monitored before and after challenge. IBDV clinical signs were recorded for 11 days after challenge (from D15 to D25). At the end of the post-challenge observation period (D33), all the surviving birds were euthanized and necropsied. Body and bursal weights were recorded. Each bursa of Fabricius (BF) was weighted then stored in individual recipients containing 4% formaldehyde for histology. Histological lesions of the bursa were scored according to the scale presented in Table 25.

TABLE 25

Scoring scale of histological lesions of the bursa of Fabricius*

| Score | Histology observation/lesions |
|---|---|
| 0 | No lesion, normal bursa |
| 1 | 1% to 25% of the follicles show lymphoid depletion (i.e. less than 50% of depletion in 1 affected follicle), influx of heterophils in lesions |
| 2 | 26% to 50% of the follicles show nearly complete lymphoid depletion (i.e. more than 75% of depletion in 1 affected follicle), affected follicles show necrosis and severe influx of heterophils may be detected |
| 3 | 51% to 75% of the follicles show lymphoid depletion; affected follicles show necrosis lesions and a severe influx of heterophils is detected |
| 4 | 76% to 100% of the follicles show nearly complete lymphoid depletion; hyperplasia and cyst structures are detected; affected follicles show necrosis and severe influx of heterophils is detected |
| 5 | 100% of the follicles show nearly complete lymphoid depletion; complete loss of follicular structure, thickened and folded epithelium, fibrosis of bursal tissue |

*sourced from Monograph No. 01/2008:0587 of EU Pharmacopoeia "Avian Infectious Bursal Disease vaccine (live)

A bird was considered as affected if it died and/or showed notable sign of disease and/or severe lesions of the bursa of Fabricius (i.e., histology score 3).

The mean ELISA IBD+ antibody titer expressed in log 10 before challenge is shown in Table 24. Significant titers were detected in all vaccinated groups that were significantly higher than that of the control group G1. The serology titer was not dose-dependent.

Severe clinical signs were observed after challenge in all birds of the control group G1. Seven out of 10 birds of that group died within the 11 days observation period indicating the high severity of challenge. None of the vaccinated birds showed severe clinical signs after challenge except 1 bird of G4 that died. Percentages of protection against severe bursal lesions are shown in the table above. Significant IBD protection was observed in all groups, the best protection being observed in G2 and G3 (vHVT13 alone). The co-administration of vSB1-008+vHVT13 and the double vHVT304 and vHVT306 constructs induced similar levels of IBD protection. The protection was not dose-dependent at the tested doses. The mean bursal/body weight ratios are also shown in Table 24. Ratios in all vaccinated groups were higher than those of the challenged control group.

In conclusion, these data indicate that both the combination of a SB1-ND vector with a single HVT-IBD or double HVT expressing both NDV-F and IBDV-VP2 induce IBD antibodies and early IBD protection in a severe IBDV challenge model.

Example 14

Efficacy of Single HVT-ND (vHVT114) or SB1-ND (vSB1-007 and vSB1-009) in Combination with vHVT13 Recombinant Vaccines, Against Challenge with a Very Virulent IBDV Isolate on D23 in Commercial Broiler Chickens The aim of the study was to assess the IBD efficacy of vHVT13 co-administered with an HVT-ND (vHVT114) or SB1-ND (vSB1-007 and vSB1-009) recombinant constructs against a very virulent infectious bursal disease virus (vvIBDV) challenge (91-168/980702) performed at 23 days of age in commercial broiler chickens.

The characteristics of these 4 vaccine candidates are described in Tables 14 and 16. On D0, 90 one-day-old broiler chickens were randomly allocated into 7 groups of 12 birds and 1 group of 6 birds (unvaccinated unchallenged control group). The birds were injected by subcutaneous injection in the neck at D0 with 0.2 mL of recombinant vaccines containing a target dose of 3000 pfu as described in the Table 26. On D14, blood sample was collected from 5 birds per group for serological testing with the Kit ProFLOK® plus IBD (Synbiotics Corp). The serum of 10 extra one-day-old broiler chickens was tested at D0 with the same kit to evaluate the level of IBDV maternal antibody. The birds (10 birds per group) were challenged by the eye drop (0.05 mL per bird) on D23 with 4.3 log 10 EID50 of the vvIBDV 91-168 isolate.

Each group was monitored before and after challenge. IBDV clinical signs were recorded for 11 days after challenge (from D23 to D33). At the end of the post-challenge observation period (D33), all the surviving birds were euthanized and necropsied. Body and bursal weights were recorded. Each bursa of Fabricius (BF) was weighted then stored in individual recipients containing 4% formaldehyde for histology. Histological lesions of the bursa were scored according to the scale presented in Table 25.

A bird was considered as affected if it died and/or showed notable signs of disease and/or severe lesions of the bursa of Fabricius (i.e., histology score ≥3).

TABLE 26

Study design and serology results

| Group | Vaccine at day-old (D0) | IBD+ ELISA titer at D23[1] | Mean bursal/body weight ratio[2] |
|---|---|---|---|
| G1 | — | 3.9 | 0.0007 |
| G2 | vHVT13 | 4.0 | 0.0015 |
| G3 | vHVT114 + vHVT13 | 4.1 | 0.0015 |
| G4 | vSB1-007 + vHVT13 | 3.8 | 0.0018 |
| G5 | vSB1-009 + vHVT13 | 4.0 | 0.0019 |

[1]Mean IBD+ ELISA titers expressed in log10 in the serum of 5 birds per group sampled at D23 before challenge;
[2]The bursal/body weight ratio of the unvaccinated/unchallenged group was 0.0047

The mean ELISA IBD+ serological titer at D0 was 4.36±0.01 log 10 indicating a very high level of IBD maternal antibody at hatch. At D23, the mean ELISA IBD+ titer was still high (3.9) in the control G1. ELISA mean titers in the vaccinated groups were not significantly different from those of the control group.

Neither morbidity nor mortality was observed in any of the groups after challenge. Percentages of protection against severe bursal lesions are shown in the table 26 above. The result showed that co-administration of vHVT114, vSB1-007 or vSB1-009 did not interfere with vHVT13-induced IBD protection indicating a lack of interference. Similarly, the mean bursal/body weight ratios of the vaccinated groups were similar and clearly higher than that of the control group, indicating IBD protection and no difference between the vaccination regimens.

In conclusion, the data indicate the compatibility between vHVT114, vSB1-007 or vSB1-009 and vHVT13 for IBD protection. The lack of interference between the two HVT vectors for IBD protection was again surprising and confirmed the results observed for ND protection (see example 10), Example 15

Efficacy of Double HVT-ND+IBD (vHVT304 and vHVT306) Associated or not with SB-1 and of SB1-ND (vSB1-007 and vSB1-008) in Combination with vHVT13 Recombinant Vaccines, Against Challenge with a Variant E IBDV Isolate on D28 in SPF Chickens The aim of the study was to assess the efficacy of two double HVT (HVT-ND+IBD: vHVT304 and vHVT306) or two vSB-1-NDV in combination with vHVT13 (vSB1-007+ vHVT13, vSB1-008+vHVT13) vectored vaccines administered subcutaneously (SC) to day-old SPF chicks and challenged with IBDV-Variant (VAR-E) 28 days post-vaccination.

On D0, 105 one-day-old SPF chickens were randomly allocated into 7 groups of 15 birds including a group of challenged controls (G6) and unchallenged controls (G7). The birds of groups G1 to G5 were injected by subcutaneous injection in the neck at D0 with 0.2 mL of recombinant and/or SB-1 vaccines containing each a target dose of 2000 pfu. The design of the study is shown in Table 27 below. On D28, all birds from groups G1 to G6 were challenged by the eye drop (0.03 mL containing 3 log 10 EID50 per bird) of the IBDV variant E isolate from University of Delaware (USA). Each group was monitored before and after challenge. Eleven days post-challenge, birds were weighed and necropsied. The bursa were collected and weighed. The bursal/body weight ratios (bursa weight/body weight ratio×100) were calculated.

TABLE 27

Study design and results of IBD efficacy

| Group | Vaccine at day-old | Mean bursal/body weight ratio (*100) |
|---|---|---|
| G1 | vHVT304 | 0.33 |
| G2 | vHVT304 + SB-1 | 0.33 |
| G3 | vHVT306 | 0.29 |
| G4 | vHVT13 + vSB1-007 | 0.49 |
| G5 | vHVT13 + vSB1-008 | 0.47 |
| G6 | - (challenged) | 0.13 |
| G7 | - (unchallenged) | 0.46 |

The mean bursal/body weight ratios are shown in the Table 27. The challenged control birds had a severe bursal atrophy compared to unchallenged ones. The vSB1-007 and vSB1-008 vaccines did not interfere on vHVT13-induced protection (G4 and G5). The bursal/body weight ratios of birds vaccinated with the double HVT (HVT-ND+IBD) were slightly lower than the unchallenged control group but were clearly higher than the challenged control groups. Furthermore, the SB-1 serotype 2 Marek's disease vaccine did not interfere with vHVT304-induced IBD protection.

In conclusion, these data indicate that both the combination of a SB1-ND vector with a single HVT-IBD or double HVT expressing both NDV-F and IBDV-VP2 induce IBD protection in a variant E IBDV challenge model.

Example 16

Lack of Interference of vHVT114, vSB1-009 and/or SB-1 on vHVT13 Induced Variant E IBD Protection in SPF Chickens The aim of the study was to assess the IBD efficacy of vHVT13 when administered by SC or in ovo route concomitantly with vHVT114, vSB1-009 and/or SB-1 in SPF chicks in an IBDV-Variant (VAR-E) at D28 challenge model.

75 one-day-old SPF chickens and 75 SPF 18 to 19 day-old chicken embryo were randomly allocated into 5 groups (G1 to G5 and G6 to G10, respectively) including a group of challenged controls (G4 and G9, respectively) and unchallenged controls (G5 and G10, respectively). The birds of groups G1 to G3 were injected by subcutaneous injection in the neck at D0 with 0.2 mL of vaccines containing each a target dose of 3000 pfu except for SB-1 which had a target dose of 1000 PFU. Birds from G6 to G8 received the same vaccine doses but in 0.05 mL volume by the in ovo route 2-3 days before hatch. The design of the study is shown in Table 28 below. At 28 days of age, all birds from groups G1 to G4 and G6 to G9 were challenged by the eye drop (0.03 mL containing 3 log 10 EID50 per bird) of the IBDV variant E isolate from University of Delaware (USA). Each group was monitored before and after challenge. Eleven days post-challenge, birds were weighed and necropsied. The bursa were collected and weighed. The bursal/body weight ratios (bursa weight/body weight ratio×100) were calculated.

TABLE 28

Study design and results of IBD efficacy

| Group | Vaccine at day-old | Administration route | Mean bursal/body weight ratio (*100) |
|---|---|---|---|
| G1 | vHVT13 + vHVT114 + SB-1 | SC | 0.56 |
| G2 | vHVT13 + vHVT114 + vSB1-009 | SC | 0.58 |
| G3 | vHVT13 + vSB1-009 | SC | 0.52 |
| G4 | - (challenged) | SC | 0.13 |
| G5 | - (unchallenged) | SC | 0.51 |
| G6 | vHVT13 + vHVT114 + SB-1 | In ovo | 0.54 |
| G7 | vHVT13 + vHVT114 + vSB1-009 | In ovo | 0.47 |
| G8 | vHVT13 + vSB1-009 | In ovo | 0.53 |
| G9 | - (challenged) | In ovo | 0.14 |
| G10 | - (unchallenged) | In ovo | 0.58 |

The mean bursal/body weight ratios are shown in the Table 28. The challenged control birds (G4 and G9) had a severe bursal atrophy compared to unchallenged ones. The bursal/body weight ratios of the vaccinated groups (G1 to G3 and G6 to G8) were similar to those of the unchallenged control groups (G5 and G10) and well above those of the challenged control groups (G4 and G9). The lack of interference of vHVT114 on vHVT13-induced IBD protection after both SC or in ovo routes was surprising and confirmed data obtained in examples 10 and 14.

In conclusion, these data indicate clearly the compatibility of vHVT114+vSB1-009 or +SB-1 and of vSB1-009 with vHVT13 when administered by SC or in ovo route in a variant E IBDV challenge model.

Example 17

Efficacy of vHVT114 and vHVT13 and SB1 or vSB1-009 Vectors Against Very Virulent Plus Marek's Disease Challenge The aim of this study was to evaluate the Marek's disease efficacy induced by different combinations of vaccines including vHVT114, vHVT13, SB-1 and/or vSB1-009 administered by the SC route to one-day-old SPF chicks and challenged 4 days later with the very virulent plus Marek's disease virus (vv+MDV) T-King isolate.

On D0, 100 one-day-old SPF chickens were randomly allocated into 5 groups of 20 birds. The birds from groups 1 to 3 were injected by subcutaneous injection in the neck at D0 with 0.2 mL of vaccines containing a target dose of 2000 pfu for each vaccine except for SB-1 for which the target dose was 1000 pfu. Birds from groups 4 and 5 were non-vaccinated and were used as sham controls challenged (group 4) or unchallenged (group 5). The study design is shown in the Table 29. On D4, All birds from groups 1 to 4 were challenged with 0.2 mL of the vv+MDV T-King isolate using the intraperitoneal route of administration.

TABLE 29

Study design and MD protection results

| Group | Vaccine at day-old (D0) | Number of MD positive/total | Percentage of protection |
|---|---|---|---|
| G1 | vHVT13 + SB-1 | 7/20 | 65% |
| G2 | vHVT114 + SB-1 | 7/20 | 65% |
| G3 | vHVT13 + vHVT114 + vSB1-009 | 7/20 | 65% |
| G4 | - (challenged) | 20/20 | 0% |
| G5 | - (unchallenged) | 0/20 | 100% |

Each group was monitored daily for any unfavourable reactions before and after challenge. At day 49, all live birds were terminated and necropsied to examine for gross lesions associated with Marek's disease. Chickens were classified as positive for infection with Marek's disease if nervous signs, such as paralysis, locomotive signs attributable to the disease, and severe emaciation or depression are observed, if mortality directly attributable to Marek's Disease occurs, or if gross lesions are observed at necropsy. Lesions might include, but not be limited to, the following: liver, heart, spleen, gonads, kidneys, and muscle lesions Results of protection are shown in the Table 29 above. All vaccinated groups (G1 to G3) performed equally, inducing a partial (65%) MD protection as expected in this very severe and early challenge model. These results indicated that the vector vaccine candidates retain their ability to protect against Marek's disease.

Example 18

Efficacy of Recombinant HVT and SB1 Vectors Against Marek's Disease

Marek's disease efficacy is also demonstrated for the HVT vectored recombinants and the SB-1 vectored recombinants either alone or in combination. The challenge strains include a virulent Marek's disease (vMD) challenge such as GA22, a very virulent Marek's disease (vvMD) challenge such as RB1B and/or a very virulent plus Marek's disease (vv+MD) challenge such as the T. King virus. One-day-old chickens are inoculated subcutaneously or 18-19-day-old embryonated eggs are inoculated with a 0.2 ml dose or 0.05 ml dose, respectively, of the test viruses. At five days of age the vaccinated chickens and naïve controls are challenged with the relevant Marek's challenge virus (v, vv, or vv+MDV). The challenged birds are observed until seven weeks of age. All birds are terminated and necropsied to observe for grossly visible lesions associated with Marek's disease as described in Example 17.

Example 19

Interference of HVT on vHVT13-Induced IBDV Antibodies in Commercial Pullets

The objective of this study was to determine if co-administration of HVT with vHVT13 had an impact on vHVT13-induced IBDV antibody response in commercial pullets.

Eighty day-old commercial brown pullets were used in three isolation units. Fifteen were blood sampled at day-old to test IBD maternally derived antibodies (MDA). The remaining birds were split into three groups as shown in Table 30. Birds from group 2 and 3 were vaccinated by the SC route in the nape of the neck with commercial doses of vHVT13 (VAXXITEK HVT+IBD; Merial SAS, Lyon, France) and/or HVT cell-associated Bio HVT (Merial S.p.A., Noventa, Italy). Blood sampling was performed at the age of 25, 35 and 45 days of age. The ELISA kit used to evaluate IBDV serological response was the PROFLOK PLUS IBD (IBD+) Ab ELISA kit from Synbiotics (Synbiotics Corp., Kansas City, Mo., USA).

TABLE 30

Study design and serology results

| Group | Vaccine at day-old (D 0) | ELISA titre D 1 | ELISA titre D 25 | ELISA titre D 35 | ELISA titre D 45 |
|---|---|---|---|---|---|
| G1 | — | 10,502 | 7,814 | 6,237 | 3,664 |
| G2 | vHVT13 | 10,502 | 8,023 | 9,360 | 9,486 |
| G3 | vHVT13 + HVT | 10,502 | 6,896 | 4,763 | 3,795 |

Mean ELISA titers are shown in Table 30. Titers in the unvaccinated group G1 decreased from D1 to D45, which corresponded to the decline of IBDV maternal antibodies. As expected; ELISA titers in the vHVT13 group G2, remains high up to D45 indicating maternal antibodies were progressively replaced by vHVT13-induced antibodies. The addition of HVT to vHVT13 had a clear negative impact since the antibody titers observed in G3 were similar to G1. These results contrast with those obtained with vHVT114+vHVT13 since the vHVT114 did not decrease vHVT13-induced IBD+ ELISA titers (see example 14, Table 26). They confirm the unexpected property of vHVT114 in not interfering with vHVT13 immunogenicity.

In conclusion, in contrast to what was observed with vHVT114, the addition of HVT to vHVT13 had a clear negative impact on vHVT13-induced IBDV humoral immunity.

Example 20

Interference of Commercial HVT-ND on vHVT13-Induced IBD Protection

The objective of this study was to determine if co-administration of commercial HVT-ND vector vaccines with vHVT13 had an impact on vHVT13-induced IBD protection in SPF chickens.

Seventy five SPF chickens (3 groups (G2, G3 and G4) of 25) were vaccinated at one day-of-age by the SC route with a commercial dose of vHVT13 (VAXXITEK HVT+IBD) with or without one commercial dose of licensed HVT-vectored ND vaccine (vHVT-ND1 and vHVT-ND2) as shown in the Table 31. Fifteen birds were kept as non-vaccinated controls (G1). Three weeks post-vaccination, birds (20 chickens in G2, G3 and G4 and 10 chickens in G1) were challenged with at least 2.0 log 10 EID50 in 0.05 ml of IBD virus Ph/B1 strain (isolated in the Philippines) administered via ocular route. All chickens were observed for 5 days for clinical signs or death from causes attributable to IBD challenge virus and euthanatized humanely at end of post-challenge observation for necropsy examination of IBD lesion, especially from the bursa of Fabricius. Birds were considered as protected if their bursa did not show bursal lesions typical of IBD: bursal atrophy, peri-bursa edema and/or hemorrhages in bursa tissues.

TABLE 31

Study design and IBD protection data

| Group | Vaccine at day-old (D 0) | Number of sick (dead)/total | Number of positive bursa/total | Percent of protection |
|---|---|---|---|---|
| G1 | — | 10(8)/10 | 10/10 | 0% |
| G2 | vHVT13 + vHVT-ND 1 | 3(3)/20 | 9/20 | 55% |
| G3 | vHVT13 + vHVT-ND2 | 3(1)/20 | 7/20 | 65% |
| G4 | vHVT13 | 0(0)/20 | 0/20 | 100% |

Results are shown in Table 31. All 10 challenged control birds showed clinical signs and 8 out of 10 died 4 or 5 dpi indicating that the IBDV challenge was very severe. All of them had severe lesions of bursa including severe atrophy and haemorrhagic patches. The vHVT13 alone induced full protection whereas both combinations with vHVT-ND induced partial clinical and bursal protection.

In conclusion, these results clearly indicate that the 2 commercial HVT-vectored ND vaccines interfere with vHVT13-induced IBD protection.

Example 21

Efficacy of vSB1-004, vSB1-006, vSB1-007, vSB1-008, SB1-Vectored ND Vaccine Alone or in Association with vHVT13 HVT-Vectored IBD Vaccine, and the vHVT302 and vHVT304 Vaccines Against Challenges with NDV Texas GB Strain at 14 and/or 28 Days of Age in SPF Chickens The aim of the study was to assess the efficacy of combinations of different Marek's disease vector vaccines expressing the NDV F and/or the IBDV VP2 gene against Newcastle disease challenge (Texas GB strain, genotype II) performed at 14 and/or 28 days of age in SPF chickens.

The characteristics of the 6 NDV recombinant vaccine candidates tested in this study are described in the Table 32 below.

TABLE 32 characteristics of the 6 NDV recombinant vaccine candidates tested in this study

| Name | Parental virus | Promoter | F gene | Poly-A | Locus |
|---|---|---|---|---|---|
| vSB1-004 | SB-1* | mCMV IE | Wt-VIId | SV40 | SORF4/US10 |
| vSB1-006 | SB-1 | SV40 | Opt-VIId | Synthetic | UL55/LORF5 |
| vSB1-007 | SB-1 | SV40 | Opt-VIId | (endogeneous from gC gene) | gC |
| vSB1-008 | SB-1 | SV40 | Opt-CA02 | Synthetic | UL55/LORF5 |
| vHVT302 | vHVT13 | US10 | Opt-VIId | US10 | US10 |
| vHVT304 | vHVT13 | SV40 | Opt-VIId | Synthetic | IG2 |

On D0, 225 one-day-old SPF chickens were randomly allocated into 9 groups of 15 birds (G1a to G9a challenged at D14) and 6 groups of 15 birds (G1b, G3b, G4b, G5b, G8b, G9b challenged at D28). The birds were injected by subcutaneous injection in the neck at D0 with 0.2 mL containing a target dose of 2000 pfu for recombinant vaccines. The design of the study is shown in Table 33 below. The birds were challenged by the intramuscular route on D14 or D28 with 4.3 and 4.2 log 10 EID50 (0.1 mL) velogenic ND Texas GB (genotype II) strain, respectively.

TABLE 33

Results of ND efficacy

| Group | Vaccine at day-old (D 0) | % ND protection after ND challenge at 14 days of age | % ND protection after ND challenge at 28 days of age |
|---|---|---|---|
| G1a & 1b | — | 0% | 0% |
| G2a | vSB1-004 | 20% | ND* |
| G3a & 3b | vSB1-006 | 26.6% | 73.3% |
| G4a & 4b | vSB1-007 | 33.3% | 93.3% |
| G5a & 5b | vSB1-008 | 46.6% | 86.6% |
| G6a | vSB1-006 + vHVT13 | 14% | ND |
| G7a | vSB1-008 + vHVT13 | 21.4% | ND |
| G8a & 8b | vHVT302 | 13.3% | 80% |
| G9a & 9b | vHVT304 | 33.3% | 93.3% |

*ND = not done

Each group was monitored before and after challenge. NDV clinical signs after challenge were recorded. One bird died in G6 and G7 before challenge reducing the number of birds from 15 to 14 in these groups.

Percentages of clinical protection (including protection against both mortality and morbidity) are reported in Table 33 above. Full susceptibility was observed in the non-vaccinated challenged control group G1a and G1b thus validating the high severity of challenge. Partial protections ranging from 13.3 to 46.6% were observed after challenge at D14, the highest levels of protection being induced by vSB1-008, vSB1-007 and vHVT304. Protection levels after ND challenge at D28 were much higher for all vaccinated groups and were again slightly higher in the groups vaccinates with vSB1-008, vSB1-007 or vHVT304. These results indicated that ND protection levels were dependent on the date of challenge and on the construct. The vSB1-008 and vSB1-007 constructs performed slightly better than vSB1-004 and vSB1-006, and the vHVT304 performed slightly better than vHVT302, indicating that different characteristics of the constructs are playing a role in the performances of MDV-based vector vaccines.

In conclusion, the results of this study showed that ND protection levels induced by Marek's disease vectors expressing NDV F gene may depend on different parameters including the vector, the locus of insertion, the F gene, the promoter, the poly-adenylation site and the challenge conditions.

Example 22

Efficacy of Double HVT-ND+IBD vHVT304 and vHVT306 Vaccines Against Challenges with NDV Texas GB Strain at 14 and/or 28 Days of Age in SPF Chickens The aim of the study was to assess the efficacy of HVT-vectored vaccine expressing both NDV F and IBDV VP2 genes against Newcastle disease challenge (Texas GB strain, genotype II) performed at 14 and/or 28 days of age in SPF chickens.

The characteristics of the 2 recombinant vaccine candidates tested in this study are described in the Table 34 below.

TABLE 34

Characteristics of the recombinant vaccine candidates used in this study

| Name | Parental virus | Promoter | F gene | Poly-A | Locus |
|---|---|---|---|---|---|
| vHVT304 | vHVT13 | SV40 | Opt-VIId | Synthetic | IG2 |
| vHVT306 | vHVT13 | SV40 | Opt-VIId | Synthetic | SORF3-US2 |

On D0, 90 one-day-old SPF chickens were randomly allocated into 3 groups of 15 birds (G1a to G3a challenged at D14) and 3 groups of 15 birds (G1b to G3b challenged at D28). The birds were injected by subcutaneous injection in the neck at D0 with 0.2 mL containing a target dose of 2000 pfu for recombinant vaccines. The design of the study is shown in Table 35 below. The birds were challenged by the intramuscular route on D14 or D28 with a target dose of 4.0 log 10 EID50 (0.1 mL) velogenic ND Texas GB (genotype II) strain.

TABLE 35

Results of ND efficacy

| Group | Vaccine at day-old (D 0) | % ND protection after ND challenge at 14 days of age | % ND protection after ND challenge at 28 days of age |
|---|---|---|---|
| G1a & 1b | — | 0% | 0% |
| G2a & 2b | vHVT304 | 26.7% | 92.9% |
| G3a & 3b | vHVT306 | 33.3% | 86.7% |

Each group was monitored before and after challenge. NDV clinical signs after challenge were recorded. One bird died in G2b before challenge reducing the number of birds from 15 to 14 in this group.

Percentages of clinical protection (including protection against both mortality and morbidity) are reported in Table 35 above. Full susceptibility was observed in the non-vaccinated challenged control group G1a and G1b thus validating the high severity of challenge. Protections levels after challenge at D14 were much lower than those obtained after challenge at D28. These vaccine candidates had the same NDV F expression cassette inserted into 2 different loci of vHVT13 genome. They performed equally in terms of ND protection in the tested conditions, indicating that both insertion loci (IG2 and SORF3-US2) are equally suitable for NDV F cassette insertion.

In conclusion, the results of this study showed that ND protection levels induced by Marek's disease vectors expressing NDV F gene depend on different parameters including the vector, the locus of insertion, the F gene, the promoter, the poly-adenylation site and the challenge conditions.

Example 23

ND Early Efficacy Induced by Double HVT-ND+IBD (vHVT302, vHVT303, and vHVT304) or SB1-Vectors (vSB1-006 and vSB1-007) in One Day-Old SPF Chickens Against a Velogenic Genotype V NDV Challenge The objective of the study was to evaluate the efficacy of three double HVT-ND+IBD (vHVT302, vHVT303, and vHVT304) and two SB1-ND vectors (vSB1-006 and vSB1-007) in one day-old SPF chickens against a velogenic genotype V (Chimalhuacan) NDV challenge performed at D14.

The characteristics of the 5 recombinant vaccine candidates tested in this study are described in Table 36 below.

TABLE 36

Characteristics of the recombinant vaccine candidates used in this study

| Name | Parental virus | Promoter | F gene | Poly-A | Locus |
|---|---|---|---|---|---|
| vHVT302 | vHVT13 | US10 | Opt-VIId | US10 | US10 |
| vHVT303 | vHVT13 | US10 | Opt-V (CA02) | US10 | US10 |
| vHVT304 | vHVT13 | SV40 | Opt-VIId | Synthetic | IG2 |
| vSB1-006 | SB-1 | SV40 | Opt-VIId | Synthetic | UL55/LORF5 |
| vSB1-007 | SB-1 | SV40 | Opt-VIId | (endogenous from gC gene) | gC |

Six groups (1 and 2) of ten one-day-old specific pathogen free (SPF) white Leghorn chicks were randomly constituted. Birds from groups 2 to 6 were vaccinated by the subcutaneous route (nape of the neck) with a target dose of 2000 PFU as shown in the Table 37 below. Chickens from group 1 were not vaccinated and were kept as control birds. At 2 week-of-age, all birds were challenged with the genotype V Mexican Chimalhuacan (Mex V) velogenic NDV strain. The challenge was performed by the intramuscular (IM) route using $10^5$ Egg Infectious Dose 50 (EID50) diluted in 0.2 ml of physiological sterile water. All birds were monitored until 14 days post-challenge. After challenge, health status of each bird was scored daily as follows: healthy/with specific symptoms (ruffled feathers, prostration, torticollis, tremor)/dead. Any bird that showed specific symptoms for more than 2 days or was noted sick on D28 was taken into account for calculation of morbidity.

TABLE 37

Results of early ND protection induced by different MDV vectored candidates expressing NDV F gene in SPF day-old chicks

| Group | Vaccine | Target dose (PFU) under 0.2 mL (actual dose) | Protection against mortality | Protection against morbidity |
|---|---|---|---|---|
| G1 | — | — | 0% | 0% |
| G2 | vHVT302 | 2000 (4427) | 50% | 10% |
| G3 | vHVT303 | 2000 (ND) | 10% | 0% |
| G4 | vHVT304 | 2000 (1169) | 80% | 60% |
| G5 | vSB1-006 | 2000 (1720) | 60% | 40% |
| G6 | vSB1-007 | 2000 (1564) | 80% | 50% |

Results of protection are summarized in Table 37. All control birds died after ND challenge. Variable levels of ND protection were induced by the different tested vaccines ranging from 10% to 80% and from 0% and 60% in terms of protection against mortality and morbidity, respectively. The vHVT304 candidate induced a better protection than the vHVT303 and vHVT302 candidates; this may be due to the exogenous SV40 promoter placed in front of the NDV F gene. The vSB1-007 performed slightly better than the vSB1-006. Furthermore, performances obtained with vHVT304 were comparable to those obtained with vSB1-007 indicating that different Marek's disease vectors can reach the same level of ND protection.

In conclusion, this study demonstrates that both double HVT-ND+IBD and SB1-ND vectored vaccines can reach significant levels of ND protection in a very severe and early NDV challenge model.

Example 24

ND Efficacy Induced by the Double HVT-ND+IBD vHVT306 Administered by in Ovo or SC Route to One Day-Old SPF Chickens Against a Velogenic Genotype V NDV Challenge Performed at D28

The objective of the study was to evaluate the efficacy of one double HVT-ND+IBD (vHVT306) administered by the in ovo or SC route to SPF chickens against a velogenic genotype V (Chimalhuacan) NDV challenge performed at 28 days of age.

The characteristics of the vHVT306 recombinant vaccine candidate tested in this study are described in Table 38 below. The single HVT-IBD vector vaccine vHVT13 was used as a control.

TABLE 38

Characteristics of the recombinant vaccine candidate used in this study

| Name | Parental virus | Promoter | F gene | Poly-A | Locus |
|---|---|---|---|---|---|
| vHVT306 | vHVT13 | SV40 | Opt-VIId | Synthetic | SORF3-US2 |

On day −3, 40 SPF embryonated eggs aged around 18 days and 18 hours of incubation were randomly allocated into 2 groups of 20 eggs each. On D0, one group of 12 day-old SPF chicks was added. The definition of groups is given in Table 39 below. The vaccination was performed on D-3 (in ovo route) or on D0 (SC route, in the back of the neck) and the target dose of vHVT306 and vHVT13 was 2000 PFU/bird. For the in ovo route, hatchability, viability (until D28) and growth of the birds (between hatching and D28) were monitored.

On D28, 10 birds per group were challenged with virulent ND Chimalhuacan strain. The challenge was performed by the intramuscular (IM) route using $10^5$ Egg Infectious Dose 50 (EID50) diluted in 0.2 ml of physiological sterile water. Birds were monitored until 14 days post-challenge. Specific clinical signs and mortality were recorded. Any bird that showed specific symptoms for more than 2 days or was noted sick on D42 was taken into account for calculation of morbidity. Five and seven days post-challenge (i.e. on D33 and D35), oropharyngeal swab was taken from each surviving bird. All the swabs were analyzed by specific NDV qRT-PCR.

TABLE 39

Results of ND protection induced by vHVT306 MDV vectored candidate expressing both NDV F and IBDV VP2 genes administered by the SC or in ovo route into SPF chicks

| Group | Vaccine/ route | Hatchability/ viability (%) | Protection against mortality/ morbidity | % birds shedding at 5 dpi/7 dpi (mean log 10 titer*) |
|---|---|---|---|---|
| G1 | vHVT13/ in ovo | 100%/100% | 0%/0% | (not tested) |
| G2 | vVHT306/ in ovo | 100%/100% | 100%/100% | 0% (2.7)/0% (2.7) |
| G3 | vHVT306/ SC | — | 100%/100% | 20% (3.2)/10% (2.9) |

*The threshold titer of the real time RT PCR was set at 2.7 log10 equivalent EID50

Full hatchability was recorded after in ovo vaccination in groups 1 and 2 and all hatched birds survived up to D28. No difference in body weights was detected between the two groups at both D0 and D28 confirming the perfect safety of vHVT306 when administered in ovo. Results of protection are summarized in Table 39. All vHVT13-vaccinated control birds died by 4 days after ND challenge. Full clinical ND protection was induced by vHVT306 administered by both routes. Furthermore, no shedding was detected after in ovo administration whereas only a few birds shed detectable amount of challenge virus after SC administration.

In conclusion, this study demonstrates that the double HVT-ND+IBD vHVT306 induce excellent level of ND protection by SC or in ovo administration routes in a very severe heterologous NDV challenge model.

Example 25

Efficacy of Double HVT-ND+IBD (vHVT302, vHVT303 and vHVT304) Recombinant Vaccines, Against Challenge with a Classical IBDV Isolate on D15 in SPF Chickens The aim of the study was to assess the early IBD efficacy of double HVT recombinants vHVT302, vHVT303 and vHVT304 recombinant constructs against a virulent infectious bursal disease virus (vIBDV) challenge (Faragher 52/70 strain) performed at 15 days of age in SPF chickens.

The characteristics of the 3 double HVT-ND+IBD recombinant vaccine candidates tested in this study are described in the Table 40 below.

TABLE 40

Characteristics of the expression cassettes of double HVT recombinants

| Name | Parental virus | Promoter | F gene | Poly-A | Locus |
|---|---|---|---|---|---|
| vHVT302 | vHVT13 | US10 | Opt-VIId | US10 | US10 |
| vHVT303 | vHVT13 | US10 | Opt-V (CA02) | US10 | US10 |
| vHVT304 | vHVT13 | SV40 | Opt-VIId | Synthetic | IG2 |

On D0, 40 one-day-old SPF chickens were randomly allocated into 4 groups of 10 birds including one control groups (G1) that was vaccinated with vSB1-004, a SB-1 vector expressing NDV F gene. Five other SPF birds were kept unvaccinated and unchallenged for bursal/body weights evaluation. The birds were injected by subcutaneous injection in the neck at D0 with 0.2 mL of recombinant vaccines containing a target dose of 2000 pfu as described in the Table 41 below. On D15, blood sample was collected from all birds per group (10 birds per group except for groups 1 and 3 in which 1 bird died before blood sampling) for serological testing with the Kit ProFLOK® plus IBD (Synbiotics Corp). On D15, birds from all 4 groups were challenged by the eye drop (0.05 mL per bird) with 2.5 log 10 EID50.

TABLE 41

Study design and results of IBD efficacy

| Group | Vaccine at day-old | ELISA IBD+ titer (log10) | Number Dead/Sick (total)[1] | % protection[2] | Mean bursal/body weight ratio[4] |
|---|---|---|---|---|---|
| G1 | vSB1-004 | 0.25 | 1/9 (9) | 0% | 0.0014 |
| G2 | vHVT302 | 2.6 | 0/1 (10) | 80% | 0.0043 |

TABLE 41-continued

Study design and results of IBD efficacy

| Group | Vaccine at day-old | ELISA IBD+ titer (log10) | Number Dead/Sick (total)[1] | % protection[2] | Mean bursal/body weight ratio[4] |
|---|---|---|---|---|---|
| G3 | vHVT303 | 3.0 | 0/0 (9) | 100% | 0.0053 |
| G4 | vHVT304 | 2.4 | 0/0 (10) | 80% | 0.0034 |

[1]Birds sick for more than 2 days or still sick on D 25 were considered as sick. The number in brackets is the total number of birds in the group that were challenged.
[2]Protection against clinical signs and severe bursal lesion (bursal score <3)
[4]The bursal/body weight ratio of the unvaccinated/unchallenged group was 0.0043.

Each group was monitored before and after challenge. IBDV clinical signs were recorded for 11 days after challenge (from D15 to D25). At the end of the post-challenge observation period (D25), all the surviving birds were euthanized and necropsied. Body and bursal weights were recorded. Each bursa of Fabricius (BF) was weighted then stored in individual recipients containing 4% formaldehyde for histology. Histological lesions of the bursa were scored according to the scale presented in Table 42.

TABLE 42

Scoring scale of histological lesions of the bursa of Fabricius*

| Score | Histology observation/lesions |
|---|---|
| 0 | No lesion, normal bursa |
| 1 | 1% to 25% of the follicles show lymphoid depletion (i.e. less than 50% of depletion in 1 affected follicle), influx of heterophils in lesions |
| 2 | 26% to 50% of the follicles show nearly complete lymphoid depletion (i.e. more than 75% of depletion in 1 affected follicle), affected follicles show necrosis and severe influx of heterophils may be detected |
| 3 | 51% to 75% of the follicles show lymphoid depletion; affected follicles show necrosis lesions and a severe influx of heterophils is detected |
| 4 | 76% to 100% of the follicles show nearly complete lymphoid depletion; hyperplasia and cyst structures are detected; affected follicles show necrosis and severe influx of heterophils is detected |
| 5 | 100% of the follicles show nearly complete lymphoid depletion; complete loss of follicular structure, thickened and folded epithelium, fibrosis of bursal tissue |

*sourced from Monograph No. 01/2008: 0587 of EU Pharmacopoeia "Avian Infectious Bursal Disease vaccine (live)

A bird was considered as affected if it died and/or showed notable sign of disease and/or severe lesions of the bursa of Fabricius (i.e., histology score 3).

The mean ELISA IBD+ antibody titer expressed in log 10 before challenge is shown in Table 41. Significant titers were detected in all vaccinated groups that were significantly higher than that of the control group G1. The serology titer was slightly higher in G3 (vHVT303).

Severe clinical signs were observed after challenge in all 9 birds of the control group G1, which lead to the death of 1 bird. Only one vaccinated bird in G2 (vHVT302) showed clinical signs after challenge. Percentages of protection against severe bursal lesions are shown in Table 41 above. Significant IBD protection was observed in all vaccinated groups, a full protection being observed in G3 (vHVT303). The mean bursal/body weight ratios are also shown in Table 41. Ratios in all vaccinated groups were higher than those of the challenged control group G1 and not significantly different from the unvaccinated and unchallenged control group.

In conclusion, these data indicate that the three double HVT-IBD+ND tested in this study induced IBD antibodies and early IBD protection in a severe IBDV challenge model.

Example 26

Efficacy of Five Different HVT-ND Vaccine Candidates Against Challenges with Velogenic NDV ZJ1 (Genotype VIId) Isolate at 14 Days of Age in SPF Chickens The aim of the study was to assess the efficacy of 5 single HVT recombinant constructs (vHVT39, vHVT110, vHVT111, vHVT112 and vHVT113) expressing the NDV F gene against Newcastle disease challenge with velogenic NDV ZJ1 (genotype VIId) isolate performed at 14 days of age in SPF chickens.

The characteristics of these 5 vaccine candidates are described in Table 43 below.

TABLE 43

Characteristics of the HVT-ND recombinant viruses used in the challenge study

| Name | Parental virus | Promoter | F gene* | Poly-A | Locus |
|---|---|---|---|---|---|
| vHVT039 | HVT | MDV gB | Wtnm-Texas | SV40 | IG1 |
| vHVT110 | HVT | MCMV IE | Wt-VIId | SV40 | IG1 |
| vHVT111 | HVT | SV40 | Wt-VIId | SV40 | IG1 |
| vHVT112 | HVT | MCMV IE | Wt-YZCQ | SV40 | IG1 |
| vHVT113 | HVT | MCMV IE | Wt-Texas | SV40 | IG1 |

*Wt means that the wild type velogenic F gene sequence was used but the cleavage site was modified to that of a lentogenic virus. Wtnm means that the cleavage site of the wild type sequence was not modified. The Texas velogenic strain belongs to genotype IV and YZCQ to the genotype VIId.

On D0, 72 one-day-old SPF chickens were randomly allocated into 5 groups of 12 birds (vaccinated) and 1 group of 12 birds (non-vaccinated controls). The birds were injected by subcutaneous injection in the neck at D0 with 0.2 mL of recombinant vaccines containing a target dose of 6000 pfu as described in Table 44 below. The birds were challenged by the intramuscular route on D14 with 5 log 10 EID50 of NDV ZJ1/2000 (genotype VIId) velogenic strain.

TABLE 44

Results of ND efficacy

| | | % clinical protection | |
|---|---|---|---|
| Group | Vaccine at day-old (D 0) | Protection against mortality/ morbidity | Mean shedding titer (log10) at 2/4 dpi |
| G1 | — | 0%/0% | 3.5/— (all dead) |
| G2 | vHVT039 | 25%/8% | 2.5/4.8 |
| G3 | vHVT110 | 100%/83% | 1.8/2.0 |
| G4 | vHVT111 | 100%/67% | 1.8/2.8 |
| G5 | vHVT112 | 75%/42% | 1.7/3.4 |
| G6 | vHVT113 | 83%/25% | 1.4/3.3 |

Each group was monitored before and after challenge. NDV clinical signs and mortality were recorded after challenge. Oropharyngeal swabs were taken at 2 and 4 days post-infection (dpi) for evaluation of viral load by real time RT-PCR using the method described by Wise et al. (2004; Development of a Real-Time Reverse-Transcription PCR for Detection of Newcastle Disease Virus RNA in Clinical Samples. J Clin Microbiol 42, 329-338).

Percentages of protection against mortality and morbidity are reported in the table 44 above. Full susceptibility was observed in the non-vaccinated challenged control group G1 thus validating the high severity of the challenge. Vaccines induced variable levels of protection against mortality (25-100%) or against morbidity (8%-83%). The best protection level was induced by vHVT110 whereas the lowest one was induced by vHVT039, the other candidates giving intermediate results. Results of oropharyngeal shedding at 2 and 4 dpi are also shown in Table 44 above and are in line with those of clinical protection. These vaccine candidates differ in their promoter and F gene sequence. These results show that both of these parameters are important for the design of optimal HVT-ND vaccine candidate.

In conclusion, the results of this study showed the importance of promoter and F gene sequence in the ND efficacy induced by HVT-vectored ND vaccine candidates.

Example 27

Evaluation of the Newcastle Disease Efficacy Induced by Double SB1 Constructs Expressing IBDV VP2 and NDV F The aim of the study is to assess the efficacy of double SB1 constructs expressing IBDV VP2 and NDV F against Newcastle disease challenge.

On D0, one-day-old SPF chickens are randomly allocated into several groups of 10-20 birds, including vaccinated and non-vaccinated groups. The birds of the vaccinated groups are injected by subcutaneous injection in the neck at D0 with 0.2 mL containing a target dose of 1000 to 5000 pfu of recombinant vaccines. Alternatively, the same dose in 0.05 mL may be administered in ovo 2 or 3 days before hatch. The birds (at least one vaccinated and one non vaccinated group) are challenged by the intramuscular route at different time after vaccination: for instance, D14, D28 or D42 with about 4.0 log 10 EID50 (0.1 mL) of a velogenic NDV strain such as Texas GB (genotype II), ZJ1 (genotype VIId), Chimalhuacan (genotype V) strain.

Each group is monitored clinically before and after challenge. NDV clinical signs (morbidity) and mortality are recorded after challenge. Percentages of clinical protection in all groups are calculated. At least 90% of non-vaccinated challenged SPF birds should die or be severely sick after challenge to validate the severity of challenge. Oropharyngeal and cloacal swabs can be samples at different times after challenge such as 3, 5, 7 and 9 days post-challenge and the viral load can be estimated by real-time RT-PCR. The best candidates will be those who induced the highest level of clinical protection and the lowest level of viral load in the swabs. A similar study can be performed in broilers containing NDV maternal antibodies; however, these maternal antibodies may potentially protect the non-vaccinated birds if the challenge is performed early. The double SB1 construct may also be tested in combination with other Marek's disease vaccine or vector vaccines.

Example 28

Evaluation of the Infectious Bursal Disease Efficacy Induced by Double SB1 Constructs Expressing IBDV VP2 and NDV F The aim of the study is to assess the IBD efficacy of double SB1 expressing both the IBDV VP2 and the NDV F.

One-day-old SPF chickens are randomly allocated into several groups of 10 to 20 birds including vaccinated and non-vaccinated controls. Non-vaccinated controls will be separated into 2 subgroups including challenged and unchallenged birds. The birds of vaccinated groups are injected by subcutaneous injection in the neck at D0 with 0.2 mL of vaccines containing each a target dose of 1000 to 5000 pfu. Alternatively, the same dose in 0.05 mL may be administered in ovo 2 or 3 days before hatch. At different times after vaccination such as 14, 21, 28 or 42 days post-vaccination, all birds from vaccinated groups and the challenged controls are challenged by the eye drop (0.03 mL containing 2 to 4 log 10 EID50 per bird) of a virulent IBDV (such as the Faragher or the US standard strain), a very virulent IBDV such as the 91-168 isolate or a variant IBDV isolate such as the US Delaware variant E isolate. Each group is clinically monitored before and after challenge. Birds can be necropsied 4 or 5 days post-challenge for bursal gross lesions evaluation. They can also be necropsied 10 to 11 days post-challenge. Gross and/or histological lesions can be evaluated. Furthermore, birds and bursa are weighed the bursal/body weight. ratios (bursa weight/body weight ratio×100) are calculated compared to those of the non-vaccinated unchallenged group. Control SPF challenged birds must show clinical signs and/or have significant gross and/or histological lesions, and/or should have a bursal/body weight ratio significantly lower than the unvaccinated unchallenged control birds to validate the severity of challenge. The efficacy of the vaccine is evaluated by comparing these parameters with unvaccinated/challenged and unvaccinated/unchallenged groups. Such study may be performed in broiler chickens containing IBDV maternal antibodies; however, these maternal antibodies may potentially protect the non-vaccinated birds if the challenge is performed early. The double SB1 construct may also be tested in combination with other Marek's disease vaccine or vector vaccines.

Example 29

Evaluation of the Marek's Disease Efficacy Induced by Double SB1 Constructs Expressing IBDV VP2 and NDV F The aim of the study is to evaluate Marek's disease efficacy induced by the SB1 vectors expressing both IBDV VP2 and NDVF.

One-day-old SPF chickens are randomly allocated into several groups of 20 to 50 birds including vaccinated and non-vaccinated controls. Non-vaccinated controls may be separated into 2 subgroups including challenged and unchallenged birds. The birds of vaccinated groups are injected by subcutaneous injection in the neck at D0 with 0.2 mL of vaccines containing each a target dose of 1000 to 5000 pfu. Alternatively, the same dose in 0.05 mL may be administered in ovo 2 or 3 days before hatch. At different times after vaccination such as 3 to 10 days post-vaccination, all birds from vaccinated groups and the challenged controls are challenged by the intraperitoneal route with 0.2 mL of a Marek's disease virus (MDV) strain. MDV strain may be of several pathotypes such as virulent MDV (vMDV) including the JM or GA22 isolate, very virulent MDV (vvMDV) such as the RB-1B or Md5 isolate, very virulent plus (vv+MDV) such as the T-King or 648A isolate. MDV challenge strain inoculum are prepared by infecting chickens, harvesting and freezing their blood cells into liquid nitrogen in presence of a cryopreservative such as DMSO. The chicken infectious dose 50 (CID50) is established for each challenge batch before performing vaccination/challenge studies. Each group is clinically monitored before and after challenge. Birds are necropsied after at least 7 weeks post-vaccination and the presence Marek's disease gross lesions is checked in each bird. Lesions might include, but not be limited to, the following: liver, heart, spleen, gonads, kidneys, nerve and muscle lesions. Such study may be performed in broiler chickens containing MDV maternal antibodies. The double SB1 construct may also be tested in combination with other Marek's disease vaccine (for instance HVT and or CVI988 Rispens strains) or MD vector vaccines. MD challenge may also be performed by contact between vaccinated birds and MDV infected non-vaccinated SPF chicks.

Having thus described in detail preferred embodiments of the present invention, it is to be understood that the invention defined by the above examples is not to be limited to particular details set forth in the above description as many apparent variations thereof are possible without departing from the spirit or scope of the present invention.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. A composition or vaccine comprising one recombinant herpesvirus of turkeys (HVT) vector comprising at least one or more heterologous polynucleotides coding for and expressing at least one antigen of an avian pathogen, wherein the polynucleotide encodes a Newcastle Disease Virus F (NDV-F) polypeptide and is operably linked to an SV40 promoter, and wherein the polynucleotide is codon-optimized.

2. The composition or vaccine of claim 1, wherein the NDV-F polypeptide has at least 95% sequence identity to the amino acid sequence as set forth in SEQ ID NO:2, 4, 6, 33, 35, or 37.

3. The composition or vaccine of claim 1, wherein the polynucleotide encoding the NDV-F polypeptide is operably linked to an SV40 polyA signal.

4. The composition or vaccine of claim 3, wherein the polynucleotide encoding the NDV-F polypeptide, the operably linked SV40 promoter, and the SV40 polyA signal are inserted in the IG1 (intergenic region 1) locus of HVT genome.

5. The composition or vaccine of claim 1, wherein the composition or vaccine further comprises a second recombinant HVT vector comprising a heterologous polynucleotide coding for and expressing IBDV VP2 antigen.

6. The composition or vaccine of claim 5, wherein the second recombinant HVT vector is the HVT vector included in VAXXITEK™ HVT+IBD.

7. The composition or vaccine of claim 1 or 5, wherein the composition or vaccine is a multivalent composition further comprising one or more recombinant SB1 vectors or the parental SB1 strain.

8. The composition or vaccine of claim 7, wherein the recombinant SB1 vector comprises one or more heterologous polynucleotides coding for and expressing a Newcastle Disease Virus F (NDV-F) antigen.

9. The composition or vaccine of claim 8, wherein the SB1 vector is selected from the group consisting of an SB1 vector comprising an SV40 promoter and a polynucleotide encoding an NDV-F antigen inserted in the region coding for glycoprotein C (UL44) of the SB1 vector, an SB1 vector comprising a guinea pig CMV promoter and a polynucleotide encoding an NDV-F antigen inserted in the region between SORF4 and US2 of the SB1 vector, an SB1 vector comprising an mCMV IE promoter and a polynucleotide encoding an NDV-F antigen inserted in the region US10 of the SB1 vector, and an SB1 vector comprising an SV40 promoter and a polynucleotide encoding an NDV-F antigen inserted in the region between UL55 and LORF5 of the SB1 vector.

10. The composition or vaccine of claim 1, wherein the HVT vector comprises a first heterologous polynucleotide coding for and expressing a Newcastle Disease Virus F (NDV-F) antigen having at least 95% sequence identity to the amino acid sequence as set forth in SEQ ID NO:2, 4, 6, 33, 35, or 37 and a second heterologous polynucleotide coding for and expressing an Infectious Bursal Disease Virus (IBDV) VP2 antigen having at least 95% sequence identity to the amino acid sequence as set forth in SEQ ID NO:8 or 42.

11. The composition or vaccine of claim 10, wherein the polynucleotide encoding the IBDV VP2 antigen is operably linked to a CMV promoter.

12. The composition or vaccine of claim 11, wherein the polynucleotide encoding the NDV-F antigen is operably linked to an SV40 polyA signal and the polynucleotide encoding the IBDV VP2 antigen is operably linked to an SV40 polyA signal.

13. The composition or vaccine of claim 12, wherein the polynucleotide encoding the NDV-F antigen, the operably linked SV40 promoter, and the SV40 polyA signal are inserted in the IG1 locus of the HVT genome, and wherein the polynucleotide encoding the IBDV VP2 antigen, the operably linked CMV promoter, and the SV40 polyA signal are inserted in the IG1 locus or the SORF3-US2 locus of the HVT genome.

14. The composition or vaccine of claim 10, wherein the composition or vaccine further comprises a second recombinant HVT vector comprising a heterologous polynucleotide coding for and expressing an IBDV VP2 antigen.

15. The composition or vaccine of claim 14, wherein the recombinant HVT vector is the HVT vector included in VAXXITEK™ HVT+IBD.

16. The composition or vaccine of claim 10, wherein the composition or vaccine is a multivalent composition or vaccine further comprising one or more recombinant SB1 vectors or the parental SB1 strain.

17. The composition or vaccine of claim 16, wherein the recombinant SB1 vector comprises one or more heterologous polynucleotides coding for and expressing a Newcastle Disease Virus F (NDV-F) antigen.

18. The composition or vaccine of claim 17, wherein the SB1 vector is selected from the group consisting of an SB1 vector comprising an SV40 promoter and a polynucleotide encoding an NDV-F antigen inserted in the region coding for glycoprotein C (UL44) of the SB1 vector, an SB1 vector comprising a guinea pig CMV promoter and a polynucleotide encoding an NDV-F antigen inserted in the region between SORF4 and US2 of the SB1 vector, an SB1 vector comprising an mCMV IE promoter and a polynucleotide encoding an NDV-F antigen inserted in the region US10 of the SB1 vector, and an SB1 vector comprising an SV40 promoter and a polynucleotide encoding an NDV-F antigen inserted in the region between UL55 and LORF5 of the SB1 vector.

19. A method of vaccinating an animal comprising at least one administration of the composition or vaccine of claim 1, wherein the animal is avian.

20. A method for inducing an immunogenic or protective response in an animal against one or more avian pathogens comprising at least one administration of the composition or vaccine of claim 1, wherein the animal is avian.

21. The method of claim 20, wherein the avian pathogen is selected from the group consisting of Newcastle Disease Virus (NDV), Infectious Bursal Disease Virus (i.e., IBDV or Gumboro Disease virus), Marek's Disease Virus (MDV), Infectious Laryngotracheitis Virus (ILTV), avian encephalomyelitis virus, avian reovirus, avian paramyxovirus, avian metapneumovirus, avian influenza virus, avian adenovirus, fowl pox virus, avian coronavirus, avian rotavirus, avian parvovirus, avian astrovirus and chick anemia virus coccidiosis (*Eimeria* sp.), *Campylobacter* sp., *Salmonella* sp., *Mycoplasma* gallisepticum, *Mycoplasma* synoviae, *Pasteurella* sp., *Avibacterium* sp., *E. coli* and *Clostridium* sp.

* * * * *

SEQUENCE LISTING

```
<160> NUMBER OF SEQ ID NOS: 47

<210> SEQ ID NO 1
<211> LENGTH: 1665
<212> TYPE: DNA
<213> ORGANISM: artificial sequence
<220> FEATURE:
<223> OTHER INFORMATION: NDV-F VIId codon-optimized DNA sequence

<400> SEQUENCE: 1
atgggcagca agcccagcac aagaatccca gcccccctga tgctgatcac ccgcatcatg      60
ctgatcctgg gctgcatcag acccacaagc tccctggatg gacgccccct ggccgctgcc     120
ggcatcgtgg tgaccggcga caaggccgtg aacgtgtaca ccagcagcca gaccggcagc     180
```

```
atcatcgtga agctgctgcc caacatgccc agagacaaag aggcctgcgc caaggccccc     240
ctggaagcct acaacagaac cctgaccacc ctgctgaccc ccctgggcga cagcatcaga     300
aagatccagg gctccgtgag cacaagcggc ggaggaaagc agggcagact gatcggcgcc     360
gtgatcggca gcgtggccct gggagtggct acagctgccc agattaccgc tgcagccgcc     420
ctgatccagg ccaaccagaa cgccgccaac atcctgagac tgaaagagag cattgccgcc     480
accaacgagg ccgtgcacga agtgaccgac ggcctgagcc agctgtccgt ggccgtgggc     540
aagatgcagc agttcgtgaa cgaccagttc aacaacaccg ccagagagct ggactgcatc     600
aagatcaccc cagcaggtgg gcgtggagct aacctgtacc tgaccgagct gaccacagtg     660
ttcggccccc agatcacaag cccagccctg acacagctga ccatccaggc cctgtacaac     720
ctggctggcg gcaacatgga ctatctgctg acaaagctgg gaatcggcaa caaccagctg     780
tccagcctga tcggaagcgg cctgatcacc ggctaccccaa tcctgtacga cagccagaca     840
cagctgctgg gcatccaggt gaacctgccc agcgtgggca acctgaacaa catgcgcgcc     900
acctacctgg aaaccctgag cgtgtccacc accaagggct acgccagcgc cctggtgccc     960
aaggtggtga cacaggtggg cagcgtgatc gaggaactgg acaccagcta ctgcatcgag    1020
agcgacctgg acctgtactg caccagaatc gtgaccttcc caatgagccc cggcatctac    1080
agctgcctga cggcaacac cagcgcctgc atgtacagca agaccgaagg cgcactgaca    1140
acaccctaca tggccctgaa gggaagcgtg atcgccaact gcaagatcac cacctgcaga    1200
tgcaccgacc ccccaggcat catcagccag aactacggcg aggccgtgag cctgatcgat    1260
cgccattcct gtaacgtgct gtccctggac ggcatcacac tgagactgag cggcgagttc    1320
gatgccacct accagaagaa catcagcatc ctggacagcc aggtgatcgt gaccggcaac    1380
ctggacatca gcaccgagct gggcaacgtg aataacagca tcagcaacgc cctggacaga    1440
ctggccgaga gcaacagcaa gctggaaaaa gtgaacgtgc gcctgacatc cacttccgct    1500
ctgatcacct acatcgtgct gaccgtgatc agcctggtgt tcggcgccct gagcctggtg    1560
ctggcctgct acctgatgta caagcagaag gcccagcaga aaacctgct gtggctgggc    1620 aacaacaccc tggaccagat gagagccacc accagagcct gatga                   1665
```

<210> SEQ ID NO 2
<211> LENGTH: 553
<212> TYPE: PRT
<213> ORGANISM: artificial sequence
<220> FEATURE:
<223> OTHER INFORMATION: NDV-F protein sequence from codon-optimized
      VIId gene

<400> SEQUENCE: 2

```
Met Gly Ser Lys Pro Ser Thr Arg Ile Pro Ala Pro Leu Met Leu Ile
1               5                   10                  15

Thr Arg Ile Met Leu Ile Leu Gly Cys Ile Arg Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Val Tyr Thr Ser Ser Gln Thr Gly Ser Ile Ile Val Lys
    50                  55                  60

Leu Leu Pro Asn Met Pro Arg Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95
```

```
Asp Ser Ile Arg Lys Ile Gln Gly Ser Val Ser Thr Ser Gly Gly
            100                 105                 110

Lys Gln Gly Arg Leu Ile Gly Ala Val Ile Gly Ser Val Ala Leu Gly
            115                 120                 125

Val Ala Thr Ala Ala Gln Ile Thr Ala Ala Ala Leu Ile Gln Ala
            130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                    165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
            195                 200                 205

Glu Leu Asn Leu Tyr Leu Thr Glu Leu Thr Thr Val Phe Gly Pro Gln
210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
            245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
            275                 280                 285

Leu Pro Ser Val Gly Asn Leu Asn Asn Met Arg Ala Thr Tyr Leu Glu
            290                 295                 300

Thr Leu Ser Val Ser Thr Thr Lys Gly Tyr Ala Ser Ala Leu Val Pro
305                 310                 315                 320

Lys Val Val Thr Gln Val Gly Ser Val Ile Glu Glu Leu Asp Thr Ser
                    325                 330                 335

Tyr Cys Ile Glu Ser Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
            355                 360                 365

Ala Cys Met Tyr Ser Lys Thr Glu Gly Ala Leu Thr Thr Pro Tyr Met
            370                 375                 380

Ala Leu Lys Gly Ser Val Ile Ala Asn Cys Lys Ile Thr Thr Cys Arg
385                 390                 395                 400

Cys Thr Asp Pro Pro Gly Ile Ile Ser Gln Asn Tyr Gly Glu Ala Val
                    405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
            435                 440                 445

Ser Ile Leu Asp Ser Gln Val Ile Val Thr Gly Asn Leu Asp Ile Ser
            450                 455                 460

Thr Glu Leu Gly Asn Val Asn Asn Ser Ile Ser Asn Ala Leu Asp Arg
465                 470                 475                 480

Leu Ala Glu Ser Asn Ser Lys Leu Glu Lys Val Asn Val Arg Leu Thr
                    485                 490                 495

Ser Thr Ser Ala Leu Ile Thr Tyr Ile Val Leu Thr Val Ile Ser Leu
            500                 505                 510

Val Phe Gly Ala Leu Ser Leu Val Leu Ala Cys Tyr Leu Met Tyr Lys
```

Gln Lys Ala Gln Gln Lys Thr Leu Leu Trp Leu Gly Asn Asn Thr Leu
    530                 535                 540

Asp Gln Met Arg Ala Thr Thr Arg Ala
545                 550

<210> SEQ ID NO 3
<211> LENGTH: 1662
<212> TYPE: DNA
<213> ORGANISM: artificial sequence
<220> FEATURE:
<223> OTHER INFORMATION: NDV-F VIId wildtype DNA sequence

<400> SEQUENCE: 3

| | | | | | |
|---|---|---|---|---|---|
| atgggctcca | aaccttctac | caggatccca | gcacctctga | tgctgatcac | ccggattatg | 60 |
| ctgatattgg | gctgtatccg | tccgacaagc | tctcttgacg | gcaggcctct | tgcagctgca | 120 |
| ggaattgtag | taacaggaga | taaggcagtc | aatgtataca | cttcgtctca | gacagggtca | 180 |
| atcatagtca | agttgctccc | gaatatgccc | agggataagg | aggcgtgtgc | aaaagcccca | 240 |
| ttagaggcat | ataacagaac | actgactact | ttgctcactc | tcttggcga | ctccatccgc | 300 |
| aagatccaag | ggtctgtgtc | cacatctgga | ggaggcaagc | aaggccgcct | gataggtgct | 360 |
| gttattggca | gtgtagctct | tggggttgca | acagcggcac | agataacagc | agctgcggcc | 420 |
| ctaatacaag | ccaaccagaa | tgccgccaac | atcctccggc | ttaaggagag | cattgctgca | 480 |
| accaatgaag | ctgtgcatga | agtcaccgac | ggattatcac | aactatcagt | ggcagttggg | 540 |
| aagatgcagc | agtttgtcaa | tgaccagttt | aataatacgg | cgcgagaatt | ggactgtata | 600 |
| aaaatcacac | aacaggttgg | tgtagaactc | aacctatacc | taactgaatt | gactacagta | 660 |
| ttcgggccac | agatcacctc | ccctgcatta | actcagctga | ccatccaggc | actttataat | 720 |
| ttagctggtg | gcaatatgga | ttacttatta | actaagttag | gtataggga | caatcaactc | 780 |
| agctcgttaa | ttggtagcgg | cctgatcact | ggttacccta | tactgtatga | ctcacagact | 840 |
| caactcttgg | gcatacaagt | gaatttaccc | tcagtcggga | acttaaataa | tatgcgtgcc | 900 |
| acctatttgg | agaccttatc | tgtaagtaca | accaaaggat | atgcctcagc | acttgtcccg | 960 |
| aaagtagtga | cacaagtcgg | ttccgtgata | aagagcttg | acacctcata | ctgtatagag | 1020 |
| tccgatctgg | atttatattg | tactagaata | gtgacattcc | ccatgtcccc | aggtatttat | 1080 |
| tcctgtttga | gcggcaacac | atcagcttgc | atgtattcaa | agactgaagg | cgcactcact | 1140 |
| acgccgtata | tggcccttaa | aggctcagtt | attgccaatt | gtaaaataac | aacatgtaga | 1200 |
| tgtacagacc | ctcctggtat | catatcgcaa | aattatggag | aagctgtatc | cctgatagat | 1260 |
| agacattcgt | gcaatgtctt | atcattagac | gggataactc | taaggctcag | tggggaattt | 1320 |
| gatgcaactt | atcaaaagaa | catctcaata | ctagattctc | aagtcatcgt | gacaggcaat | 1380 |
| cttgatatat | caactgaact | tggaaacgtc | aacaattcaa | tcagcaatgc | cttgatagg | 1440 |
| ttggcagaaa | gcaacagcaa | gctagaaaaa | gtcaatgtca | gactaaccag | cacatctgct | 1500 |
| ctcattacct | atattgttct | aactgtcatt | tctctagttt | tcggtgcact | tagtctggtg | 1560 |
| ttagcgtgtt | acctgatgta | caaacagaag | gcacaacaaa | agaccttgct | atggcttggg | 1620 |
| aataatccc | tcgatcagat | gagagccact | acaagagcat | ga | | 1662 |

<210> SEQ ID NO 4
<211> LENGTH: 553
<212> TYPE: PRT
<213> ORGANISM: artificial sequence
<220> FEATURE:
<223> OTHER INFORMATION: NDV-F protein from wildtype VIId DNA sequence

<400> SEQUENCE: 4

```
Met Gly Ser Lys Pro Ser Thr Arg Ile Pro Ala Pro Leu Met Leu Ile
1               5                   10                  15

Thr Arg Ile Met Leu Ile Leu Gly Cys Ile Arg Pro Thr Ser Ser Leu
            20                  25                  30

Asp Gly Arg Pro Leu Ala Ala Gly Ile Val Val Thr Gly Asp Lys
        35                  40                  45

Ala Val Asn Val Tyr Thr Ser Ser Gln Thr Gly Ser Ile Ile Val Lys
    50                  55                  60

Leu Leu Pro Asn Met Pro Arg Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Lys Ile Gln Gly Ser Val Ser Thr Ser Gly Gly Gly
            100                 105                 110

Lys Gln Gly Arg Leu Ile Gly Ala Val Ile Gly Ser Val Ala Leu Gly
        115                 120                 125

Val Ala Thr Ala Ala Gln Ile Thr Ala Ala Ala Ala Leu Ile Gln Ala
130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
        195                 200                 205

Glu Leu Asn Leu Tyr Leu Thr Glu Leu Thr Thr Val Phe Gly Pro Gln
210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
        275                 280                 285

Leu Pro Ser Val Gly Asn Leu Asn Asn Met Arg Ala Thr Tyr Leu Glu
290                 295                 300

Thr Leu Ser Val Ser Thr Thr Lys Gly Tyr Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
370                 375                 380

Ala Leu Lys Gly Ser Val Ile Ala Asn Cys Lys Ile Thr Thr Cys Arg
385                 390                 395                 400
```

-continued

```
Cys Thr Asp Pro Pro Gly Ile Ile Ser Gln Asn Tyr Gly Glu Ala Val
                405                 410                 415
Ser Leu Ile Asp Arg His Ser Cys Asn Val Leu Ser Leu Asp Gly Ile
            420                 425                 430
Thr Leu Arg Leu Ser Gly Glu Phe Asp Ala Thr Tyr Gln Lys Asn Ile
        435                 440                 445
Ser Ile Leu Asp Ser Gln Val Ile Val Thr Gly Asn Leu Asp Ile Ser
    450                 455                 460
Thr Glu Leu Gly Asn Val Asn Asn Ser Ile Ser Asn Ala Leu Asp Arg
465                 470                 475                 480
Leu Ala Glu Ser Asn Ser Lys Leu Glu Lys Val Asn Val Arg Leu Thr
                485                 490                 495
Ser Thr Ser Ala Leu Ile Thr Tyr Ile Val Leu Thr Val Ile Ser Leu
            500                 505                 510
Val Phe Gly Ala Leu Ser Leu Val Leu Ala Cys Tyr Leu Met Tyr Lys
        515                 520                 525
Gln Lys Ala Gln Gln Lys Thr Leu Leu Trp Leu Gly Asn Asn Thr Leu
    530                 535                 540
Asp Gln Met Arg Ala Thr Thr Arg Ala
545                 550

<210> SEQ ID NO 5
<211> LENGTH: 1665
<212> TYPE: DNA
<213> ORGANISM: artificial sequence
<220> FEATURE:
<223> OTHER INFORMATION: NDV-F Ca02 codon-optimized DNA sequence

<400> SEQUENCE: 5
atgggcagca agcccagcac ctggatcagc gtgaccctga tgctgatcac cagaaccatg      60
ctgatcctga gctgcatctg ccccacaagc agcctggacg gcagacccct ggccgctgcc     120
ggcatcgtgg tgaccggcga caaggccgtg aacatctaca ccagcagcca gaccggcagc     180
atcatcatca agctgctgcc caacatgccc aaggacaaag aggcctgcgc caaggccccc     240
ctggaagcct acaacagaac cctgaccacc ctgctgaccc ccctgggcga cagcatcaga     300
agaatccagg gcagcgccac cacaagcggc ggaggaaagc agggcagact ggtgggcgct     360
atcatcggga gcgtggccct gggcgtggcc acagctgccc agattaccgc tgcagccgcc     420
ctgattcagg ccaatcagaa cgccgccaac atcctgagac tgaaagagag cattgccgcc     480
accaacgacg ccgtgcacga agtgacaaac ggactgtccc agctggctgt cgctgtcggc     540
aagatgcagc agttcgtgaa caaccagttc aacaacaccg ccagagagct ggactgcatc     600
aagatcgccc agcaggtggg cgtggagctg aacctgtacc tgaccgagct gaccacagtg     660
ttcggccccc agatcacaag ccccgctctg acccagctga caatccaggc cctgtacaac     720
ctggctggcg gcaacatgga ctatctgctg actaagctgg gagtgggcaa caaccagctg     780
tccagcctga tcgggtccgg gctgatcaca ggcaacccca tcctgtacga cagccagaca     840
cagctgctgg gcatccagat caacctgcca tccgtgggaa gcctgaacaa catgagagcc     900
acctacctgg aaaccctgag cgtgtccacc accaagggct tcgccagcgc cctggtgccc     960
aaggtggtga cacaggtggg cagcgtgatc gaggaactgg acaccagcta ctgcatcgag    1020
agcgacatcg acctgtactg caccagagtg gtgaccttcc caatgagccc cggcatctac    1080
agctgcctga gcggcaacac cagcgcctgc atgtacagca agaccgaagg agcactgaca    1140
```

```
acaccctaca tggccctgaa gggaagcgtg atcgccaact gcaagatgac cacctgcaga    1200
tgcgccgacc ccccaggcat catcagccag aactacggcg aggccgtgag cctgatcgac    1260
aaacattcct gtagcgtgct gtccctggat ggcatcacac tgagactgag cggcgagttc    1320
gacgccacct accagaagaa catcagcatc ctggacagcc aggtgatcgt gaccggcaac    1380
ctggacatca gcaccgagct gggcaacgtg aacaacagca tcagcagcac cctggacaag    1440
ctggccgagt ccaacaacaa gctgaacaaa gtgaacgtga acctgaccag cacaagcgcc    1500
ctgatcacct acatcgtgct ggccatcgtg tccctggcct tcggcgtgat cagcctggtg    1560
ctggcctgct acctgatgta caagcagaga gcccagcaga aaccctgctg tggctgggc     1620 aataacaccc tggaccagat gagggccacc accagaacct gatga                   1665
```

<210> SEQ ID NO 6
<211> LENGTH: 553
<212> TYPE: PRT
<213> ORGANISM: artificial sequence
<220> FEATURE:
<223> OTHER INFORMATION: NDV-F protein sequence from codon-optimized CA02 gene

<400> SEQUENCE: 6

```
Met Gly Ser Lys Pro Ser Thr Trp Ile Ser Val Thr Leu Met Leu Ile
1               5                   10                  15

Thr Arg Thr Met Leu Ile Leu Ser Cys Ile Cys Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Ile Lys
    50                  55                  60

Leu Leu Pro Asn Met Pro Lys Asp Lys Glu Ala Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Gly Ser Ala Thr Thr Ser Gly Gly Gly
            100                 105                 110

Lys Gln Gly Arg Leu Val Gly Ala Ile Ile Gly Ser Val Ala Leu Gly
        115                 120                 125

Val Ala Thr Ala Ala Gln Ile Thr Ala Ala Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Asp Ala Val His Glu Val Thr Asn Gly Leu Ser Gln Leu Ala
                165                 170                 175

Val Ala Val Gly Lys Met Gln Gln Phe Val Asn Asn Gln Phe Asn Asn
            180                 185                 190

Thr Ala Arg Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270
```

-continued

```
Pro Ile Leu Tyr Asp Ser Gln Thr Gln Leu Leu Gly Ile Gln Ile Asn
        275                 280                 285

Leu Pro Ser Val Gly Ser Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Ile Asp Leu Tyr Cys Thr Arg Val Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Met Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Lys His Ser Cys Ser Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Ser Thr Leu Asp Lys
465                 470                 475                 480

Leu Ala Glu Ser Asn Asn Lys Leu Asn Lys Val Asn Val Asn Leu Thr
                485                 490                 495

Ser Thr Ser Ala Leu Ile Thr Tyr Ile Val Leu Ala Ile Val Ser Leu
            500                 505                 510

Ala Phe Gly Val Ile Ser Leu Val Leu Ala Cys Tyr Leu Met Tyr Lys
        515                 520                 525

Gln Arg Ala Gln Gln Lys Thr Leu Leu Trp Leu Gly Asn Asn Thr Leu
    530                 535                 540

Asp Gln Met Arg Ala Thr Thr Arg Thr
545                 550
```

<210> SEQ ID NO 7
<211> LENGTH: 1362
<212> TYPE: DNA
<213> ORGANISM: artificial sequence
<220> FEATURE:
<223> OTHER INFORMATION: IBDV DNA sequence encoding VP2

<400> SEQUENCE: 7

```
atgacaaacc tgcaagatca aacccaacag attgttccgt tcatacggag ccttctgatg      60
ccaacaaccg gaccggcgtc cattccggac gacaccctgg agaagcacac tctcaggtca     120
gagacctcga cctacaattt gactgtgggg gacacagggt cagggctaat tgtctttttc     180
cctggattcc ctggctcaat tgtgggtgct cactacacac tgcagagcaa tgggaactac     240
aagttcgatc agatgctcct gactgcccag aacctaccgg ccagctacaa ctactgcaga     300
ctagtgagtc ggagtctcac agtgaggtca agcacactcc ctggtggcgt ttatgcacta     360
aacggcacca taaacgccgt gaccttccaa ggaagcctga gtgaactgac agatgttagc     420
```

-continued

```
tacaatgggt tgatgtctgc aacagccaac atcaacgaca aaattgggaa tgtcctggta    480
ggggaagggg tcactgtcct cagcctaccc acatcatatg atcttgggta tgtgaggctt    540
ggtgacccca ttcccgctat agggcttgac ccaaaaatgg tagctacatg cgacagcagt    600
gacaggccca gagtctacac cataactgca gccgatgatt accaattctc atcacagtac    660
caaccaggtg gggtaacaat cacactgttc tcagccaaca ttgatgctat cacaagcctc    720
agcattgggg agagctcgt gtttcaaaca agcgtccaag gccttgtact gggcgccacc    780
atctacctta taggctttga tgggactgcg gtaatcacca gagctgtagc cgcagataat    840
gggctgacgg ccggcaccga caatcttatg ccattcaatc ttgtcattcc aaccaatgag    900
ataacccagc caatcacatc catcaaactg gagatagtga cctccaaaag tggtggtcag    960
gcagggatc agatgtcatg gtcggcaagt gggagcctag cagtgacgat ccatggtggc    1020
aactatccag gggccctccg tcccgtcaca ctagtagcct acgaaagagt ggcaacagga    1080
tccgtcgtta cggtcgctgg ggtgagtaac ttcgagctga ttccaaatcc tgaactagca    1140
aagaacctgg ttacagaata cggccgattt gacccaggag ccatgaacta cacaaaattg    1200
atactgagtg agagggaccg tcttggcatc aagaccgtct ggccaacaag ggagtacact    1260
gattttcgtg agtacttcat ggaggtggcc gacctcaact ctcccctgaa gattgcagga    1320
gcatttggct tcaaagacat aatccgggct ataaggaggt aa                       1362
```

```
<210> SEQ ID NO 8
<211> LENGTH: 453
<212> TYPE: PRT
<213> ORGANISM: artificial sequence
<220> FEATURE:
<223> OTHER INFORMATION: IBDV VP2 protein

<400> SEQUENCE: 8
```

Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile

```
                195                 200                 205
Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Ile Gly Gly Glu Leu Val Phe Gln Thr Ser Val Gln Gly Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asp Asn Gly Leu Thr Ala Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg
    450

<210> SEQ ID NO 9
<211> LENGTH: 368
<212> TYPE: DNA
<213> ORGANISM: artificial sequence
<220> FEATURE:
<223> OTHER INFORMATION: SV40 promoter

<400> SEQUENCE: 9
gaattcgagc tcggtacagc ttggctgtgg aatgtgtgtc agttagggtg tggaaagtcc     60
ccaggctccc cagcaggcag aagtatgcaa agcatgcatc tcaattagtc agcaaccagg    120
tgtggaaagt ccccaggctc cccagcaggc agaagtatgc aaagcatgca tctcaattag    180
tcagcaacca tagtcccgcc cctaactccg cccatcccgc ccctaactcc gcccagttcc    240
gcccattctc cgccccatgg ctgactaatt ttttttattt atgcagaggc cgaggccgcc    300
tcggcctctg agctattcca gaagtagtga ggaggctttt ttggaggcct aggcttttgc    360
aaaaagct                                                            368

<210> SEQ ID NO 10
<211> LENGTH: 1391
<212> TYPE: DNA
<213> ORGANISM: artificial sequence
```

```
<220> FEATURE:
<223> OTHER INFORMATION: CMV-IE promoter

<400> SEQUENCE: 10
aactccgccc gttttatgac tagaaccaat agttttaat gccaaatgca ctgaaatccc        60
ctaatttgca aagccaaacg ccccctatgt gagtaatacg gggacttttt acccaatttc       120
ccaagcggaa agcccctaa tacactcata tggcatatga atcagcacgg tcatgcactc       180
taatggcggc ccatagggac tttccacata ggggcgttc accatttccc agcatagggg       240
tggtgactca atggccttta cccaagtaca ttgggtcaat gggaggtaag ccaatgggtt       300
tttcccatta ctggcaagca cactgagtca aatgggactt tccactgggt tttgcccaag       360
tacattgggt caatgggagg tgagccaatg ggaaaaaccc attgctgcca agtacactga       420
ctcaataggg actttccaat gggttttttcc attgttggca agcatataag gtcaatgtgg       480
gtgagtcaat agggactttc cattgtattc tgcccagtac ataaggtcaa tagggggtga       540
atcaacagga aagtcccatt ggagccaagt acactgcgtc aatagggact ttccattggg       600
ttttgcccag tacataaggt caataggggga tgagtcaatg gaaaaaccc attggagcca       660
agtacactga ctcaataggg actttccatt gggttttgcc cagtacataa ggtcaatagg       720
gggtgagtca acaggaaagt cccattggag ccaagtacat tgagtcaata gggacttttcc      780
aatgggtttt gcccagtaca taaggtcaat gggaggtaag ccaatgggtt tttcccatta       840
ctggcacgta tactgagtca ttagggactt tccaatgggt tttgcccagt acataaggtc       900
aatagggggtg aatcaacagg aaagtcccat tggagccaag tacactgagt caataggggac      960
tttccattgg gttttgccca gtacaaaagg tcaataggg gtgagtcaat gggttttttcc      1020
cattattggc acgtacataa ggtcaatagg ggtgagtcat tgggttttttc cagccaattt      1080
aattaaaacg ccatgtactt tcccaccatt gacgtcaatg gctattgaa actaatgcaa       1140
cgtgaccttt aaacggtact ttcccatagc tgattaatgg gaaagtaccg ttctcgagcc       1200
aatacacgtc aatgggaagt gaaagggcag ccaaaacgta acaccgcccc ggttttcccc       1260
tggaaattcc atattggcac gcattctatt ggctgagctg cgttctacgt gggtataaga       1320
ggcgcgacca gcgtcggtac cgtcgcagtc ttcggtctga ccaccgtaga acgcagagct       1380
cctcgctgca g                                                          1391

<210> SEQ ID NO 11
<211> LENGTH: 218
<212> TYPE: DNA
<213> ORGANISM: artificial sequence
<220> FEATURE:
<223> OTHER INFORMATION: SV40 polyA signal

<400> SEQUENCE: 11
ggggatccag acatgataag atacattgat gagtttggac aaaccacaac tagaatgcag        60
tgaaaaaaat gctttatttg tgaaatttgt gatgctattg cttatttgt aaccattata       120
agctgcaata acaagttaa caacaacaat tgcattgatt ttatgtttca ggttcagggg       180
gaggtgtggg aggtttttc ggatcctcta gagtcgac                              218

<210> SEQ ID NO 12
<211> LENGTH: 155
<212> TYPE: DNA
<213> ORGANISM: artificial sequence
<220> FEATURE:
<223> OTHER INFORMATION: Synthetic polyA signal
```

-continued

```
<400> SEQUENCE: 12
aataaaatat ctttattttc attacatctg tgtgttggtt ttttgtgtga atcgatagta    60
ctaacatacg ctctccatca aaacaaaacg aaacaaaaca aactagcaaa ataggctgtc   120
cccagtgcaa gtgcaggtgc cagaacattt ctctt                             155

<210> SEQ ID NO 13
<211> LENGTH: 22
<212> TYPE: DNA
<213> ORGANISM: artificial sequence
<220> FEATURE:
<223> OTHER INFORMATION: primer

<400> SEQUENCE: 13
cgaacaaact tcatcgctat gc                                            22

<210> SEQ ID NO 14
<211> LENGTH: 22
<212> TYPE: DNA
<213> ORGANISM: artificial sequence
<220> FEATURE:
<223> OTHER INFORMATION: primer

<400> SEQUENCE: 14
taactcaaat gcgaagcgtt gc                                            22

<210> SEQ ID NO 15
<211> LENGTH: 21
<212> TYPE: DNA
<213> ORGANISM: artificial sequence
<220> FEATURE:
<223> OTHER INFORMATION: primer

<400> SEQUENCE: 15
actgacaaca ccctacatgg c                                             21

<210> SEQ ID NO 16
<211> LENGTH: 19
<212> TYPE: DNA
<213> ORGANISM: artificial sequence
<220> FEATURE:
<223> OTHER INFORMATION: VIioptF RP primer

<400> SEQUENCE: 16
gccagcacca ggctcaggg                                                19

<210> SEQ ID NO 17
<211> LENGTH: 18
<212> TYPE: DNA
<213> ORGANISM: artificial sequence
<220> FEATURE:
<223> OTHER INFORMATION: primer

<400> SEQUENCE: 17
agcttggctg tggaatgt                                                 18

<210> SEQ ID NO 18
<211> LENGTH: 4344
<212> TYPE: DNA
<213> ORGANISM: artificial sequence
<220> FEATURE:
<223> OTHER INFORMATION: Partial plasmid pHM103+Fopt DNA sequence

<400> SEQUENCE: 18
gagctcaggg tatgatactc agctgttatt gtggccgacc aggaggactc caatgcttag    60
```

```
cattcataag aacgctagag atgctattta acgatgtgct gtcgtctaaa gaatttgtgc    120
atttagcctt taaatgtaaa accaatgacg cattcactac gctcgtgcgt gcaatttctg    180
ggccagggta tgcatattcc ataacagaaa tcgacacttg agaagaggat ctgactgttt    240
gggataaagg tcgtttgggt ctgtcctagc gatataattt atatgacgat atacattaaa    300
catctgtgtg cagtacttag gtatttaatc atgtcgatga aatgttatgt gtaaatatcg    360
gacaatatag ataacgggca cgctgctatt gtaacgtgcg cccgcgcgct agtgctgact    420
aatagtgtgg atgatgtata cagtatatta caaacggaaa tgatacgtaa taaattatgt    480
actcttattg atttataaaa acatacatgc agtgttgcta tgtcacataa ttagcctcgc    540
ccgtctacgc tccactgaag ataatgggct cccgctgttc aaaaaaatca gcgtgcgtcg    600
ataagacttt ggtgcagtct cttcggggtc gcaatttaga tttgccgcat ggagggtatc    660
tggggatttt tgccaatgct ggagcgacga ctgtacgatt cgtcccatcg ggatctagca    720
gaccaatgat gttgacacac atcggccatg catgtacgga cggtctattg cgcgagtttg    780
ttattttcga aggacaagat ggaagtgtat atggaaccga caataatgtt agtttgcatt    840
tcttagggcg gaatctacat gatatcttat ccaagcgggg tatgagccag agagatgtga    900
tggtcataaa gggtaaattt tttagatctg aaataacgca gttgcccaaa caacgatcgc    960
gattaaaaga aaaatcggat ggttcaatta ggacatgcat ggattctgtg cgcataaacc   1020
ataaccgcag cactgttggg cacttcggta actcaaatgc gaagcgttgc acgtctgcga   1080
taactacgcc tactatgcac attgttactc ctgcatctta aaaatatatc ctgtagtaat   1140
tttcacagca atgtcataac atcatctcgc taaagaatga cctgggattg gagaagtaat   1200
gaatatttgc aaccaatgca ttgaataaac taacattaaa cgaattcgag ctcggtacag   1260
cttggctgtg gaatgtgtgt cagttagggt gtggaaagtc cccaggctcc ccagcaggca   1320
gaagtatgca aagcatgcat ctcaattagt cagcaaccag gtgtggaaag tccccaggct   1380
ccccagcagg cagaagtatg caaagcatgc atctcaatta gtcagcaacc atagtcccgc   1440
ccctaactcc gcccatcccg ccctaactc cgcccagttc cgcccattct ccgcccatg    1500 gctgactaat ttttttatt tatgcagagg ccgaggccgc ctcggcctct gagctattcc   1560
agaagtagtg aggaggcttt tttggaggcc taggcttttg caaaaagctg cggccgccac   1620
catgggcagc aagcccagca caagaatccc agcccccctg atgctgatca cccgcatcat   1680
gctgatcctg ggctgcatca gacccacaag ctccctggat ggacgccccc tggccgctgc   1740
cggcatcgtg gtgaccggcg acaaggccgt gaacgtgtac accagcagcc agaccggcag   1800
catcatcgtg aagctgctgc ccaacatgcc cagagacaaa gaggcctgcg ccaaggcccc   1860
cctggaagcc tacaacagaa ccctgaccac cctgctgacc cccctgggcg acagcatcag   1920
aaagatccag ggctccgtga gcacaagcgg cggaggaaag cagggcagac tgatcggcgc   1980
cgtgatcggc agcgtggccc tgggagtggc tacagctgcc cagattaccg ctgcagccgc   2040
cctgatccag gccaaccaga acgccgccaa catcctgaga ctgaaagaga gcattgccgc   2100
caccaacgag gccgtgcacg aagtgaccga cggcctgagc cagctgtccg tggccgtggg   2160
caagatgcag cagttcgtga acgaccagtt caacaacacc gccagagagc tggactgcat   2220
caagatcacc cagcaggtgg gcgtggagct gaacctgtac ctgaccgagc tgaccacagt   2280
gttcggcccc cagatcacaa gcccagccct gacacagctg accatccagg ccctgtacaa   2340
cctggctggc ggcaacatgg actatctgct gacaaagctg ggaatcggca acaaccagct   2400
```

| | |
|---|---|
| gtccagcctg atcggaagcg gcctgatcac cggctacccc atcctgtacg acagccagac | 2460 |
| acagctgctg ggcatccagg tgaacctgcc cagcgtgggc aacctgaaca acatgcgcgc | 2520 |
| cacctacctg gaaaccctga gcgtgtccac caccaagggc tacgccagcg ccctggtgcc | 2580 |
| caaggtggtg acacaggtgg gcagcgtgat cgaggaactg gacaccagct actgcatcga | 2640 |
| gagcgacctg gacctgtact gcaccagaat cgtgaccttc ccaatgagcc ccggcatcta | 2700 |
| cagctgcctg agcggcaaca ccagcgcctg catgtacagc aagaccgaag cgcactgac | 2760 |
| aacaccctac atggccctga agggaagcgt gatcgccaac tgcaagatca ccacctgcag | 2820 |
| atgcaccgac cccccaggca tcatcagcca gaactacggc gaggccgtga gcctgatcga | 2880 |
| tcgccattcc tgtaacgtgc tgtccctgga cggcatcaca ctgagactga gcggcgagtt | 2940 |
| cgatgccacc taccagaaga acatcagcat cctggacagc caggtgatcg tgaccggcaa | 3000 |
| cctggacatc agcaccgagc tgggcaacgt gaataacagc atcagcaacg ccctggacag | 3060 |
| actggccgag agcaacagca agctggaaaa agtgaacgtg cgcctgacat ccacttccgc | 3120 |
| tctgatcacc tacatcgtgc tgaccgtgat cagcctggtg ttcggcgccc tgagcctggt | 3180 |
| gctggcctgc tacctgatgt acaagcagaa ggcccagcag aaaaccctgc tgtggctggg | 3240 |
| caacaacacc ctggaccaga tgagagccac caccagagcc tgatgagcgg ccgcggggat | 3300 |
| ccagacatga taagatacat tgatgagttt ggacaaacca caactagaat gcagtgaaaa | 3360 |
| aaatgcttta tttgtgaaat ttgtgatgct attgctttat ttgtaaccat tataagctgc | 3420 |
| aataaacaag ttaacaacaa caattgcatt gattttatgt ttcaggttca gggggaggtg | 3480 |
| tgggaggttt tttcggatcc tctagagtcg acaattattt tatttaataa catatagccc | 3540 |
| aaagacctct atgaacattt agtttcccgt atactcaacg gcgcgtgtac acacgcatct | 3600 |
| ctttgcatag cgatgaagtt tgttcggcag cagaaaatgc agatatccaa caatctggag | 3660 |
| aaaacttatc atcacagtgg cagtggaaac atacccctc tatattcatg gtataattat | 3720 |
| cgtctacagc gtccaggata gtggcgtgag aaaatggaga tctgcagccc tccttttccat | 3780 |
| ggcatgccgc tttattgttc attaaacgca caatggtctc aacgccagat atgggcatag | 3840 |
| attctgaaga acccgttgac aatccgaaga agaaggcgtg caggtctttg aagactcgc | 3900 |
| acgttggtct tataatgtat gatcgagatg tcaccctaat gccacatggt acaggcttat | 3960 |
| cgcggtcatg gcgatcggac ttgtaatttg caacgatggg caaaggatcg acgacatgcc | 4020 |
| aaacattctg aacccgtaga gatgttaacg atgacgagga tgaatatccc atgctcgctg | 4080 |
| ccatagtatc aagtacaccg cgaataagga gcgcgtccaac atcgttatat gcacacaatg | 4140 |
| ggctacacgt gactaacacc cccgaatatt agtcatatgt gagtttcagt ctggctccca | 4200 |
| tatagcctgt agactatttg tggtttaagt gtgaacgagg cgctgtgaac gagactcggg | 4260 |
| ccgattgtaa gaacaagcaa atgcactttc catttaacaa gaagtgtaga gagaatactc | 4320 |
| aacctctttg gatgtatcct cgag | 4344 |

<210> SEQ ID NO 19
<211> LENGTH: 4085
<212> TYPE: DNA
<213> ORGANISM: artificial sequence
<220> FEATURE:
<223> OTHER INFORMATION: Partial plasmid pSB1 44cds SV FCAopt sequence
      for vSB1-009

<400> SEQUENCE: 19
cttttgtcat gctcggagct ctgatcgcat cttatcatta cgtctgcata gcaacgtctg    60

-continued

| | |
|---|---|
| gagacgtgac gtggaagacc gggttttag ttgtggcggc agggacgatt gccggcatca | 120 |
| cggctccgta tggagacatt tctcctctag ccggctttct ttcggcgtat acggcgttag | 180 |
| ctattcacgt ggtcagagac gccagtcggt ctctaatgaa cacgtgctac taccgtgcac | 240 |
| gtcgggaaat tactgtgaac ggtgcatatc gcctcggtcg cgcgcgtctc ccgcccagca | 300 |
| cggacgccga ggcgacgcgc gaagaagacg tatccagtta cgatacgctg ggggggaata | 360 |
| ttcctacgat aattctgagc ctcatagcgg tcatctcgat ccagccata gccagctttc | 420 |
| aaaagtacat gtcgaacgca actaagcacc agtcaacatt gactgacacg ttacgcagta | 480 |
| tatgcggttt cttggtgggt acaagtgtcg cgatattcct tccgtcgcgc taccacgagg | 540 |
| ttctgttccg tccaattctt gtattactgt taatattcgg ggcaatggct actaccttag | 600 |
| ccggcttcgg tttacttctc gggccgacat tgttttccgc gacagccgcg gttctgtgct | 660 |
| gctacacttg tataaatgta cgcaacgcga atagcggaat aaagcaattg gcggccgccg | 720 |
| cagctggtaa atgcatatta ggaactgcca tctcgagcat gttggtttgc gtgttaatac | 780 |
| aatattcctg atcgcggagc gattaatttt tatatcatgt gctcatagcg ttctttcgaa | 840 |
| ctgcgaataa aactttcgtg gctactaaag gggcctatcg tgggtttatg cgctgtcgaa | 900 |
| aacatgaaag ggccgattta aagctaagtt gcgcaggcag aggccactcc atatacgctc | 960 |
| tcggagacgc ggctcgcacg ccagctgaaa tattttcccc cctgcaggtc gacccaattc | 1020 |
| gagctcggta cagcttggct gtggaatgtg tgtcagttag ggtgtggaaa gtccccaggc | 1080 |
| tccccagcag gcagaagtat gcaaagcatg catctcaatt agtcagcaac caggtgtgga | 1140 |
| aagtccccag gctccccagc aggcagaagt atgcaaagca tgcatctcaa ttagtcagca | 1200 |
| accatagtcc cgcccctaac tccgcccatc ccgcccctaa ctccgcccag ttccgcccat | 1260 |
| tctccgcccc atggctgact aatttttttt atttatgcag aggccgaggc cgcctcggcc | 1320 |
| tctgagctat tccagaagta gtgaggaggc ttttttggag gcctaggctt ttgcaaaaag | 1380 |
| ctcccggggc ggccgccacc atgggcagca agcccagcac ctggatcagc gtgaccctga | 1440 |
| tgctgatcac cagaaccatg ctgatcctga gctgcatctg ccccacaagc agcctggacg | 1500 |
| gcagaccect ggccgctgcc ggcatcgtgg tgaccggcga caaggccgtg aacatctaca | 1560 |
| ccagcagcca gaccggcagc atcatcatca gctgctgcc caacatgccc aaggacaaag | 1620 |
| aggcctgcgc caaggccccc ctggaagcct acaacagaac cctgaccacc ctgctgaccc | 1680 |
| ccctgggcga cagcatcaga agaatccagg gcagcgccac cacaagcggc ggaggaaagc | 1740 |
| agggcagact ggtgggcgct atcatcggga gcgtggccct gggcgtggcc acagctgccc | 1800 |
| agattaccgc tgcagccgcc ctgattcagg ccaatcagaa cgccgccaac atcctgagac | 1860 |
| tgaaagagag cattgccgcc accaacgacg ccgtgcacga agtgacaaac ggactgtccc | 1920 |
| agctggctgt cgctgtcggc aagatgcagc agttcgtgaa caaccagttc aacaacaccg | 1980 |
| ccagagagct ggactgcatc aagatcgccc agcaggtggg cgtggagctg aacctgtacc | 2040 |
| tgaccgagct gaccacagtg ttcggccccc agatcacaag ccccgctctg acccagctga | 2100 |
| caatccaggc cctgtacaac ctggctggcg gcaacatgga ctatctgctg actaagctgg | 2160 |
| gagtgggcaa caaccagctg tccagcctga tcgggtccgg gctgatcaca ggcaacccca | 2220 |
| tcctgtacga cagccagaca cagctgctgg gcatccagat caacctgcca tccgtgggaa | 2280 |
| gcctgaacaa catgagagcc acctacctgg aaaccctgag cgtgtccacc accaagggct | 2340 |
| tcgccagcgc cctggtgccc aaggtggtga cacaggtggg cagcgtgatc gaggaactgg | 2400 |
| acaccagcta ctgcatcgag agcgacatcg acctgtactg caccagagtg gtgaccttcc | 2460 |

```
caatgagccc cggcatctac agctgcctga gcggcaacac cagcgcctgc atgtacagca    2520
agaccgaagg agcactgaca acaccctaca tggccctgaa gggaagcgtg atcgccaact    2580
gcaagatgac cacctgcaga tgcgccgacc ccccaggcat catcagccag aactacggcg    2640
aggccgtgag cctgatcgac aaacattcct gtagcgtgct gtccctggat ggcatcacac    2700
tgagactgag cggcgagttc gacgccacct accagaagaa catcagcatc ctggacagcc    2760
aggtgatcgt gaccggcaac ctggacatca gcaccgagct gggcaacgtg aacaacagca    2820
tcagcagcac cctggacaag ctggccgagt ccaacaacaa gctgaacaaa gtgaacgtga    2880
acctgaccag cacaagcgcc ctgatcacct acatcgtgct ggccatcgtg tccctggcct    2940
tcggcgtgat cagcctggtg ctggcctgct acctgatgta caagcagaga gcccagcaga    3000
aaaccctgct gtggctgggc aataacaccc tggaccagat gagggccacc accagaacct    3060
gatgagcggc cgcgatacct gcaggtttgc ggtgacattg atctggctca ttatatgccc    3120
cgagctcttg taacatcgcg gacgcgattt ccgtagtagg cacatctcaa atgcaaaagc    3180
ggcatgtcaa ccgtataggt acatccggcc ctgcttacag tcggtagggc atatatccac    3240
cggaaaactt cagctttaga ctcctcaggt gatgaggaat agtatgtaac cctctagcag    3300
tacggtattt ctaaaaaaag gtagatcctt ttccacacgg cacagactaa ataacgtaca    3360
ctacacaggt tctctcgaac ttcgtttgga ccggaattat tccctcggca gcgcctaaaa    3420
agcaaacctc tagagtagat aagtgtcagt gaacctaggc cttctttgtt ccacggctgg    3480
aaagctaagg gacgaggtac acgcgacccc agccacgcac gaacagagtt taacggaagc    3540
gtcgtttgcg ggataaggtt gtcggacccc gcgggtccgt tgaaaagtgg ctgcgcgcct    3600
accgacgaat acgtcggtaa caattttaga aatcgaatat gactgcgagt accgtacaat    3660
cgcgaaatac ggtctctata tagctactcg gtccttaaat atgtaagtat gatgtcccct    3720
actcccgaag acgaccgcga cttggtcgca gtacgtgggc tgctccggat gatggacgag    3780
accacatctg agcgacacaa acgttcgcgt tcaggatgcc cccggttgtt atgcggttgt    3840
acgatcggga tcgctcttac tgtgttcgtc atcacagcta cggtcgtgct agcttcgctg    3900
tttgcattct cttacatgtc cctggagtcc ggtacatgtc ctcacgaatg gatcggttta    3960
ggctatagtt gtatgcgcgc gatggggagc aacgctaccg agctagaagc cctagatacg    4020
tgctcccgac ataacagcaa gcttgtcgac tttactcatg cgaaaattct aatcgaagct    4080
atcgc    4085
```

<210> SEQ ID NO 20
<211> LENGTH: 4335
<212> TYPE: DNA
<213> ORGANISM: artificial sequence
<220> FEATURE:
<223> OTHER INFORMATION: Partial plasmid pHVT US2 SV-Fopt-SynPA for vHVT306

<400> SEQUENCE: 20

```
taaaatggga tctatcatta cattcgttaa gagtctggat aattttactg tttgccagct      60
tcgatcttgg aacgtactgt ggatagtgcc ttacttggaa tcgtgaaaat ttgaaacgtc     120
cattatttgg atatcttccg gttgtcccat atcccgccct ggtaccgctc ggataccttg     180
cccgtatgga ttcgtattga cagtcgcgca atcggggacc aacaacgcgt gggtccacac     240
tcattccgaa attttccgat gattctgaat atttattgcc gctcgttacg agtcgttgga     300
catatctgta atacatttct tcttctgaag gatcgctgca catttgatct atacattggc     360
```

```
caggatgttc aagtctcaga tgttgcattc tggcacagca caactttatg gcatttccga    420
tgtaatcgtc cggcagccct gggggagttc tatattcgca tattgggatg gtaaggacaa    480
tagcagatct cgcaacctcc agggaggcta taataacgtt tttaaaggat ggatttctca    540
taaaaatctg tcgcaaatta cactgagaat atcctttact agcgccgatt gagagcatcg    600
tcgtccaatt ttctaaatgg aaagaaaaca aggcgggcaa gagtgttcca acattttca     660 ttttcggcga atctctcaaa tcccatggcg tgcaattgat tgcaaaattg cacttccgt     720 tcacgtttgt atctccaaac tctaagacac ttttaattga aaaactacgt tctagtgtgg    780
aaagaaacct ataggcagac catagaacta tttgacacca catatctttt tgtatgtcaa    840
actgaccatg atcgtatgtt gctgaatgca ctagggcaat tcgctcgcgc gactccatac    900
attgaataat tccacacgtc agctcatcgg ttagcaaggt ccagtagttg aagtcattta    960 ttttcccg cggctggcca atctacctc tgggaatatc aagttgtcg aatatgatcg      1020 caccggctct ggtcatggtg aaggaacttg tagcataaag acgcaggtat cataggggta   1080
atattttttt attcactcac atactaaaag taacgcatat tagcaccatg tatgggctat   1140
caattgacat ttgcgtagca ctacatcacg attatgtaca acataatggg acaacatatg   1200
cctgcaggtc gacccaattc gagctcggta cagcttggct gtggaatgtg tgtcagttag   1260
ggtgtggaaa gtccccaggc tccccagcag gcagaagtat gcaaagcatg catctcaatt   1320
agtcagcaac caggtgtgga agtccccag gctccccagc aggcagaagt atgcaaagca   1380
tgcatctcaa ttagtcagca accatagtcc cgccctaac tccgcccatc ccgccctaa    1440 ctccgcccag ttccgcccat tctccgcccc atggctgact aatttttttt atttatgcag   1500
aggccgaggc cgcctcggcc tctgagctat tccagaagta gtgaggaggc ttttttggag   1560
gcctaggctt ttgcaaaaag ctcccggggc ggccgccacc atgggcagca agcccagcac   1620
aagaatccca gccccctga tgctgatcac ccgcatcatg ctgatcctgg gctgcatcag   1680
acccacaagc tccctggatg gacgcccct ggccgctgcc ggcatcgtgg tgaccggcga   1740
caaggccgtg aacgtgtaca ccagcagcca gaccggcagc atcatcgtga agctgctgcc   1800
caacatgccc agagacaaag aggcctgcgc caaggccccc ctggaagcct acaacagaac   1860
cctgaccacc ctgctgaccc ccctgggcga cagcatcaga agatccagg gctccgtgag   1920 cacaagcggc ggaggaaagc agggcagact gatcggcgcc gtgatcggca gcgtggccct   1980
gggagtggct acagctgccc agattaccgc tgcagccgcc ctgatccagg ccaaccagaa   2040
cgccgccaac atcctgagac tgaaagagag cattgccgcc accaacgagg ccgtgcacga   2100
agtgaccgac ggcctgagcc agctgtccgt ggccgtgggc aagatgcagc agttcgtgaa   2160
cgaccagttc aacaacaccg ccagagagct ggactgcatc aagatcaccc agcaggtggg   2220
cgtggagctg aacctgtacc tgaccgagct gaccacagtg ttcggccccc agatcacaag   2280
cccagccctg acacagctga ccatccaggc cctgtacaac ctggctggcg caacatgga    2340 ctatctgctg acaaagctgg gaatcggcaa caaccagctg tccagcctga tcggaagcgg   2400
cctgatcacc ggctacccca tcctgtacga cagccagaca cagctgctgg catccaggt   2460 gaacctgccc agcgtgggca acctgaacaa catgcgcgcc acctacctgg aaaccctgag   2520
cgtgtccacc accaagggct acgccagcgc cctggtgccc aaggtggtga cacaggtggg   2580
cagcgtgatc gaggaactgg acaccagcta ctgcatcgag agcgacctgg acctgtactg   2640
caccagaatc gtgaccttcc caatgagccc cggcatctac agctgcctga gcggcaacac   2700
```

| | |
|---|---|
| cagcgcctgc atgtacagca agaccgaagg cgcactgaca acaccctaca tggccctgaa | 2760 |
| gggaagcgtg atcgccaact gcaagatcac cacctgcaga tgcaccgacc ccccaggcat | 2820 |
| catcagccag aactacggcg aggccgtgag cctgatcgat cgccattcct gtaacgtgct | 2880 |
| gtccctggac ggcatcacac tgagactgag cggcgagttc gatgccacct accagaagaa | 2940 |
| catcagcatc ctggacagcc aggtgatcgt gaccggcaac ctggacatca gcaccgagct | 3000 |
| gggcaacgtg aataacagca tcagcaacgc cctggacaga ctggccgaga gcaacagcaa | 3060 |
| gctggaaaaa gtgaacgtgc gcctgacatc cacttccgct ctgatcacct acatcgtgct | 3120 |
| gaccgtgatc agcctggtgt tcggcgccct gagcctggtg ctggcctgct acctgatgta | 3180 |
| caagcagaag gcccagcaga aaccctgct gtggctgggc aacaacaccc tggaccagat | 3240 |
| gagagccacc accagagcct gatgagcggc cgcgatatca ataaaatatc tttattttca | 3300 |
| ttacatctgt gtgttggttt tttgtgtgaa tcgatagtac taacatacgc tctccatcaa | 3360 |
| aacaaaacga aacaaaacaa actagcaaaa taggctgtcc ccagtgcaag tgcaggtgcc | 3420 |
| agaacatttc tcttctagac ctgcaggccc gggcaagtag atgcaatttc ctcacactag | 3480 |
| ttgggtttat ctactattga attttcccct atctgtgata cacttgggag cctctacaag | 3540 |
| catattgcca tcatgtacgt ttttatctac tgtcttaacg cccatgggaa cggaggcgtc | 3600 |
| gtcgtcatgt attggacggc aacataggca gcaacacaaa ttgcgtttag gtggggtgca | 3660 |
| tgtggactcg ataccaagcc cctgcagctg ggaacgtct ggtggagagc cgataatttg | 3720 |
| atatacgcac gccatattac tgtcgttgaa gtacgcctta tcttctatgt tttcaaattt | 3780 |
| aggttcccaa gtgacgtga gaagtgtttg tatctcacat ggaatggccc aaggcattcc | 3840 |
| agcccaggtg cctggtactt taatggcaaa caaacgtttt ggtagaggta ttgattctat | 3900 |
| tgcagttctg cagatatctg cagccccgag tatccacagg ctatacgata cgttatcgga | 3960 |
| ggcctccgat tctagcatta catagccggt cagtagatcc tgccattcgg tagcgcaacc | 4020 |
| ggctacatct tcaaacagtc tcacaataaa tgcatctctc gttcctgcca atccggaacc | 4080 |
| gggcatacca ctcccgcctg ccgatttaat tctcacaatt gggcgatgcc ggcggggcaa | 4140 |
| aacgaatgtg gatttggcaa accgacacag gtctgctgta cggactaata tgggcacacc | 4200 |
| cacatcattc ttcagatgct ccatgcattg ttctatgaga aagatccata gggtggaggc | 4260 |
| agcgtcacga gatcgcccag gcaatcgatc gcattcgtct agtaaagtga cgagagttat | 4320 |
| catgcacaca cccat | 4335 |

<210> SEQ ID NO 21
<211> LENGTH: 5381
<212> TYPE: DNA
<213> ORGANISM: artificial sequence
<220> FEATURE:
<223> OTHER INFORMATION: plasmid pCD046+NDV-F wt for vHVT110

<400> SEQUENCE: 21

```
gagctcaggg tatgatactc agctgttatt gtggccgacc aggaggactc caatgcttag     60
cattcataag aacgctagag atgctattta acgatgtgct gtcgtctaaa gaatttgtgc    120
atttagcctt taaatgtaaa accaatgacg cattcactac gctcgtgcgt gcaatttctg    180
ggccagggta tgcatattcc ataacagaaa tcgacacttg agaagaggat ctgactgttt    240
gggataaagg tcgtttgggt ctgtcctagc gatataattt atatgacgat atacattaaa    300
catctgtgtg cagtacttag gtatttaatc atgtcgatga aatgttatgt gtaaatatcg    360
gacaatatag ataacgggca cgctgctatt gtaacgtgcg cccgcgcgct agtgctgact    420
```

```
aatagtgtgg atgatgtata cagtatatta caaacggaaa tgatacgtaa taaattatgt      480
actcttattg atttataaaa acatacatgc agtgttgcta tgtcacataa ttagcctcgc      540
ccgtctacgc tccactgaag ataatgggct cccgctgttc aaaaaaatca gcgtgcgtcg      600
ataagacttt ggtgcagtct cttcggggtc gcaatttaga tttgccgcat ggagggtatc      660
tggggatttt tgccaatgct ggagcgacga ctgtacgatt cgtcccatcg ggatctagca      720
gaccaatgat gttgacacac atcggccatg catgtacgga cggtctattg cgcgagtttg      780
ttattttcga aggacaagat ggaagtgtat atggaaccga caataatgtt agtttgcatt      840
tcttagggcg gaatctacat gatatcttat ccaagcgggg tatgagccag agagatgtga      900
tggtcataaa gggtaaattt tttagatctg aaataacgca gttgcccaaa caacgatcgc      960
gattaaaaga aaaatcggat ggttcaatta ggacatgcat ggattctgtg cgcataaacc     1020
ataaccgcag cactgttggg cacttcggta actcaaatgc gaagcgttgc acgtctgcga     1080
taactacgcc tactatgcac attgttactc ctgcatctta aaaatatatc ctgtagtaat     1140
tttcacagca atgtcataac atcatctcgc taaagaatga cctgggattg gagaagtaat     1200
gaatatttgc aaccaatgca ttgaataaac taacattaaa cgaattcaat agtggatccc     1260
ccaactccgc ccgttttatg actagaacca atagttttta atgccaaatg cactgaaatc     1320
ccctaatttg caaagccaaa cgcccccctat gtgagtaata cggggacttt ttacccaatt     1380
tcccacgcgg aaagccccct aatacactca tatggcatat gaatcagcac ggtcatgcac     1440
tctaatggcg gcccataggg actttccaca taggggcgt tcaccatttc ccagcatagg      1500
ggtggtgact caatggcctt tacccaagta cattgggtca atgggaggta agccaatggg     1560 ttttcccat tactgcaag cacactgagt caaatgggac tttccactgg gttttgccca      1620
agtacattgg gtcaatggga ggtgagccaa tgggaaaaac ccattgctgc caagtacact      1680
gactcaatag ggacttttcca atgggttttt ccattgttgg caagcatata aggtcaatgt     1740
gggtgagtca atagggactt tccattgtat tctgcccagt acataaggtc aatagggggt     1800
gaatcaacag gaaagtccca ttggagccaa gtacactgcg tcaataggga ctttccattg     1860
ggttttgccc agtacataag gtcaataggg gatgagtcaa tgggaaaaac ccattggagc     1920
caagtacact gactcaatag ggacttttcca ttgggttttg cccagtacat aaggtcaata     1980
gggggtgagt caacaggaaa gttccattgg agccaagtac attgagtcaa tagggacttt     2040
ccaatgggtt tgcccagta cataaggtca tgggaggta agccaatggg ttttcccat      2100 tactggcacg tatactgagt cattagggac tttccaatgg gttttgccca gtacataagg     2160
tcaatagggg tgaatcaaca ggaaagtccc attggagcca agtacactga gtcaataggg     2220
actttccatt gggttttgcc cagtacaaaa ggtcaatagg gggtgagtca atgggttttt     2280
cccattattg gcacgtacat aaggtcaata ggggtgagtc attgggtttt tccagccaat     2340
ttaattaaaa cgccatgtac tttcccacca ttgacgtcaa tgggctattg aaactaatgc     2400
aacgtgacct ttaaacggta ctttcccata gctgattaat gggaaagtac cgttctcgag     2460
ccaatacacg tcaatgggaa gtgaaagggc agccaaaacg taacaccgcc ccggttttcc     2520
cctggaaatt ccatattggc acgcattcta ttggctgagc tgcgttctac gtgggtataa     2580
gaggcgcgac cagcgtcggt accgtcgcag tcttcggtct gaccaccgta gaacgcagag     2640
ctcctcgctg caggcggccg catgggctcc aaaccttcta ccaggatccc agcacctctg     2700
atgctgatca cccggattat gctgatattg ggctgtatcc gtccgacaag ctctcttgac     2760
```

```
ggcaggcctc ttgcagctgc aggaattgta gtaacaggag ataaggcagt caatgtatac    2820
acttcgtctc agacagggtc aatcatagtc aagttgctcc cgaatatgcc cagggataag    2880
gaggcgtgtg caaaagcccc attagaggca tataacagaa cactgactac tttgctcact    2940
cctcttggcg actccatccg caagatccaa gggtctgtgt ccacatctgg aggaggcaag    3000
caaggccgcc tgataggtgc tgttattggc agtgtagctc ttggggttgc aacagcggca    3060
cagataacag cagctgcggc cctaatacaa gccaaccaga atgccgccaa catcctccgg    3120
cttaaggaga gcattgctgc aaccaatgaa gctgtgcatg aagtcaccga cggattatca    3180
caactatcag tggcagttgg gaagatgcag cagtttgtca atgaccagtt taataatacg    3240
gcgcgagaat tggactgtat aaaaatcaca caacaggttg gtgtagaact caacctatac    3300
ctaactgaat tgactacagt attcgggcca cagatcacct cccctgcatt aactcagctg    3360
accatccagg cactttataa tttagctggt ggcaatatgg attacttatt aactaagtta    3420
ggtataggga caatcaact cagctcgtta attggtagcg gcctgatcac tggttaccct    3480
atactgtatg actcacagac tcaactcttg ggcatacaag tgaatttacc ctcagtcggg    3540
aacttaaata atatgcgtgc cacctatttg gagaccttat ctgtaagtac aaccaaagga    3600
tatgcctcag cacttgtccc gaaagtagtg acacaagtcg gttccgtgat agaagagctt    3660
gacacctcat actgtatga gtccgatctg gatttatatt gtactagaat agtgacattc    3720
cccatgtccc caggtattta ttcctgtttg agcggcaaca catcagcttg catgtattca    3780
aagactgaag gcgcactcac tacgccgtat atggccctta aaggctcagt tattgccaat    3840
tgtaaaataa caacatgtag atgtacagac cctcctggta tcatatcgca aaattatgga    3900
gaagctgtat ccctgataga tagacattcg tgcaatgtct tatcattaga cgggataact    3960
ctaaggctca gtggggaatt tgatgcaact tatcaaaaga acatctcaat actagattct    4020
caagtcatcg tgacaggcaa tcttgatata tcaactgaac ttggaaacgt caacaattca    4080
atcagcaatg ccttggatag gttggcagaa agcaacagca agctagaaaa agtcaatgtc    4140
agactaacca gcacatctgc tctcattacc tatattgttc taactgtcat ttctctagtt    4200
ttcggtgcac ttagtctggt gttagcgtgt acctgatgt acaaacagaa ggcacaacaa    4260
aagaccttgc tatggcttgg gaataatacc ctcgatcaga tgagagccac tacaagagca    4320
tgagcggccg cggggatcca gacatgataa gatacattga tgagtttgga caaaccacaa    4380
ctagaatgca gtgaaaaaaa tgctttattt gtgaaatttg tgatgctatt gctttatttg    4440
taaccattat aagctgcaat aaacaagtta acaacaacaa ttgcattgat tttatgtttc    4500
aggttcaggg ggaggtgtgg gaggtttttt cggatcctct agagtcgaca attatttat    4560 ttaataacat atagcccaaa gacctctatg aacatttagt ttcccgtata ctcaacggcg    4620
cgtgtacaca cgcatctctt tgcatagcga tgaagtttgt tcggcagcag aaaatgcaga    4680
tatccaacaa tctggagaaa acttatcatc acagtggcag tggaaacata ccccctctat    4740
attcatggta aattatcgt ctacagcgtc caggatagtg gcgtgagaaa atggagatct    4800
gcagccctcc tttccatggc atgccgcttt attgttcatt aaacgcacaa tggtctcaac    4860
gccagatatg gcatagatt ctgaagaacc cgttgacaat ccgaagaaga aggcgtgcag    4920
gtctttggaa gactcgcacg ttggtcttat aatgtatgat cgagatgtca ccctaatgcc    4980
acatggtaca ggcttatcgc ggtcatggcg atcggacttg taatttgcaa cgatgggcaa    5040
aggatcgacg acatgccaaa cattctgaac ccgtagagat gttaacgatg acgaggatga    5100
atatcccatg ctcgctgcca tagtatcaag tacaccgcga ataaggacgc gtccaacatc    5160
```

-continued gttatatgca cacaatgggc tacacgtgac taacaccccc gaatattagt catatgtgag 5220
tttcagtctg gctcccatat agcctgtaga ctatttgtgg tttaagtgtg aacgaggcgc 5280
tgtgaacgag actcgggccg attgtaagaa caagcaaatg cactttccat ttaacaagaa 5340
gtgtagagag aatactcaac ctctttggat gtatcctcga g 5381

<210> SEQ ID NO 22
<211> LENGTH: 4337
<212> TYPE: DNA
<213> ORGANISM: artificial sequence
<220> FEATURE:
<223> OTHER INFORMATION: Partial plasmid pHM103+NDV-F wt sequence for vHVT111

<400> SEQUENCE: 22
gagctcaggg tatgatactc agctgttatt gtggccgacc aggaggactc caatgcttag 60
cattcataag aacgctagag atgctattta acgatgtgct gtcgtctaaa gaatttgtgc 120
atttagcctt taaatgtaaa accaatgacg cattcactac gctcgtgcgt gcaatttctg 180
ggccagggta tgcatattcc ataacagaaa tcgacacttg agaagaggat ctgactgttt 240
gggataaagg tcgtttgggt ctgtcctagc gatataattt atatgacgat atacattaaa 300
catctgtgtg cagtacttag gtatttaatc atgtcgatga aatgttatgt gtaaatatcg 360
gacaatatag ataacgggca cgctgctatt gtaacgtgcg cccgcgcgct agtgctgact 420
aatagtgtgg atgatgtata cagtatatta caaacggaaa tgatacgtaa taaattatgt 480
actcttattg atttataaaa acatacatgc agtgttgcta tgtcacataa ttagcctcgc 540
ccgtctacgc tccactgaag ataatgggct cccgctgttc aaaaaaatca gcgtgcgtcg 600
ataagacttt ggtgcagtct cttcggggtc gcaatttaga tttgccgcat ggagggtatc 660
tggggatttt tgccaatgct ggagcgacga ctgtacgatt cgtcccatcg ggatctagca 720
gaccaatgat gttgacacac atcggccatg catgtacgga cggtctattg cgcgagtttg 780
ttattttcga aggacaagat ggaagtgtat atggaaccga caataatgtt agtttgcatt 840
tcttagggcg gaatctacat gatatcttat ccaagcgggg tatgagccag agagatgtga 900
tggtcataaa gggtaaattt tttagatctg aaataacgca gttgcccaaa caacgatcgc 960
gattaaaaga aaaatcggat ggttcaatta ggacatgcat ggattctgtg cgcataaacc 1020
ataaccgcag cactgttggg cacttcggta actcaaatgc gaagcgttgc acgtctgcga 1080
taactacgcc tactatgcac attgttactc ctgcatctta aaaatatatc ctgtagtaat 1140
tttcacagca atgtcataac atcatctcgc taaagaatga cctgggattg gagaagtaat 1200
gaatatttgc aaccaatgca ttgaataaac taacattaaa cgaattcgag ctcggtacag 1260
cttggctgtg gaatgtgtgt cagttagggt gtggaaagtc cccaggctcc ccagcaggca 1320
gaagtatgca aagcatgcat ctcaattagt cagcaaccag gtgtggaaag tccccaggct 1380
ccccagcagg cagaagtatg caaagcatgc atctcaatta gtcagcaacc atagtcccgc 1440
ccctaactcc gcccatcccg cccctaactc cgcccagttc cgcccattct ccgccccatg 1500
gctgactaat tttttttatt tatgcagagg ccgaggccgc ctcggcctct gagctattcc 1560
agaagtagtg aggaggcttt tttggaggcc taggcttttg caaaaagctg cggccgcatg 1620
ggctccaaac cttctaccag gatcccagca cctctgatgc tgatcacccg gattatgctg 1680
atattgggct gtatccgtcc gacaagctct cttgacggca ggcctcttgc agctgcagga 1740
attgtagtaa caggagataa ggcagtcaat gtatacactt cgtctcagac agggtcaatc 1800

```
atagtcaagt tgctcccgaa tatgcccagg gataaggagg cgtgtgcaaa agccccatta    1860
gaggcatata acagaacact gactactttg ctcactcctc ttggcgactc catccgcaag    1920
atccaagggt ctgtgtccac atctggagga ggcaagcaag gccgcctgat aggtgctgtt    1980
attggcagtg tagctcttgg ggttgcaaca gcggcacaga taacagcagc tgcggcccta    2040
atacaagcca accagaatgc cgccaacatc ctccggctta aggagagcat tgctgcaacc    2100
aatgaagctg tgcatgaagt caccgacgga ttatcacaac tatcagtggc agttgggaag    2160
atgcagcagt ttgtcaatga ccagtttaat aatacggcgc gagaattgga ctgtataaaa    2220
atcacacaac aggttggtgt agaactcaac ctatacctaa ctgaattgac tacagtattc    2280
gggccacaga tcacctcccc tgcattaact cagctgacca tccaggcact ttataattta    2340
gctggtggca atatggatta cttattaact aagttaggta tagggaacaa tcaactcagc    2400
tcgttaattg gtagcggcct gatcactggt taccctatac tgtatgactc acagactcaa    2460
ctcttgggca tacaagtgaa tttaccctca gtcgggaact taaataatat gcgtgccacc    2520
tatttggaga ccttatctgt aagtacaacc aaaggatatg cctcagcact tgtcccgaaa    2580
gtagtgacac aagtcggttc cgtgatgaaa gagcttgaca cctcatactg tatagagtcc    2640
gatctggatt tatattgtac tagaatagtg acattcccca tgtccccagg tatttattcc    2700
tgtttgagcg gcaacacatc agcttgcatg tattcaaaga ctgaaggcgc actcactacg    2760
ccgtatatgg cccttaaagg ctcagttatt gccaattgta aaataacaac atgtagatgt    2820
acagaccctc ctggtatcat atcgcaaaat tatggagaag ctgtatccct gatagataga    2880
cattcgtgca atgtcttatc attagacggg ataactctaa ggctcagtgg ggaatttgat    2940
gcaacttatc aaaagaacat ctcaatacta gattctcaag tcatcgtgac aggcaatctt    3000
gatatatcaa ctgaacttgg aaacgtcaac aattcaatca gcaatgcctt ggataggttg    3060
gcagaaagca acagcaagct agaaaaagtc aatgtcagac taaccagcac atctgctctc    3120
attacctata ttgttctaac tgtcatttct ctagttttcg gtgcacttag tctggtgtta    3180
gcgtgttacc tgatgtacaa acagaaggca caacaaaaga ccttgctatg gcttgggaat    3240
aataccctcg atcagatgag agccactaca agagcatgag cggccgcggg gatccagaca    3300
tgataagata cattgatgag tttggacaaa ccacaactag aatgcagtga aaaaaatgct    3360
ttatttgtga aatttgtgat gctattgctt tatttgtaac cattataagc tgcaataaac    3420
aagttaacaa caacaattgc attgatttta tgtttcaggt tcaggggag gtgtgggagg    3480 ttttttcgga tcctctagag tcgacaatta ttttatttaa taacatatag cccaaagacc    3540
tctatgaaca tttagtttcc cgtatactca acggcgcgtg tacacacgca tctctttgca    3600
tagcgatgaa gtttgttcgg cagcagaaaa tgcagatatc caacaatctg agaaaacttt    3660
atcatcacag tggcagtgga aacatacccc ctctatattc atggtataat tatcgtctac    3720
agcgtccagg atagtggcgt gagaaaatgg agatctgcag ccctcctttc catggcatgc    3780
cgctttattg ttcattaaac gcacaatggt ctcaacgcca gatatgggca tagattctga    3840
agaacccgtt gacaatccga agaagaaggc gtgcaggtct ttggaagact cgcacgttgg    3900
tcttataatg tatgatcgag atgtcaccct aatgccacat ggtacaggct tatcgcggtc    3960
atggcgatcg gacttgtaat ttgcaacgat gggcaaagga tcgacgacat gccaaacatt    4020
ctgaacccgt agagatgtta acgatgacga ggatgaatat cccatgctcg ctgccatagt    4080
atcaagtaca ccgcgaataa ggacgcgtcc aacatcgtta tatgcacaca atgggctaca    4140
```
cgtgactaac acccccgaat attagtcata tgtgagtttc agtctggctc ccatatagcc 4200
tgtagactat ttgtggttta agtgtgaacg aggcgctgtg aacgagactc gggccgattg 4260
taagaacaag caaatgcact ttccatttaa caagaagtgt agagagaata ctcaacctct 4320
ttggatgtat cctcgag 4337

<210> SEQ ID NO 23
<211> LENGTH: 4344
<212> TYPE: DNA
<213> ORGANISM: artificial sequence
<220> FEATURE:
<223> OTHER INFORMATION: Partial plasmid pHM103+NDV-F CA02 for vHVT116

<400> SEQUENCE: 23
gagctcaggg tatgatactc agctgttatt gtggccgacc aggaggactc caatgcttag 60
cattcataag aacgctagag atgctattta acgatgtgct gtcgtctaaa gaatttgtgc 120
atttagcctt taaatgtaaa accaatgacg cattcactac gctcgtgcgt gcaatttctg 180
ggccagggta tgcatattcc ataacagaaa tcgacacttg agaagaggat ctgactgttt 240
gggataaagg tcgtttgggt ctgtcctagc gatataattt atatgacgat atacattaaa 300
catctgtgtg cagtacttag gtatttaatc atgtcgatga aatgttatgt gtaaatatcg 360
gacaatatag ataacgggca cgctgctatt gtaacgtgcg cccgcgcgct agtgctgact 420
aatagtgtgg atgatgtata cagtatatta caaacggaaa tgatacgtaa taaattatgt 480
actcttattg atttataaaa acatacatgc agtgttgcta tgtcacataa ttagcctcgc 540
ccgtctacgc tccactgaag ataatgggct cccgctgttc aaaaaaatca gcgtgcgtcg 600
ataagacttt ggtgcagtct cttcggggtc gcaatttaga tttgccgcat ggagggtatc 660
tggggatttt tgccaatgct ggagcgacga ctgtacgatt cgtcccatcg ggatctagca 720
gaccaatgat gttgacacac atcggccatg catgtacgga cggtctattg cgcgagtttg 780
ttattttcga aggacaagat ggaagtgtat atggaaccga caataatgtt agtttgcatt 840
tcttagggcg gaatctacat gatatcttat ccaagcgggg tatgagccag agagatgtga 900
tggtcataaa gggtaaattt tttagatctg aaataacgca gttgcccaaa caacgatcgc 960
gattaaaaga aaaatcggat ggttcaatta ggacatgcat ggattctgtg cgcataaacc 1020
ataaccgcag cactgttggg cacttcggta actcaaatgc gaagcgttgc acgtctgcga 1080
taactacgcc tactatgcac attgttactc ctgcatctta aaaatatatc ctgtagtaat 1140
tttcacagca atgtcataac atcatctcgc taaagaatga cctgggattg gagaagtaat 1200
gaatatttgc aaccaatgca ttgaataaac taacattaaa cgaattcgag ctcggtacag 1260
cttggctgtg gaatgtgtgt cagttagggt gtggaaagtc cccaggctcc ccagcaggca 1320
gaagtatgca aagcatgcat ctcaattagt cagcaaccag gtgtggaaag tccccaggct 1380
ccccagcagg cagaagtatg caaagcatgc atctcaatta gtcagcaacc atagtcccgc 1440
ccctaactcc gcccatcccg cccctaactc cgcccagttc cgcccattct ccgccccatg 1500
gctgactaat tttttttatt tatgcagagg ccgaggccgc ctcggcctct gagctattcc 1560
agaagtagtg aggaggcttt tttggaggcc taggcttttg caaaaagctg cggccgccac 1620
catgggcagc aagcccagca cctggatcag cgtgaccctg atgctgatca ccagaaccat 1680
gctgatcctg agctgcatct gccccacaag cagcctggac ggcagacccc tggccgctgc 1740
cggcatcgtg gtgaccggcg acaaggccgt gaacatctac accagcagcc agaccggcag 1800
catcatcatc aagctgctgc ccaacatgcc caaggacaaa gaggcctgcg ccaaggcccc 1860

-continued

```
cctggaagcc tacaacagaa ccctgaccac cctgctgacc ccctgggcg acagcatcag   1920
aagaatccag ggcagcgcca ccacaagcgg cggaggaaag cagggcagac tggtgggcgc   1980
tatcatcggg agcgtggccc tgggcgtggc cacagctgcc cagattaccg ctgcagccgc   2040
cctgattcag gccaatcaga acgccgccaa catcctgaga ctgaaagaga gcattgccgc   2100
caccaacgac gccgtgcacg aagtgacaaa cggactgtcc cagctggctg tcgctgtcgg   2160
caagatgcag cagttcgtga acaaccagtt caacaacacc gccagagagc tggactgcat   2220
caagatcgcc cagcaggtgg gcgtggagct gaacctgtac ctgaccgagc tgaccacagt   2280
gttcggcccc cagatcacaa gccccgctct gacccagctg acaatccagg ccctgtacaa   2340
cctggctggc ggcaacatgg actatctgct gactaagctg ggagtgggca caaccagct   2400
gtccagcctg atcgggtccg ggctgatcac aggcaacccc atcctgtacg acagccagac   2460
acagctgctg ggcatccaga tcaacctgcc atccgtggga agcctgaaca catgagagc   2520
cacctacctg gaaaccctga gcgtgtccac caccaagggc ttcgccagcg ccctggtgcc   2580
caaggtggtg acacaggtgg gcagcgtgat cgaggaactg gacaccagct actgcatcga   2640
gagcgacatc gacctgtact gcaccagagt ggtgaccttc ccaatgagcc ccggcatcta   2700
cagctgcctg agcggcaaca ccagcgcctg catgtacagc aagaccgaag gagcactgac   2760
aacaccctac atggccctga gggaagcgt gatcgccaac tgcaagatga ccacctgcag   2820
atgcgccgac cccccaggca tcatcagcca gaactacggc gaggccgtga gcctgatcga   2880
caaacattcc tgtagcgtgc tgtccctgga tggcatcaca ctgagactga gcggcgagtt   2940
cgacgccacc taccagaaga acatcagcat cctggacagc caggtgatcg tgaccggcaa   3000
cctggacatc agcaccgagc tgggcaacgt gaacaacagc atcagcagca ccctggacaa   3060
gctggccgag tccaacaaca agctgaacaa agtgaacgtg aacctgacca gcacaagcgc   3120
cctgatcacc tacatcgtgc tggccatcgt gtccctggcc ttcggcgtga tcagcctggt   3180
gctggcctgc tacctgatgt acaagcagag agcccagcag aaaaaccctg ctgtggctggg   3240
caataacacc ctggaccaga tgagggccac caccagaacc tgatgagcgg ccgcggggat   3300
ccagacatga taagatacat tgatgagttt ggacaaacca caactagaat gcagtgaaaa   3360
aaatgcttta tttgtgaaat ttgtgatgct attgctttat tgtaaccat tataagctgc   3420
aataaacaag ttaacaacaa caattgcatt gattttatgt ttcaggttca ggggaggtg   3480
tgggaggttt ttccgatcc tctagagtcg acaattattt tatttaataa catatagccc   3540
aaagacctct atgaacattt agtttcccgt atactcaacg gcgcgtgtac acacgcatct   3600
ctttgcatag cgatgaagtt tgttcggcag cagaaaatgc agatatccaa caatctggag   3660
aaaacttatc atcacagtgg cagtggaaac ataccccctc tatattcatg gtataattat   3720
cgtctacagc gtccaggata gtggcgtgag aaaatggaga tctgcagccc tccttttccat   3780
ggcatgccgc tttattgttc attaaacgca caatggtctc aacgccagat atgggcatag   3840
attctgaaga acccgttgac aatccgaaga agaaggcgtg caggtctttg aaagactcgc   3900
acgttggtct tataatgtat gatcgagatg tcaccctaat gccacatggt acaggcttat   3960
cgcggtcatg gcgatcggac ttgtaatttg caacgatggg caaggatcg acgacatgcc   4020
aaacattctg aacccgtaga gatgttaacg atgacgagga tgaatatccc atgctcgctg   4080
ccatagtatc aagtacaccg cgaataagga gcgttccaac atcgttatat gcacacaatg   4140
ggctacacgt gactaacacc cccgaatatt agtcatatgt gagtttcagt ctggctccca   4200
```

```
tatagcctgt agactatttg tggtttaagt gtgaacgagg cgctgtgaac gagactcggg    4260
ccgattgtaa gaacaagcaa atgcactttc catttaacaa gaagtgtaga gagaatactc    4320
aacctctttg gatgtatcct cgag                                            4344

<210> SEQ ID NO 24
<211> LENGTH: 3988
<212> TYPE: DNA
<213> ORGANISM: artificial sequence
<220> FEATURE:
<223> OTHER INFORMATION: Partial plasmid HVTIG2 SV Fwt SbfI sequence for
      vHVT301

<400> SEQUENCE: 24
tgtttcgcac catatccaag ctggctgtcc ctaagagctt attcctgcaa gacctcatac      60
ggaataattg cccgaccaat acttattacg gacataggta ggccgataaa tattatgttg     120
actggaggat ggaaggagg ttttgtaaca gctacatcgc tcgttcatca gcaagcgata     180
ctttggatat ccgagcttca aaagccgcat aaaccccgct ttatttctga atacgcccca    240
acagtaacac atgcgtggtt cctggcactt ggaacgccgt gttttatagg caagaacata    300
ctacccaaag aggtcttggg atttctggcg cgtcgttgca atgaagaaat gaattctttg    360
ttccttgaaa tgccgacaac tctaaaaacg gtattcgagc accattactt tacgcgtgga    420
tctgaagtaa atccagcgtt gttgatgag cctaacagat ttttgcaact gatggattcg    480
cggaaaatcc tatgtttata cgaatccgct atgtgcgaca accccggagc tcagggtatg    540
atactcagct gttattgtgg ccgaccagga ggactccaat gcttagcatt cataagaacg    600
ctagagatgc tatttaacga tgtgctgtcg tctaaagaat ttgtgcattt agcctttaaa    660
tgtaaaacca atgacgcatt cactacgctc gtgcgtgcaa tttctgggcc agggtatgca    720
tattccataa cagaaatcga cacttgagaa gaggatctga ctgtttggga taaaggtcgt    780
ttgggtctgt cctagcgata taatttatat gacgatatac attaaacatc tgtgtgcagt    840
acttaggtat ttaatcatgt cgatgaaatg ttatgtgtaa atatcggaca atatagataa    900
cgggcacgct gctattgtaa cgtgcgcccg cgcgctagtg ctgactaata gtgtggatga    960
tgtatacagt atattacaaa cggaaatgat acgtaataaa cctgcaggtc gacccaattc   1020
gagctcggta cagcttggct gtggaatgtg tgtcagttag ggtgtggaaa gtccccaggc   1080
tccccagcag gcagaagtat gcaaagcatg catctcaatt agtcagcaac caggtgtgga   1140
aagtccccag gctccccagc aggcagaagt atgcaaagca tgcatctcaa ttagtcagca   1200
accatagtcc cgcccctaac tccgcccatc ccgccctaa ctccgcccag ttccgcccat   1260
tctccgcccc atggctgact aattttttt atttatgcag aggccgaggc cgcctcggcc   1320
tctgagctat tccagaagta gtgaggaggc ttttttggag gcctaggctt ttgcaaaaag   1380
ctgcggccgc atgggctcca aaccttctac caggatccca gcacctctga tgctgatcac   1440
ccggattatg ctgatattgg gctgtatccg tccgacaagc tctcttgacg gcaggcctct   1500
tgcagctgca ggaattgtag taacaggaga taaggcagtc aatgtatca cttcgtctca   1560 gacagggtca atcatagtca agttgctccc gaatatgccc agggataagg aggcgtgtgc   1620
aaaagcccca ttagaggcat ataacagaac actgactact tgctcactc ctcttggcga   1680 ctccatccgc aagatccaag ggtctgtgtc cacatctgga ggaggcaagc aaggccgcct   1740
gataggtgct gttattggca gtgtagctct tggggttgca acagcggcac agataacagc   1800
agctgcggcc ctaatacaag ccaaccagaa tgccgccaac atcctccggc ttaaggagag   1860
```

| | |
|---|---|
| cattgctgca accaatgaag ctgtgcatga agtcaccgac ggattatcac aactatcagt | 1920 |
| ggcagttggg aagatgcagc agtttgtcaa tgaccagttt aataatacgg cgcgagaatt | 1980 |
| ggactgtata aaaatcacac aacaggttgg tgtagaactc aacctatacc taactgaatt | 2040 |
| gactacagta ttcgggccac agatcacctc ccctgcatta actcagctga ccatccaggc | 2100 |
| actttataat ttagctggtg gcaatatgga ttacttatta actaagttag gtataggggaa | 2160 |
| caatcaactc agctcgttaa ttggtagcgg cctgatcact ggttacccta tactgtatga | 2220 |
| ctcacagact caactcttgg gcatacaagt gaatttaccc tcagtcggga acttaaataa | 2280 |
| tatgcgtgcc acctatttgg agaccttatc tgtaagtaca accaaaggat atgcctcagc | 2340 |
| acttgtcccg aaagtagtga cacaagtcgg ttccgtgata aagagcttg acacctcata | 2400 |
| ctgtatagag tccgatctgg atttatattg tactagaata gtgacattcc ccatgtcccc | 2460 |
| aggtatttat tcctgtttga gcggcaacac atcagcttgc atgtattcaa agactgaagg | 2520 |
| cgcactcact acgccgtata tggcccttaa aggctcagtt attgccaatt gtaaaataac | 2580 |
| aacatgtaga tgtacagacc ctcctggtat catatcgcaa aattatggag aagctgtatc | 2640 |
| cctgatagat agacattcgt gcaatgtctt atcattagac gggataactc taaggctcag | 2700 |
| tggggaattt gatgcaactt atcaaaagaa catctcaata ctagattctc aagtcatcgt | 2760 |
| gacaggcaat cttgatatat caactgaact tggaaacgtc aacaattcaa tcagcaatgc | 2820 |
| cttggatagg ttggcagaaa gcaacagcaa gctagaaaaa gtcaatgtca gactaaccag | 2880 |
| cacatctgct ctcattaccct atattgttct aactgtcatt tctctagttt tcggtgcact | 2940 |
| tagtctggtg ttagcgtgtt acctgatgta caaacagaag gcacaacaaa agaccttgct | 3000 |
| atggcttggg aataataccc tcgatcagat gagagccact acaagagcat gagcggccgc | 3060 |
| ggggatccag acatgataag atacattgat gagtttggac aaaccacaac tagaatgcag | 3120 |
| tgaaaaaaat gctttatttg tgaaatttgt gatgctattg ctttatttgt aaccattata | 3180 |
| agctgcaata aacaagttaa caacaacaat tgcattgatt ttatgtttca ggttcagggg | 3240 |
| gaggtgtggg aggttttttc ggatcctcta gagggggatta atcctgcagg ttatgtactc | 3300 |
| ttattgattt ataaaaacat acatgcagtg ttgctatgtc acataattag cctcgccccgt | 3360 |
| ctacgctcca ctgaagataa tgggctcccg ctgttcaaaa aaatcagcgt gcgtcgataa | 3420 |
| gactttggtg cagtctcttc ggggtcgcaa tttagatttg ccgcatggag ggtatctggg | 3480 |
| gattttgcc aatgctggag cgacgactgt acgattcgtc ccatcgggat ctagcagacc | 3540 |
| aatgatgttg acacacatcg gccatgcatg tacggacggt ctattgcgcg agtttgttat | 3600 |
| tttcgaagga caagatggaa gtgtatatgg aaccgacaat aatgttagtt tgcatttctt | 3660 |
| agggcggaat ctacatgata tcttatccaa gcgggggtatg agccagagag atgtgatggt | 3720 |
| cataaagggt aaatttttta gatctgaaat aacgcagttg cccaaacaac gatcgcgatt | 3780 |
| aaaagaaaaa tcggatggtt caattaggac atgcatggat tctgtgcgca taaaccataa | 3840 |
| ccgcagcact gttgggcact tcggtaactc aaatgcgaag cgttgcacgt ctgcgataac | 3900 |
| tacgcctact atgcacattg ttactcctgc atcttaaaaa tatatcctgt agtaattttc | 3960 |
| acagcaatgt cataacatca tctcgcta | 3988 |

<210> SEQ ID NO 25
<211> LENGTH: 3707
<212> TYPE: DNA
<213> ORGANISM: artificial sequence
<220> FEATURE:
<223> OTHER INFORMATION: Partial plasmid pHVTUS10 cds F opt plasmid for vHVT302

<400> SEQUENCE: 25

```
tcccttacgg cggatcgaaa cgacattagg catactcggg taccattttg cattccgatc      60
agcacggatg aaattaggca ggaatgcggt ttatattatg cggcattgga caaacgatat     120
ggcattgatt ggcagtttat gaatgtcttc atgttgggcg taaacggatt cctattggtt     180
cagaagacaa cgacgatata tttagagaga aaaagctacc cagcatagga taaacacaca     240
ttgagcattg agagacatag gtatcggtat ggatgggaaa actacacacg tgaacaccaa     300
acgacttata tactcgagcg gtgatactac tgagcaagaa tgcactgcat ctgagccact     360
gaatgaagac tgtgatgaaa atgtgaccat cgatggaatt ggagaagaat atgcgcagtt     420
cttcatgtcc ccgcaatggg tcccaaatct acatcgcttg agcgaggata ccaaaaaggt     480
ataccgatgt atggtttcca acagactcaa ttattttccc tattatgagg cgttcaggcg     540
gtctttgttt gatatgtata tgctaggtcg gttgggcgt cgacttaagc gatctgactg      600
ggagactatt atgcatctgt caccaacgca agtcggcgt ctacatagaa ctttaagatt      660
tgtggagcgt agaattatcc catctaacag ttatatacgc acatcgggcc acgttccgcc     720
ttcgagggca cttccgacag atacgaattt aaagatggat gaataattaa attggaaaga     780
gtaactacat taatcgagcg tcatgacggc gtcccgtgaa aatgggaatt ttctactcga     840
aacaccgtga catttgacag acctggaatt gttattctga tatatagtgg gtgtgtctgg     900
ccggcaacat acataatgtg catgcgaaac cactttttca gtgtacgctg acattgtgca     960
acacggaggg gtagcatcta catacaatat atgttgatta cctgcagggc ggccgccacc    1020
atgggcagca agcccagcac aagaatccca gcccccctga tgctgatcac ccgcatcatg    1080
ctgatcctgg gctgcatcag acccacaagc tccctggatg acgcccct ggccgctgcc     1140
ggcatcgtgg tgaccggcga caaggccgtg aacgtgtaca ccagcagcca gaccggcagc    1200
atcatcgtga gctgctgcc caacatgccc agagacaaag aggcctgcgc caaggccccc    1260
ctggaagcct acaacagaac cctgaccacc ctgctgaccc cctgggcga cagcatcaga    1320
aagatccagg gctccgtgag cacaagcggc ggaggaaagc agggcagact gatcggcgcc    1380
gtgatcggca gcgtggccct gggagtggct acagctgccc agattaccgc tgcagccgcc    1440
ctgatccagg ccaaccagaa cgccgccaac atcctgagac tgaaagagag cattgccgcc    1500
accaacgagg ccgtgcacga agtgaccgac ggcctgagcc agctgtccgt ggccgtgggc    1560
aagatgcagc agttcgtgaa cgaccagttc aacaacaccg ccagagagct ggactgcatc    1620
aagatcaccc agcaggtggg cgtggagctg aacctgtacc tgaccgagct gaccacagtg    1680
ttcggccccc agatcacaag cccagccctg acacagctga ccatccaggc cctgtacaac    1740
ctggctggcg gcaacatgga ctatctgctg acaaagctgg gaatcggcaa caccagctg     1800
tccagcctga tcggaagcgg cctgatcacc ggctacccca tcctgtacga cagccagaca    1860
cagctgctgg gcatccaggt gaacctgccc agcgtgggca acctgaacaa catgcgcgcc    1920
acctacctgg aaaccctgag cgtgtccacc accaagggct acgccagcgc cctggtgccc    1980
aaggtggtga cacaggtggg cagcgtgatc gaggaactgg acaccagcta ctgcatcgag    2040
agcgacctgg acctgtactg caccagaatc gtgaccttcc caatgagccc cggcatctac    2100
agctgcctga gcggcaacac cagcgcctgc atgtacagca agaccgaagg cgcactgaca    2160
acaccctaca tggcccctga gggaagcgtg atcgccaact gcaagatcac cacctgcaga    2220
tgcaccgacc ccccaggcat catcagccag aactacggcg aggccgtgag cctgatcgat    2280
```

```
cgccattcct gtaacgtgct gtccctggac ggcatcacac tgagactgag cggcgagttc 2340
gatgccacct accagaagaa catcagcatc ctggacagcc aggtgatcgt gaccggcaac 2400
ctggacatca gcaccgagct gggcaacgtg aataacagca tcagcaacgc cctggacaga 2460
ctggccgaga gcaacagcaa gctggaaaaa gtgaacgtgc gcctgacatc cacttccgct 2520
ctgatcacct acatcgtgct gaccgtgatc agcctggtgt tcggcgccct gagcctggtg 2580
ctggcctgct acctgatgta caagcagaag gcccagcaga aaccctgct gtggctgggc 2640
aacaacaccc tggaccagat gagagccacc accagagcct gatgagcggc cgccccgggc 2700
ctgcaggcat aggcacgctc tgatgttaca gaccacaata ccgcatacat ttattgtaag 2760
gttgttaata aaggtttatt ctatgtaaga ctacaatact ttcgacattg cttgtataca 2820
tattaaatac tttctcaagt tcctattaca taaaatggga tctatcatta cattcgttaa 2880
gagtctggat aattttactg tttgccagct tcgatcttgg aacgtactgt ggatagtgcc 2940
ttacttggaa tcgtgaaaat ttgaaacgtc cattatttgg atatcttccg gttgtcccat 3000
atcccgccct ggtaccgctc ggataccttg cccgtatgga ttcgtattga cagtcgcgca 3060
atcggggacc aacaacgcgt gggtccacac tcattcggaa attttccgat gattctgaat 3120
atttattgcc gctcgttacg agtcgttgga catatctgta atacatttct tcttctgaag 3180
gatcgctgca catttgatct atacattggc caggatgttc aagtctcaga tgttgcattc 3240
tggcacagca caactttatg gcatttccga tgtaatcgtc cggcagccct gggggagttc 3300
tatattcgca tattgggatg gtaaggacaa tagcagatct cgcaacctcc agggaggcta 3360
taataacgtt tttaaaggat ggatttctca taaaaatctg tcgcaaatta cactgagaat 3420
atcctttact agcgccgatt gagagcatcg tcgtccaatt ttctaaatgg aaagaaaaca 3480
aggcgggcaa gagtgttcca aacattttca ttttcggcga atctctcaaa tcccatggcg 3540
tgcaattgat tgcaaaattg gcacttccgt tcacgtttgt atctccaaac tctaagacac 3600
ttttaattga aaaactacgt tctagtgtgg aaagaaacct ataggcagac catagaacta 3660
tttgacacca catatctttt tgtatgtcaa actgaccatg atcgtat 3707
```

<210> SEQ ID NO 26
<211> LENGTH: 3707
<212> TYPE: DNA
<213> ORGANISM: artificial sequence
<220> FEATURE:
<223> OTHER INFORMATION: Partial plasmid pHVT US20 cds F CA02 opt sequence for vHVT303

<400> SEQUENCE: 26

```
tcccttacgg cggatcgaaa cgacattagg catactcggg taccattttg cattccgatc 60
agcacggatg aaattaggca ggaatgcggt ttatattatg cggcattgga caaacgatat 120
ggcattgatt ggcagtttat gaatgtcttc atgttgggcg taaacggatt cctattggtt 180
cagaagacaa cgacgatata tttagagaga aaaagctacc cagcatagga taaacacaca 240
ttgagcattg agagacatag gtatcggtat ggatgggaaa actacacacg tgaacaccaa 300
acgacttata tactcgagcg gtgatactac tgagcaagaa tgcactgcat ctgagccact 360
gaatgaagac tgtgatgaaa atgtgaccat cgatggaatt ggagaagaat atgcgcagtt 420
cttcatgtcc ccgcaatggg tcccaaatct acatcgcttg agcgaggata ccaaaaaggt 480
ataccgatgt atggtttcca acagactcaa ttattttccc tattatgagg cgttcaggcg 540
gtctttgttt gatatgtata tgctaggtcg gttggggcgt cgacttaagc gatctgactg 600
```

```
ggagactatt atgcatctgt caccaacgca aagtcggcgt ctacatagaa ctttaagatt    660
tgtggagcgt agaattatcc catctaacag ttatatacgc acatcgggcc acgttccgcc    720
ttcgagggca cttccgacag atacgaattt aaagatggat gaataattaa attggaaaga    780
gtaactacat taatcgagcg tcatgacggc gtcccgtgaa aatgggaatt ttctactcga    840
aacaccgtga catttgacag acctggaatt gttattctga tatatagtgg gtgtgtctgg    900
ccggcaacat acataatgtg catgcgaaac cactttttca gtgtacgctg acattgtgca    960
acacggaggg gtagcatcta catacaatat atgttgatta cctgcagggc ggccgccacc   1020
atgggcagca agcccagcac ctggatcagc gtgaccctga tgctgatcac cagaaccatg   1080
ctgatcctga gctgcatctg ccccacaagc agcctggacg gcagacccct ggccgctgcc   1140
ggcatcgtgg tgaccggcga caaggccgtg aacatctaca ccagcagcca gaccggcagc   1200
atcatcatca agctgctgcc caacatgccc aaggacaaag aggcctgcgc caaggccccc   1260
ctggaagcct acaacagaac cctgaccacc ctgctgaccc ccctgggcga cagcatcaga   1320
agaatccagg gcagcgccac cacaagcggc ggaggaaagc agggcagact ggtgggcgct   1380
atcatcggga gcgtggccct gggcgtggcc acagctgccc agattaccgc tgcagccgcc   1440
ctgattcagg ccaatcagaa cgccgccaac atcctgagac tgaaagagag cattgccgcc   1500
accaacgacg ccgtgcacga agtgacaaac ggactgtccc agctggctgt cgctgtcggc   1560
aagatgcagc agttcgtgaa caaccagttc aacaacaccg ccagagagct ggactgcatc   1620
aagatcgccc agcaggtggg cgtggagctg aacctgtacc tgaccgagct gaccacagtg   1680
ttcggccccc agatcacaag ccccgctctg acccagctga caatccaggc cctgtacaac   1740
ctggctggcg gcaacatgga ctatctgctg actaagctgg gagtgggcaa caaccagctg   1800
tccagcctga tcgggtccgg gctgatcaca ggcaaccccca tcctgtacga cagccagaca   1860
cagctgctgg gcatccagat caacctgcca tccgtgggaa gcctgaacaa catgagagcc   1920
acctacctgg aaaccctgag cgtgtccacc accaagggct cgccagcgc cctggtgccc   1980 aaggtggtga cacaggtggg cagcgtgatc gaggaactgg acaccagcta ctgcatcgag   2040
agcgacatcg acctgtactg caccagagtg gtgaccttcc caatgagccc cggcatctac   2100
agctgcctga gcggcaacac cagcgcctgc atgtacagca gaccgaagg agcactgaca   2160 acaccctaca tggccctgaa gggaagcgtg atcgccaact gcaagatgac cacctgcaga   2220
tgcgccgacc ccccaggcat catcagccag aactacggcg aggccgtgag cctgatcgac   2280
aaacattcct gtagcgtgct gtccctggat ggcatcacac tgagactgag cggcgagttc   2340
gacgccacct accagaagaa catcagcatc ctggacagcc aggtgatcgt gaccggcaac   2400
ctggacatca gcaccgagct gggcaacgtg aacaacagca tcagcagcac cctggacaag   2460
ctggccgagt ccaacaacaa gctgaacaaa gtgaacgtga acctgaccag cacaagcgcc   2520
ctgatcacct acatcgtgct ggccatcgtg tccctggcct tcggcgtgat cagcctggtg   2580
ctggcctgct acctgatgta caagcagaga gcccagcaga aaaccctgct gtggctgggc   2640
aataacaccc tggaccagat gagggccacc accagaacct gatgagcggc cgccccgggc   2700
ctgcaggcat aggcacgctc tgatgttaca gaccacaata ccgcatacat ttattgtaag   2760
gttgttaata aaggtttatt ctatgtaaga ctacaatact ttcgacattg cttgtataca   2820
tattaaatac tttctcaagt tcctattaca taaaatggga tctatcatta cattcgttaa   2880
gagtctggat aattttactg tttgccagct tcgatcttgg aacgtactgt ggatagtgcc   2940
```

| | |
|---|---|
| ttacttggaa tcgtgaaaat ttgaaacgtc cattatttgg atatcttccg gttgtcccat | 3000 |
| atcccgccct ggtaccgctc ggataccttg cccgtatgga ttcgtattga cagtcgcgca | 3060 |
| atcggggacc aacaacgcgt gggtccacac tcattcggaa attttccgat gattctgaat | 3120 |
| atttattgcc gctcgttacg agtcgttgga catatctgta atacatttct tcttctgaag | 3180 |
| gatcgctgca catttgatct atacattggc caggatgttc aagtctcaga tgttgcattc | 3240 |
| tggcacagca caactttatg gcatttccga tgtaatcgtc cggcagccct ggggagttc | 3300 |
| tatattcgca tattgggatg gtaaggacaa tagcagatct cgcaacctcc agggaggcta | 3360 |
| taataacgtt tttaaaggat ggatttctca taaaaatctg tcgcaaatta cactgagaat | 3420 |
| atcctttact agcgccgatt gagagcatcg tcgtccaatt ttctaaatgg aaagaaaaca | 3480 |
| aggcgggcaa gagtgttcca acatttttca ttttcggcga atctctcaaa tcccatggcg | 3540 |
| tgcaattgat tgcaaaattg gcacttccgt tcacgtttgt atctccaaac tctaagacac | 3600 |
| ttttaattga aaaactacgt tctagtgtgg aaagaaacct ataggcagac catagaacta | 3660 |
| tttgacacca catatctttt tgtatgtcaa actgaccatg atcgtat | 3707 |

<210> SEQ ID NO 27
<211> LENGTH: 3946
<212> TYPE: DNA
<213> ORGANISM: artificial sequence
<220> FEATURE:
<223> OTHER INFORMATION: Partial plasmid HVT IG2 SVFopt syn tail
      sequence for vHVT304

<400> SEQUENCE: 27

| | |
|---|---|
| tgtttcgcac catatccaag ctggctgtcc ctaagagctt attcctgcaa gacctcatac | 60 |
| ggataattg cccgaccaat acttattacg gacataggta ggccgataaa tattatgttg | 120 |
| actggaggat ggaaaggagg ttttgtaaca gctacatcgc tcgttcatca gcaagcgata | 180 |
| ctttggatat ccgagcttca aaagccgcat aaaccccgct ttatttctga atacgcccca | 240 |
| acagtaacac atgcgtggtt cctggcactt ggaacgccgt gttttatagg caagaacata | 300 |
| ctacccaaag aggtcttggg atttctggcg cgtcgttgca atgaagaaat gaattctttg | 360 |
| ttccttgaaa tgccgacaac tctaaaaacg gtattcgagc accattactt tacgcgtgga | 420 |
| tctgaagtaa atccagcgtt gttgatggag cctaacagat ttttgcaact gatggattcg | 480 |
| cggaaaatcc tatgtttata cgaatccgct atgtgcgaca ccccggagc tcagggtatg | 540 |
| atactcagct gttattgtgg ccgaccagga ggactccaat gcttagcatt cataagaacg | 600 |
| ctagagatgc tatttaacga tgtgctgtcg tctaaagaat ttgtgcattt agccttaaa | 660 |
| tgtaaaacca atgacgcatt cactacgctc gtgcgtgcaa tttctgggcc agggtatgca | 720 |
| tattccataa cagaaatcga cacttgagaa gaggatctga ctgtttggga taaggtcgt | 780 |
| ttgggtctgt cctagcgata taatttatat gacgatatac attaaacatc tgtgtgcagt | 840 |
| acttaggtat ttaatcatgt cgatgaaatg ttatgtgtaa atatcggaca atatagataa | 900 |
| cgggcacgct gctattgtaa cgtgcgcccg cgcgctagtg ctgactaata gtgtggatga | 960 |
| tgtatacagt atattacaaa cggaaatgat acgtaataaa cctgcaggtc gacccaattc | 1020 |
| gagctcggta cagcttggct gtggaatgtg tgtcagttag ggtgtggaaa gtccccaggc | 1080 |
| tccccagcag gcagaagtat gcaaagcatg catctcaatt agtcagcaac caggtgtgga | 1140 |
| aagtccccag gctccccagc aggcagaagt atgcaaagca tgcatctcaa ttagtcagca | 1200 |
| accatagtcc cgcccctaac tccgcccatc ccgccctaa ctccgcccag ttccgcccat | 1260 |

```
tctccgcccc atggctgact aattttttt  atttatgcag aggccgaggc cgcctcggcc   1320
tctgagctat tccagaagta gtgaggaggc ttttttggag gcctaggctt ttgcaaaaag   1380
ctcccggggc ggccgccacc atgggcagca agcccagcac aagaatccca gcccccctga   1440
tgctgatcac ccgcatcatg ctgatcctgg gctgcatcag acccacaagc tccctggatg   1500
gacgccccct ggccgctgcc ggcatcgtgg tgaccggcga caaggccgtg aacgtgtaca   1560
ccagcagcca gaccggcagc atcatcgtga agctgctgcc caacatgccc agagacaaag   1620
aggcctgcgc caaggccccc tggaagcct  acaacagaac cctgaccacc ctgctgaccc   1680
ccctgggcga cagcatcaga aagatccagg gctccgtgag cacaagcggc ggaggaaagc   1740
agggcagact gatcggcgcc gtgatcggca gcgtggccct gggagtggct acagctgccc   1800
agattaccgc tgcagccgcc ctgatccagg ccaaccagaa cgccgccaac atcctgagac   1860
tgaaagagag cattgccgcc accaacgagg ccgtgcacga agtgaccgac ggcctgagcc   1920
agctgtccgt ggccgtgggc aagatgcagc agttcgtgaa cgaccagttc aacaacaccg   1980
ccagagagct ggactgcatc aagatcaccc agcaggtggg cgtggagctg aacctgtacc   2040
tgaccgagct gaccacagtg ttcggccccc agatcacaag cccagccctg acacagctga   2100
ccatccaggc cctgtacaac ctggctggcg gcaacatgga ctatctgctg acaaagctgg   2160
gaatcggcaa caaccagctg tccagcctga tcggaagcgg cctgatcacc ggctacccca   2220
tcctgtacga cagccagaca cagctgctgg gcatccaggt gaacctgccc agcgtgggca   2280
acctgaacaa catgcgcgcc acctacctgg aaaccctgag cgtgtccacc accaagggct   2340
acgccagcgc cctggtgccc aaggtggtga cacaggtggg cagcgtgatc gaggaactgg   2400
acaccagcta ctgcatcgag agcgacctgg acctgtactg caccagaatc gtgaccttcc   2460
caatgagccc cggcatctac agctgcctga gcggcaacac cagcgcctgc atgtacagca   2520
agaccgaagg cgcactgaca acaccctaca tggcccctga gggaagcgtg atcgccaact   2580
gcaagatcac cacctgcaga tgcaccgacc ccccaggcat catcagccag aactacggcg   2640
aggccgtgag cctgatcgat cgccattcct gtaacgtgct gtccctggac ggcatcacac   2700
tgagactgag cggcgagttc gatgccacct accagaagaa catcagcatc ctggacagcc   2760
aggtgatcgt gaccggcaac ctggacatca gcaccgagct gggcaacgtg aataacagca   2820
tcagcaacgc cctggacaga ctggccgaga gcaacagcaa gctggaaaaa gtgaacgtgc   2880
gcctgacatc cacttccgct ctgatcacct acatcgtgct gaccgtgatc agcctggtgt   2940
tcggcgccct gagcctggtg ctggcctgct acctgatgta caagcagaag gcccagcaga   3000 aaacccctgct gtggctgggc aacaacaccc tggaccagat gagagccacc accagagcct   3060
gatgagcggc cgcgatatca ataaaatatc tttattttca ttacatctgt gtgttggttt   3120
tttgtgtgaa tcgatagtac taacatacgc tctccatcaa acaaaacga aacaaaacaa   3180 actagcaaaa taggctgtcc ccagtgcaag tgcaggtgcc agaacatttc tcttctagac   3240
ctgcaggtta tgtactctta ttgatttata aaaacataca tgcagtgttg ctatgtcaca   3300
taattagcct cgcccgtcta cgctccactg aagataatgg gctcccgctg ttcaaaaaaa   3360
tcagcgtgcg tcgataagac tttggtgcag tctcttcggg gtcgcaattt agatttgccg   3420
catggagggt atctggggat ttttgccaat gctggagcga cgactgtacg attcgtccca   3480
tcgggatcta gcagaccaat gatgttgaca cacatcggcc atgcatgtac ggacggtcta   3540
ttgcgcgagt ttgttatttt cgaaggacaa gatggaagtg tatatggaac cgacaataat   3600
gttagtttgc atttcttagg gcggaatcta catgatatct tatccaagcg gggtatgagc   3660
```

```
cagagagatg tgatggtcat aaagggtaaa ttttttagat ctgaaataac gcagttgccc    3720
aaacaacgat cgcgattaaa agaaaaatcg atggttcaa ttaggacatg catggattct     3780
gtgcgcataa accataaccg cagcactgtt gggcacttcg gtaactcaaa tgcgaagcgt    3840
tgcacgtctg cgataactac gcctactatg cacattgtta ctcctgcatc ttaaaaatat    3900
atcctgtagt aattttcaca gcaatgtcat aacatcatct cgctaa                   3946
```

<210> SEQ ID NO 28
<211> LENGTH: 4654
<212> TYPE: DNA
<213> ORGANISM: artificial sequence
<220> FEATURE:
<223> OTHER INFORMATION: Partial plasmid pHVT US2 SV-FCA02 opt-synPA for vHVT307

<400> SEQUENCE: 28

```
tatctccaca tcgtattcag gcccacggaa gtcttcgtta tcgaagctat tgttactagt      60
atctggcgac atcgacggtt ctgcaaccgt cgtaccgctt tcgatatttt cacagacaat     120
acccatattc gaggcactta ctttcgaaga ctcaacatct acttccatcg ccgccacgta     180
tgtaatttcg ggacgttgga tgatataaaa tatatagtac gcgtccgggt atacacctgt     240
gcgaaagtag tacgagaccg gcagtcaaaa agacgtttcc gatcttccac agctccagtt     300
attcggaagg cgtgggcatg ggtgtgtgca tgataactct cgtcacttta ctagacgaat     360
gcgatcgatt gcctgggcga tctcgtgacg ctgcctccac cctatggatc tttctcatag     420
aacaatgcat ggagcatctg aagaatgatg tgggtgtgcc catattagtc cgtacagcag     480
acctgtgtcg gtttgccaaa tccacattcg ttttgccccg ccggcatcgc ccaattgtga     540
gaattaaatc ggcaggcggg agtggtatgc ccggttccgg attggcagga acgagagatg     600
catttattgt gagactgttt gaagatgtag ccggttgcgc taccgaatgg caggatctac     660
tgaccggcta tgtaatgcta gaatcggagg cctccgataa cgtatcgtat agcctgtgga     720
tactcggggc tgcagatatc tgcagaactg caatagaatc aatacctcta ccaaaacgtt     780
tgtttgccat taaagtacca ggcacctggg ctggaatgcc ttgggccatt ccatgtgaga     840
tacaaacact tctcacgtcc acttgggaac ctaaatttga aaacatagaa gataaggcgt     900
acttcaacga cagtaatatg gcgtgcgtat atcaaattat cggctctcca ccagacgttc     960
cccagctgca ggggcttggt atcgagtcca catgcaccc acctaaacgc aatttgtgtt    1020
gctgcctatg ttgccgtcca atacatgacg acgacgcctc cgttcccatg ggcgttaaga    1080
cagtagataa aaacgtacat gatggcaata tgcttgtaga ggctcccaag tgtatcacag    1140
ataggggaaa attcaatagt agataaaccc aactagtgtg aggaaattgc atctacttgc    1200
ccccgggcct gcaggtcgac ccaattcgag ctcggtacag cttggctgtg aatgtgtgt    1260 cagttagggt gtgaaagtc cccaggctcc ccagcaggca gaagtatgca agcatgcat      1320 ctcaattagt cagcaaccag gtgtggaaag tccccaggct cccagcagg cagaagtatg    1380 caaagcatgc atctcaatta gtcagcaacc atagtcccgc ccctaactcc gcccatcccg    1440
cccctaactc cgcccagttc cgcccattct ccgccccatg ctgactaat ttttttatt      1500 tatgcagagg ccgaggccgc ctcggcctct gagctattcc agaagtagtg aggaggcttt    1560
tttggaggcc taggcttttg caaaaagctc ccggggcggc cgccaccatg ggcagcaagc    1620
ccagcacctg gatcagcgtg accctgatgc tgatcaccag aacctgctg atcctgagct    1680 gcatctgccc cacaagcagc ctggacggca gaccctggc cgctgccggc atcgtggtga    1740
```

```
ccggcgacaa ggccgtgaac atctacacca gcagccagac cggcagcatc atcatcaagc    1800
tgctgcccaa catgcccaag gacaaagagg cctgcgccaa gccccccctg gaagcctaca    1860
acagaaccct gaccaccctg ctgacccccc tgggcgacag catcagaaga atccagggca    1920
gcgccaccac aagcggcgga ggaaagcagg gcagactggt gggcgctatc atcgggagcg    1980
tggccctggg cgtggccaca gctgcccaga ttaccgctgc agccgccctg attcaggcca    2040
atcagaacgc cgccaacatc ctgagactga aagagagcat tgccgccacc aacgacgccg    2100
tgcacgaagt gacaaacgga ctgtcccagc tggctgtcgc tgtcggcaag atgcagcagt    2160
tcgtgaacaa ccagttcaac aacaccgcca gagagctgga ctgcatcaag atcgcccagc    2220
aggtgggcgt ggagctgaac ctgtacctga ccagctgac cacagtgttc ggcccccaga    2280
```

| | |
|---|---|
| ggatattctc agtgtaattt gcgacagatt tttatgagaa atccatcctt taaaaacgtt | 4140 |
| attatagcct ccctggaggt tgcgagatct gctattgtcc ttaccatccc aatatgcgaa | 4200 |
| tatagaactc ccccagggct gccggacgat tacatcggaa atgccataaa gttgtgctgt | 4260 |
| gccagaatgc aacatctgag acttgaacat cctggccaat gtatagatca aatgtgcagc | 4320 |
| gatccttcag aagaagaaat gtattacaga tatgtccaac gactcgtaac gagcggcaat | 4380 |
| aaatattcag aatcatcgga aaatttccga atgagtgtgg acccacgcgt tgttggtccc | 4440 |
| cgattgcgcg actgtcaata cgaatccata cgggcaaggt atccgagcgg taccagggcg | 4500 |
| ggatatggga caaccggaag atatccaaat aatggacgtt tcaaattttc acgattccaa | 4560 |
| gtaaggcact atccacagta cgttccaaga tcgaagctgg caaacagtaa aattatccag | 4620 |
| actcttaacg aatgtaatga tagatcccat ttta | 4654 |

<210> SEQ ID NO 29
<211> LENGTH: 5381
<212> TYPE: DNA
<213> ORGANISM: artificial sequence
<220> FEATURE:
<223> OTHER INFORMATION: partial plasmid pCD046+NDV-F VII YZCQ sequence for HVT112

<400> SEQUENCE: 29

| | |
|---|---|
| gagctcaggg tatgatactc agctgttatt gtggccgacc aggaggactc caatgcttag | 60 |
| cattcataag aacgctagag atgctatttta acgatgtgct gtcgtctaaa gaatttgtgc | 120 |
| atttagcctt taaatgtaaa accaatgacg cattcactac gctcgtgcgt gcaatttctg | 180 |
| ggccagggta tgcatattcc ataacagaaa tcgacacttg agaagaggat ctgactgttt | 240 |
| gggataaagg tcgtttgggt ctgtcctagc gatataattt tatgacgat atacattaaa | 300 |
| catctgtgtg cagtacttag gtatttaatc atgtcgatga atgttatgt gtaaatatcg | 360 |
| gacaatatag ataacgggca cgctgctatt gtaacgtgcg cccgcgcgct agtgctgact | 420 |
| aatagtgtgg atgatgtata cagtatatta caaacggaaa tgatacgtaa taaattatgt | 480 |
| actcttattg atttataaaa acatacatgc agtgttgcta tgtcacataa ttagcctcgc | 540 |
| ccgtctacgc tccactgaag ataatgggct cccgctgttc aaaaaaatca gcgtgcgtcg | 600 |
| ataagacttt ggtgcagtct cttcgggggtc gcaatttaga tttgccgcat ggagggtatc | 660 |
| tggggatttt tgccaatgct ggagcgacga ctgtacgatt cgtcccatcg ggatctagca | 720 |
| gaccaatgat gttgacacac atcggccatg catgtacgga cggtctattg cgcgagtttg | 780 |
| ttattttcga aggacaagat ggaagtgtat atggaaccga caataatgtt agtttgcatt | 840 |
| tcttagggcg gaatctacat gatatcttat ccaagcgggg tatgagccag agagatgtga | 900 |
| tggtcataaa gggtaaattt tttagatctg aaataacgca gttgcccaaa caacgatcgc | 960 |
| gattaaaaga aaaatcggat ggttcaatta ggacatgcat ggattctgtg cgcataaacc | 1020 |
| ataaccgcag cactgttggg cacttcggta actcaaatgc gaagcgttgc acgtctgcga | 1080 |
| taactacgcc tactatgcac attgttactc ctgcatctta aaaatatatc ctgtagtaat | 1140 |
| tttcacagca atgtcataac atcatctcgc taaagaatga cctgggattg gagaagtaat | 1200 |
| gaatatttgc aaccaatgca ttgaataaac taacattaaa cgaattcaat agtggatccc | 1260 |
| ccaactccgc ccgttttatg actagaacca atagttttta atgccaaatg cactgaaatc | 1320 |
| ccctaatttg caaagccaaa cgcccccctat gtgagtaata cggggacttt ttacccaatt | 1380 |
| tcccacgcgg aaagccccct aatacactca tatggcatat gaatcagcac ggtcatgcac | 1440 |

-continued

```
tctaatggcg gcccataggg actttccaca tagggggcgt tcaccatttc ccagcatagg    1500
ggtggtgact caatggcctt tacccaagta cattgggtca atgggaggta agccaatggg    1560
ttttcccat tactggcaag cacactgagt caaatgggac tttccactgg ttttgccca    1620
agtacattgg gtcaatggga ggtgagccaa tgggaaaaac ccattgctgc caagtacact    1680
gactcaatag ggactttcca tgggttttt ccattgttgg caagcatata aggtcaatgt    1740
gggtgagtca atagggactt tccattgtat tctgcccagt acataaggtc aataggggt    1800
gaatcaacag gaaagtccca ttggagccaa gtacactgcg tcaataggga ctttccattg    1860
ggttttgccc agtacataag gtcaataggg gatgagtcaa tgggaaaaac ccattggagc    1920
caagtacact gactcaatag ggactttcca ttgggttttg cccagtacat aaggtcaata    1980
gggggtgagt caacaggaaa gttccattgg agccaagtac attgagtcaa tagggacttt    2040
ccaatgggtt ttgcccagta cataaggtca atggaggta agccaatggg ttttcccat    2100
tactggcacg tatactgagt cattagggac tttccaatgg ttttgccca gtacataagg    2160
tcaataggg tgaatcaaca ggaaagtccc attggagcca agtacactga gtcaataggg    2220
actttccatt gggttttgcc cagtacaaaa ggtcaatagg gggtgagtca atgggttttt    2280
cccattattg gcacgtacat aaggtcaata ggggtgagtc attgggtttt ccagccaat    2340
ttaattaaaa cgccatgtac tttcccacca ttgacgtcaa tgggctattg aaactaatgc    2400
aacgtgacct ttaaacggta ctttcccata gctgattaat gggaaagtac cgttctcgag    2460
ccaatacacg tcaatgggaa gtgaagggc agccaaaacg taacaccgcc ccggttttcc    2520
cctgaaaatt ccatattggc acgcattcta ttggctgagc tgcgttctac gtgggtataa    2580
gaggcgcgac cagcgtcggt accgtcgcag tcttcggtct gaccaccgta gaacgcagag    2640
ctcctcgctg caggcggccg catgggctct aaaccttcta ccaggatccc agcacctctg    2700
atgctgatca cccggattat gctgatattg gactgtatcc gtccgacaag ctctcttgac    2760
ggcaggcctc ttgcagctgc aggaattgta gtaacaggag ataaggcagt caatgtatat    2820
acctcgtctc agacagggtc aatcatagtc aagttgctcc cgaatatgcc caaggataag    2880
gaggcgtgtg cgaaagaccc attagaggca tataacagaa cactgactac tttgctcact    2940
cctcttggcg aatccatccg caagatccaa gggtctgtgt ccacgtctgg aggaggcaag    3000
caaggccgcc tgataggtgc tgttattggt agtgtagctc ttgggggttgc aacagcggca    3060
caaataacag cagctgcggc cctaatacaa gccaaccaga atgctgccaa catccttcgg    3120
cttaaggaga gcattgctgc aaccaatgaa gctgtgcatg aagtcaccga cggattatca    3180
caactatcag tggcagttgg gaagatgcag cagtttgtca atgaccagtt taataataca    3240
gcgcgagaat tggactgtat aaaaatcaca caacaggttg gtgtagaact caacctatac    3300
ctaactgaat tgactacagt attcgggcca cagatcacct ccctgcatt aactcagctg    3360
accatccagg cactttataa tttagctggt ggcaatatgg attacttatt aactaagtta    3420
ggtatagga acaatcaact cagctcatta attggcagcg gcctgatcac tggttaccct    3480
atattgtatg actcacagac tcaactcttg ggcatacaag tgaatttgcc ctcagtcggg    3540
aacttaaata atatgcgtgc cacctattta gagaccttat ctgtaagtac agccaaagga    3600
tatgcctcag cacttgttcc aaaagtagtg acacaagtcg gttctgtgat agaagagctt    3660
gacacctcat actgtatga gtccgatctg gatttatatt gtactagaat agtgacattc    3720
cccatgtccc caggtattta ttcctgttta agcggcaaca catcagcttg catgtattca    3780
aagactgaag gcgcactcac tacgccgtat atggccctta aaggctcagt tattgccaat    3840
```

| | | |
|---|---|---|
| tgtaagataa caacatgtag atgtacagac cctcctggta tcatatcgca aaattatgga | 3900 |
| gaagctgtat ccctgataga tagacattcg tgcaatgtct tatcattaga cgggataact | 3960 |
| ctgaggctca gtggagaatt tgatgcaact tatcaaaaga acatctcaat actagattct | 4020 |
| caagtcatcg tgacaggcaa tcttgatata tcaactgaac ttggaaacgt caacaattca | 4080 |
| atcagcaatg ccttggataa gttggcaaaa agcaacagca agctagaaaa agtcaatgtc | 4140 |
| agactaacca gcacatccgc tctcattacc tatattgttc tgactgtcat ttctctagtt | 4200 |
| ttcggtgcac taagtctggg tttaacatgt tacctgatgt acaaacaaaa ggcacaacaa | 4260 |
| aagaccttgc tatggcttgg gaataatacc ctcgatcaga tgagagccac tacaagagca | 4320 |
| tgagcggccg cggggatcca gacatgataa gatacattga tgagtttgga caaccacaa | 4380 |
| ctagaatgca gtgaaaaaaa tgctttattt gtgaaatttg tgatgctatt gcttatttg | 4440 |
| taaccattat aagctgcaat aaacaagtta acaacaacaa ttgcattgat tttatgtttc | 4500 |
| aggttcaggg ggaggtgtgg gaggtttttt cggatcctct agagtcgaca attattttat | 4560 |
| ttaataacat atagcccaaa gacctctatg aacatttagt ttcccgtata ctcaacggcg | 4620 |
| cgtgtacaca cgcatctctt tgcatagcga tgaagtttgt tcggcagcag aaaatgcaga | 4680 |
| tatccaacaa tctggagaaa acttatcatc acagtggcag tggaaacata cccctctat | 4740 |
| attcatggta taattatcgt ctacagcgtc caggatagtg gcgtgagaaa atggagatct | 4800 |
| gcagccctcc tttccatggc atgccgcttt attgttcatt aaacgcacaa tggtctcaac | 4860 |
| gccagatatg ggcatagatt ctgaagaacc cgttgacaat ccgaagaaga aggcgtgcag | 4920 |
| gtctttggaa gactcgcacg ttggtcttat aatgtatgat cgagatgtca ccctaatgcc | 4980 |
| acatggtaca ggcttatcgc ggtcatggcg atcggacttg taatttgcaa cgatgggcaa | 5040 |
| aggatcgacg acatgccaaa cattctgaac ccgtagagat gttaacgatg acgaggatga | 5100 |
| atatcccatg ctcgctgcca tagtatcaag tacaccgcga ataaggacgc gtccaacatc | 5160 |
| gttatatgca cacaatgggc tacacgtgac taacacccccc gaatattagt catatgtgag | 5220 |
| tttcagtctg gctcccatat agcctgtaga ctatttgtgg tttaagtgtg aacgaggcgc | 5280 |
| tgtgaacgag actcgggccg attgtaagaa caagcaaatg cactttccat ttaacaagaa | 5340 |
| gtgtagagag aatactcaac ctcttttggat gtatcctcga g | 5381 |

<210> SEQ ID NO 30
<211> LENGTH: 5381
<212> TYPE: DNA
<213> ORGANISM: artificial sequence
<220> FEATURE:
<223> OTHER INFORMATION: partial plasmid pCD046+Texas NDV-F sequence for HVT113

<400> SEQUENCE: 30

| | | |
|---|---|---|
| gagctcaggg tatgatactc agctgttatt gtggccgacc aggaggactc caatgcttag | 60 |
| cattcataag aacgctagag atgctattta acgatgtgct gtcgtctaaa gaatttgtgc | 120 |
| atttagcctt taaatgtaaa accaatgacg cattcactac gctcgtgcgt gcaatttctg | 180 |
| ggccagggta tgcatattcc ataacagaaa tcgacacttg agaagaggat ctgactgttt | 240 |
| gggataaagg tcgtttgggt ctgtcctagc gatataattt atatgacgat atacattaaa | 300 |
| catctgtgtg cagtacttag gtatttaatc atgtcgatga atgttatgt gtaaatatcg | 360 |
| gacaatatag ataacgggca cgctgctatt gtaacgtgcg cccgcgcgct agtgctgact | 420 |
| aatagtgtgg atgatgtata cagtatatta caaacggaaa tgatacgtaa taaattatgt | 480 |

```
actcttattg atttataaaa acatacatgc agtgttgcta tgtcacataa ttagcctcgc    540
ccgtctacgc tccactgaag ataatgggct cccgctgttc aaaaaaatca gcgtgcgtcg    600
ataagacttt ggtgcagtct cttcggggtc gcaatttaga tttgccgcat ggagggtatc    660
tggggatttt tgccaatgct ggagcgacga ctgtacgatt cgtcccatcg ggatctagca    720
gaccaatgat gttgacacac atcggccatg catgtacgga cggtctattg cgcgagtttg    780
ttattttcga aggacaagat ggaagtgtat atggaaccga caataatgtt agtttgcatt    840
tcttagggcg gaatctacat gatatcttat ccaagcgggg tatgagccag agagatgtga    900
tggtcataaa gggtaaattt tttagatctg aaataacgca gttgcccaaa caacgatcgc    960
gattaaaaga aaaatcggat ggttcaatta ggacatgcat ggattctgtg cgcataaacc   1020
ataaccgcag cactgttggg cacttcggta actcaaatgc gaagcgttgc acgtctgcga   1080
taactacgcc tactatgcac attgttactc ctgcatctta aaaatatatc ctgtagtaat   1140
tttcacagca atgtcataac atcatctcgc taaagaatga cctgggattg gagaagtaat   1200
gaatatttgc aaccaatgca ttgaataaac taacattaaa cgaattcaat agtggatccc   1260
ccaactccgc ccgttttatg actagaacca atagttttta atgccaaatg cactgaaatc   1320
ccctaatttg caaagccaaa cgcccccctat gtgagtaata cggggacttt ttacccaatt   1380
tcccacgcgg aaagcccccc t aatacactca tatggcatat gaatcagcac ggtcatgcac  1440
tctaatggcg gcccataggg actttccaca tagggggcgt tcaccatttc ccagcatagg   1500
ggtggtgact caatggcctt tacccaagta cattgggtca atggaggta agccaatggg    1560 ttttcccat tactggcaag cacactgagt caaatgggac tttccactgg gttttgccca    1620
agtacattgg gtcaatggga ggtgagccaa tgggaaaaac ccattgctgc caagtacact   1680
gactcaatag ggacttttcca atgggttttt ccattgttgg caagcatata aggtcaatgt   1740
gggtgagtca atagggactt tccattgtat tctgcccagt acataaggtc aataggggt    1800 gaatcaacag gaaagtccca ttggagccaa gtacactgcg tcaatagga ctttccattg    1860 ggttttgccc agtacataag gtcaataggg gatgagtcaa tgggaaaaac ccattggagc   1920
caagtacact gactcaatag ggactttcca ttgggttttg cccagtacat aaggtcaata   1980
gggggtgagt caacaggaaa gttccattgg agccaagtac attgagtcaa tagggacttt   2040
ccaatgggtt ttgcccagta cataaggtca atggaggta agccaatggg ttttccccat    2100
tactggcacg tatactgagt cattagggac tttccaatgg gttttgccca gtacataagg   2160 tcaataggg tgaatcaaca ggaaagtccc attggagcca agtacactga gtcaataggg    2220
actttccatt gggttttgcc cagtacaaaa ggtcaatagg gggtgagtca atgggttttt   2280
cccattattg gcacgtacat aaggtcaata ggggtgagtc attgggtttt tccagccaat   2340
ttaattaaaa cgccatgtac tttcccacca ttgacgtcaa tgggctattg aaactaatgc   2400
aacgtgacct ttaaacggta ctttcccata gctgattaat gggaaagtac cgttctcgag   2460
ccaatacacg tcaatgggaa gtgaaagggc agccaaaacg taacaccgcc ccggtttttcc   2520 cctggaaatt ccatattggc acgcattcta ttggctgagc tgcgttctac gtgggtataa   2580
gaggcgcgac cagcgtcggt accgtcgcag tcttcggtct gaccaccgta gaacgcagag   2640
ctcctcgctg caggcggccg catgggctcc agatcttcta ccaggatccc ggtacctcta   2700
atgctgatca tccgaaccgc gctgacactg agctgtatcc gtctgacaag ctctcttgat   2760
ggcaggcctc ttgcggctgc agggatcgtg gtaacaggag ataaagcagt caacatatac   2820
```

```
acctcatccc agacagggtc aatcatagtt aagttactcc cgaatatgcc caaggacaaa    2880
gaggtgtgtg caaaagcccc attggaggca tacaacagga cactgactac tttactcacc    2940 cccttggtg attctatccg caggatacaa gagtctgtga ctacttccgg aggaggcaag     3000
caaggccgcc tgataggtgc cattatcggc agtgtagctc ttggggttgc gacagctgca    3060
cagataacag cagcttcggc cctgatacaa gccaaccaga atgctgccaa catcctccgg    3120
cttaaagaga gcattgctgc aaccaatgaa gctgtgcacg aggtcactga cggattatca    3180
caactagcag tggcagtagg gaagatgcaa cagtttgtca atgaccagtt caataataca    3240
gcgcaagaat tggactgtat aaaaattgca cagcaggtcg gtgtagaact caacttgtac    3300
ctaactgaat tgactacagt atttgggcca caaatcactt cccctgcctt aactcagctg    3360
actatccaag cgctttacaa tctagctggt ggtaatatgg attacttgct gactaagtta    3420
ggtgtaggga acaaccaact cagctcatta attggtagcg gcttgatcac cggcaaccct    3480
attctgtacg actcacagac tcagatcttg ggtatacagg taactttgcc ttcagttggg    3540
aacctgaata atatgcgtgc cacctacctg agagccttat ctgtaagcac aaccaaggga    3600
tttgcctcag cacttgtccc aaaagtggtg acacaggtcg gttccgtgat agaagaactt    3660
gacacctcat actgtataqg gaccgacttg gatttatact gtacaagaat agtgacattc    3720
cctatgtctc ctggtattta ttcttgtctg agcggtaata tcggcttg catgtattca     3780 aagactgaag gcgcacttac tacgccatat atggctctca aaggctcagt tattgccaat    3840
tgcaagctga caacatgtag atgtgcagat cccccaggta tcatatcgca aaattatgga    3900
gaagctgtgt ccttaataga taggcactca tgcaacgtct tatccttaga cgggataact    3960
ctgaggctca gtggggaatt tgatgcaacc tatcaaaaga atatctctat actagattct    4020
caagttatag tgacaggcaa tcttgatata tcaactgagc ttgggaatgt caacaactca    4080
ataagtaatg ccctgaataa gttagaggaa agcaacagca aactagacaa agtcaatgtc    4140
aaactgacca gcacatctgc tctcattacc tacatcgttt taactgtcat atctcttgtt    4200
tttggtgtac ttagcctggt tctagcatgc tacctgatgt acaagcaaaa ggcacaacaa    4260
aagaccttgt tatggcttgg gaataatacc cttgatcaga tgagagccac tacaaaaata    4320
tgagcggccg cggggatcca gacatgataa gatacattga tgagtttgga caaaccacaa    4380
ctagaatgca gtgaaaaaaa tgctttattt gtgaaatttg tgatgctatt gctttatttg    4440
taaccattat aagctgcaat aaacaagtta acaacaacaa ttgcattgat tttatgtttc    4500
aggttcaggg ggaggtgtgg gaggttttt cggatcctct agagtcgaca attatttat     4560 ttaataacat atagcccaaa gacctctatg aacatttagt ttcccgtata ctcaacggcg    4620
cgtgtacaca cgcatctctt tgcatagcga tgaagtttgt tcggcagcag aaaatgcaga    4680
tatccaacaa tctggagaaa acttatcatc acagtggcag tggaaacata cccctctat    4740 attcatggta taattatcgt ctacagcgtc caggatagtg gcgtgagaaa atggagatct    4800
gcagccctcc tttccatggc atgccgcttt attgttcatt aaacgcacaa tggtctcaac    4860
gccagatatg ggcatagatt ctgaagaacc cgttgacaat ccgaagaaga aggcgtgcag    4920
gtctttggaa gactcgcacg ttggtcttat aatgtatgat cgagatgtca ccctaatgcc    4980
acatggtaca ggcttatcgc ggtcatggcg atcggacttg taatttgcaa cgatgggcaa    5040
aggatcgacg acatgccaaa cattctgaac ccgtagagat gttaacgatg acgaggatga    5100
atatcccatg ctcgctgcca tagtatcaag tacaccgcga ataaggacgc gtccaacatc    5160
gttatatgca cacaatgggc tacacgtgac taacacccc gaatattagt catatgtgag     5220
```

```
tttcagtctg gctcccatat agcctgtaga ctatttgtgg tttaagtgtg aacgaggcgc    5280
tgtgaacgag actcgggccg attgtaagaa caagcaaatg cactttccat ttaacaagaa    5340
gtgtagagag aatactcaac ctctttggat gtatcctcga g                       5381
```

<210> SEQ ID NO 31
<211> LENGTH: 4600
<212> TYPE: DNA
<213> ORGANISM: artificial sequence
<220> FEATURE:
<223> OTHER INFORMATION: partial plasmid pHM119 sequence for vHVT039

<400> SEQUENCE: 31

```
gagctcaggg tatgatactc agctgttatt gtggccgacc aggaggactc caatgcttag      60
cattcataag aacgctagag atgctattta acgatgtgct gtcgtctaaa gaatttgtgc     120
atttagcctt taaatgtaaa accaatgacg cattcactac gctcgtgcgt gcaatttctg     180
ggccagggta tgcatattcc ataacagaaa tcgacacttg agaagaggat ctgactgttt     240
gggataaagg tcgtttgggt ctgtcctagc gatataattt atatgacgat atacattaaa     300
catctgtgtg cagtacttag gtatttaatc atgtcgatga aatgttatgt gtaaatatcg     360
gacaatatag ataacgggca cgctgctatt gtaacgtgcg cccgcgcgct agtgctgact     420
aatagtgtgg atgatgtata cagtatatta caaacggaaa tgatacgtaa taaattatgt     480
actcttattg atttataaaa acatacatgc agtgttgcta tgtcacataa ttagcctcgc     540
ccgtctacgc tccactgaag ataatgggct cccgctgttc aaaaaaatca gcgtgcgtcg     600
ataagacttt ggtgcagtct cttcggggtc gcaatttaga tttgccgcat ggagggtatc     660
tggggatttt tgccaatgct ggagcgacga ctgtacgatt cgtcccatcg ggatctagca     720
gaccaatgat gttgacacac atcggccatg catgtacgga cggtctattg cgcgagtttg     780
ttattttcga aggacaagat ggaagtgtat atggaaccga caataatgtt agtttgcatt     840
tcttagggcg gaatctacat gatatcttat ccaagcgggg tatgagccag agagatgtga     900
tggtcataaa gggtaaattt tttagatctg aaataacgca gttgcccaaa caacgatcgc     960
gattaaaaga aaaatcggat ggttcaatta ggacatgcat ggattctgtg cgcataaacc    1020
ataaccgcag cactgttggg cacttcggta actcaaatgc gaagcgttgc acgtctgcga    1080
taactacgcc tactatgcac attgttactc ctgcatctta aaaatatatc ctgtagtaat    1140
tttcacagca atgtcataac atcatctcgc taaagaatga cctgggattg gagaagtaat    1200
gaatatttgc aaccaatgca ttgaataaac taacattaaa cgaattccga tgtttagtca    1260
cgatagacat cggttcgccc agccgtcgaa tacagcatta tattttagtg ttgaaaatgt    1320
agggctgctt cctcacttaa aggaggaaat ggctcgattc atgtttcata gcagtagaaa    1380
aacagattgg accgtcagta agtttagagg gttttatgac tttagcacta tagataatgt    1440
aactgcggcc catcgcatgg cttggaaata tatcaaagaa ctgattttg caacagcttt     1500 attttcttct gtatttaaat gtggcgaatt gcacatctgt cgtgccgaca gtttgcagat    1560
caacagcaat ggagactatg tatggaaaaa tggaatatat ataacatatg aaaccgaata    1620
tccacttata atgattctgg ggtcagaatc aagcacttca gaaacgcaaa atatgactgc    1680
aattattgat acagatgttt tttcgttgct ttattctatt ttgcagtata tggcccccgt    1740
tacggcagat caggtgcgag tagaacagat taccaacagc cacgcccccca tctgacccgt    1800 ccaatattct tgtgtccctg catttttatct cacacaattt atgaacagca tcattaagat    1860
```

```
catctcactg cggccgcaag atgggctcca gatcttctac caggatcccg gtacctctaa    1920
tgctgatcat ccgaaccgcg ctgacactga gctgtatccg tctgacaagc tctcttgatg    1980
gcaggcctct tgcggctgca gggatcgtgg taacaggaga taaagcagtc aacatataca    2040
cctcatccca gacagggtca atcatagtta agttactccc gaatatgccc aaggacaaag    2100
aggtgtgtgc aaaagcccca ttggaggcat acaacaggac actgactact ttactcaccc    2160
cccttggtga ttctatccgc aggatacaag agtctgtgac tacttccgga ggaaggagac    2220
agagacgctt tataggtgcc attatcggca gtgtagctct tggggttgcg acagctgcac    2280
agataacagc agcttcggcc ctgatacaag ccaaccagaa tgctgccaac atcctccggc    2340
ttaaagagag cattgctgca accaatgaag ctgtgcacga ggtcactgac ggattatcac    2400
aactagcagt ggcagtaggg aagatgcaac agtttgtcaa tgaccagttc aataatacag    2460
cgcaagaatt ggactgtata aaaattgcac agcaggtcgg tgtagaactc aacttgtacc    2520
taactgaatt gactacagta tttgggccac aaatcacttc ccctgcctta actcagctga    2580
ctatccaagc gctttacaat ctagctgtg gtaatatgga ttacttgctg actaagttag    2640
gtgtagggaa caaccaactc agctcattaa ttggtagcgg cttgatcacc ggcaacccta    2700
ttctgtacga ctcacagact cagatcttgg gtatacaggt aactttgcct tcagttggga    2760
acctgaataa tatgcgtgcc acctacctgg agaccttatc tgtaagcaca accaagggat    2820
tgcctcagc acttgtccca aaagtggtga cacaggtcgg ttccgtgata aagaacttg     2880
acacctcata ctgtataggg accgacttgg atttatactg tacaagaata gtgacattcc    2940
ctatgtctcc tggtatttat tcttgtctga gcggtaatac atcggcttgc atgtattcaa    3000
agactgaagg cgcacttact acgccatata tggctctcaa aggctcagtt attgccaatt    3060
gcaagctgac aacatgtaga tgtgcagatc ccccaggtat catatcgcaa aattatggag    3120
aagctgtgtc cttaatagat aggcactcat gcaacgtctt atccttagac gggataactc    3180
tgaggctcag tggggaattt gatgcaacct atcaaaagaa tatctctata ctagattctc    3240
aagttatagt gacaggcaat cttgatatat caactgagct tgggaatgtc aacaactcaa    3300
taagtaatgc cctgaataag ttagaggaaa gcaacagcaa actagacaaa gtcaatgtca    3360
aactgaccag cacatctgct ctcattacct acatcgtttt aactgtcata tctcttgttt    3420
ttggtgtact tagcctggtt ctagcatgct acctgatgta caagcaaaag gcacaacaaa    3480
agaccttgtt atggcttggg aataataccc ttgatcagat gagagccact acaaaaatat    3540
gagcggccgc ggggatccag acatgataag atacattgat gagtttggac aaaccacaac    3600
tagaatgcag tgaaaaaaat gctttatttg tgaaatttgt gatgctattg ctttatttgt    3660
aaccattata agctgcaata acaagttaa caacaacaat tgcattcatt ttatgtttca     3720
ggttcagggg gaggtgtggg aggtttttc ggatcctcta gagtcgacaa ttatttt att    3780
taataacata tagcccaaag acctctatga acatttagtt tcccgtatac tcaacgcgc    3840
gtgtacacac gcatctcttt gcatagcgat gaagtttgtt cggcagcaga aaatgcagat    3900
atccaacaat ctggagaaaa cttatcatca cagtggcagt ggaaacatac cccctctata    3960
ttcatggtat aattatcgtc tacagcgtcc aggatagtgg cgtgagaaaa tggagatctg    4020
cagccctcct ttccatggca tgccgcttta ttgttcatta aacgcacaat ggtctcaacg    4080
ccagatatgg gcatagattc tgaagaaccc gttgacaatc cgaagaagaa ggcgtgcagg    4140
tctttggaag actcgcacgt tggtcttata atgtatgatc gagatgtcac cctaatgcca    4200
catggtacag gcttatcgcg gtcatggcga tcggacttgt aatttgcaac gatgggcaaa    4260
```

```
ggatcgacga catgccaaac attctgaacc cgtagagatg ttaacgatga cgaggatgaa    4320
tatcccatgc tcgctgccat agtatcaagt acaccgcgaa taaggacgcg tccaacatcg    4380
ttatatgcac acaatgggct acacgtgact aacaccccg aatattagtc atatgtgagt    4440
ttcagtctgg ctcccatata gcctgtagac tatttgtggt ttaagtgtga acgaggcgct    4500
gtgaacgaga ctcgggccga ttgtaagaac aagcaaatgc actttccatt taacaagaag    4560
tgtagagaga atactcaacc tctttggatg tatcctcgag                          4600
```

<210> SEQ ID NO 32
<211> LENGTH: 1662
<212> TYPE: DNA
<213> ORGANISM: artificial sequence
<220> FEATURE:
<223> OTHER INFORMATION: NDV Texas F gene (wild type non-modified)

<400> SEQUENCE: 32

```
atgggctcca gatcttctac caggatcccg gtacctctaa tgctgatcat ccgaaccgcg      60
ctgacactga gctgtatccg tctgacaagc tctcttgatg gcaggcctct tgcggctgca    120
gggatcgtgg taacaggaga taaagcagtc aacatataca cctcatccca gacagggtca    180
atcatagtta agttactccc gaatatgccc aaggacaaag aggtgtgtgc aaaagcccca    240
ttggaggcat acaacaggac actgactact ttactcaccc cccttggtga ttctatccgc    300
aggatacaag agtctgtgac tacttccgga ggaaggagag agagacgctt tataggtgcc    360
attatcggca gtagctct tggggttgcg acagctgcac agataacagc agcttcggcc      420
ctgatacaag ccaaccagaa tgctgccaac atcctccggc ttaaagagag cattgctgca    480
accaatgaag ctgtgcacga ggtcactgac ggattatcac aactagcagt ggcagtaggg    540
aagatgcaac agtttgtcaa tgaccagttc aataatacag cgcaagaatt ggactgtata    600
aaaattgcac agcaggtcgg tgtagaactc aacttgtacc taactgaatt gactacagta    660
tttgggccac aaatcacttc ccctgcctta actcagctga ctatccaagc gctttacaat    720
ctagctggtg gtaatatgga ttacttgctg actaagttag gtgtagggaa caaccaactc    780
agctcattaa ttggtagcgg cttgatcacc ggcaacccta ttctgtacga ctcacagact    840
cagatcttgg gtatacaggt aactttgcct tcagttggga acctgaataa tatgcgtgcc    900
acctacctgg agaccttatc tgtaagcaca accaagggat tgcctcagc acttgtccca    960 aaagtggtga cacaggtcgg ttccgtgata gaagaacttg acacctcata ctgtatagg    1020 accgacttgg attatactg tacaagaata gtgacattcc ctatgtctcc tggtatttat    1080
tcttgtctga gcggtaatac atcggcttgc atgtattcaa agactgaagg cgcacttact    1140
acgccatata tggctctcaa aggctcagtt attgccaatt gcaagctgac aacatgtaga    1200
tgtgcagatc ccccaggtat catatcgcaa aattatggag aagctgtgtc cttaatagat    1260
aggcactcat gcaacgtctt atccttagac gggataactc tgaggctcag tggggaattt    1320
gatgcaacct atcaaaagaa tatctctata ctagattctc aagttatagt gacaggcaat    1380
cttgatatat caactgagct tgggaatgtc aacaactcaa taagtaatgc cctgaataag    1440
ttagaggaaa gcaacagcaa actagacaaa gtcaatgtca aactgaccag cacatctgct    1500
ctcattacct acatcgtttt aactgtcata tctcttgttt ttggtgtact tagcctggtt    1560
ctagcatgct acctgatgta caagcaaaag gcacaacaaa agaccttgtt atggcttggg    1620
aataataccc ttgatcagat gagagccact acaaaaatat ga                      1662
```

<210> SEQ ID NO 33
<211> LENGTH: 553
<212> TYPE: PRT
<213> ORGANISM: artificial sequence
<220> FEATURE:
<223> OTHER INFORMATION: NDV Texas F protein (wild type non-modified)

<400> SEQUENCE: 33

```
Met Gly Ser Arg Ser Ser Thr Arg Ile Pro Val Pro Leu Met Leu Ile
1               5                   10                  15

Ile Arg Thr Ala Leu Thr Leu Ser Cys Ile Arg Leu Thr Ser Ser Leu
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Met Pro Lys Asp Lys Glu Val Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Arg
            100                 105                 110

Arg Gln Arg Arg Phe Ile Gly Ala Ile Ile Gly Ser Val Ala Leu Gly
        115                 120                 125

Val Ala Thr Ala Ala Gln Ile Thr Ala Ala Ser Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Asn
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Ile Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Gly Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365
```

```
Ala Cys Met Tyr Ser Lys Thr Glu Gly Ala Leu Thr Thr Pro Tyr Met
    370             375             380
Ala Leu Lys Gly Ser Val Ile Ala Asn Cys Lys Leu Thr Thr Cys Arg
385             390             395             400
Cys Ala Asp Pro Pro Gly Ile Ile Ser Gln Asn Tyr Gly Glu Ala Val
            405             410             415
Ser Leu Ile Asp Arg His Ser Cys Asn Val Leu Ser Leu Asp Gly Ile
        420             425             430
Thr Leu Arg Leu Ser Gly Glu Phe Asp Ala Thr Tyr Gln Lys Asn Ile
    435             440             445
Ser Ile Leu Asp Ser Gln Val Ile Val Thr Gly Asn Leu Asp Ile Ser
450             455             460
Thr Glu Leu Gly Asn Val Asn Asn Ser Ile Ser Asn Ala Leu Asn Lys
465             470             475             480
Leu Glu Glu Ser Asn Ser Lys Leu Asp Lys Val Asn Val Lys Leu Thr
            485             490             495
Ser Thr Ser Ala Leu Ile Thr Tyr Ile Val Leu Thr Val Ile Ser Leu
        500             505             510
Val Phe Gly Val Leu Ser Leu Val Leu Ala Cys Tyr Leu Met Tyr Lys
    515             520             525
Gln Lys Ala Gln Gln Lys Thr Leu Leu Trp Leu Gly Asn Asn Thr Leu
530             535             540
Asp Gln Met Arg Ala Thr Thr Lys Ile
545             550
```

<210> SEQ ID NO 34
<211> LENGTH: 1662
<212> TYPE: DNA
<213> ORGANISM: artificial sequence
<220> FEATURE:
<223> OTHER INFORMATION: NDV-F YZCQ wildtype DNA sequence

<400> SEQUENCE: 34

```
atgggctcca gatcttctac caggatcccg gtacctctaa tgctgatcat ccgaaccgcg     60
ctgacactga gctgtatccg tctgacaagc tctcttgatg gcaggcctct tgcggctgca    120
gggatcgtgg taacaggaga taaagcagtc aacatataca cctcatccca gacagggtca    180
atcatagtta agttactccc gaatatgccc aaggacaaag aggtgtgtgc aaaagcccca    240
ttggaggcat acaacaggac actgactact ttactcaccc cccttggtga ttctatccgc    300
aggatacaag agtctgtgac tacttccgga ggaggcaagc aaggccgcct gataggtgcc    360
attatcggca gtgtagctct tggggttgcg acagctgcac agataacagc agcttcggcc    420
ctgatacaag ccaaccagaa tgctgccaac atcctccggc ttaaagagag cattgctgca    480
accaatgaag ctgtgcacga ggtcactgac ggattatcac aactagcagt ggcagtaggg    540
aagatgcaac agtttgtcaa tgaccagttc aataatacag cgcaagaatt ggactgtata    600
aaaattgcac agcaggtcgg tgtagaactc aacttgtacc taactgaatt gactacagta    660
tttgggccac aaatcacttc ccctgcctta actcagctga ctatccaagc gctttacaat    720
ctagctggtg gtaatatgga ttacttgctg actaagttag gtgtagggaa caaccaactc    780
agctcattaa ttggtagcgg cttgatcacc ggcaacccta ttctgtacga ctcacagact    840
cagatcttgg gtatacaggt aactttgcct tcagttggga acctgaataa tatgcgtgcc    900
acctacctgg agaccttatc tgtaagcaca accaagggat ttgcctcagc acttgtccca    960
aaagtggtga cacaggtcgg ttccgtgata gaagaacttg acacctcata ctgtataggg   1020
```

-continued

```
accgacttgg atttatactg tacaagaata gtgacattcc ctatgtctcc tggtatttat    1080
tcttgtctga gcggtaatac atcggcttgc atgtattcaa agactgaagg cgcacttact    1140
acgccatata tggctctcaa aggctcagtt attgccaatt gcaagctgac aacatgtaga    1200
tgtgcagatc ccccaggtat catatcgcaa aattatggag aagctgtgtc cttaatagat    1260
aggcactcat gcaacgtctt atccttagac gggataactc tgaggctcag tggggaattt    1320
gatgcaacct atcaaagaa tatctctata ctagattctc aagttatagt gacaggcaat    1380
cttgatatat caactgagct tgggaatgtc aacaactcaa taagtaatgc cctgaataag    1440
ttagaggaaa gcaacagcaa actagacaaa gtcaatgtca aactgaccag cacatctgct    1500
ctcattacct acatcgtttt aactgtcata tctcttgttt ttggtgtact tagcctggtt    1560
ctagcatgct acctgatgta caagcaaaag gcacaacaaa agaccttgtt atggcttggg    1620
aataataccc ttgatcagat gagagccact acaaaaatat ga                      1662
```

<210> SEQ ID NO 35
<211> LENGTH: 553
<212> TYPE: PRT
<213> ORGANISM: artificial sequence
<220> FEATURE:
<223> OTHER INFORMATION: NDV-F protein from wildtype YZCQ strain
(Amino Acid Sequence of NDV-F of Texas strain with lentogenic
cleavage site sequence)

<400> SEQUENCE: 35

```
Met Gly Ser Arg Ser Ser Thr Arg Ile Pro Val Pro Leu Met Leu Ile
1               5                   10                  15

Ile Arg Thr Ala Leu Thr Leu Ser Cys Ile Arg Leu Thr Ser Ser Leu
                20                  25                  30

Asp Gly Arg Pro Leu Ala Ala Gly Ile Val Val Thr Gly Asp Lys
            35                  40                  45

Ala Val Asn Ile Tyr Thr Ser Ser Gln Thr Gly Ser Ile Ile Val Lys
        50                  55                  60

Leu Leu Pro Asn Met Pro Lys Asp Lys Glu Val Cys Ala Lys Ala Pro
65                  70                  75                  80

Leu Glu Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Lys Gln Gly Arg Leu Ile Gly Ala Ile Ile Gly Ser Val Ala Leu Gly
        115                 120                 125

Val Ala Thr Ala Ala Gln Ile Thr Ala Ala Ser Ala Leu Ile Gln Ala
    130                 135                 140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Asn
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Thr Gln Leu Thr Ile Gln Ala Leu Tyr Asn
225                 230                 235                 240
```

Leu Ala Gly Gly Asn Met Asp Tyr Leu Leu Thr Lys Leu Gly Val Gly
            245                 250                 255

Asn Asn Gln Leu Ser Ser Leu Ile Gly Ser Gly Leu Ile Thr Gly Asn
        260                 265                 270

Pro Ile Leu Tyr Asp Ser Gln Thr Gln Ile Leu Gly Ile Gln Val Thr
            275                 280                 285

Leu Pro Ser Val Gly Asn Leu Asn Asn Met Arg Ala Thr Tyr Leu Glu
    290                 295                 300

Thr Leu Ser Val Ser Thr Thr Lys Gly Phe Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Gly Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
    370                 375                 380

Ala Leu Lys Gly Ser Val Ile Ala Asn Cys Lys Leu Thr Thr Cys Arg
385                 390                 395                 400

Cys Ala Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
        435                 440                 445

Ser Ile Leu Asp Ser Gln Val Ile Val Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Ser Lys Leu Asp Lys Val Asn Val Lys Leu Thr
                485                 490                 495

Ser Thr Ser Ala Leu Ile Thr Tyr Ile Val Leu Thr Val Ile Ser Leu
            500                 505                 510

Val Phe Gly Val Leu Ser Leu Val Leu Ala Cys Tyr Leu Met Tyr Lys
        515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Ile
545                 550

<210> SEQ ID NO 36
<211> LENGTH: 1662
<212> TYPE: DNA
<213> ORGANISM: artificial sequence
<220> FEATURE:
<223> OTHER INFORMATION: NDV-F Texas wildtype DNA sequence

<400> SEQUENCE: 36

```
atgggctcta aaccttctac caggatccca gcacctctga tgctgatcac ccggattatg      60
ctgatattgg actgtatccg tccgacaagc tctcttgacg gcaggcctct tgcagctgca     120
ggaattgtag taacaggaga taaggcagtc aatgtatata cctcgtctca gacagggtca     180
atcatagtca agttgctccc gaatatgccc aaggataagg aggcgtgtgc gaaagaccca     240
```

```
ttagaggcat ataacagaac actgactact tgctcactc ctcttggcga atccatccgc    300
aagatccaag ggtctgtgtc cacgtctgga ggaggcaagc aaggccgcct gataggtgct    360
gttattggta gtgtagctct tggggttgca acagcggcac aaataacagc agctgcggcc    420
ctaatacaag ccaaccagaa tgctgccaac atccttcggc ttaaggagag cattgctgca    480
accaatgaag ctgtgcatga agtcaccgac ggattatcac aactatcagt ggcagttggg    540
aagatgcagc agtttgtcaa tgaccagttt aataatacag cgcgagaatt ggactgtata    600
aaaatcacac aacaggttgg tgtagaactc aacctatacc taactgaatt gactacagta    660
ttcgggccac agatcacctc ccctgcatta actcagctga ccatccaggc actttataat    720
ttagctggtg gcaatatgga ttacttatta actaagttag gtataggaa caatcaactc    780
agctcattaa ttggcagcgg cctgatcact ggttaccca tattgtatga ctcacagact    840
caactcttgg gcatacaagt gaatttgccc tcagtcggga acttaaataa tatgcgtgcc    900
acctatttag agaccttatc tgtaagtaca gccaaaggat atgcctcagc acttgttcca    960
aaagtagtga cacaagtcgg ttctgtgata gaagagcttg acacctcata ctgtatagag    1020
tccgatctgg atttatattg tactagaata gtgacattcc ccatgtcccc aggtatttat    1080
tcctgtttaa gcggcaacac atcagcttgc atgtattcaa agactgaagg cgcactcact    1140
acgccgtata tggcccttaa aggctcagtt attgccaatt gtaagataac aacatgtaga    1200
tgtacagacc ctcctggtat catatcgcaa aattatggag aagctgtatc cctgatagat    1260
agacattcgt gcaatgtctt atcattagac gggataactc tgaggctcag tggagaattt    1320
gatgcaactt atcaaaagaa catctcaata ctagattctc aagtcatcgt gacaggcaat    1380
cttgatatat caactgaact tggaaacgtc aacaattcaa tcagcaatgc cttggataag    1440
ttggcaaaaa gcaacagcaa gctagaaaaa gtcaatgtca gactaaccag cacatccgct    1500
ctcattacct atattgttct gactgtcatt tctctagttt tcggtgcact aagtctgggt    1560
ttaacatgtt acctgatgta caacaaaag gcacaacaaa agaccttgct atggcttggg    1620
aataataccc tcgatcagat gagagccact acaagagcat ga                      1662
```

<210> SEQ ID NO 37
<211> LENGTH: 553
<212> TYPE: PRT
<213> ORGANISM: artificial sequence
<220> FEATURE:
<223> OTHER INFORMATION: NDV-F protein from wildtype Texas strain
    (Amino Acid Sequence of NDV-F VIId wt YZCQ with lentogenic
    cleavage site sequence)

<400> SEQUENCE: 37

Met Gly Ser Lys Pro Ser Thr Arg Ile Pro Ala Pro Leu Met Leu Ile
1               5                   10                  15

Thr Arg Ile Met Leu Ile Leu Asp Cys Ile Arg Pro Thr Ser Ser Leu
            20                  25                  30

Asp Gly Arg Pro Leu Ala Ala Ala Gly Ile Val Val Thr Gly Asp Lys
        35                  40                  45

Ala Val Asn Val Tyr Thr Ser Ser Gln Thr Gly Ser Ile Ile Val Lys
    50                  55                  60

Leu Leu Pro Asn Met Pro Lys Asp Lys Glu Ala Cys Ala Lys Asp Pro
65                  70                  75                  80

Leu Glu Ala Tyr Asn Arg Thr Leu Thr Thr Leu Leu Thr Pro Leu Gly
                85                  90                  95

Glu Ser Ile Arg Lys Ile Gln Gly Ser Val Ser Thr Ser Gly Gly Gly

```
                100             105              110
Lys Gln Gly Arg Leu Ile Gly Ala Val Ile Gly Ser Val Ala Leu Gly
            115                 120                 125

Val Ala Thr Ala Ala Gln Ile Thr Ala Ala Ala Leu Ile Gln Ala
            130                 135             140

Asn Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ser
                165                 170                 175

Val Ala Val Gly Lys Met Gln Gln Phe Val Asn Asp Gln Phe Asn Asn
            180                 185                 190

Thr Ala Arg Glu Leu Asp Cys Ile Lys Ile Thr Gln Gln Val Gly Val
            195                 200                 205

Glu Leu Asn Leu Tyr Leu Thr Glu Leu Thr Thr Val Phe Gly Pro Gln
            210                 215                 220

Ile Thr Ser Pro Ala Leu Thr Gln Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Tyr
            260                 265                 270

Pro Ile Leu Tyr Asp Ser Gln Thr Gln Leu Leu Gly Ile Gln Val Asn
            275                 280                 285

Leu Pro Ser Val Gly Asn Leu Asn Asn Met Arg Ala Thr Tyr Leu Glu
            290                 295                 300

Thr Leu Ser Val Ser Thr Ala Lys Gly Tyr Ala Ser Ala Leu Val Pro
305                 310                 315                 320

Lys Val Val Thr Gln Val Gly Ser Val Ile Glu Glu Leu Asp Thr Ser
                325                 330                 335

Tyr Cys Ile Glu Ser Asp Leu Asp Leu Tyr Cys Thr Arg Ile Val Thr
                340                 345                 350

Phe Pro Met Ser Pro Gly Ile Tyr Ser Cys Leu Ser Gly Asn Thr Ser
            355                 360                 365

Ala Cys Met Tyr Ser Lys Thr Glu Gly Ala Leu Thr Thr Pro Tyr Met
            370                 375                 380

Ala Leu Lys Gly Ser Val Ile Ala Asn Cys Lys Ile Thr Thr Cys Arg
385                 390                 395                 400

Cys Thr Asp Pro Pro Gly Ile Ile Ser Gln Asn Tyr Gly Glu Ala Val
                405                 410                 415

Ser Leu Ile Asp Arg His Ser Cys Asn Val Leu Ser Leu Asp Gly Ile
            420                 425                 430

Thr Leu Arg Leu Ser Gly Glu Phe Asp Ala Thr Tyr Gln Lys Asn Ile
            435                 440                 445

Ser Ile Leu Asp Ser Gln Val Ile Val Thr Gly Asn Leu Asp Ile Ser
            450                 455                 460

Thr Glu Leu Gly Asn Val Asn Asn Ser Ile Ser Asn Ala Leu Asp Lys
465                 470                 475                 480

Leu Ala Lys Ser Asn Ser Lys Leu Glu Lys Val Asn Val Arg Leu Thr
                485                 490                 495

Ser Thr Ser Ala Leu Ile Thr Tyr Ile Val Leu Thr Val Ile Ser Leu
            500                 505                 510

Val Phe Gly Ala Leu Ser Leu Gly Leu Thr Cys Tyr Leu Met Tyr Lys
            515                 520                 525
```

```
Gln Lys Ala Gln Gln Lys Thr Leu Leu Trp Leu Gly Asn Asn Thr Leu
    530                 535                 540

Asp Gln Met Arg Ala Thr Thr Arg Ala
545                 550
```

<210> SEQ ID NO 38
<211> LENGTH: 622
<212> TYPE: DNA
<213> ORGANISM: artificial sequence
<220> FEATURE:
<223> OTHER INFORMATION: MDV gB promoter

<400> SEQUENCE: 38

```
cgatgtttag tcacgataga catcggttcg cccagccgtc gaatacagca ttatatttta     60
gtgttgaaaa tgtagggctg cttcctcact taaaggagga aatggctcga ttcatgtttc    120
atagcagtag aaaaacagat tggaccgtca gtaagtttag agggttttat gactttagca    180
ctatagataa tgtaactgcg gcccatcgca tggcttggaa atatatcaaa gaactgattt    240
ttgcaacagc tttattttct tctgtattta aatgtggcga attgcacatc tgtcgtgccg    300
acagtttgca gatcaacagc aatggagact atgtatggaa aaatggaata tatataacat    360
atgaaaccga atatccactt ataatgattc tggggtcaga atcaagcact tcagaaacgc    420
aaaatatgac tgcaattatt gatacagatg ttttttcgtt gctttattct attttgcagt    480
atatggcccc cgttacggca gatcaggtgc gagtagaaca gattaccaac agccacgccc    540
ccatctgacc cgtccaatat tcttgtgtcc ctgcatttta tctcacacaa tttatgaaca    600
gcatcattaa gatcatctca ct                                             622
```

<210> SEQ ID NO 39
<211> LENGTH: 4850
<212> TYPE: DNA
<213> ORGANISM: artificial sequence
<220> FEATURE:
<223> OTHER INFORMATION: Partial plasmid SORF3-US2 gpVar-Ewtsyn sequence
      for vHVT202

<400> SEQUENCE: 39

```
taaaatggga tctatcatta cattcgttaa gagtctggat aattttactg tttgccagct     60
tcgatcttgg aacgtactgt ggatagtgcc ttacttggaa tcgtgaaaat ttgaaacgtc    120
cattatttgg atatcttccg gttgtcccat atcccgccct ggtaccgctc ggataccttg    180
cccgtatgga ttcgtattga cagtcgcgca atcggggacc aacaacgcgt gggtccacac    240
tcattcggaa attttccgat gattctgaat atttattgcc gctcgttacg agtcgttgga    300
catatctgta atacatttct tcttctgaag gatcgctgca catttgatct atacattggc    360
caggatgttc aagtctcaga tgttgcattc tggcacagca caactttatg gcatttccga    420
tgtaatcgtc cggcagccct gggggagttc tatattcgca tattgggatg gtaaggacaa    480
tagcagatct cgcaacctcc agggaggcta taataacgtt tttaaaggat ggatttctca    540
taaaaatctg tcgcaaatta cactgagaat atcctttact agcgccgatt gagagcatcg    600
tcgtccaatt ttctaaatgg aaagaaaaca aggcgggcaa gagtgttcca aacattttca    660
ttttcggcga atctctcaaa tcccatggcg tgcaattgat tgcaaaattg gcacttccgt    720
tcacgtttgt atctccaaac tctaagacac ttttaattga aaaactacgt tctagtgtgg    780
aaagaaacct ataggcagac catagaacta tttgacacca catatctttt tgtatgtcaa    840
actgaccatg atcgtatgtt gctgaatgca ctagggcaat tcgctcgcgc gactccatac    900
```

```
attgaataat tccacacgtc agctcatcgg ttagcaaggt ccagtagttg aagtcattta    960
tttttccccg cggctggcca aatctacctc tgggaatatc caagttgtcg aatatgatcg   1020
caccggctct ggtcatggtg aaggaacttg tagcataaag acgcaggtat catagggta    1080
atatttttt attcactcac atactaaaag taacgcatat tagcaccatg tatgggctat    1140
caattgacat ttgcgtagca ctacatcacg attatgtaca acataatggg acaacatatg   1200
cctgcaggtt agtcatatgt tacttggcag aggccgcatg gaaagtccct ggacgtggga   1260
catctgatta atacgtgagg aggtcagcca tgttcttttt ggcaaaggac tacggtcatt   1320
ggacgtttga ttggcatggg atagggtcag ccagagttaa cagtgttctt ttggcaaagg   1380
gatacgtgga aagtcccggg ccatttacag taaactgata cggggacaaa gcacagccat   1440
atttagtcat gtattgcttg cagagggtc tatggaaagt ccctggacgt gggacgtctg    1500
attaatatga agaaggtca gccagaggta gctgtgtcct ttttggcaaa gggatacggt    1560
tatgggacgt tgattggac tgggataggg tcagccagag ttaacagtgt tcttttggca    1620
aaggaaacgt ggaaagtccc gggccattta cagtaaactg atactgggac aaagtacacc   1680
catatttagt catgttcttt ttggcaaaga gcatctggaa agtcccgggc agcattatag   1740
tcacttggca gagggaaagg gtcactcaga gttaagtaca tctttccagg gccaatattc   1800
cagtaaatta cacttagttt tatgcaaatc agccacaaag gggattttcc cggtcaatta   1860
tgacttttc cttagtcatg cggtatccaa ttactgccaa attggcagta catactaggt    1920
gattcactga catttggccg tcctctggaa agtccctgga aaccgctcaa gtactgtatc   1980
atggtgactt tgcattttg gagagcacgc cccactccac cattggtcca cgtaccctat    2040
ggggagtgg tttatgagta tataaggggc tccggtttag aagccgggca gagcggccgc    2100
atgacaaacc tgcaagatca aacccaacag attgttccgt tcatacggag ccttctgatg   2160
ccaacaaccg gaccggcgtc cattccggac gacaccctgg agaagcacac tctcaggtca   2220
gagacctcga cctacaattt gactgtgggg gacacagggt cagggctaat tgtcttttc    2280
cctggattcc ctggctcaat tgtgggtgct cactacacac tgcagagcaa tgggaactac   2340
aagttcgatc agatgctcct gactgcccag aacctaccgg ccagctacaa ctactgcagg   2400
ctagtgagtc ggagtctcac agtaaggtca agcacactcc ctggtggcgt ttatgcacta   2460
aacggcacca taaacgccgt gaccttccaa ggaagcctga gtgaactgac agatgttagc   2520
tacaacgggt tgatgtctgc aacagccaac atcaacgaca aaattgggaa cgtcctagta   2580
gggaagggg taaccgtcct cagcttaccc acatcatatg atcttgggta tgtgaggctt   2640
ggtgacccca tacccgctat agggcttgac ccaaaaatgg tagcaacatg tgacagcagt   2700
gacaggccca gagtctacac cataactgca gccgataatt accaattctc atcacagtac   2760
caaacaggtg gggtaacaat cacactgttc tcagccaaca ttgatgccat cacaagtctc   2820
agcgttgggg gagagctcgt gttcaaaaca agcgtccaaa gccttgtact gggcgccacc   2880
atctacctta taggctttga tgggactgcg gtaatcacca gagctgtggc cgcaaacaat   2940
gggctgacgg ccggcatcga caatcttatg ccattcaatc ttgtgattcc aaccaatgag   3000
ataacccagc caatcacatc catcaaactg gagatagtga cctccaaaag tgatggtcag   3060
gcagggaac agatgtcatg gtcggcaagt gggagcctag cagtgacgat ccatggtggc   3120
aactatccag gagccctccg tcccgtcaca ctagtggcct acgaaagagt ggcaacagga   3180
tctgtcgtta cggtcgctgg ggtgagcaac ttcgagctga tcccaaatcc tgaactagca   3240
```

```
aagaacctgg ttacagaata tggccgattt gacccaggag ccatgaacta cacgaaattg    3300
atactgagtg agagggaccg ccttggcatc aagaccgtct ggccaacaag ggagtacact    3360
gactttcgtg agtacttcat ggaggtggcc gacctcaact ctcccctgaa gattgcagga    3420
gcatttggct tcaaagacat aatccgggcc ataaggaggt gagcggccgc gatatcaata    3480
aaatatcttt attttcatta catctgtgtg ttggtttttt gtgtgaatcg atagtactaa    3540
catacgctct ccatcaaaac aaaacgaaac aaaacaaact agcaaaatag gctgtcccca    3600
gtgcaagtgc aggtgccaga acatttctct tctagacctg caggcccggg gcaagtagat    3660
gcaatttcct cacactagtt gggtttatct actattgaat tttcccctat ctgtgataca    3720
cttgggagcc tctacaagca tattgccatc atgtacgttt ttatctactg tcttaacgcc    3780
catgggaacg gaggcgtcgt cgtcatgtat tggacggcaa cataggcagc aacacaaatt    3840
gcgtttaggt ggggtgcatg tggactcgat accaagcccc tgcagctggg aacgtctgg    3900 tggagagccg ataatttgat atacgcacgc catattactg tcgttgaagt acgccttatc    3960
ttctatgttt tcaaatttag gttcccaagt ggacgtgaga agtgtttgta tctcacatgg    4020
aatgggccaa ggcattccag cccaggtgcc tggtacttta atggcaaaca aacgttttgg    4080
tagaggtatt gattctattg cagttctgca gatatctgca gccccgagta tccacaggct    4140
atacgatacg ttatcggagg cctccgattc tagcattaca tagccggtca gtagatcctg    4200
ccattcggta gcgcaaccgg ctacatcttc aaacagtctc acaataaatg catctctcgt    4260
tcctgccaat ccggaaccgg gcataccact cccgcctgcc gatttaattc tcacaattgg    4320
gcgatgccgg cggggcaaaa cgaatgtgga tttggcaaac cgacacaggt ctgctgtacg    4380
gactaatatg ggcacaccca catcattctt cagatgctcc atgcattgtt ctatgagaaa    4440
gatccatagg gtggaggcag cgtcacgaga tcgcccaggc aatcgatcgc attcgtctag    4500
taaagtgacg agagttatca tgcacacacc catgcccacg ccttccgaat aactggagct    4560
gtggaagatc ggaaacgtct ttttgactgc cggtctcgta ctactttcgc acaggtgtat    4620
acccggacgc gtactatata ttttatatca tccaacgtcc cgaaattaca tacgtggcgg    4680
cgatggaagt agatgttgag tcttcgaaag taagtgcctc gaatatgggt attgtctgtg    4740
aaaatatcga agcggtacg acggttgcag aaccgtcgat gtcgccagat actagtaaca    4800
atagcttcga taacgaagac ttccgtgggc ctgaatacga tgtggagata             4850
```

<210> SEQ ID NO 40
<211> LENGTH: 4943
<212> TYPE: DNA
<213> ORGANISM: artificial sequence
<220> FEATURE:
<223> OTHER INFORMATION: Partial plasmid SB1US2 gpVIIdwtsyn sequence for
      vSB1-010

<400> SEQUENCE: 40
tctcgtctaa aacgctccag tgctttacag ttcgataatc tggacctggg gacgcgtata 60
ggatcgttcc tccacatgcg ctgctgtcgg tatctcgaat ccccggtatt cagttgaatc 120
gttggcggag tgtcctcctg gactctgcaa tgttccctag ccgtcttcac tatctcgtgc 180
aaggctctat aatacagttc ctctgcagac ccgtcgttgc tcttcccttc tgcgtcgtta 240
gttatttctg taggctccag acgatttgcc tgcatttgtg cgcaacataa tctgattgca 300
ttccctatct cgtcttccgg taatcccata ggtgttcggt attcgcagat aggtagagaa 360
agcaccactg caaatcgtgc aatttccatt gccccaacca atattttttt taagaacggc 420

```
atcgccgtta atgtacctcg gcattgtga cgatcgaaac ccttatggat gcctaaagag    480
agcattgcgg tccagttctc caggtgaaaa gagaatagcg cgggtagaaa cgggccgatt    540
agttttatct tcgccgcgtc cctaatatcc caagttctgc agtataactt ccatcgtccg    600
ttttcgacaa ggtccggcgc gacatagttt gaaatgtcat ctatcagaaa catctcgccc    660
atcgtagaaa aaacctgta cgcagaccat aaaaccattc ggtaccacat atccttgtgt    720
atatcaaacg atatgttggt tatgtcgttg gcggatgttg tatgaaatag agctaagcgt    780
tctctggatt ccacgcactg aacgattccg ttagtcaatt catctgctaa cataggccaa    840
aagtttattc gtgttacttt tctcggcggt ttggcaaaac gcccccttgg cacatccatg    900
tcattaaata cagcggcata actcctactc atgtgttcca tagcccaggt ttctgttcgg    960
tctgctacta cgatcagatc agtggcgcga tcagatgcgt gggatgaatg aagtgtatcc   1020
gaaagcagtt ttgagatata cgctaaactg tacgacgatt gtggcactaa cgaagctttt   1080
gcgcgacccc catcccacgc cctgcaggtt agtcatatgt tacttggcag aggccgcatg   1140
gaaagtccct ggacgtggga catctgatta atacgtgagg aggtcagcca tgttcttttt   1200
ggcaaaggac tacggtcatt ggacgtttga ttggcatggg atagggtcag ccagagttaa   1260
cagtgttctt ttggcaaagg gatacgtgga aagtcccggg ccatttacag taaactgata   1320
cggggacaaa gcacagccat atttagtcat gtattgcttg gcagagggtc tatggaaagt   1380
ccctggacgt gggacgtctg attaatatga agaaggtca gccagaggta gctgtgtcct    1440
ttttggcaaa gggatacggt tatgggacgt ttgattggac tgggataggg tcagccagag   1500
ttaacagtgt tcttttggca aaggaaacgt ggaaagtccc gggccattta cagtaaactg   1560
atactgggac aaagtacacc catatttagt catgttcttt ttggcaaaga gcatctggaa   1620
agtcccgggc agcattatag tcacttggca gagggaaagg gtcactcaga gttaagtaca   1680 tcttccagg gccaatattc cagtaaatta cacttagttt tatgcaaatc agccacaaag    1740
gggattttcc cggtcaatta tgactttttc cttagtcatg cggtatccaa ttactgccaa   1800
attggcagta catactaggt gattcactga catttggccg tcctctggaa agtccctgga   1860
aaccgctcaa gtactgtatc atggtgactt tgcattttg gagagcacgc cccactccac    1920
cattggtcca cgtaccctat ggggagtgg tttatgagta tataaggggc tccggtttag    1980
aagccgggca gagcggccgc atgggctcca aaccttctac caggatccca gcacctctga   2040
tgctgatcac ccggattatg ctgatattgg gctgtatccg tccgacaagc tctcttgacg   2100
gcaggcctct tgcagctgca ggaattgtag taacaggaga taaggcagtc aatgtataca   2160
cttcgtctca gacagggtca atcatagtca agttgctccc gaatatgccc agggataagg   2220
aggcgtgtgc aaaagcccca ttagaggcat ataacagaac actgactact ttgctcactc   2280
ctcttggcga ctccatccgc aagatccaag gtctgtgtc cacatctgga ggaggcaagc    2340
aaggccgcct gataggtgct gttattgcca gtgtagctct tggggttgca acagcggcac   2400
agataacagc agctgcggcc ctaatacaag ccaaccagaa tgccgccaac atcctccggc   2460
ttaaggagag cattgctgca accaatgaag ctgtgcatga agtcaccgac ggattatcac   2520
aactatcagt ggcagttggg aagatgcagc agtttgtcaa tgaccagttt aataatacgg   2580
cgcgagaatt ggactgtata aaaatcacac aacaggttgg tgtagaactc aacctatacc   2640
taactgaatt gactacagta ttcgggccac agatcacctc ccctgcatta actcagctga   2700
ccatccaggc actttataat ttagctggtg gcaaatgga ttacttatta actaagttag    2760
gtatagggaa caatcaactc agctcgttaa ttggtagcgg cctgatcact ggttacccta   2820
```

```
tactgtatga ctcacagact caactcttgg gcatacaagt gaatttaccc tcagtcggga    2880
acttaaataa tatgcgtgcc acctatttgg agaccttatc tgtaagtaca accaaaggat    2940
atgcctcagc acttgtcccg aaagtagtga cacaagtcgg ttccgtgata aagagcttg     3000 acacctcata ctgtatagag tccgatctgg atttatattg tactagaata gtgacattcc    3060
ccatgtcccc aggtatttat tcctgtttga gcggcaacac atcagcttgc atgtattcaa    3120
agactgaagg cgcactcact acgccgtata tgggcccttaa aggctcagtt attgccaatt   3180
gtaaaataac aacatgtaga tgtacagacc ctcctggtat catatcgcaa aattatggag    3240
aagctgtatc cctgatagat agacattcgt gcaatgtctt atcattagac gggataactc    3300
taaggctcag tggggaattt gatgcaactt atcaaaagaa catctcaata ctagattctc    3360
aagtcatcgt gacaggcaat cttgatatat caactgaact tggaaacgtc aacaattcaa    3420
tcagcaatgc cttggatagg ttggcagaaa gcaacagcaa gctagaaaaa gtcaatgtca    3480
gactaaccag cacatctgct ctcattacct atattgttct aactgtcatt tctctagttt    3540
tcggtgcact tagtctggtg ttagcgtgtt acctgatgta caaacagaag gcacaacaaa    3600
agaccttgct atggcttggg aataataccc tcgatcagat gagagccact acaagagcat    3660
gagcggccgc gatatcaata aaatatcttt attttcatta catctgtgtg ttggtttttt    3720
gtgtgaatcg atagtactaa catacgctct ccatcaaaac aaaacgaaac aaaacaaact    3780
agcaaaatag gctgtcccca gtgcaagtgc aggtgccaga acatttctct tctagacctg    3840
caggggagtc tgtgcaaggt taatgaccct cgcagttcat tcggaagtta taactgccgc    3900
cttcgcacat ttcttttttgt cctgttttgt attgccataa cagataggaa ttgaaacctg    3960
atcctcctgt tttttgcagc atggccagca acagaatact ttgtcggatc gactacttgc    4020
gcgagatggt tccgttcttg gaggtttcgg cgggtcgggt ggagaaccta ttatttttata   4080 cacacacgtc ataccgttgt cgcgaaaatg ttctttgtct tctgccgtct cgaacgtcgg    4140
ttcccacgta gacgttagga gcgttggaat ggtatcagga gagcccacg gcatgccgga     4200 ccaagtaccc gctactttga ccgcgagcag tctcttcggt aatgggatgt attccagagc    4260
agcgcggcag agatcagcgg cccccactat ccacagactg tatgaagtgt tttctgaaac    4320
atcggactcc aacatcaaat atccagacat aacatcttgc cattcggaag cacatccgcc    4380
gacatcttca aatagcctaa ctataaacga gtctctagtt cctgctaacc cagtacctcg    4440
aatgccagtc ccatccggtg ggttcgtcct gataatcggt ctctgacgcc gaggaagaac    4500
taaaaggggt ctggaaaagc ggaacagatc tgcagaccga acgactacag acacgcccac    4560
atcatcatgt atctgttcca tgcattgctt tatgagaaaa atccataagg ccgaggcggc    4620
atctctagat ctcccgggga gtctctcgca ctcatctagg agagtgacga cagttatcat    4680
agacacgccc atttgtgcac caaacgaaaa gttcctgtac tggtggagcg tcggcgcggg    4740
aatcggtccg tgctctgaaa ccagtgtcta gacagaagac catccggtaa attctggtgt    4800
atgaactgac ggtctccaga cgaacgtcga agacattaac gatggaaact aacgagcttt    4860
cttcaaaagt gtctgattac aacgctaata gaccttacga aactatacgc agcgatacca    4920
gtgacacaga tccgtcggtg tcg                                             4943
```

<210> SEQ ID NO 41
<211> LENGTH: 1362
<212> TYPE: DNA
<213> ORGANISM: artificial sequence
<220> FEATURE:

<223> OTHER INFORMATION: IBDV DNA encoding VP2 protein of IBDV E strain

<400> SEQUENCE: 41

```
atgacaaacc tgcaagatca aacccaacag attgttccgt tcatacggag ccttctgatg      60
ccaacaaccg gaccggcgtc cattccggac gacaccctgg agaagcacac tctcaggtca     120
gagacctcga cctacaattt gactgtgggg gacacagggt cagggctaat tgtcttttc     180
cctggattcc ctggctcaat tgtgggtgct cactacacac tgcagagcaa tgggaactac     240
aagttcgatc agatgctcct gactgcccag aacctaccgg ccagctacaa ctactgcagg     300
ctagtgagtc ggagtctcac agtaaggtca agcacactcc tggtggcgt ttatgcacta     360
aacggcacca taaacgccgt gaccttccaa ggaagcctga gtgaactgac agatgttagc     420
tacaacgggt tgatgtctgc aacagccaac atcaacgaca aaattgggaa cgtcctagta     480
ggggaagggg taaccgtcct cagcttaccc acatcatatg atcttgggta tgtgaggctt     540
ggtgacccca tacccgctat agggcttgac ccaaaaatgg tagcaacatg tgacagcagt     600
gacaggccca gagtctacac cataactgca gccgataatt accaattctc atcacagtac     660
caaacaggtg gggtaacaat cacactgttc tcagccaaca ttgatgccat cacaagtctc     720
agcgttgggg gagagctcgt gttcaaaaca agcgtccaaa gccttgtact gggcgccacc     780
atctacctta taggctttga tgggactgcg gtaatcacca gagctgtggc cgcaaacaat     840
gggctgacgg ccggcatcga caatcttatg ccattcaatc ttgtgattcc aaccaatgag     900
ataacccagc caatcacatc catcaaactg gagatagtga cctccaaaag tgatggtcag     960
gcagggggaac agatgtcatg gtcggcaagt gggagcctag cagtgacgat ccatggtggc    1020
aactatccag gagccctccg tcccgtcaca ctagtggcct acgaaagagt ggcaacagga    1080
tctgtcgtta cggtcgctgg ggtgagcaac ttcgagctga tcccaaatcc tgaactagca    1140
aagaacctgg ttacagaata tggccgattt gacccaggag ccatgaacta cacgaaattg    1200
atactgagtg agagggaccg ccttggcatc aagaccgtct ggccaacaag ggagtacact    1260
gactttcgtg agtacttcat ggaggtggcc gacctcaact ctcccctgaa gattgcagga    1320
gcatttggct tcaaagacat aatccgggcc ataaggaggt ga                        1362
```

<210> SEQ ID NO 42
<211> LENGTH: 453
<212> TYPE: PRT
<213> ORGANISM: artificial sequence
<220> FEATURE:
<223> OTHER INFORMATION: IBDV VP2 protein of IBDV E strain

<400> SEQUENCE: 42

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
```

```
            100                 105                 110
Leu Pro Gly Gly Val Tyr Ala Leu Asn Gly Thr Ile Asn Ala Val Thr
            115                 120                 125

Phe Gln Gly Ser Leu Ser Glu Leu Thr Asp Val Ser Tyr Asn Gly Leu
            130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                    165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
            195                 200                 205

Thr Ala Ala Asp Asn Tyr Gln Phe Ser Ser Gln Tyr Gln Thr Gly Gly
            210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                    245                 250                 255

Leu Gly Ala Thr Ile Tyr Leu Ile Gly Phe Asp Gly Thr Ala Val Ile
            260                 265                 270

Thr Arg Ala Val Ala Ala Asn Asn Gly Leu Thr Ala Gly Ile Asp Asn
            275                 280                 285

Leu Met Pro Phe Asn Leu Val Ile Pro Thr Asn Glu Ile Thr Gln Pro
            290                 295                 300

Ile Thr Ser Ile Lys Leu Glu Ile Val Thr Ser Lys Ser Asp Gly Gln
305                 310                 315                 320

Ala Gly Glu Gln Met Ser Trp Ser Ala Ser Gly Ser Leu Ala Val Thr
                    325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
            355                 360                 365

Ser Asn Phe Glu Leu Ile Pro Asn Pro Glu Leu Ala Lys Asn Leu Val
            370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                    405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
            435                 440                 445

Arg Ala Ile Arg Arg
        450

<210> SEQ ID NO 43
<211> LENGTH: 884
<212> TYPE: DNA
<213> ORGANISM: artificial sequence
<220> FEATURE:
<223> OTHER INFORMATION: Guinea pig CMV promoter

<400> SEQUENCE: 43
ttagtcatat gttacttggc agaggccgca tggaaagtcc ctggacgtgg gacatctgat      60
```

```
taatacgtga ggaggtcagc catgttctttt ttggcaaagg actacggtca ttggacgttt    120
gattggcatg ggataggtc agccagagtt aacagtgttc ttttggcaaa gggatacgtg     180
gaaagtcccg ggccatttac agtaaactga tacggggaca agcacagcc atatttagtc     240 atgtattgct tggcagaggg tctatggaaa gtccctggac gtgggacgtc tgattaatat    300
gaaagaaggt cagccagagg tagctgtgtc cttttggca agggatacg gttatgggac      360 gtttgattgg actgggatag ggtcagccag agttaacagt gttctttgg caaaggaaac     420 gtggaaagtc ccgggccatt tacagtaaac tgatactggg acaaagtaca cccatattta   480
gtcatgttct ttttggcaaa gagcatctgg aaagtcccgg gcagcattat agtcacttgg    540
cagagggaaa gggtcactca gagttaagta catctttcca gggccaatat tccagtaaat    600
tacacttagt tttatgcaaa tcagccacaa agggatttt cccggtcaat tatgactttt     660
tccttagtca tgcggtatcc aattactgcc aaattggcag tacatactag gtgattcact    720
gacatttggc cgtcctctgg aaagtccctg gaaaccgctc aagtactgta tcatggtgac    780
tttgcatttt tggagagcac gccccactcc accattggtc cacgtaccct atggggagt    840 ggtttatgag tatataaggg gctccggttt agaagccggg caga                     884
```

```
<210> SEQ ID NO 44
<211> LENGTH: 30
<212> TYPE: DNA
<213> ORGANISM: artificial sequence
<220> FEATURE:
<223> OTHER INFORMATION: primer HM101

<400> SEQUENCE: 44
ccggaattcc gatgtttagt cacgatagac                                     30
```

```
<210> SEQ ID NO 45
<211> LENGTH: 35
<212> TYPE: DNA
<213> ORGANISM: artificial sequence
<220> FEATURE:
<223> OTHER INFORMATION: Primer HM102

<400> SEQUENCE: 45
ataagagcgg ccgcagtgag atgatcttaa tgatg                               35
```

```
<210> SEQ ID NO 46
<211> LENGTH: 38
<212> TYPE: DNA
<213> ORGANISM: artificial sequence
<220> FEATURE:
<223> OTHER INFORMATION: primer F-ATG

<400> SEQUENCE: 46
tatagcggcc gcaagatggg ctccagatct tctaccag                            38
```

```
<210> SEQ ID NO 47
<211> LENGTH: 34
<212> TYPE: DNA
<213> ORGANISM: artificial sequence
<220> FEATURE:
<223> OTHER INFORMATION: Primer F-STOP

<400> SEQUENCE: 47
cgaggcggcc gctcatatttt ttgtagtggc tctc                               34
```